US012721035B2

(12) United States Patent
Dai et al.

(10) Patent No.: US 12,721,035 B2
(45) Date of Patent: Aug. 25, 2026

(54) HETEROCYCLIC AROMATIC AMINE COMPOUND AND ELECTROLUMINESCENCE USING THE SAME

(71) Applicants: Wuhan Tianma Micro-Electronics Co., Ltd., Wuhan (CN); Wuhan Tianma MicroElectronics Co., Ltd. Shanghai Branch, Shanghai (CN)

(72) Inventors: Wen Peng Dai, Shanghai (CN); Wei Gao, Shanghai (CN); Lu Zhai, Shanghai (CN); Tingting Lu, Shanghai (CN); You Gao, Shanghai (CN)

(73) Assignees: Wuhan Tianma Micro-Electronics Co., Ltd., Wuhan (CN); Wuhan Tianma MicroElectronics Co., Ltd. Shanghai Branch, Shanghai (CN)

( * ) Notice: Subject to any disclaimer, the term of this patent is extended or adjusted under 35 U.S.C. 154(b) by 922 days.

(21) Appl. No.: 18/083,291

(22) Filed: Dec. 16, 2022

(65) Prior Publication Data

US 2024/0155939 A1 May 9, 2024

(30) Foreign Application Priority Data

Oct. 9, 2022 (CN) ......................... 202211225923.8

(51) Int. Cl.

*H10K 85/60* (2023.01)
*C07D 471/04* (2006.01)
*H10K 50/86* (2023.01)

(52) U.S. Cl.

CPC ......... *H10K 85/636* (2023.02); *C07D 471/04* (2013.01); *H10K 85/633* (2023.02); *H10K 50/86* (2023.02); *H10K 85/622* (2023.02); *H10K 85/626* (2023.02); *H10K 85/657* (2023.02); *H10K 85/6572* (2023.02)

(58) Field of Classification Search

None
See application file for complete search history.

(56) References Cited

FOREIGN PATENT DOCUMENTS

| | | | |
|---|---|---|---|
| CN | 108341795 | A | 7/2018 |
| CN | 113105413 | A | 7/2021 |
| CN | 114106001 | A | 3/2022 |
| CN | 114853737 | A | 8/2022 |

OTHER PUBLICATIONS

Machine English translation of Gao et al. (CN 114106001 A). Jan. 20, 2026.*

* cited by examiner

*Primary Examiner* — Jay Yang
(74) *Attorney, Agent, or Firm* — Anova Law Group, PLLC

(57) ABSTRACT

A compound is provided as having a structure of Formula I:

Formula I

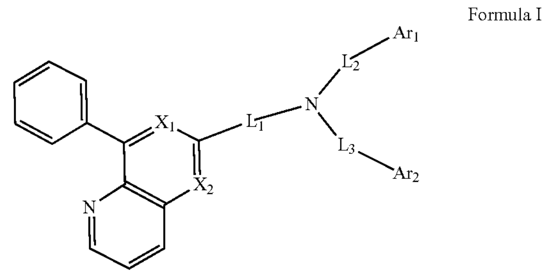

where $X_1$ and $X_2$ are each independently a nitrogen atom or a C—R group, C is a carbon atom, R is a hydrogen atom, a deuterium atom, a halogen atom, or a cyano group, CR, and at least one of $X_1$ and $X_2$ is N; $L_1$, $L_2$, and $L_3$ are each independently a single bond, a substituted or unsubstituted aryl group, or substituted or unsubstituted aryl heteroaryl group; and $Ar_1$, $Ar_2$ are each independently a substituted or unsubstituted aryl group or a substituted or unsubstituted heteroaryl group.

16 Claims, No Drawings

HETEROCYCLIC AROMATIC AMINE COMPOUND AND ELECTROLUMINESCENCE USING THE SAME

RELATED APPLICATION(S)

This application claims priority to Chinese Patent Application No. CN202211225923.8 filed with the National Intellectual Property Administration, PRC on Oct. 9, 2022, which is incorporated herein by reference in entirety.

FIELD OF THE TECHNOLOGY

The present disclosure relates to the technical field of organic electroluminescent materials, and in particular to a heterocyclic aromatic amine compound and its implementation in electroluminescence.

BACKGROUND

With decades of development, improvements have been made to OLED (organic light emitting diodes). Although its internal quantum efficiency may come close to 100%, OLED's external quantum efficiency may only be about 20%. Most of the light is confined inside the light-emitting device due to factors such as substrate mode loss, surface plasmon loss, and waveguide effect, resulting in a large amount of energy loss.

In top-emitting devices, an organic capping layer (CPL) is deposited on the translucent metal electrode Al to adjust the optical interference distance, suppress the reflection of external light, and suppress the extinction caused by the movement of surface plasmons, thereby elevating light extraction rate and improving luminous efficiency. However, certain CPL layers are met with the problem of low refractive index, where the refractive index is generally below 1.9, which may not meet the requirements of high refractive index.

SUMMARY

The present disclosure provides a heterocyclic aromatic amine compound and its implementation in electroluminescence. The heterocyclic aromatic amine compound has the structure shown in Formula I. The heterocyclic aromatic amine compound may be used as a capping layer in organic photoelectric devices, and may improve the efficiency and lifespan of OLED (organic light-emitting diode) devices.

In one aspect, the present disclosure provides a compound, having a structure of Formula I:

Formula I

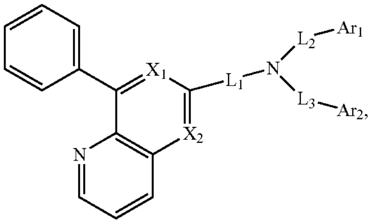

where $X_1$ and $X_2$ are each independently a nitrogen atom or a C—R group, C is a carbon atom, R is a hydrogen atom, a deuterium atom, a halogen atom, or a cyano group, and at least one of $X_1$ and $X_2$ is N; $L_1$, $L_2$, and $L_3$ are each independently a single bond, a substituted or unsubstituted aryl group, or substituted or unsubstituted aryl heteroaryl group; and $Ar_1$, $Ar_2$ are each independently a substituted or unsubstituted aryl group or a substituted or unsubstituted heteroaryl group.

In another aspect, the present disclosure provides an organic light-emitting device, including an anode, a cathode, and an organic thin film layer positioned between the anode and the cathode, the organic thin film layer including a capping layer, and the capping layer includes a compound, having a structure of Formula I:

Formula I

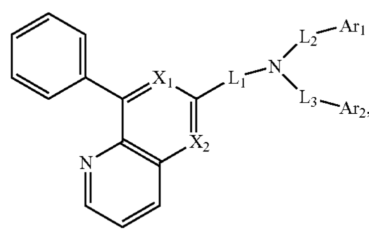

where $X_1$ and $X_2$ are each independently a nitrogen atom or a C—R group, C is a carbon atom, R is a hydrogen atom, a deuterium atom, a halogen atom, or a cyano group, and at least one of $X_1$ and $X_2$ is N; $L_1$, $L_2$, and $L_3$ are each independently a single bond, a substituted or unsubstituted aryl group, or substituted or unsubstituted aryl heteroaryl group; and $Ar_1$, $Ar_2$ are each independently a substituted or unsubstituted aryl group or a substituted or unsubstituted heteroaryl group.

In yet another aspect, the present disclosure provides a display panel, which includes an organic light-emitting device described herein.

Heterocyclic aromatic amine compound provided according to certain embodiment(s) of the present disclosure is of a structure represented by Formula I. The heterocyclic aromatic amine compound may be used as a capping layer in organic photoelectric devices. The present disclosure, in certain embodiment(s), solves a technical problem by providing a heterocyclic aromatic amine compound and its implementation in electroluminescence, which may effectively improve the luminous efficiency of devices.

DETAILED DESCRIPTION

The present disclosure provides a compound, having a structure of Formula I:

Formula I

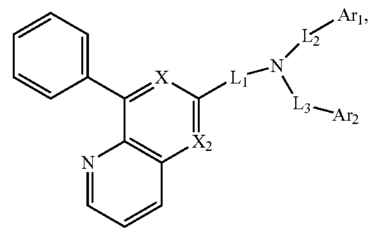

where $X_1$ and $X_2$ are each independently a nitrogen atom or a C—R group, C is a carbon atom, R is a hydrogen atom, a deuterium atom, a halogen atom, or a cyano group, and at least one of $X_1$ and $X_2$ is N; $L_1$, $L_2$, and $L_3$ are each independently a single bond, a substituted or unsubstituted aryl group, or substituted or unsubstituted aryl heteroaryl group; and $Ar_1$, $Ar_2$ are each independently a substituted or unsubstituted aryl group or a substituted or unsubstituted heteroaryl group.

In certain embodiment(s), the heterocyclic aromatic amine compound is of a structure of Formula I-a or Formula I-b:

Formula I-a

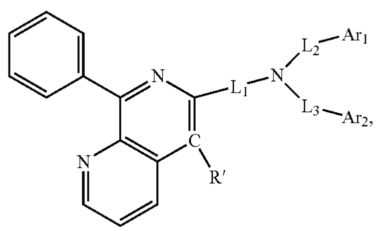

Formula I-b

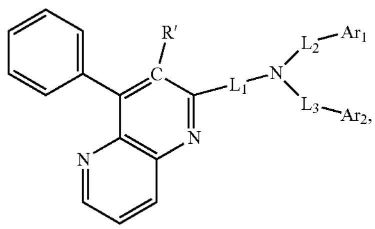

R' is the hydrogen atom, the deuterium atom, the halogen atom, or the cyano group.

In certain embodiment(s), $L_1$, $L_2$, and $L_3$ are each independently the single bond, a substituted or unsubstituted C6-C18 aryl group, or a substituted or unsubstituted C5-C18 heteroaryl group.

In certain embodiment(s), $L_1$, $L_2$, and $L_3$ are each independently the single bond, a substituted or unsubstituted monocyclic aryl group, a substituted or unsubstituted monocyclic heteroaryl group, a condensed aryl group formed by condensing 2-5 rings, or a condensed heteroaryl group formed by condensing 2 to 4 rings.

In certain embodiment(s), heteroatoms of the monocyclic heteroaryl group and the condensed heteroaryl group are each independently a nitrogen atom, an oxygen atom, or a sulfur atom.

In certain embodiment(s), $L_1$, $L_2$, and $L_3$ are each independently the single bond, a substituted or unsubstituted phenyl group, a substituted or unsubstituted furyl group, a substituted or unsubstituted thienyl group, a substituted or unsubstituted pyrrolyl group, a substituted or unsubstituted pyridyl group, a substituted or unsubstituted pyranyl group, a substituted or unsubstituted pyrimidinyl group, a substituted or unsubstituted pyrazinyl group, a substituted or unsubstituted pyridazinyl group, a substituted or unsubstituted triazinyl group, a substituted or unsubstituted naphthyl group, a substituted or unsubstituted quinolinyl group, a substituted or unsubstituted quinoxalinyl group, a substituted or unsubstituted isoquinolinyl group, a substituted or unsubstituted quinazolinyl group, a substituted or unsubstituted anthracenyl group, or a substituted or unsubstituted phenanthrenyl group.

In certain embodiment(s), $L_1$, $L_2$, and $L_3$ are each independently the single bond or the substituted or unsubstituted phenyl group.

In certain embodiment(s), $Ar_1$ and $Ar_2$ are each independently a substituted or unsubstituted C6-C30 aryl group or a substituted or unsubstituted C3-C30 heteroaryl group.

In certain embodiment(s), $Ar_1$ and $Ar_2$ are each independently the substituted or unsubstituted monocyclic aryl group, the monocyclic heteroaryl group, a condensed aryl group formed by condensing the 2-5 rings, or a condensed heteroaryl group formed by condensing 2 to 5 rings.

In certain embodiment(s), heteroatoms of the monocyclic heteroaryl group and the condensed heteroaryl group are each independently the nitrogen atom, the oxygen atom, or the sulfur atom.

In certain embodiment(s), the 2-5 rings forming the condensed heteroaryl group are each independently a phenyl group, a pyridyl group, a furyl group, a thienyl group, a pyrrolyl group, a pyranyl group, a pyrimidinyl group, a pyrazinyl group, a pyridazinyl group, a triazinyl group, an oxazolyl group, an isoxazolyl group, a pyrazolyl group, an imidazolyl group, or a thiazolyl group.

In certain embodiment(s), Ar1 and Ar2 are each independently a substituted or unsubstituted phenyl group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted perylenyl group, a substituted or unsubstituted benzophenanthrenyl group, a substituted or unsubstituted benzopyrenyl group, a substituted or unsubstituted benzanthracenyl group, a substituted or unsubstituted furyl group, a substituted or unsubstituted thienyl group, a substituted or unsubstituted pyrrolyl group, a substituted or unsubstituted pyridyl group, a substituted or unsubstituted pyranyl group, a substituted or unsubstituted pyrimidinyl group, a substituted or unsubstituted pyrazinyl group, pyridazinyl group, a substituted or unsubstituted triazinyl group, a substituted or unsubstituted quinolinyl group, a substituted or unsubstituted quinoxalinyl group, isoquinolinyl group, a substituted or unsubstituted quinazolinyl group, a substituted or unsubstituted acridinyl group, a substituted or unsubstituted carbazolyl group, a substituted or unsubstituted indolyl group, a substituted or unsubstituted benzofuryl group, a substituted or unsubstituted benzothienyl group, a substituted or unsubstituted benzoxazolyl group, a substituted or unsubstituted dibenzofuryl group, a substituted or unsubstituted dibenzothienyl group, a substituted or unsubstituted 2-N heterodibenzofuryl group, a substituted or unsubstituted 3-N heterodibenzofuryl group, a substituted or unsubstituted 4-N heterodibenzofuryl group, a substituted or unsubstituted 5-N heterodibenzofuryl group, a substituted or unsubstituted 2-N heterodibenzothienyl group, a substituted or unsubstituted 1,10-phenanthroline, 2-phenanthroline group, or a substituted or unsubstituted indolocarbazolyl group.

In certain embodiment(s), $Ar_1$ and $Ar_2$ are each independently of a structure of any one of:

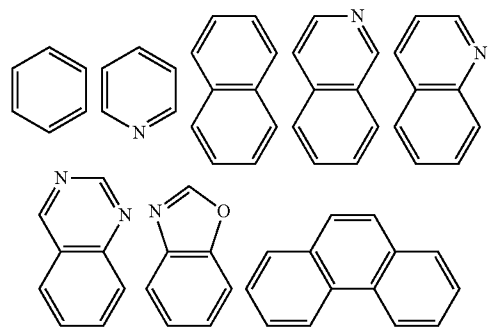

-continued
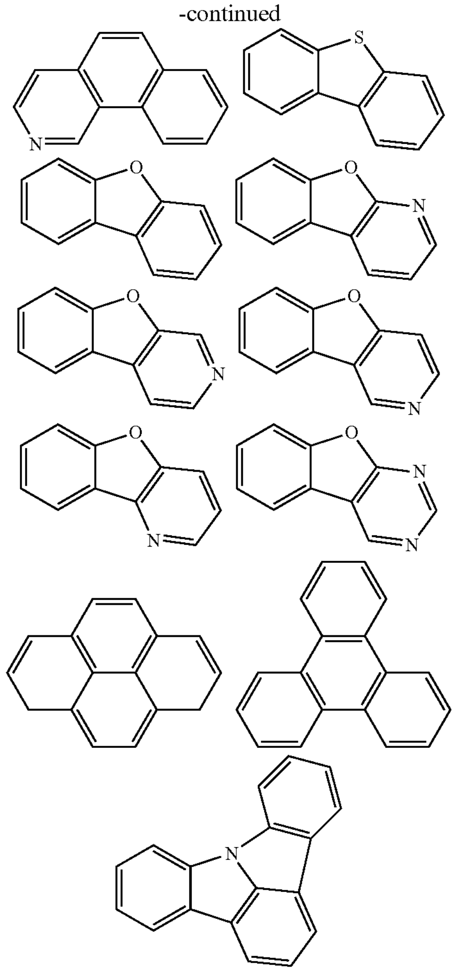
where the groups are each connected to a parent nucleus by any carbon atom.
In certain embodiment(s), the heterocyclic aromatic amine compound is of any one of the following structures.
P1
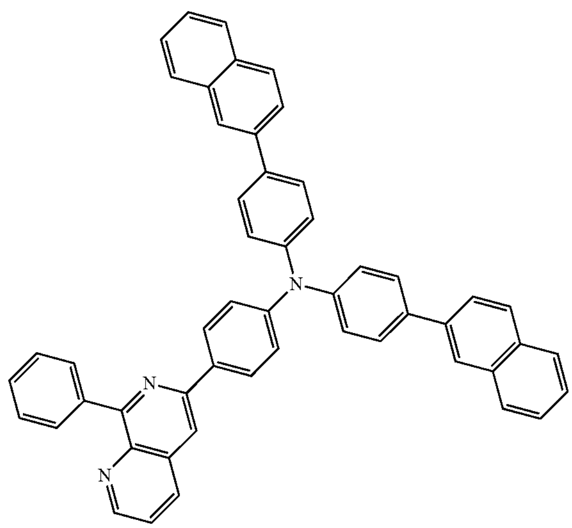
-continued
P2
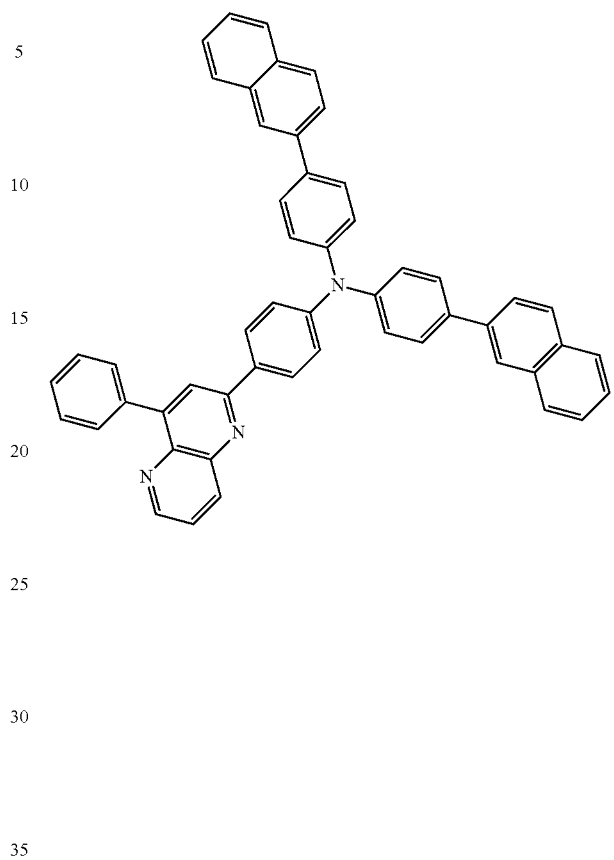
P3
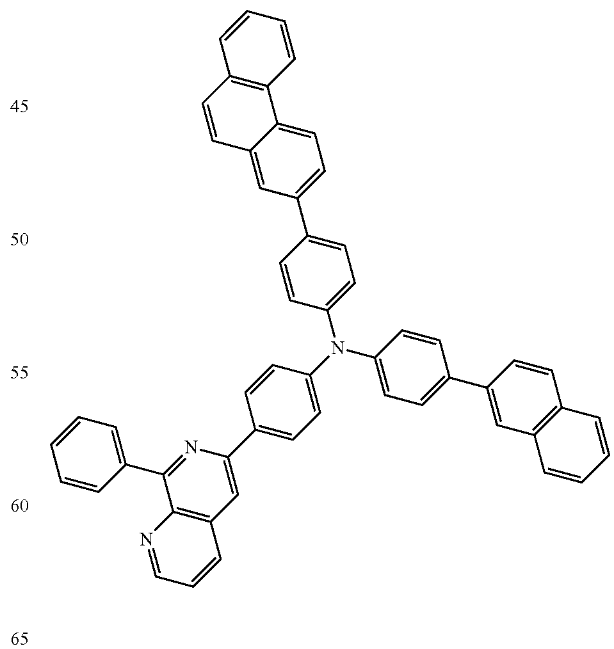

-continued
P4
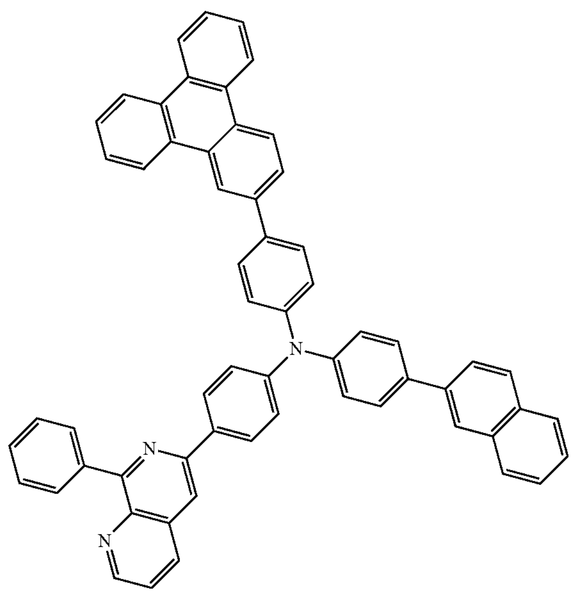
P5
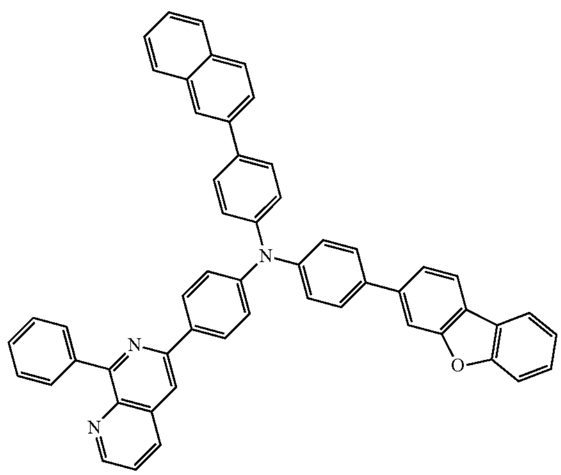
P6
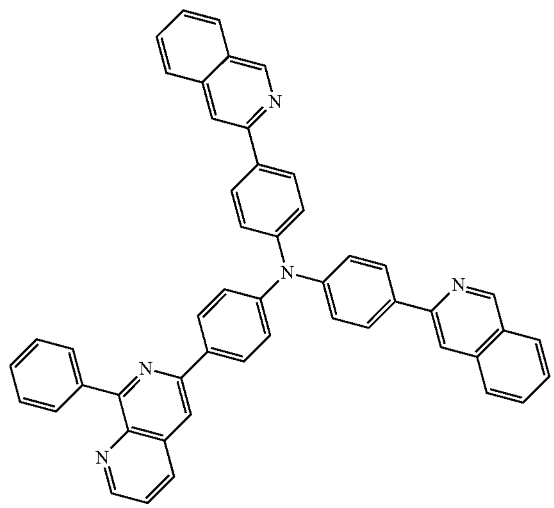
-continued
P7
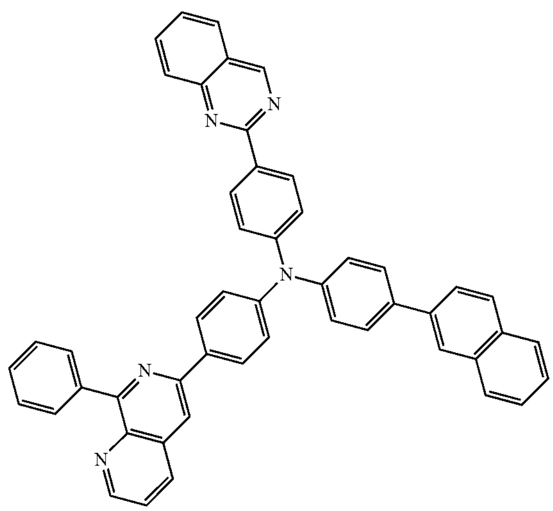
P8
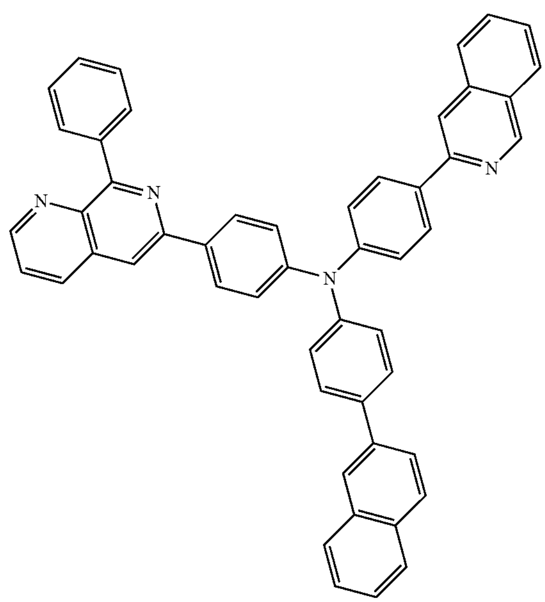
P9
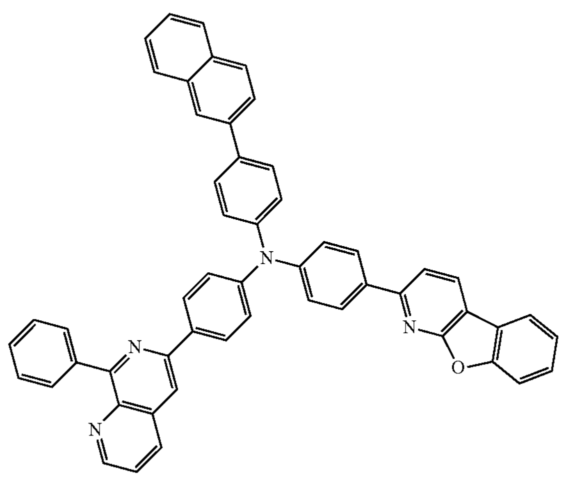

-continued
P10
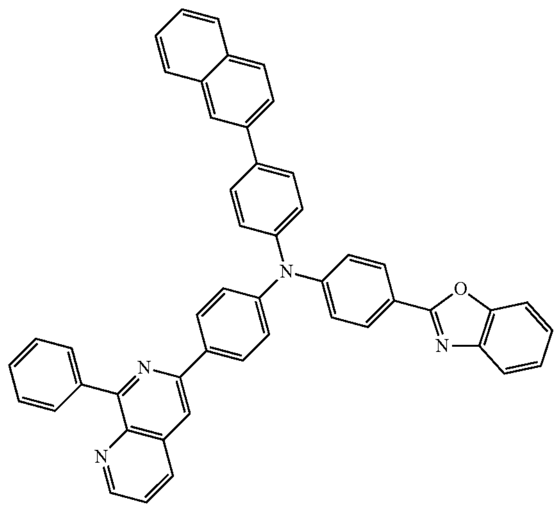
P11
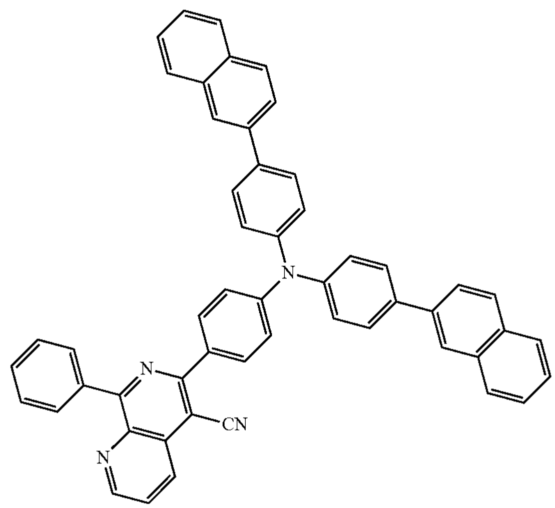
P12
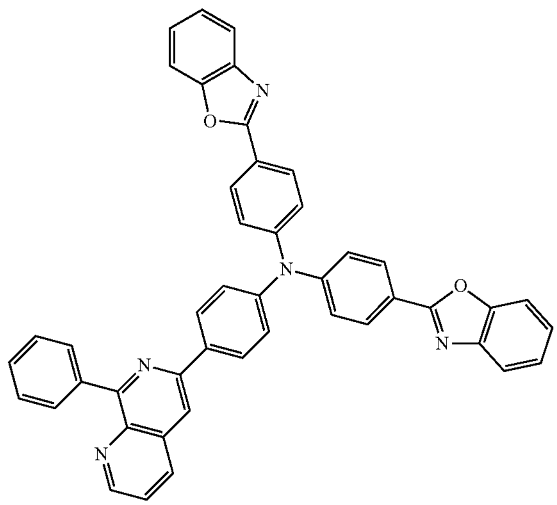
-continued
P13
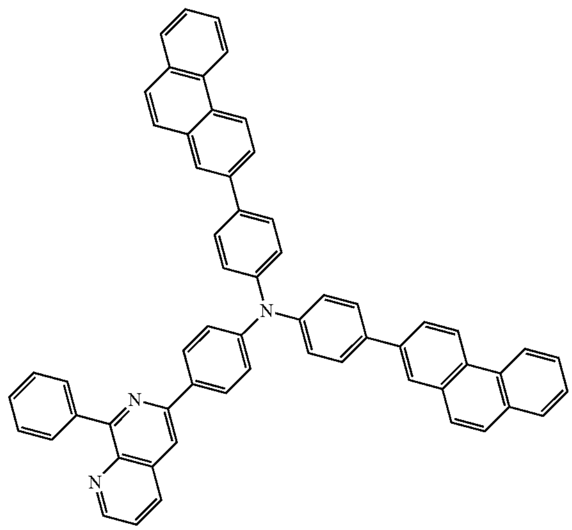
P14
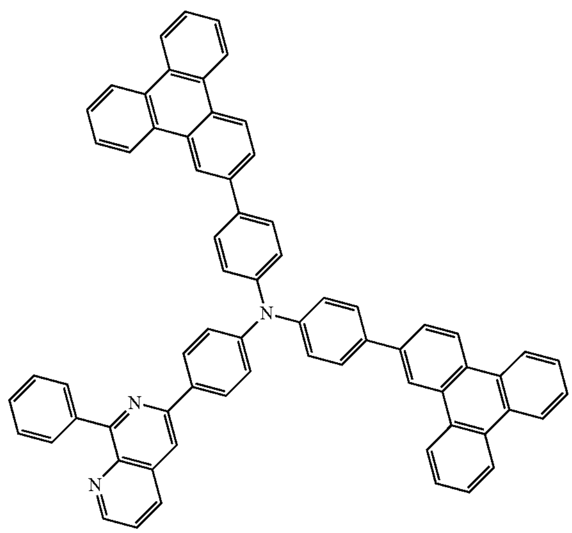
P15
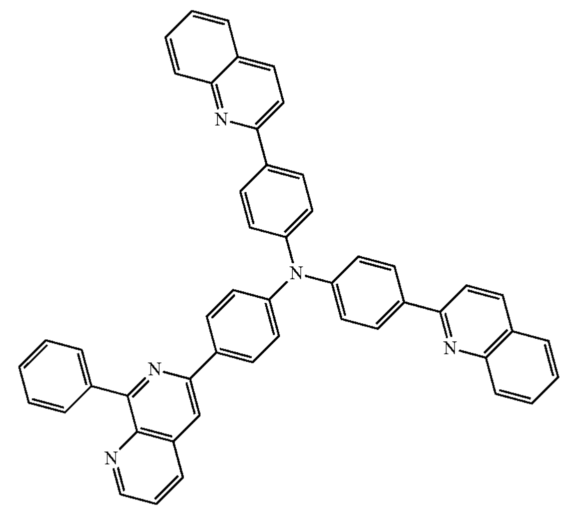

-continued
P16
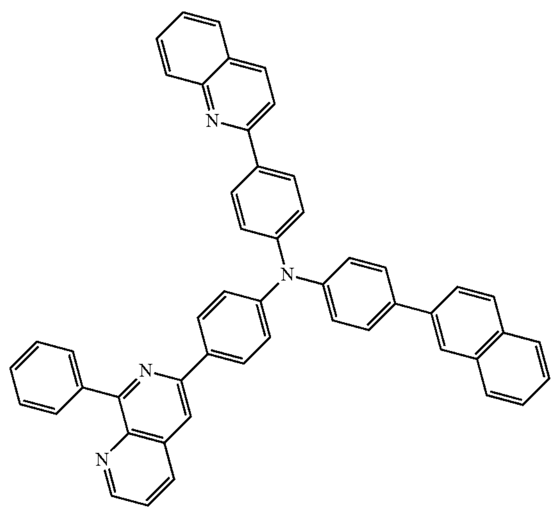
P17
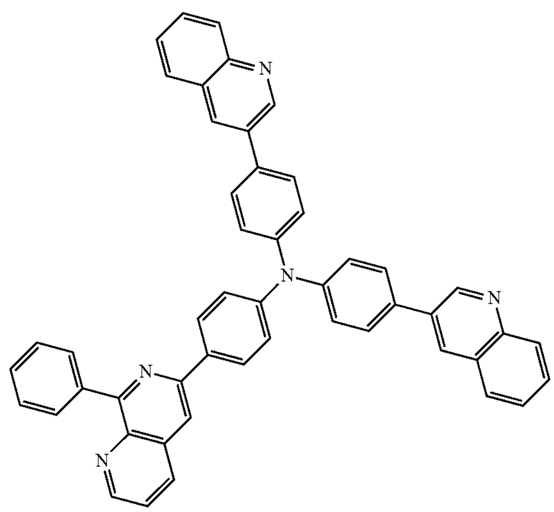
P18
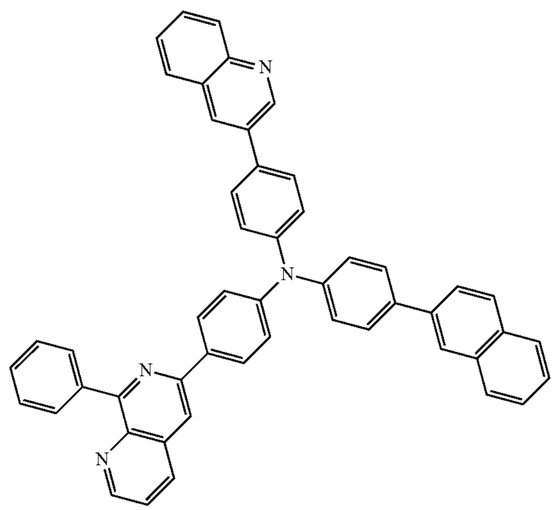
-continued
P19
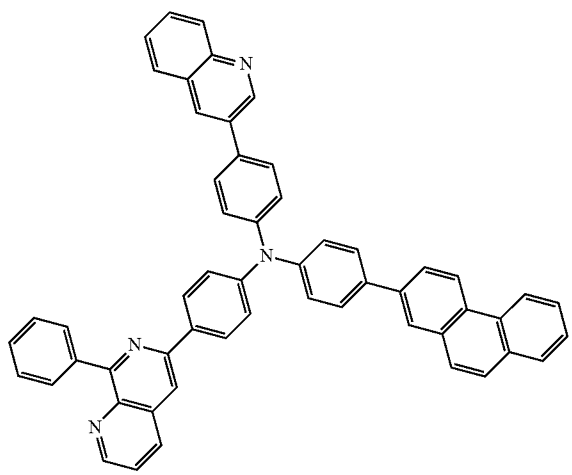
P20
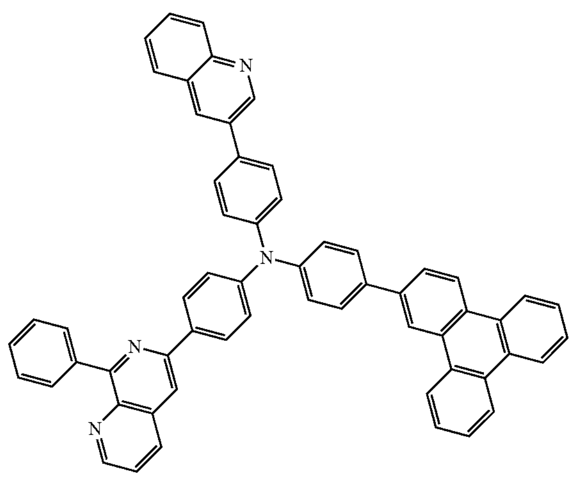
P21
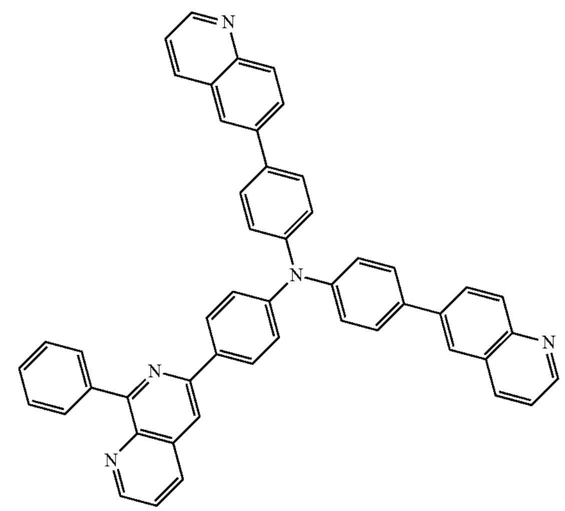

-continued
P22
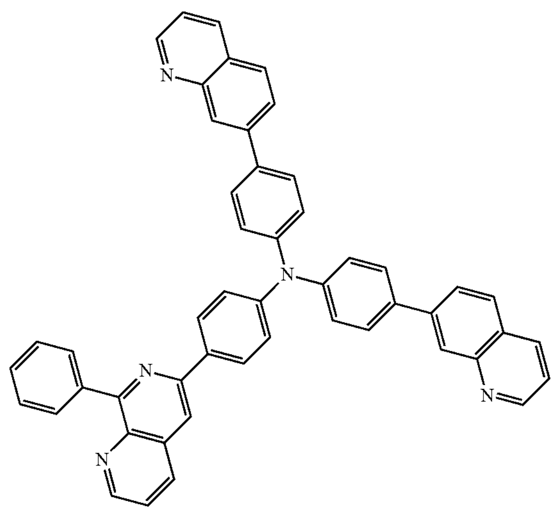
P23
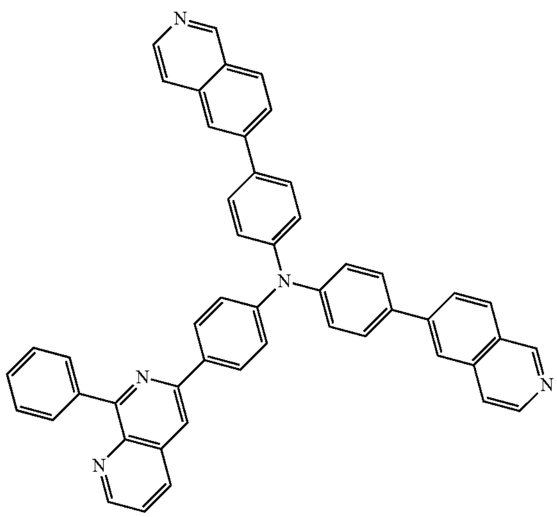
P24
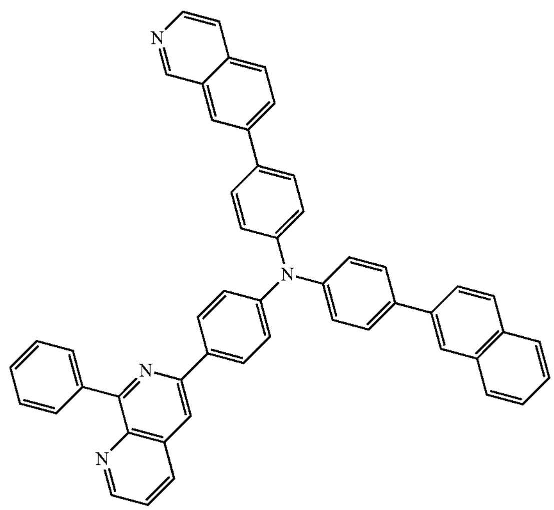
-continued
P25
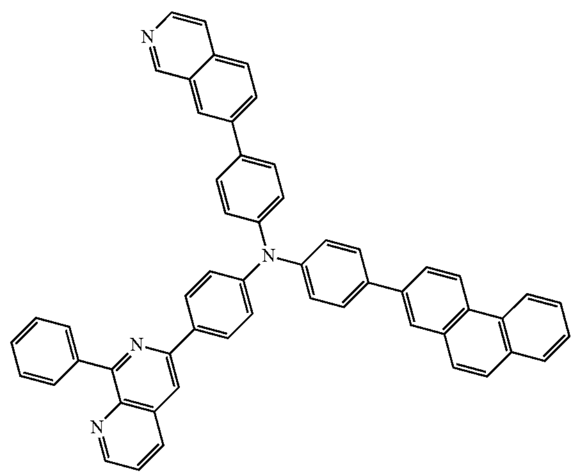
P26
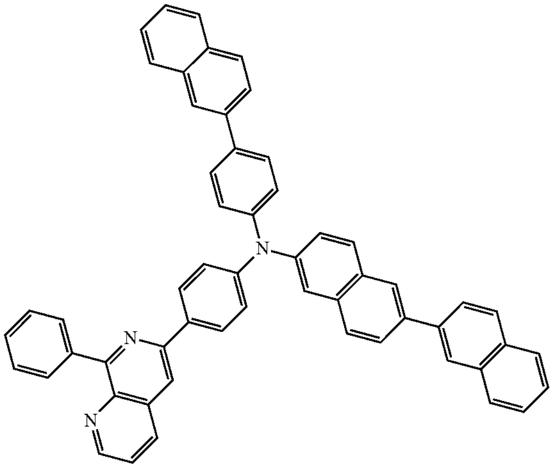
P27
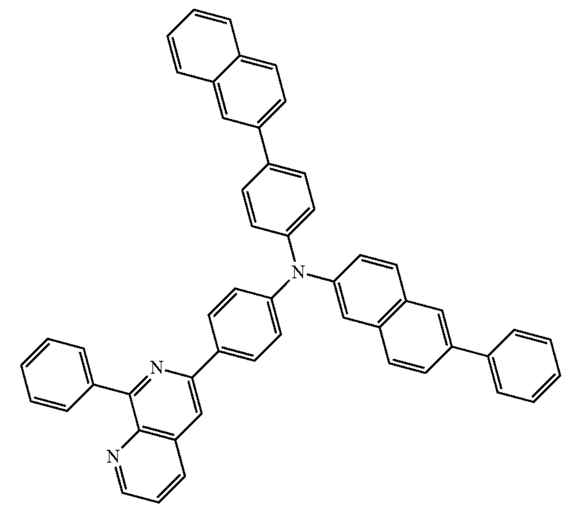

-continued
P28
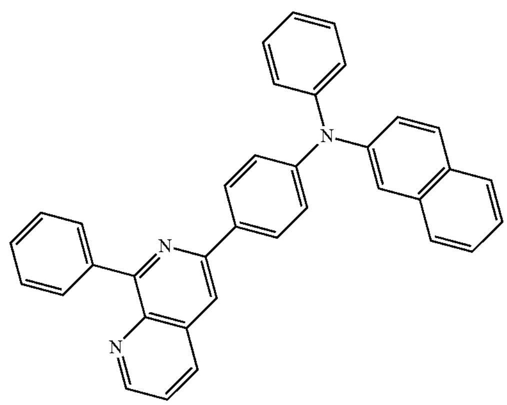
P29
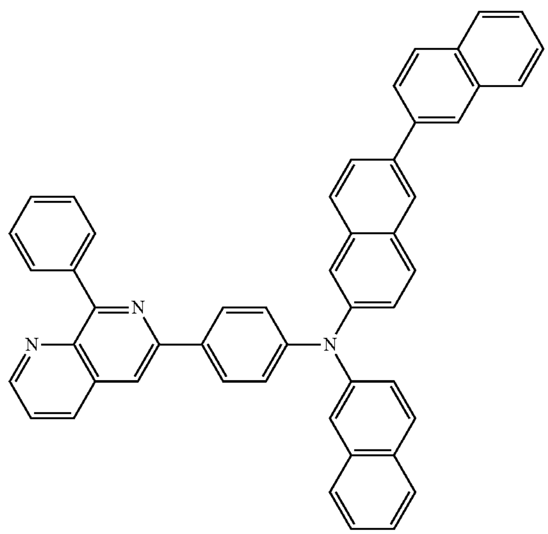
P30
-continued
P31
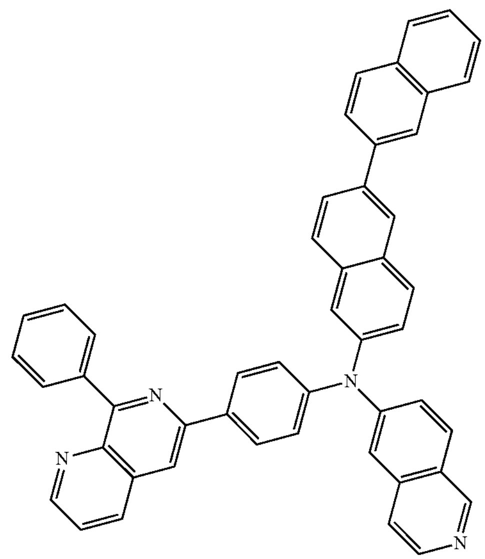
P32
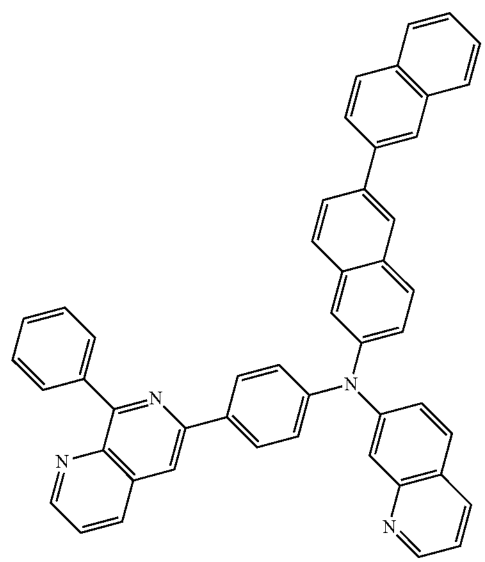
P33
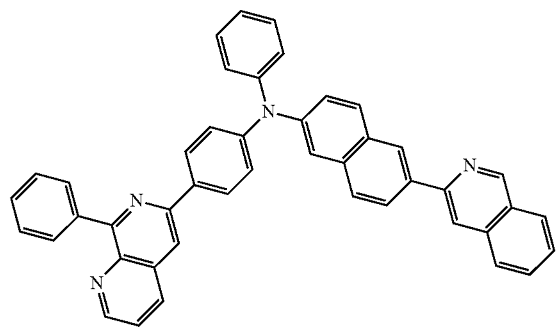

-continued
P34
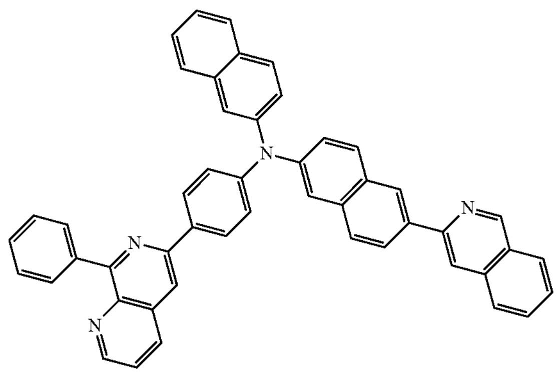
P35
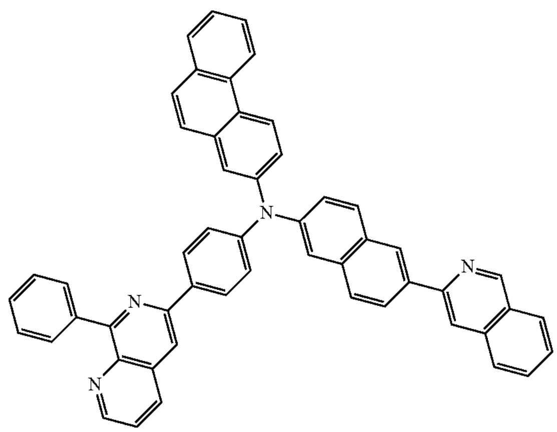
P36
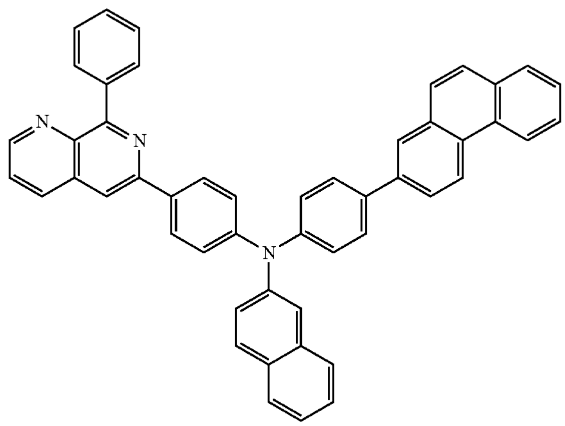
P37
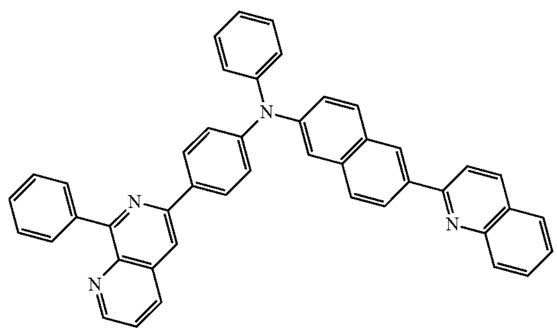
-continued
P38
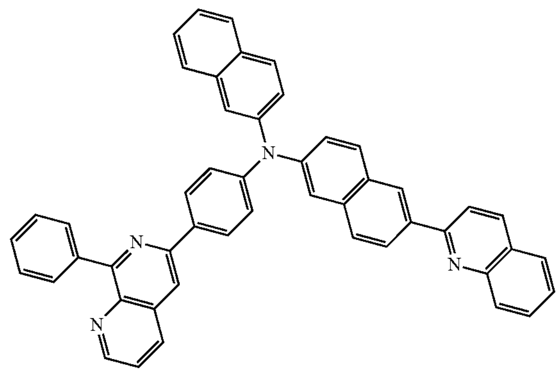
P39
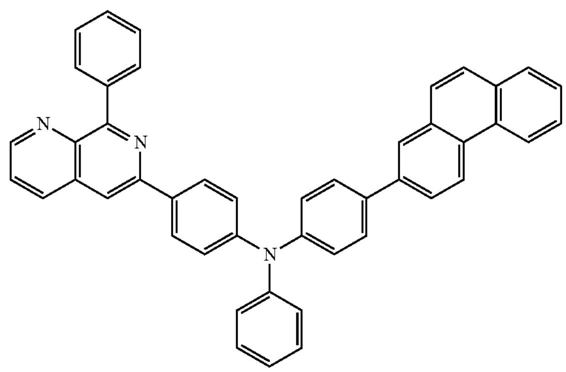
P40
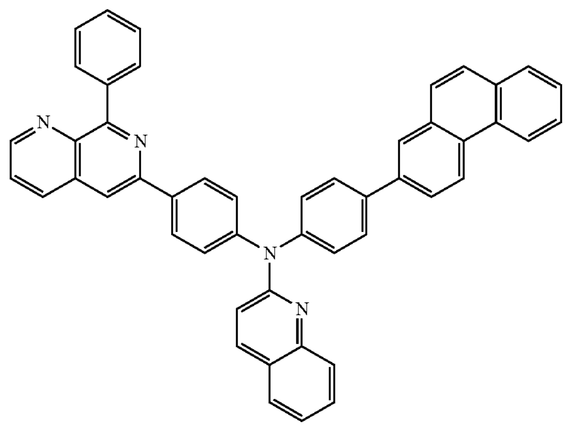

-continued
P41
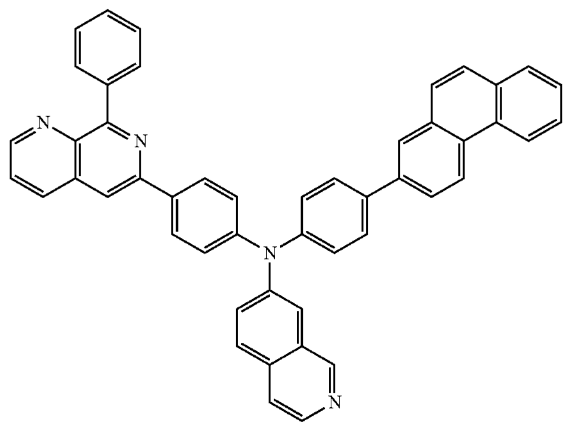
P42
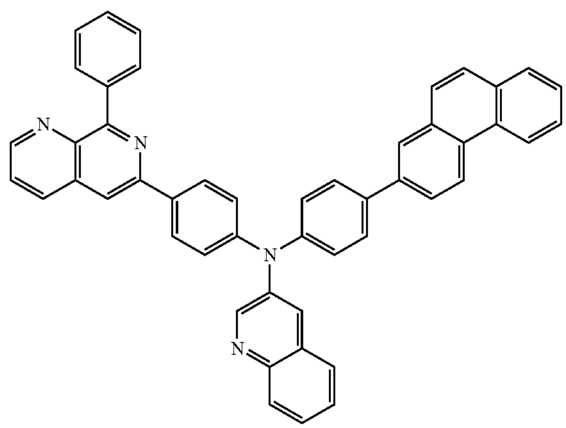
P43
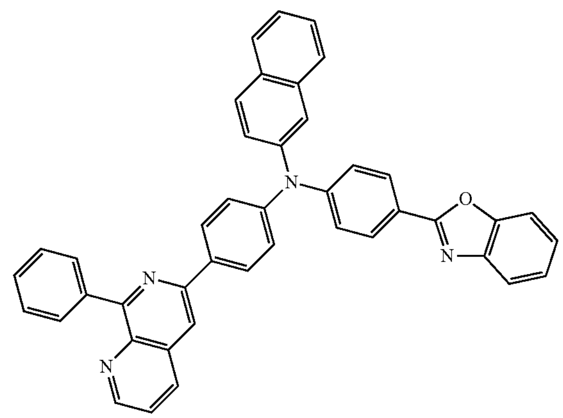
-continued
P44
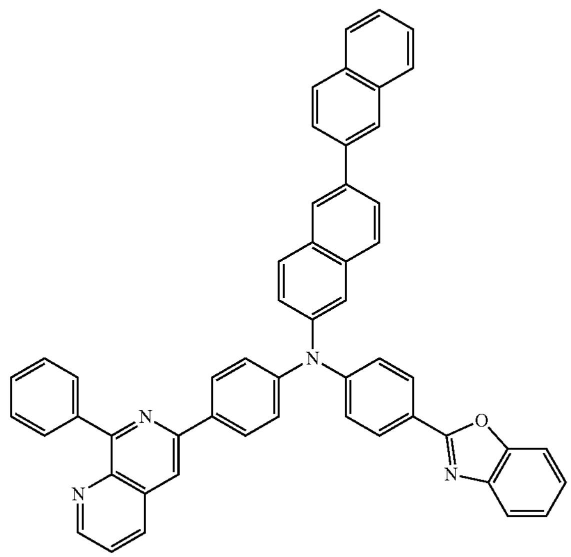
P45
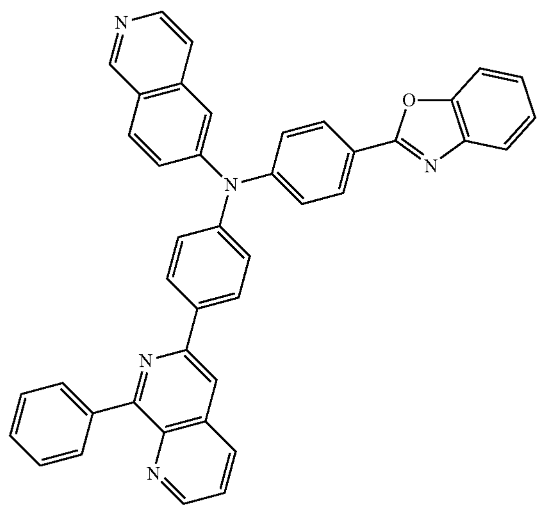
P46
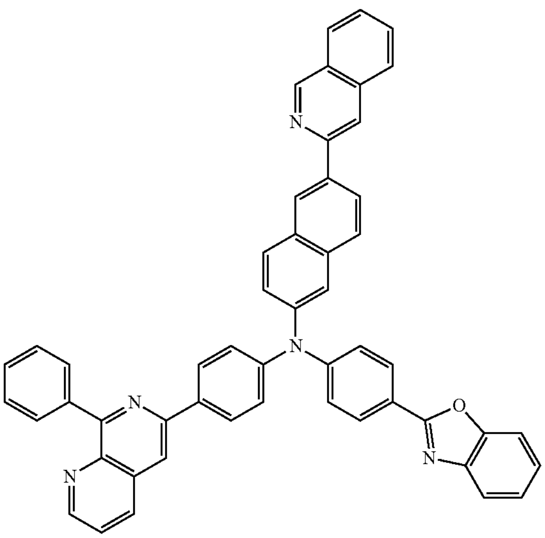

-continued
P47
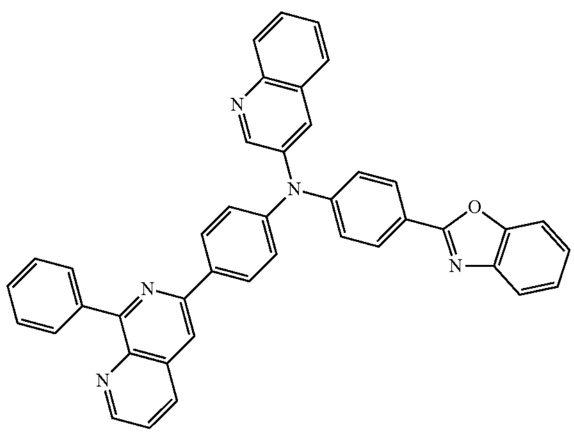
P48
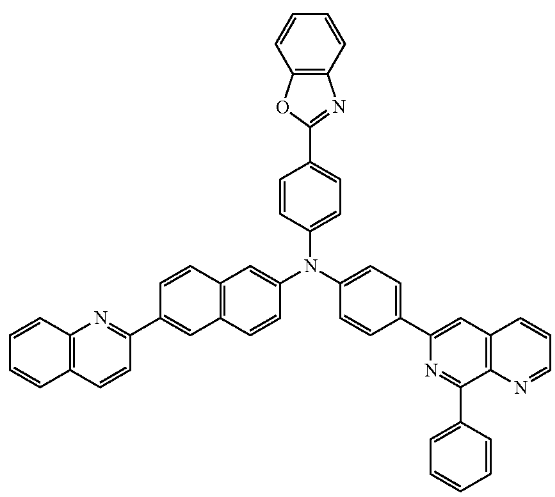
P49
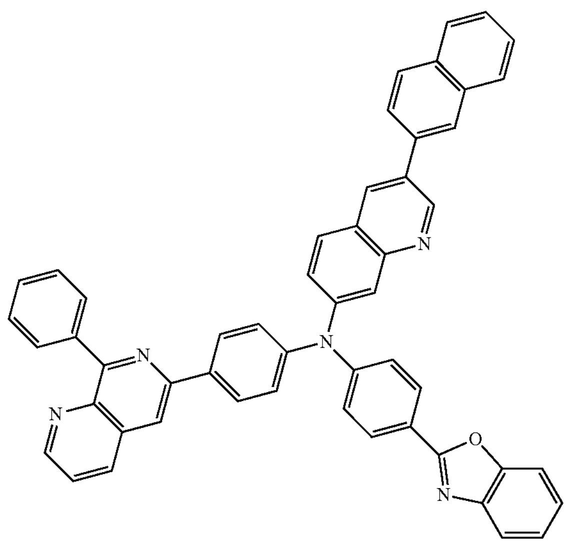
-continued
P50
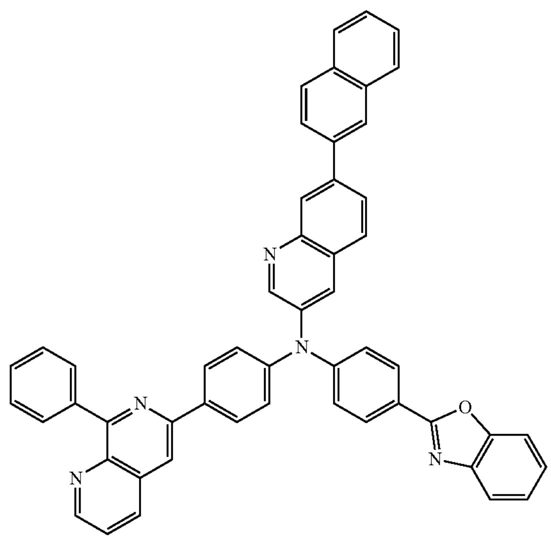
P51
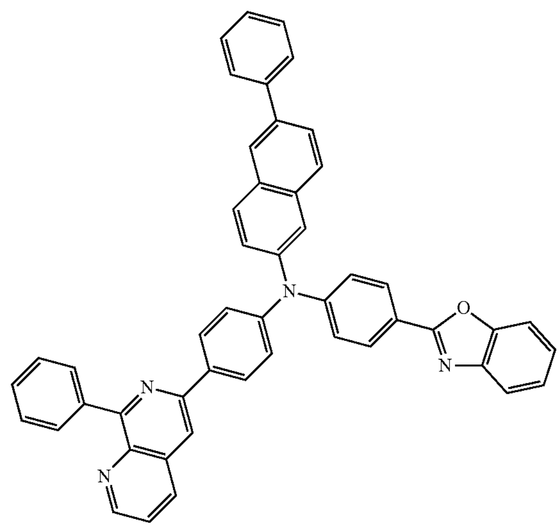
P52
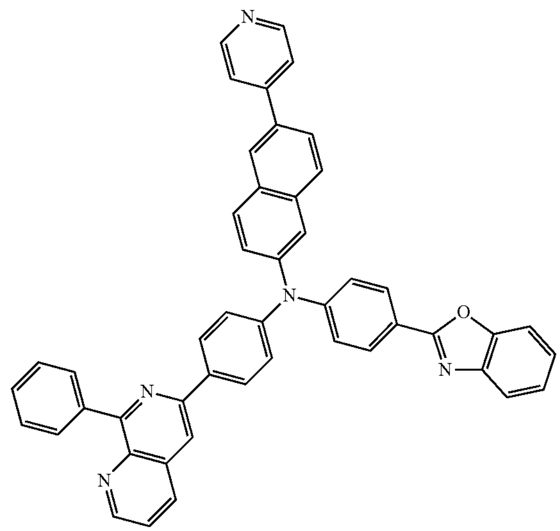

-continued
P53
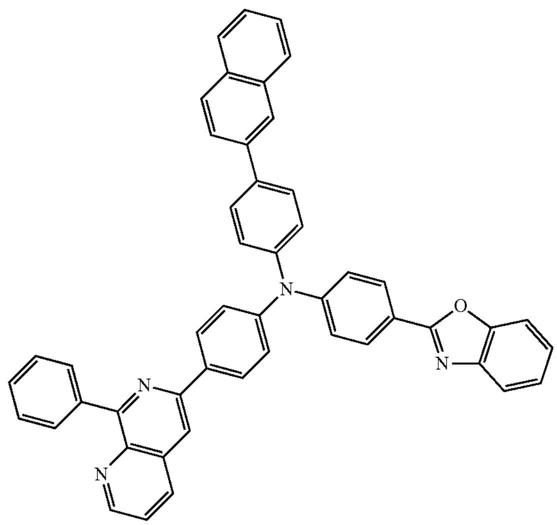
P54
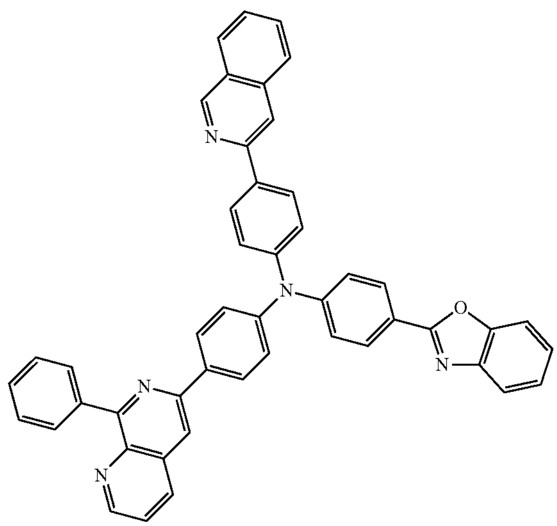
P55
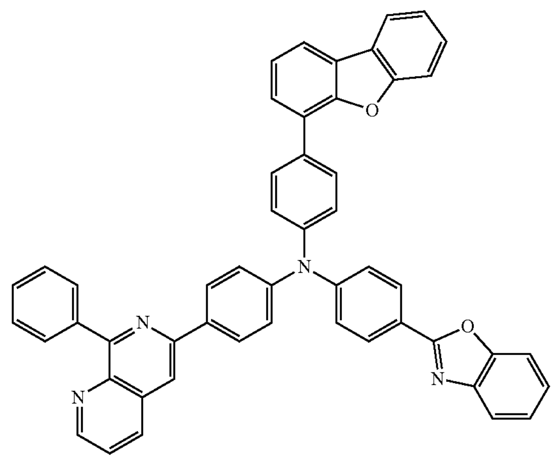
-continued
P56
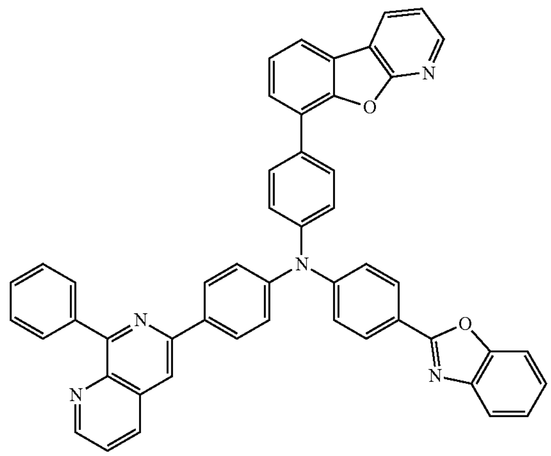
P57
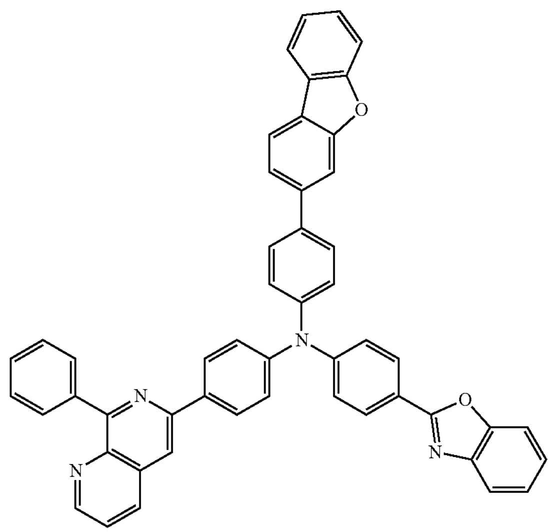
P58
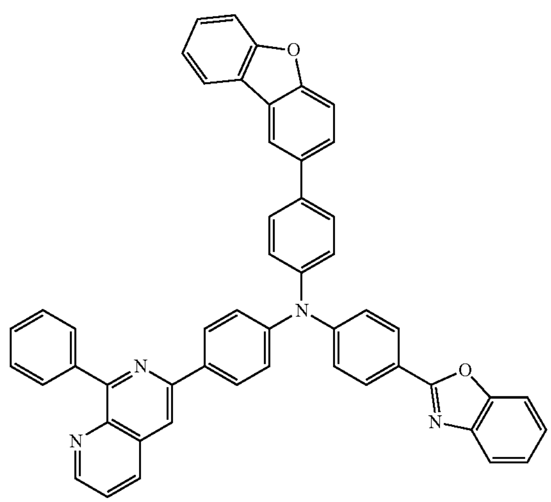

-continued
P59
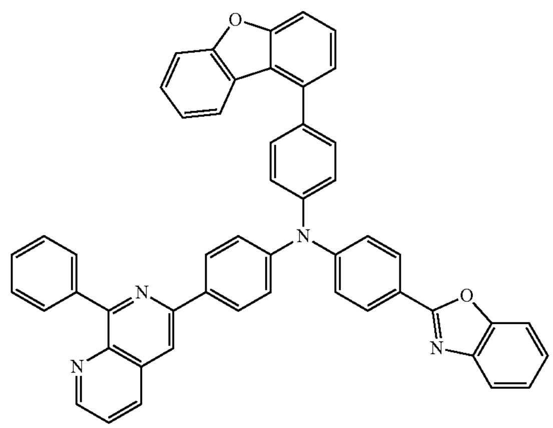
P60
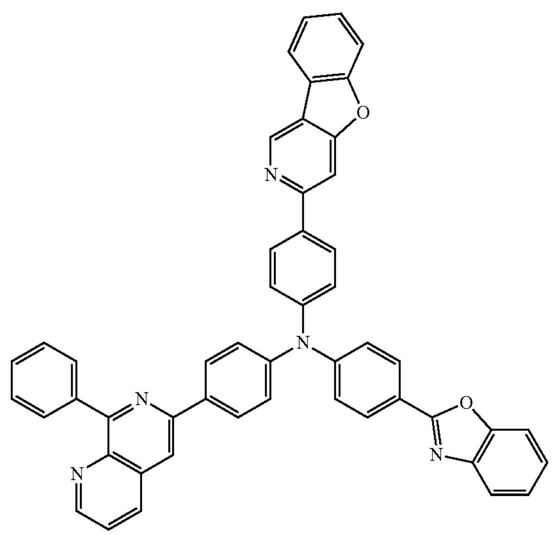
P61
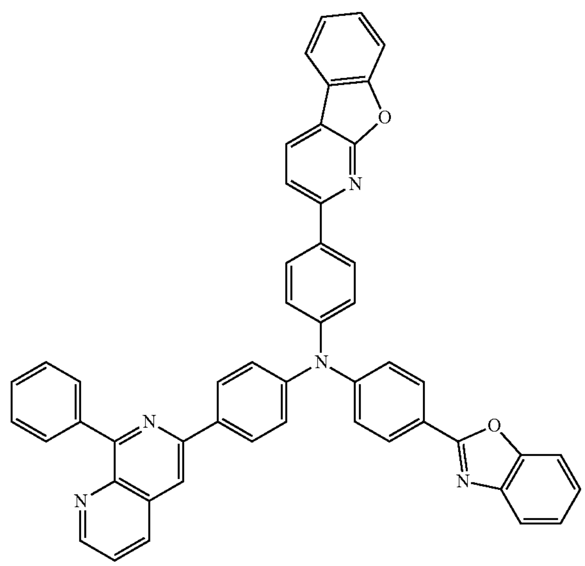
-continued
P62
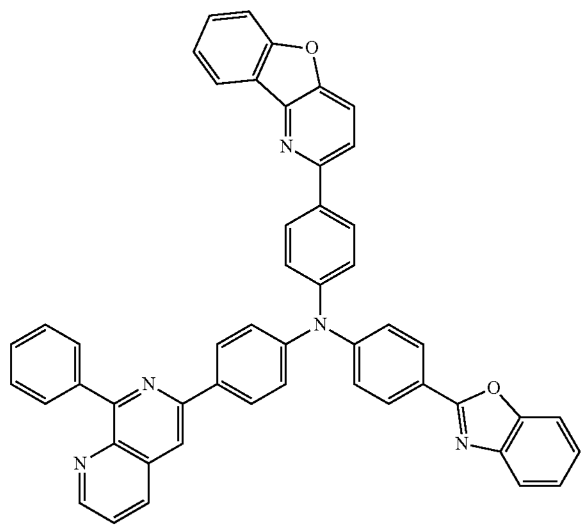
P63
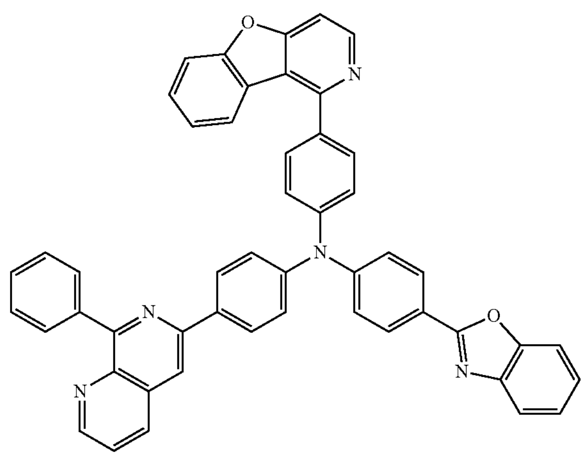
P64
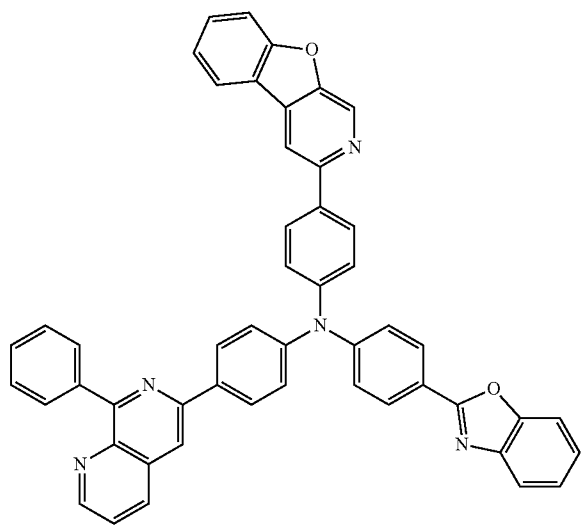

-continued
P65
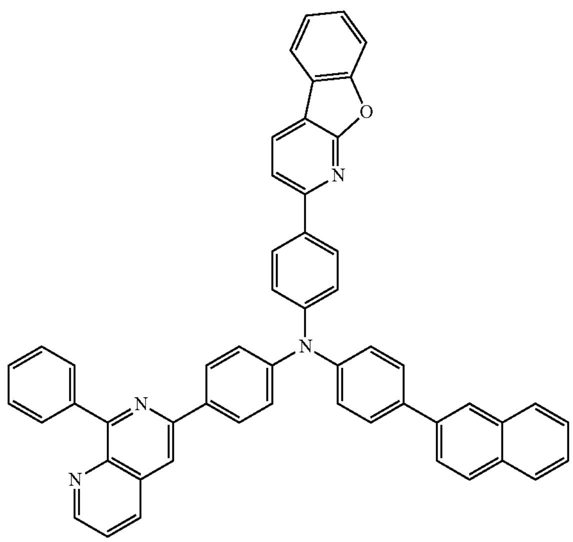
P66
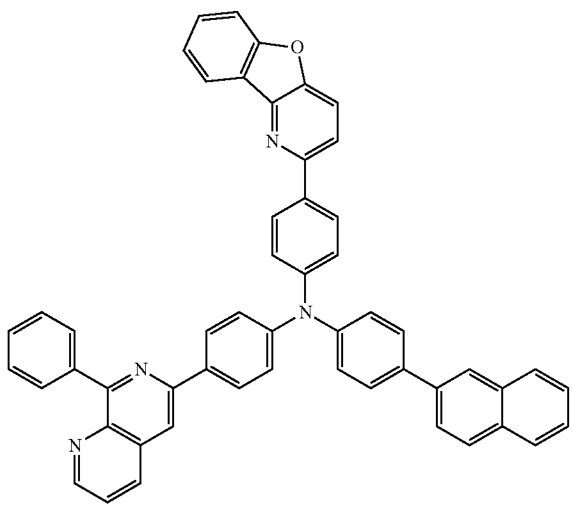
P67
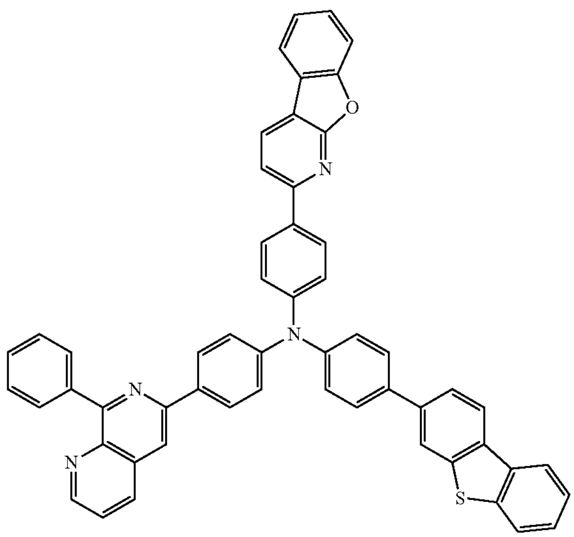
-continued
P68
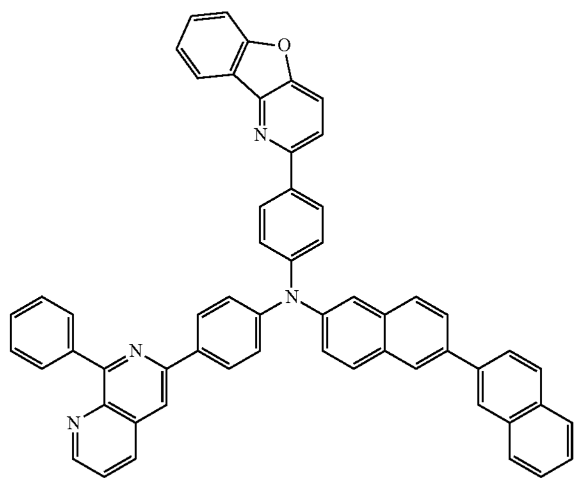
P69
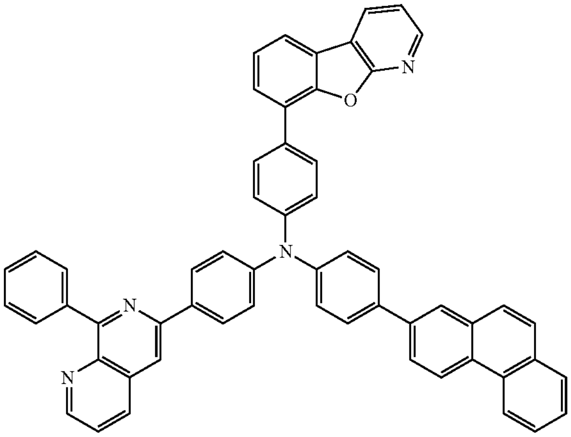
P70
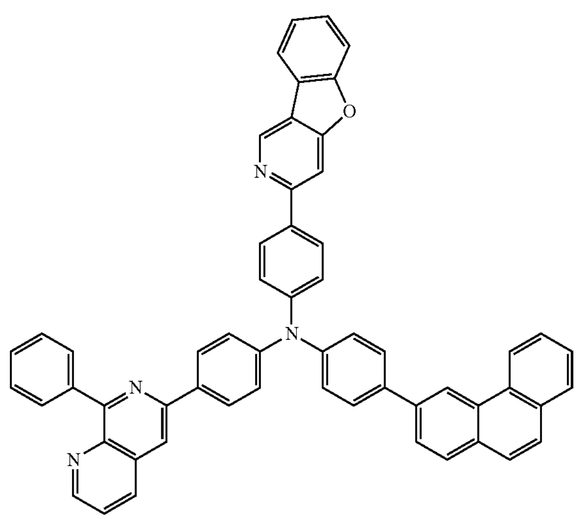

-continued
P71
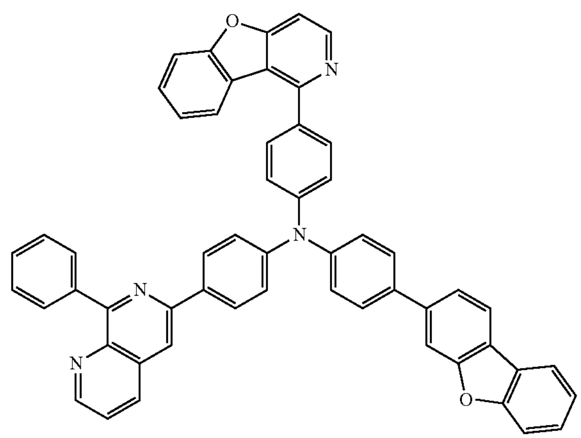
P72
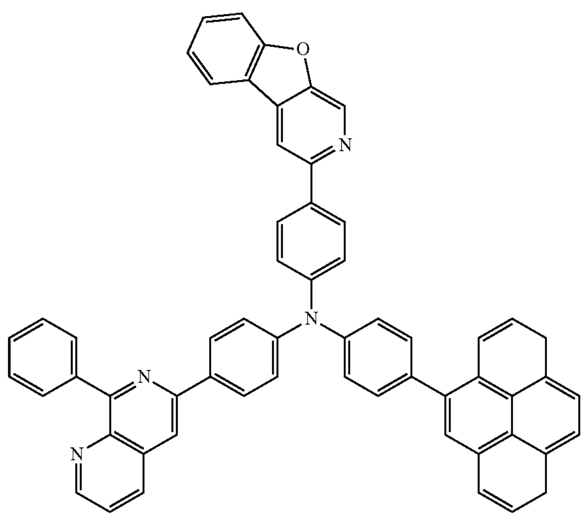
P73
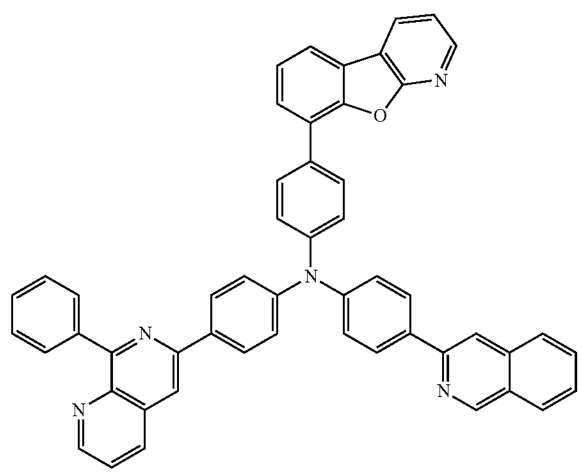
-continued
P74
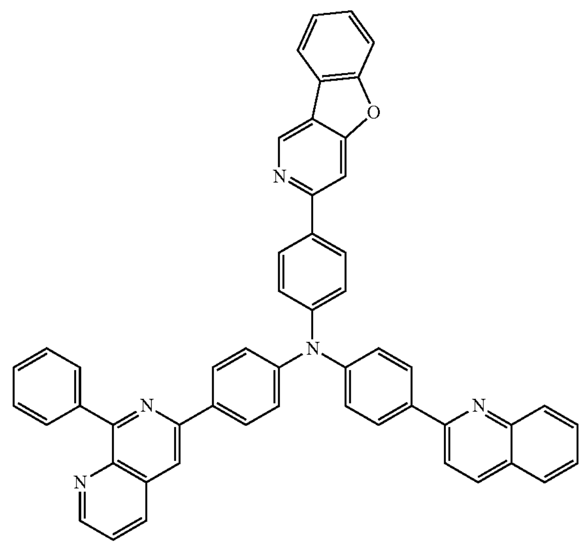
P75
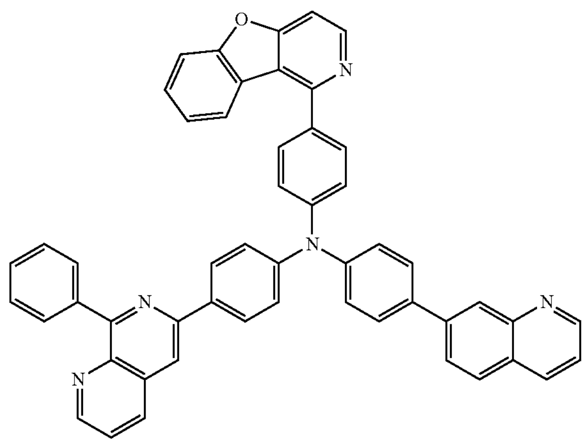
P76
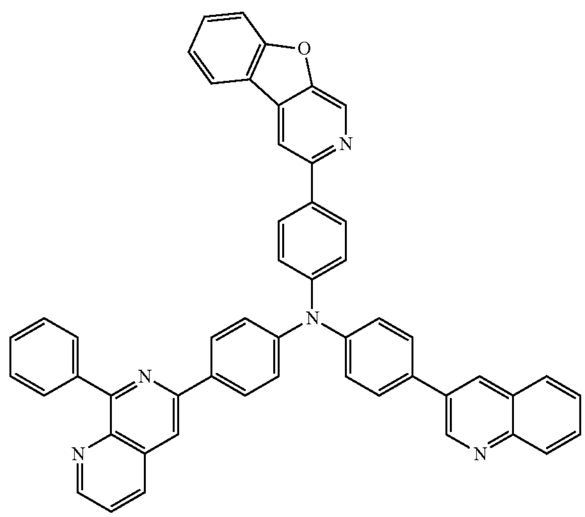

-continued
P77
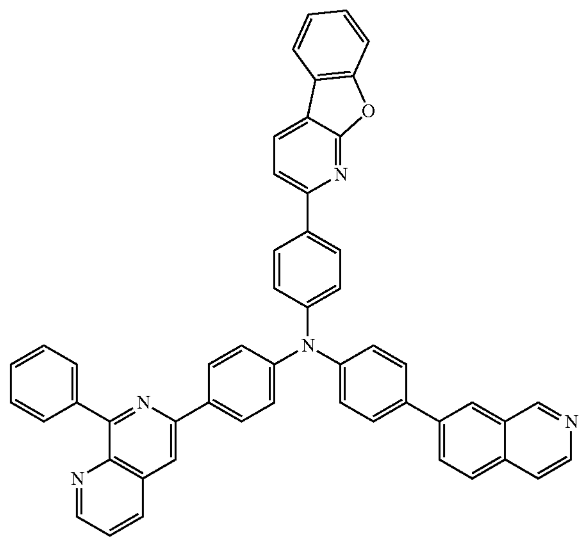
P78
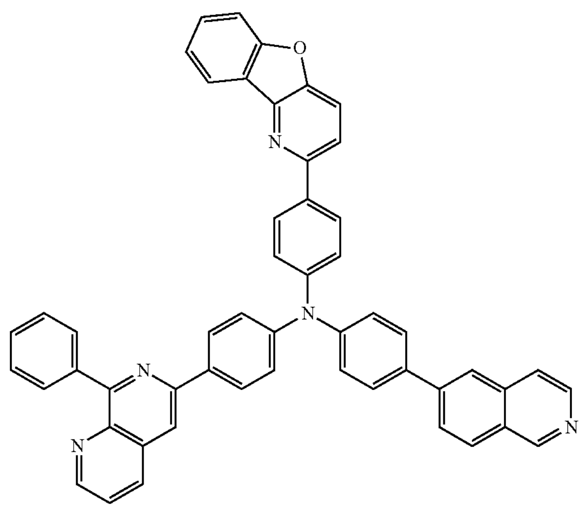
P79
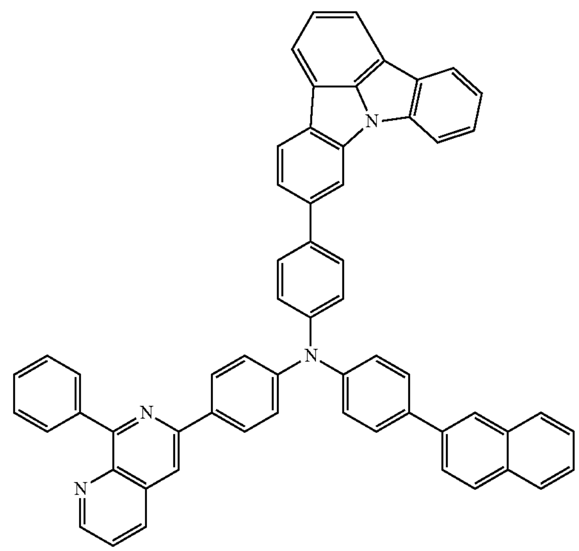
-continued
P80
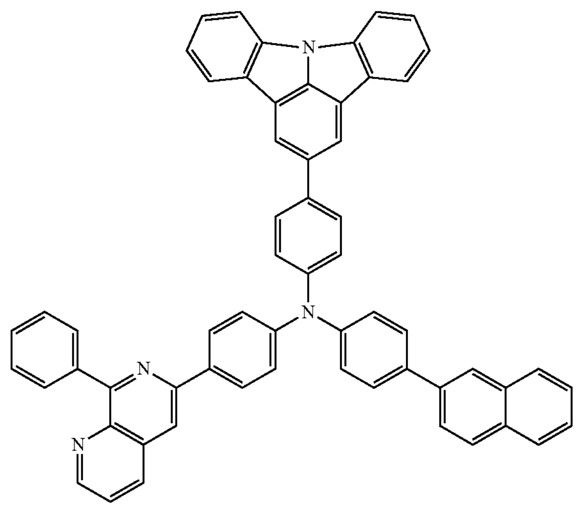
P81
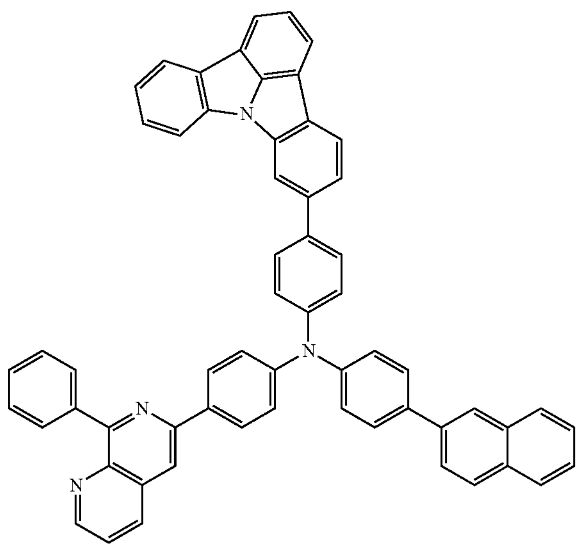
P82
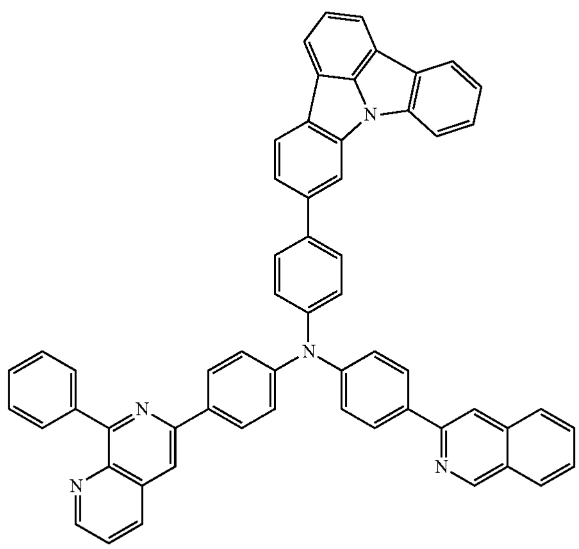

-continued
P83
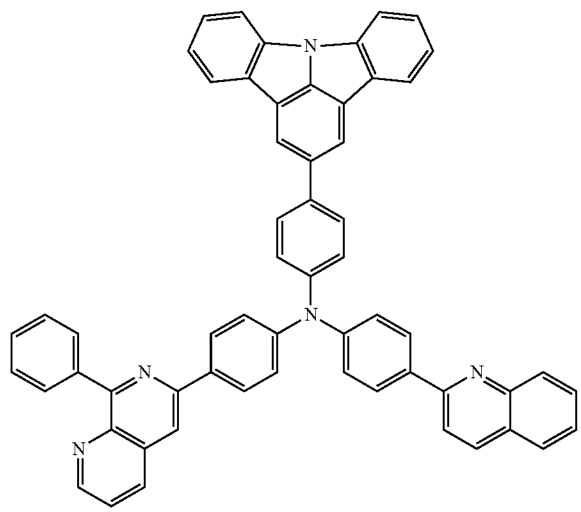
P84
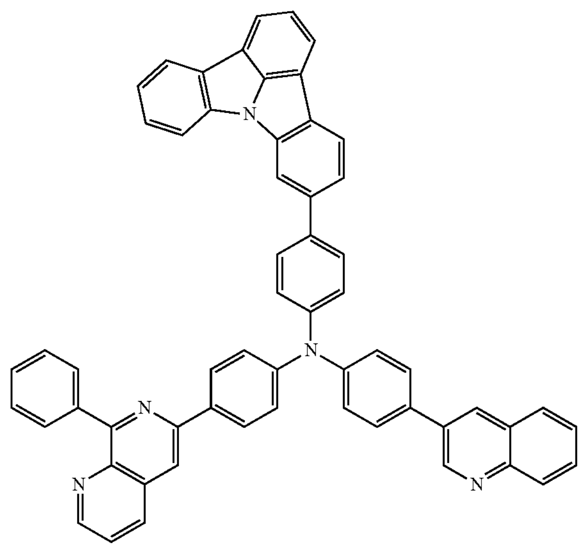
P85
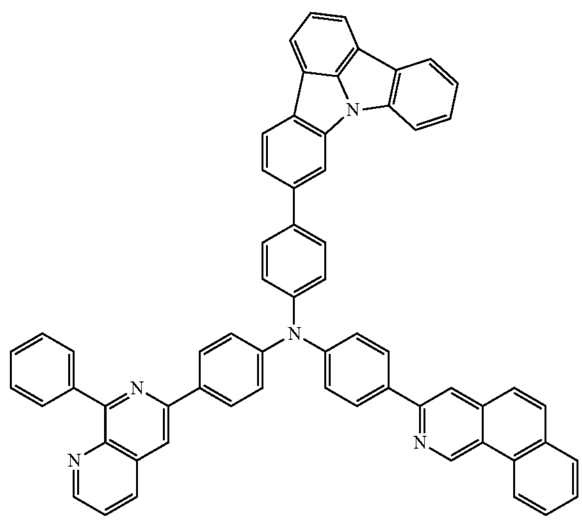
-continued
P86
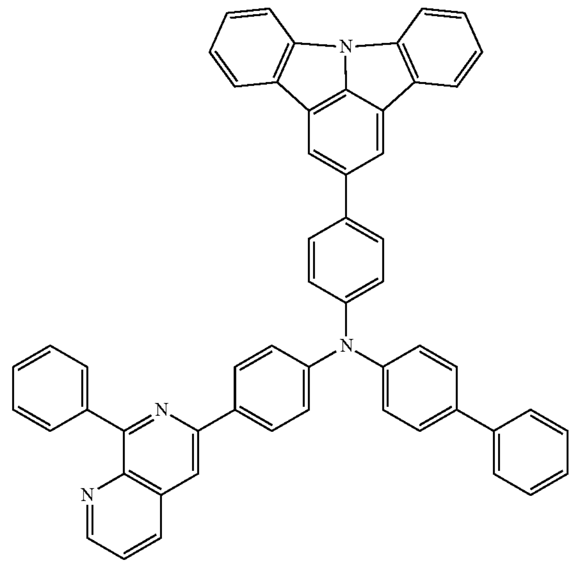
P87
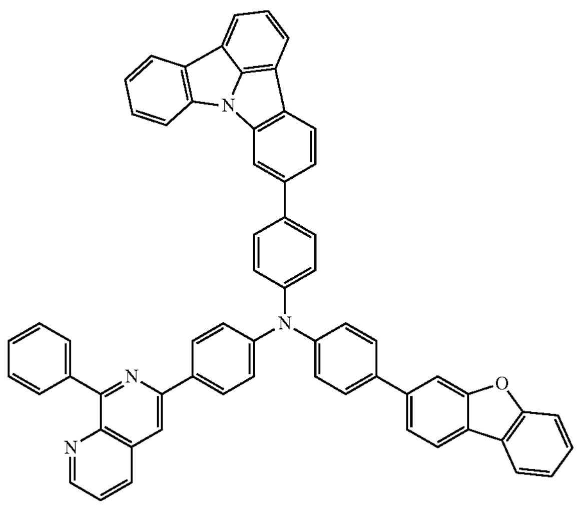
P88
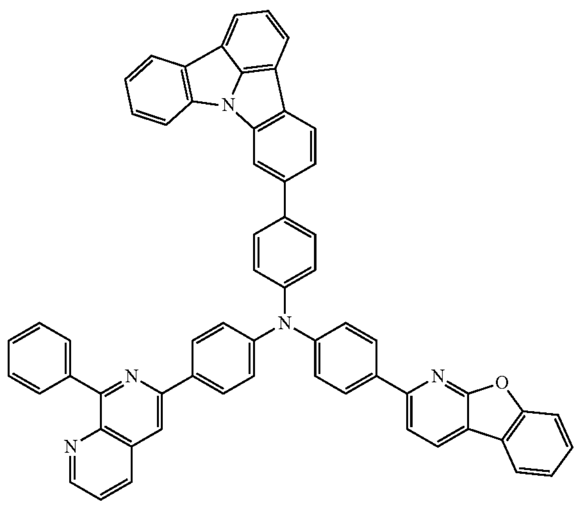

-continued
P89
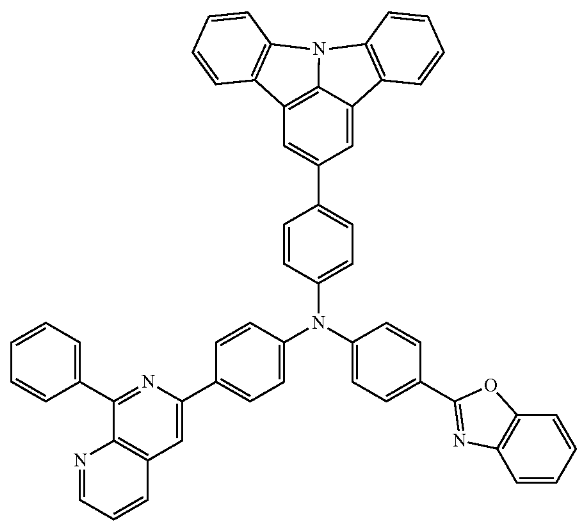
P90
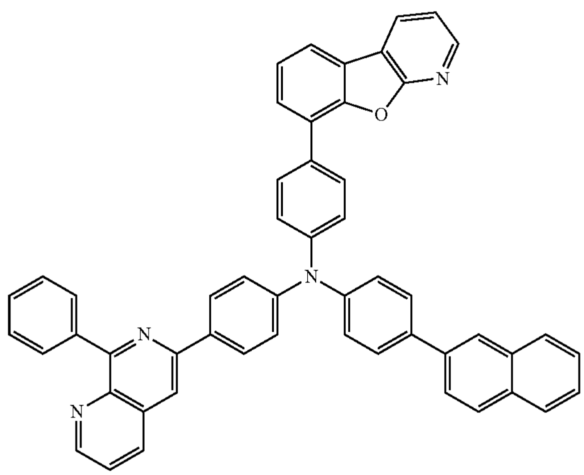
P91
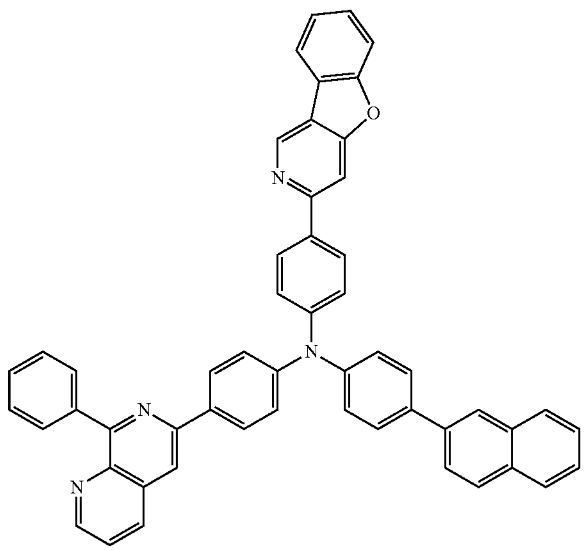
-continued
P92
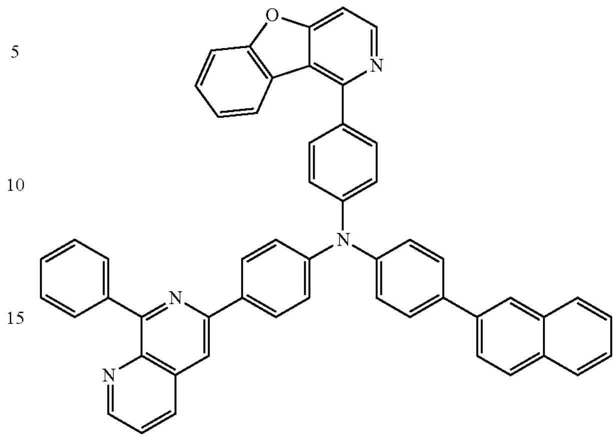
P93
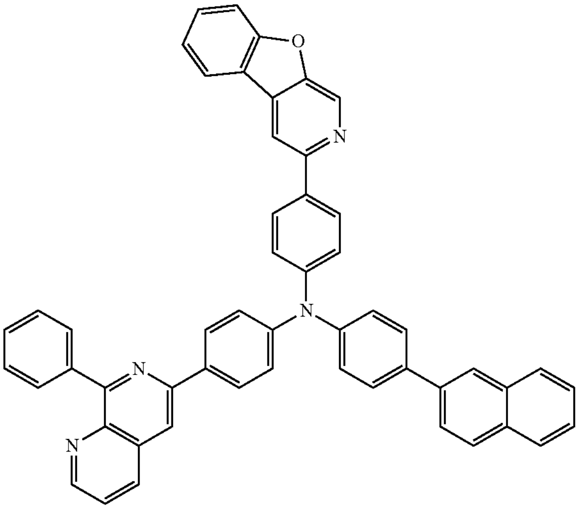
P94
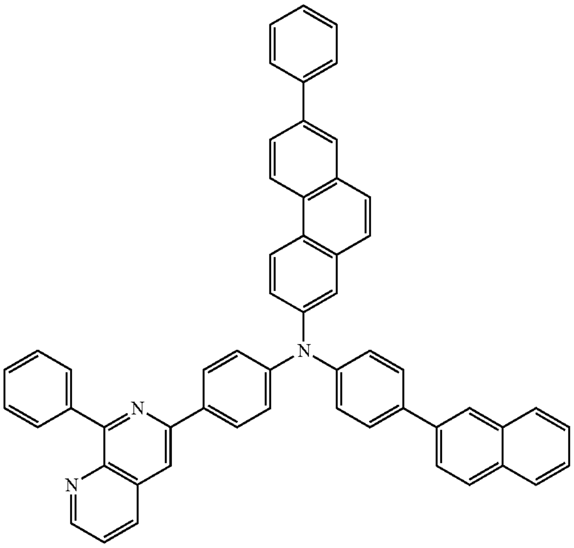

-continued
P95
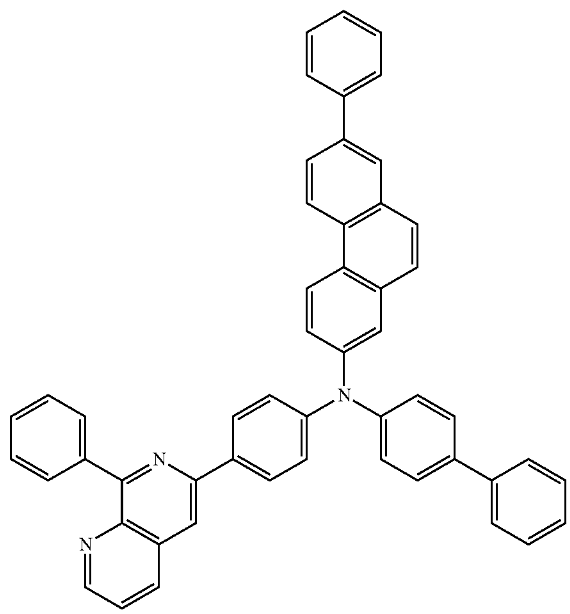
P96
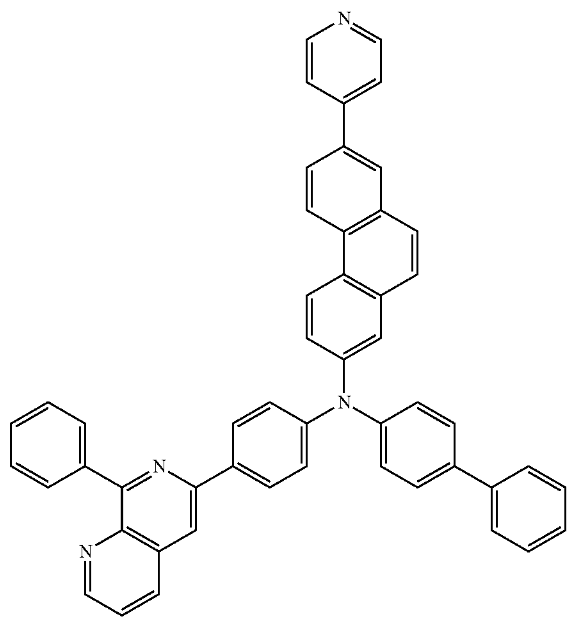
-continued
P97
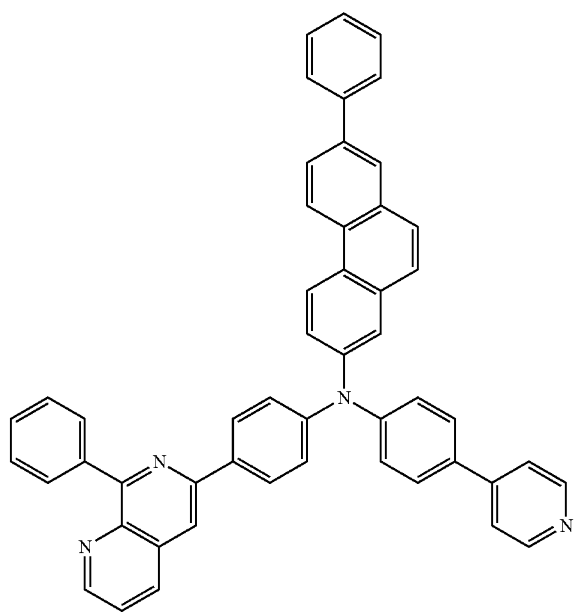
P98
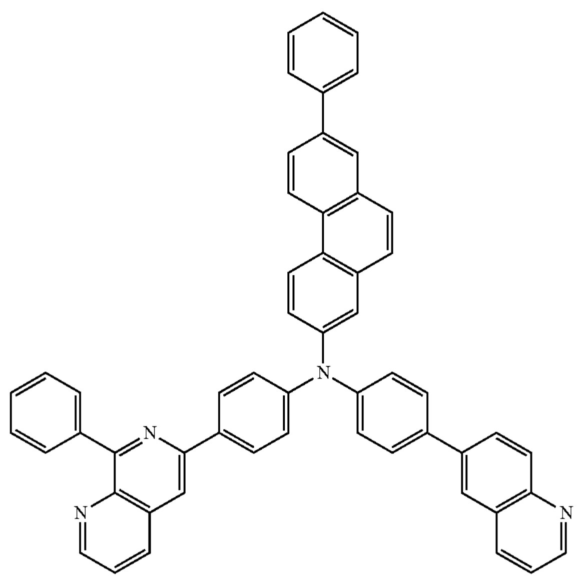

-continued
P99
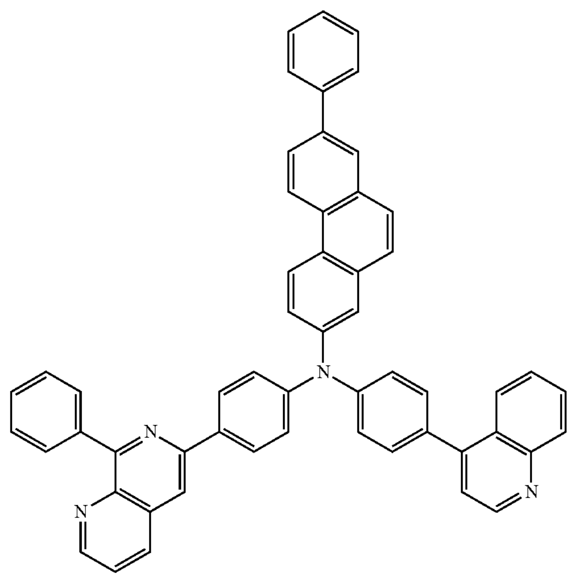
P100
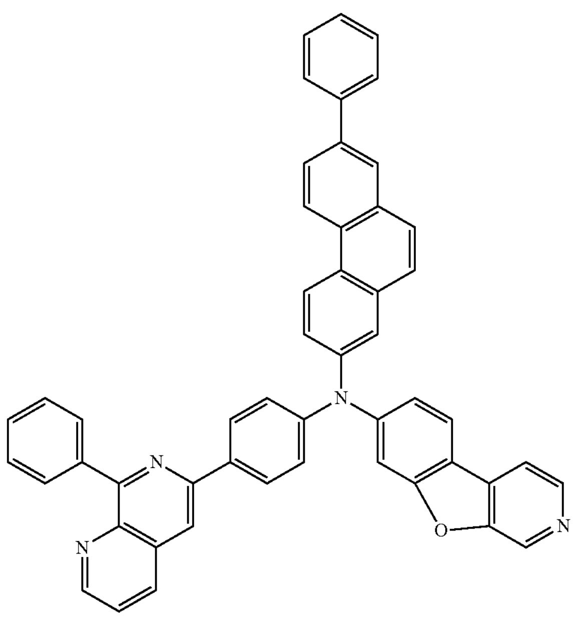
-continued
P101
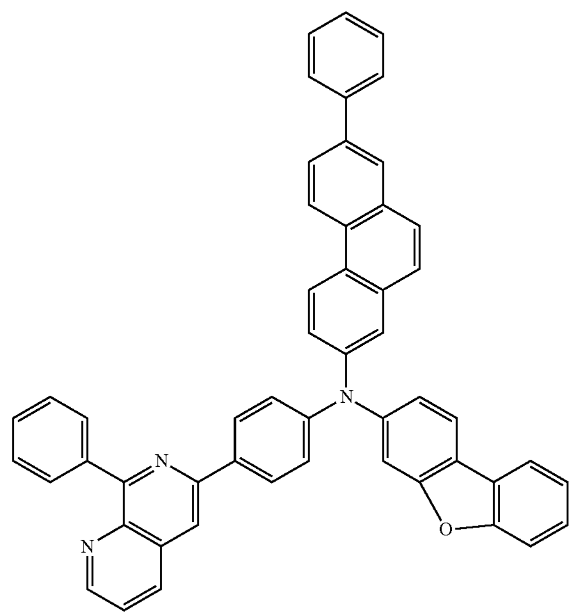
P102
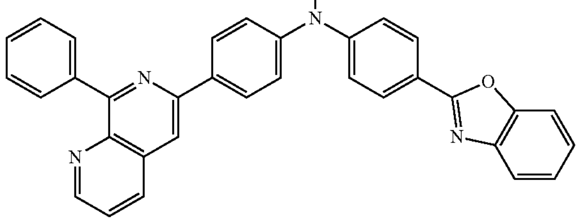

-continued
P103
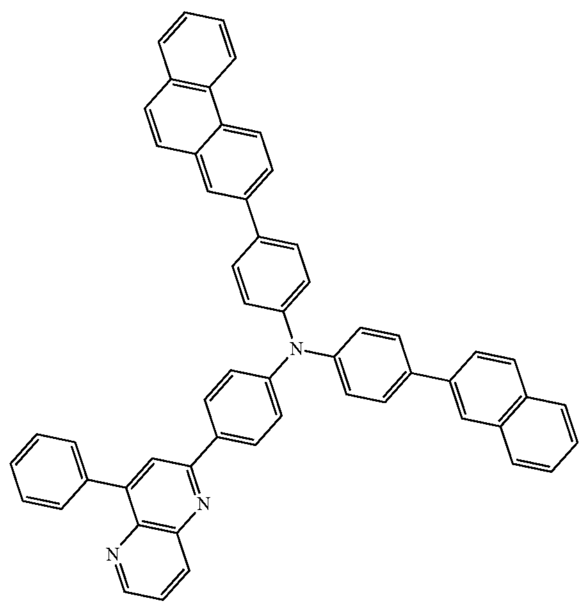
P104
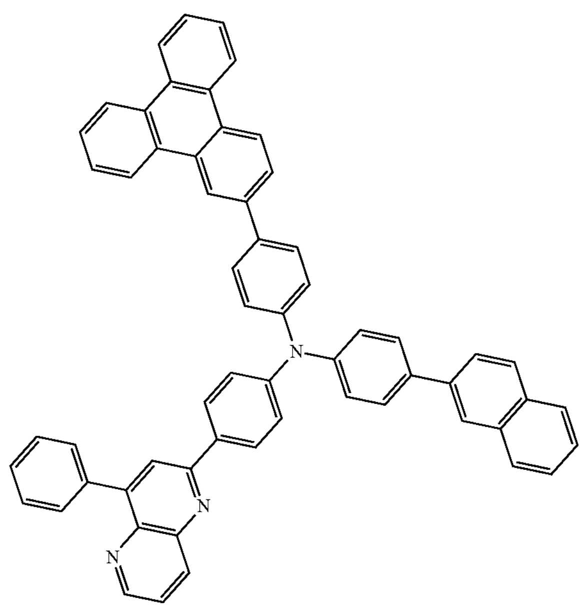
-continued
P105
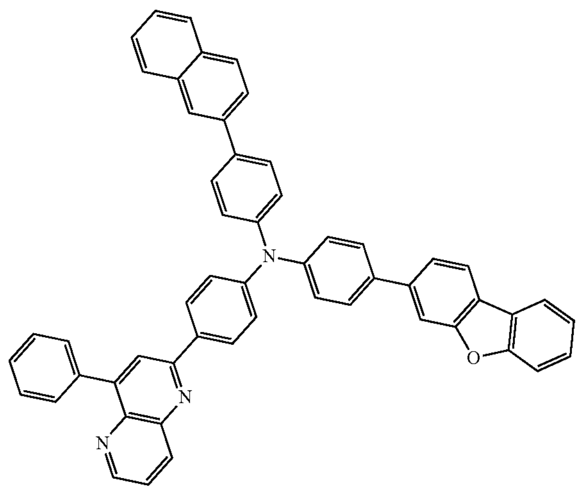
P106
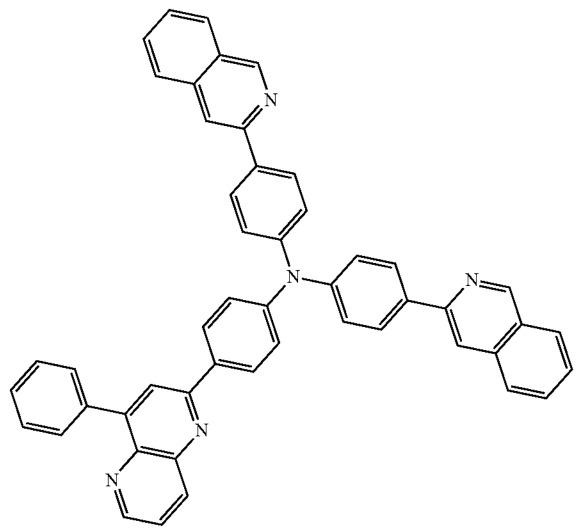
P107
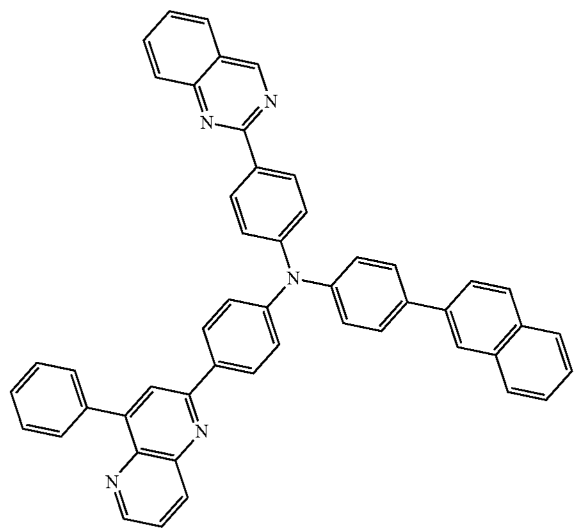

-continued
P108
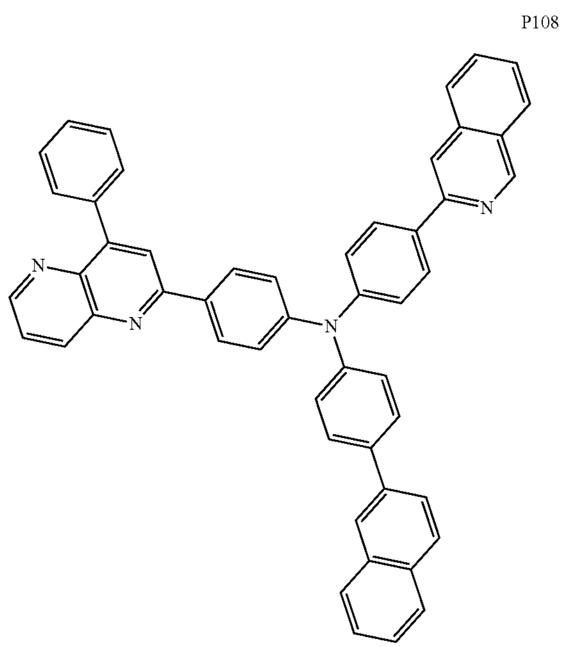
P109
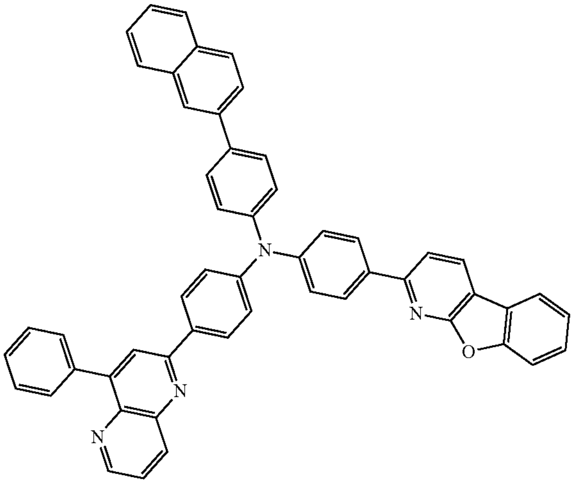
-continued
P110
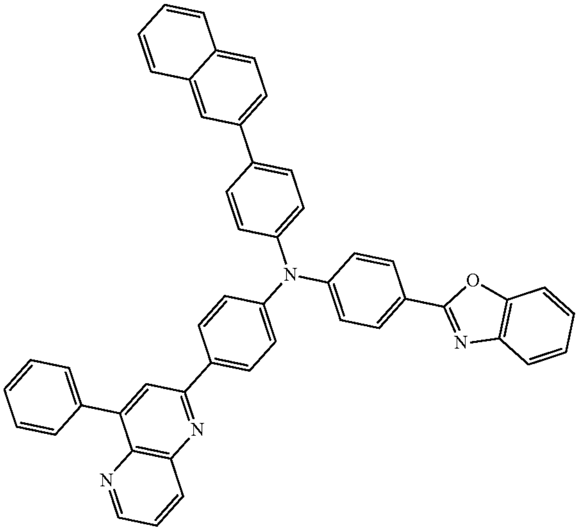
P111
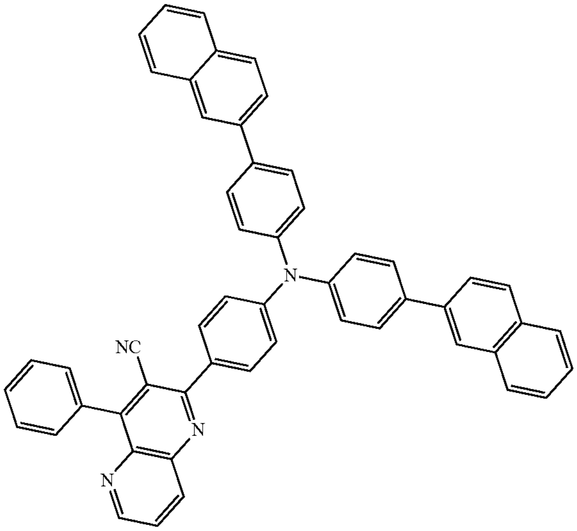
P112
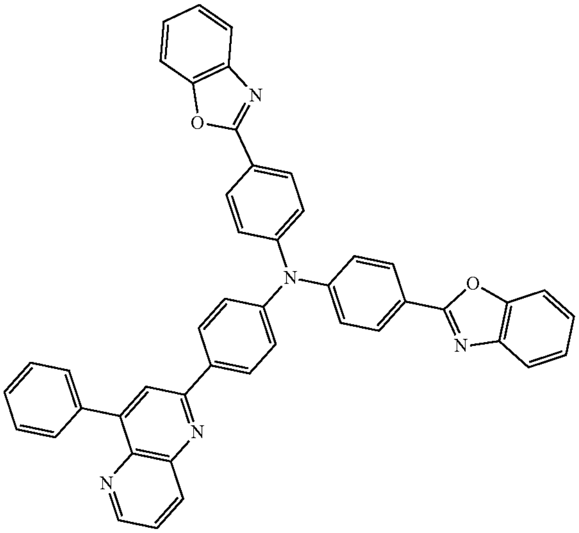

-continued
P113
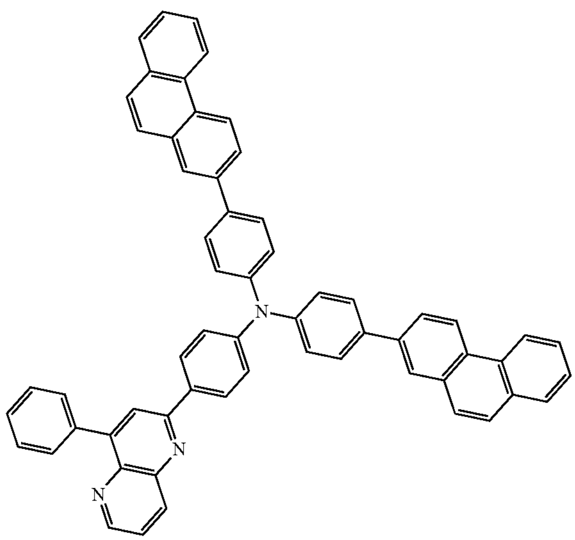
P114
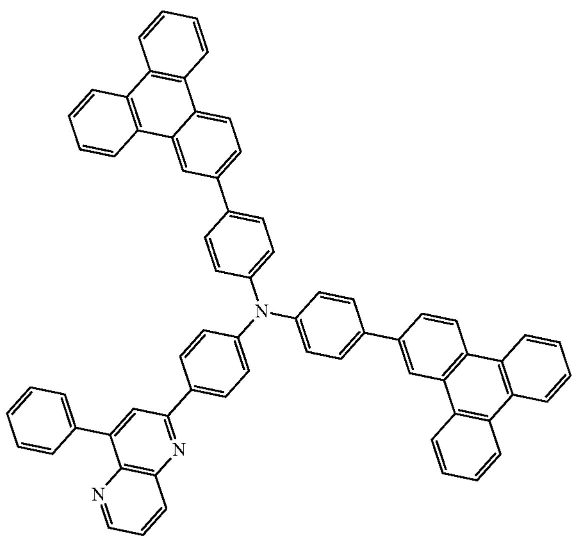
P115
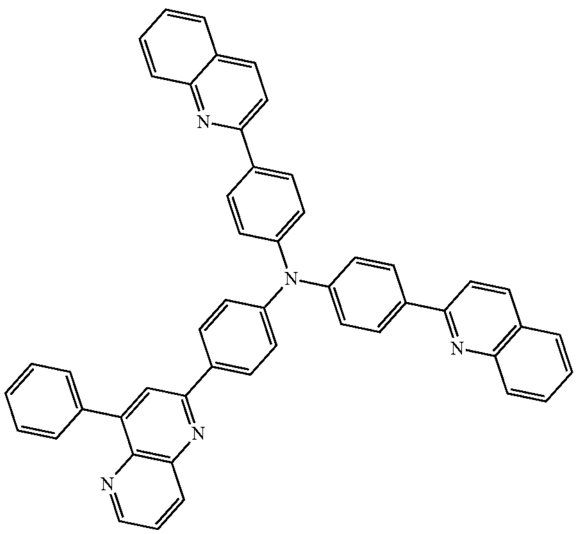
-continued
P116
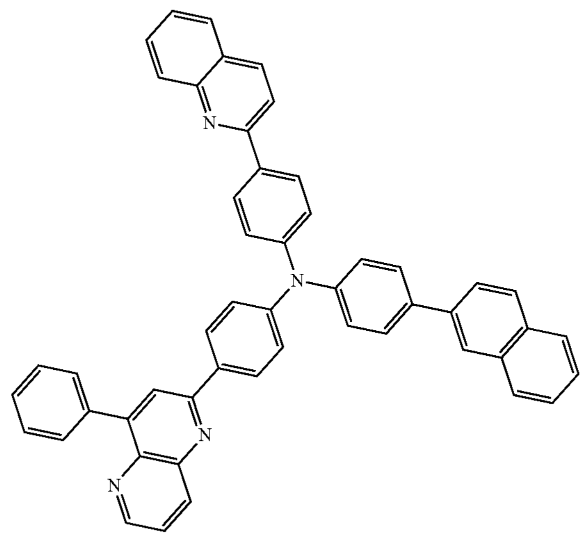
P117
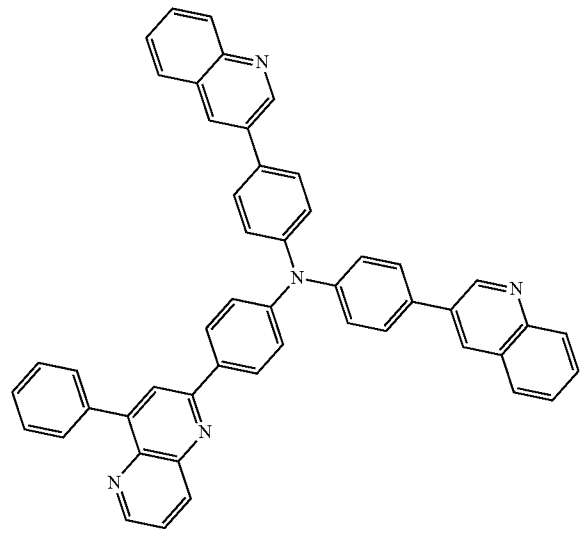
P118
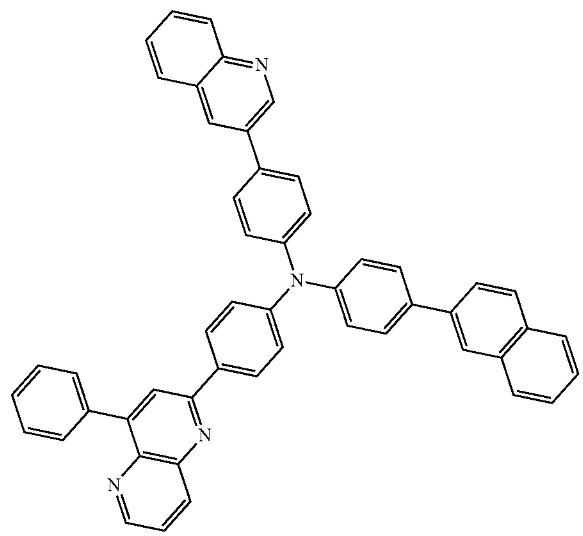

-continued
P119
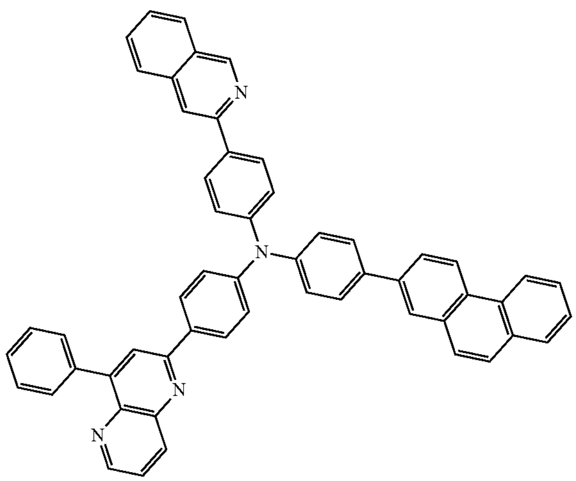
P120
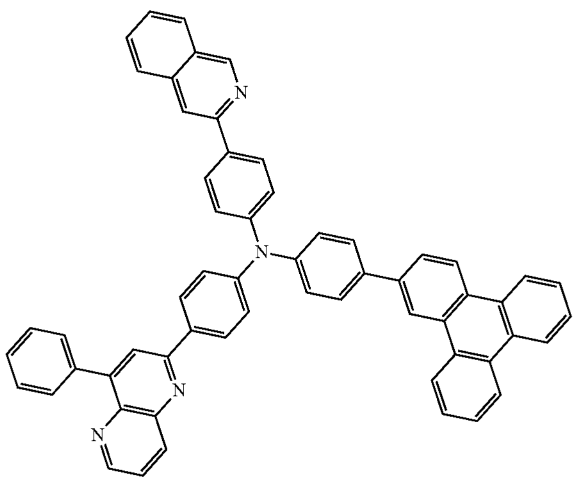
P121
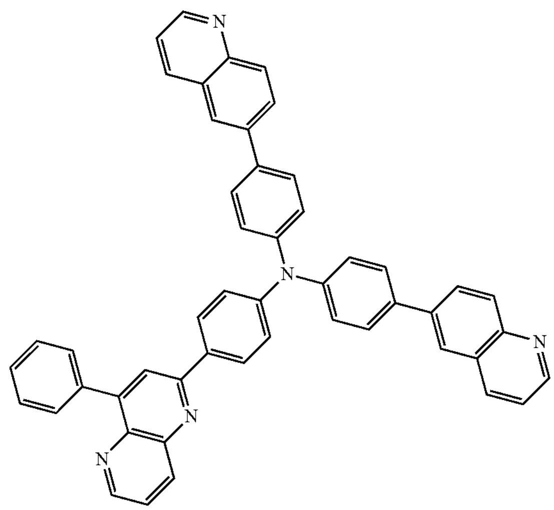
-continued
P122
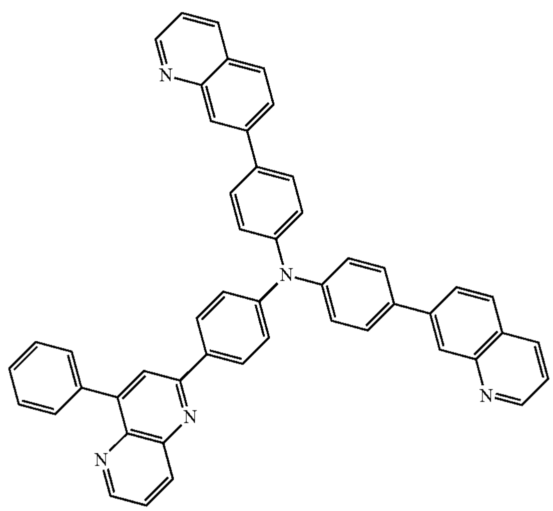
P123
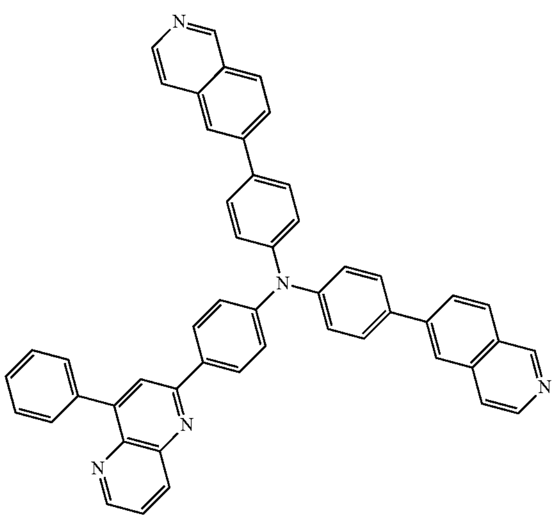
P124
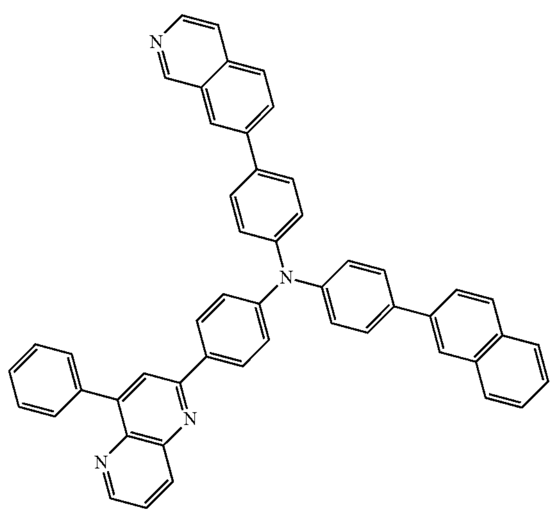

-continued
P125
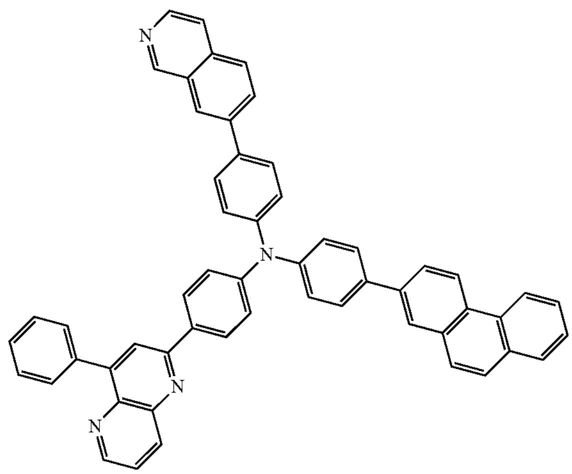
P126
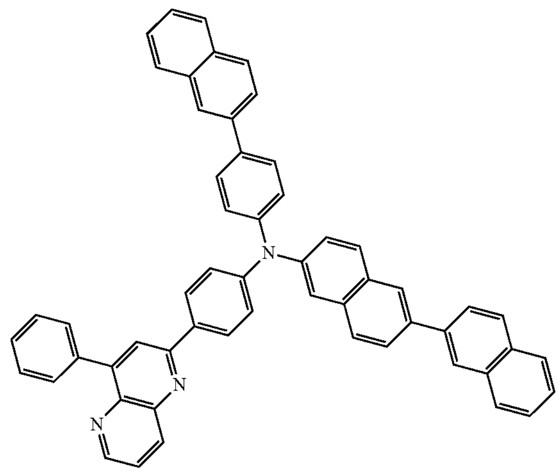
P127
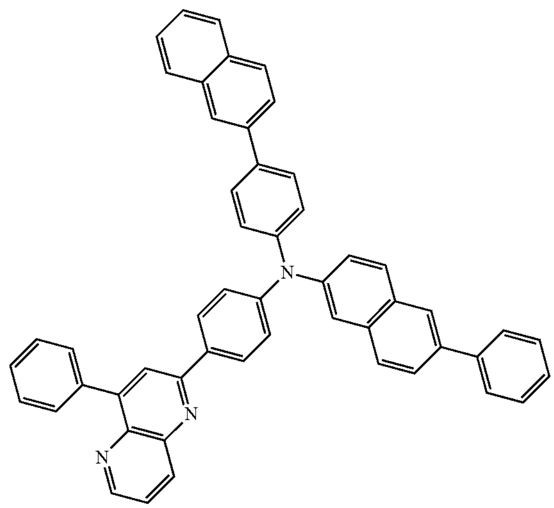
-continued
P128
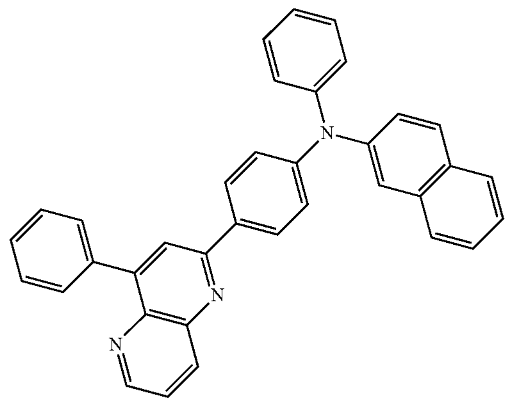
P129
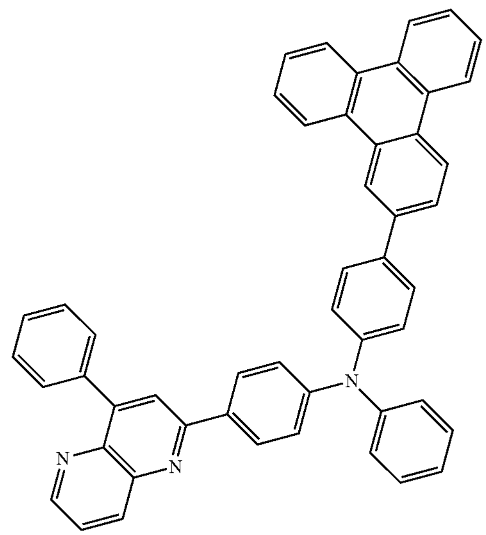
P130
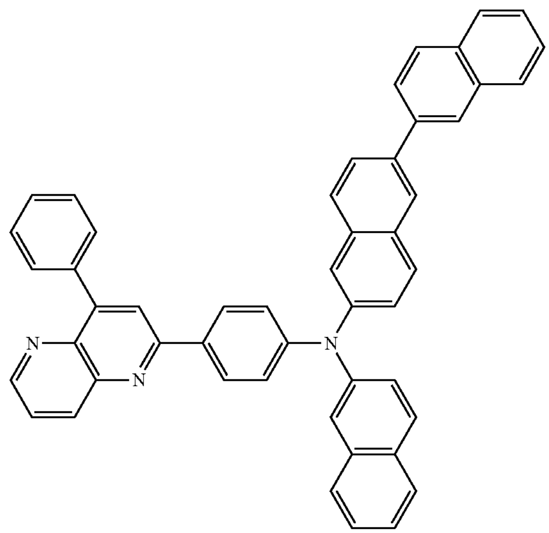

-continued
P131
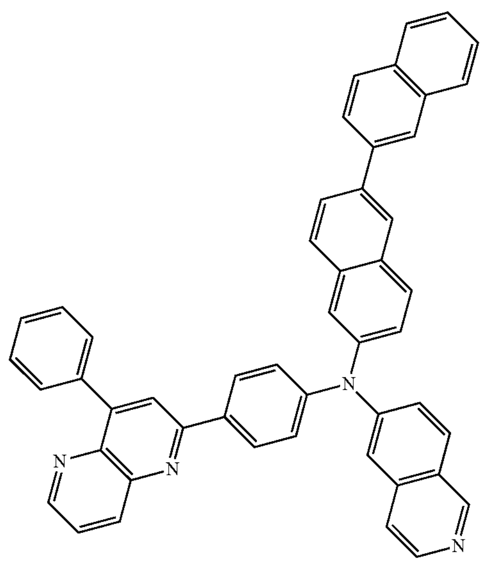
P132
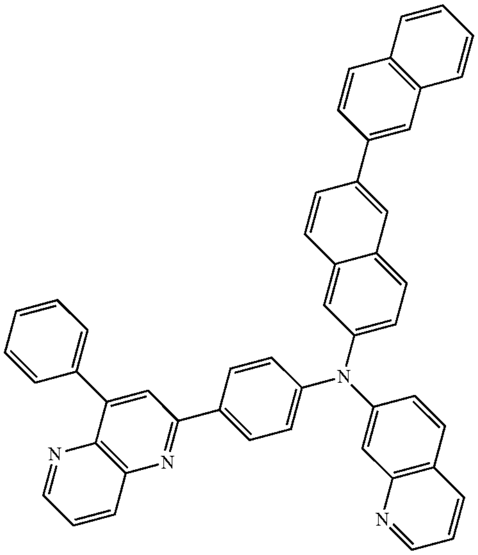
P133
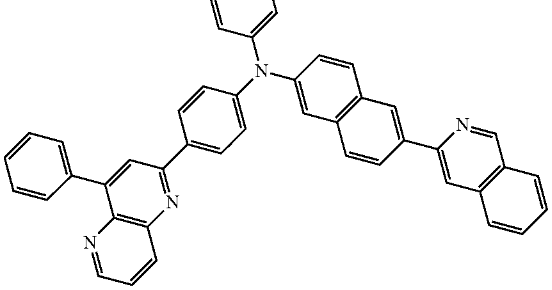
-continued
P134
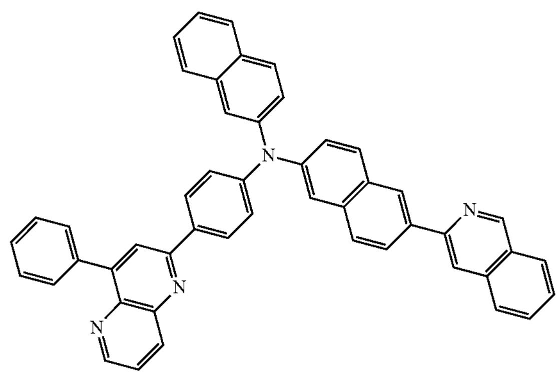
P135
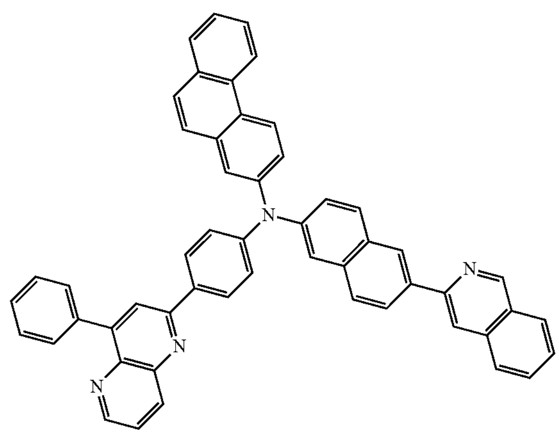
P136
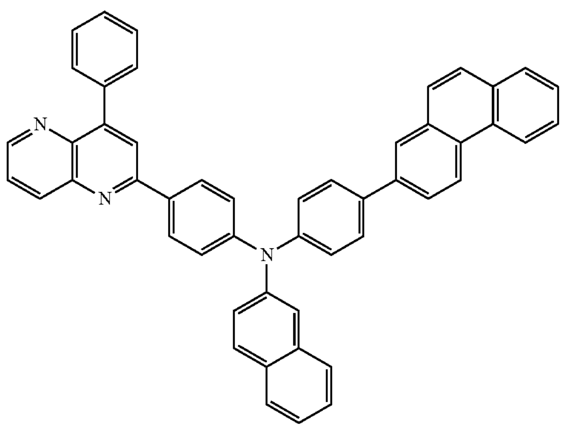
P137
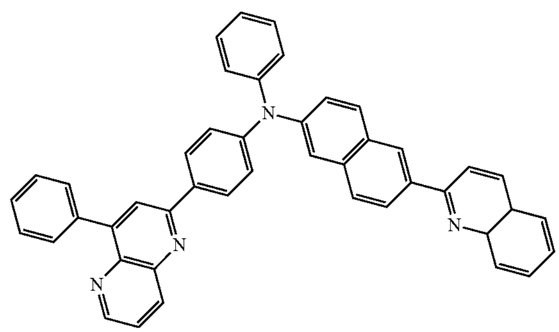

-continued
P138
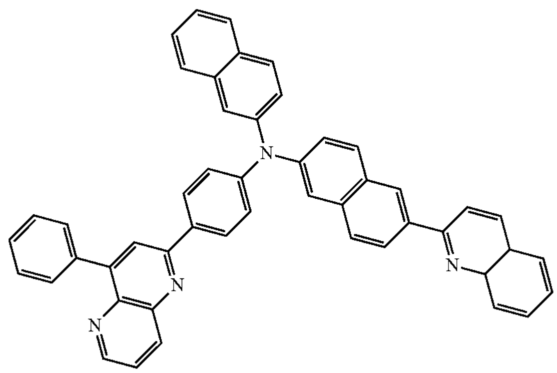
P139
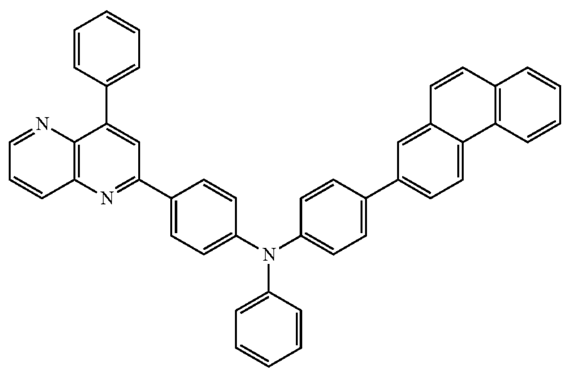
P140
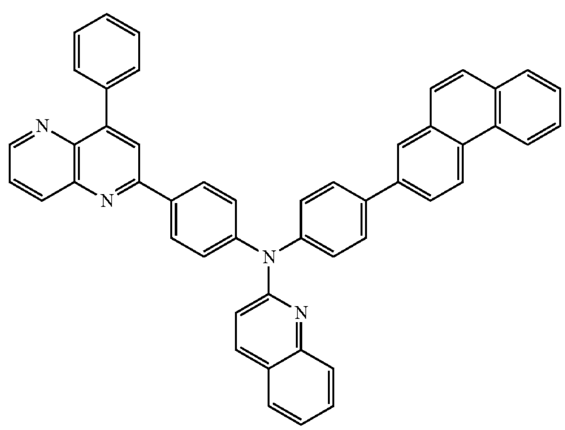
-continued
P141
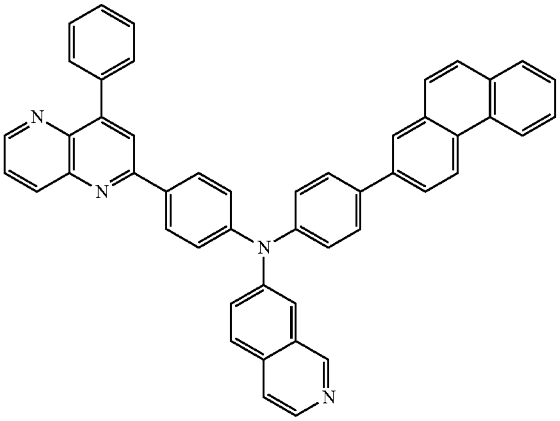
P142
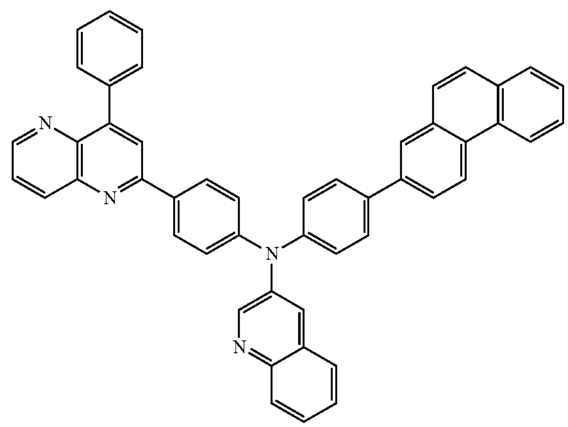
P143
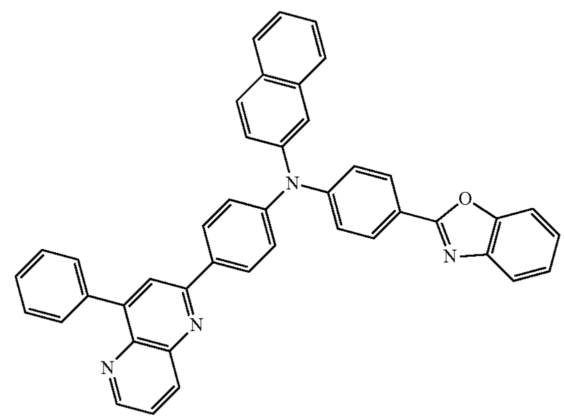

-continued
P144
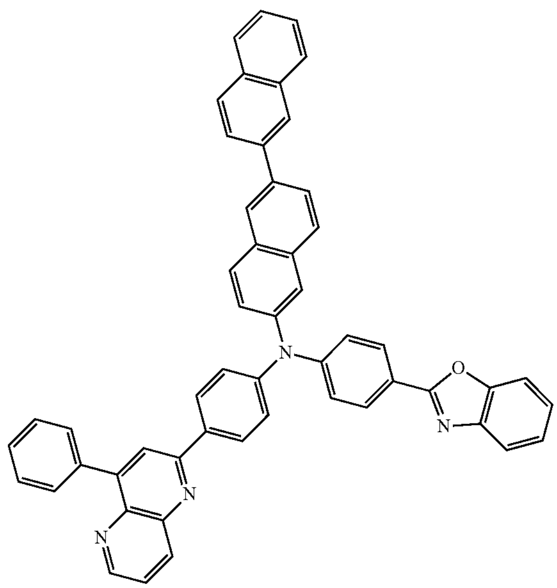
P145
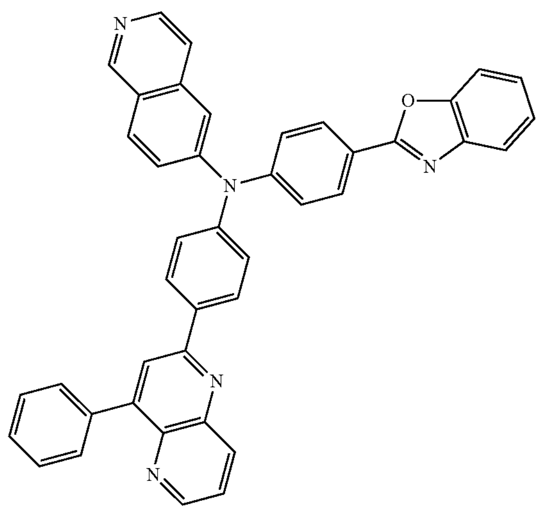
-continued
P146
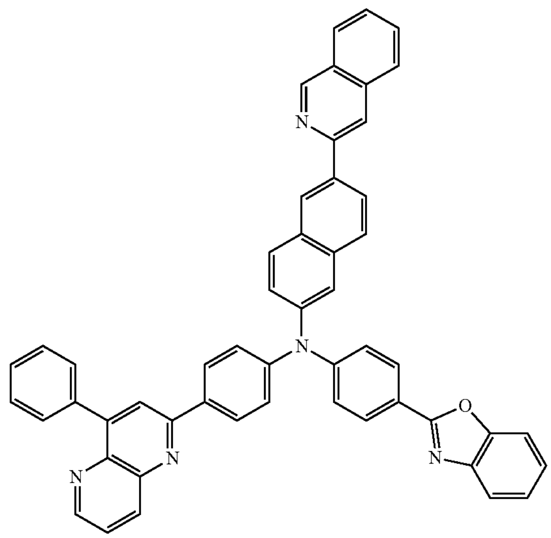
P147
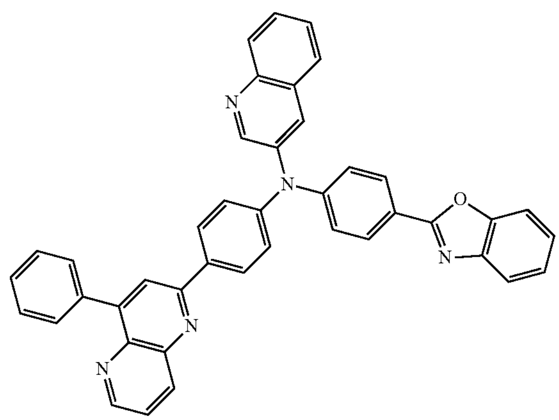
P148
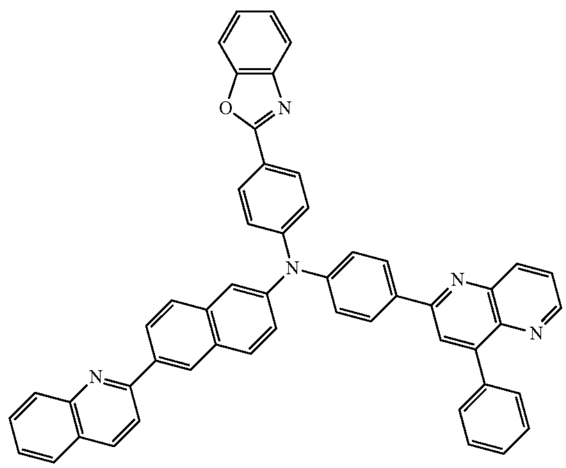

-continued
P149
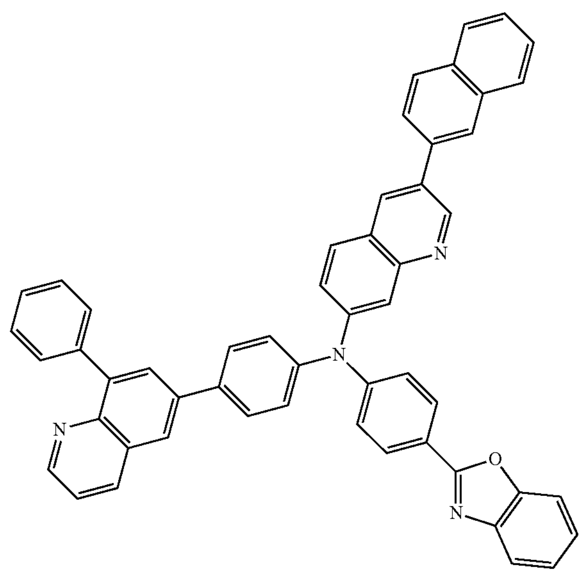
P150
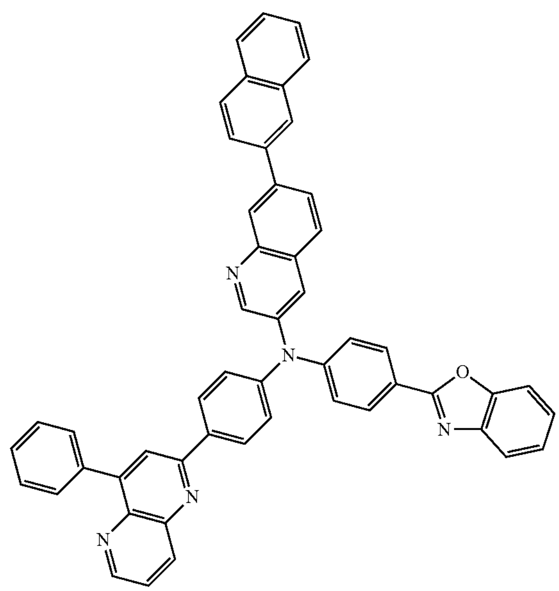
-continued
P151
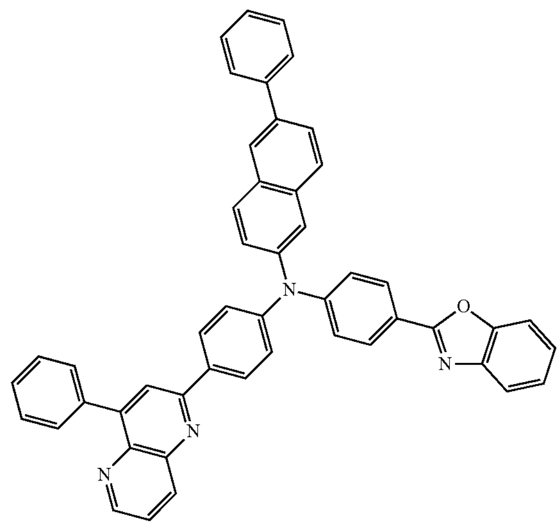
P152
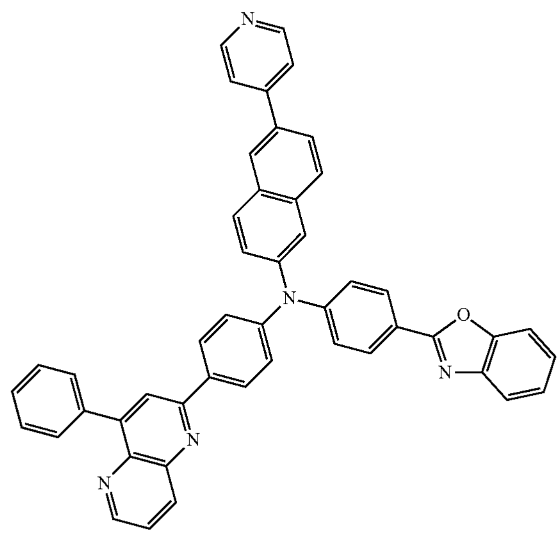
P153
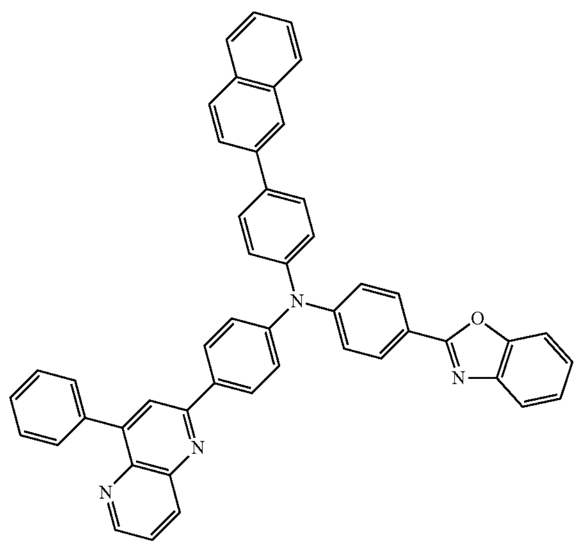

-continued
P154
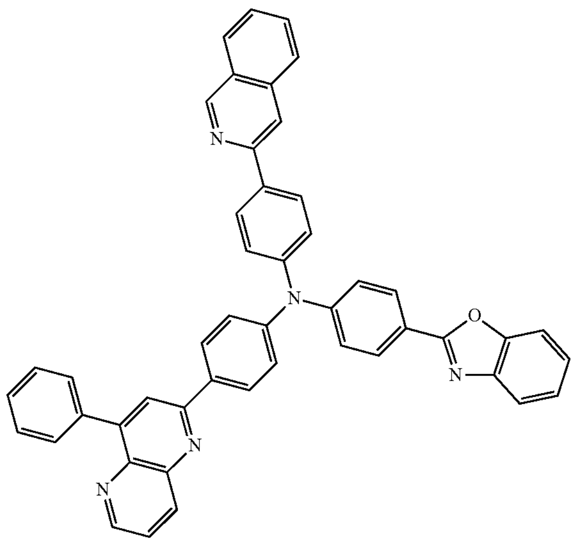
P155
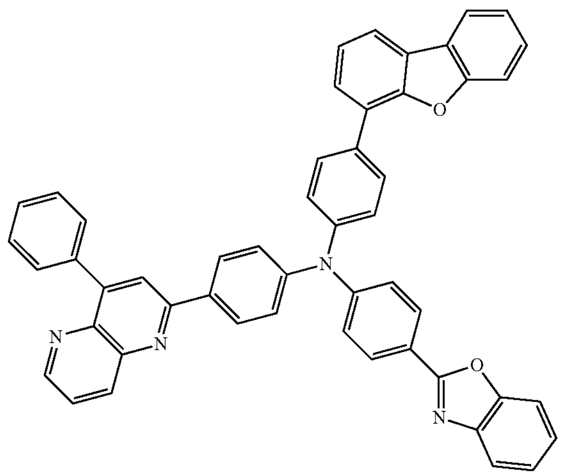
P156
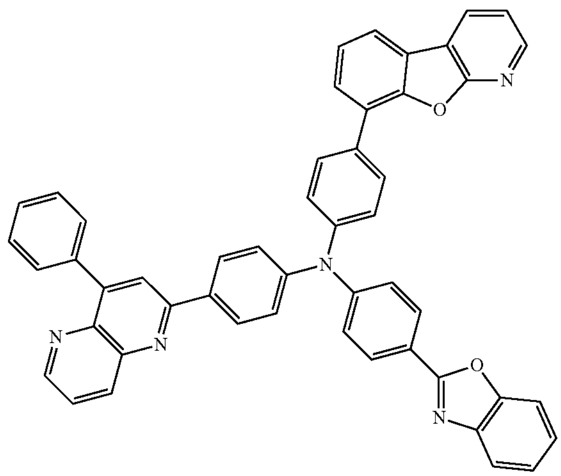
-continued
P157
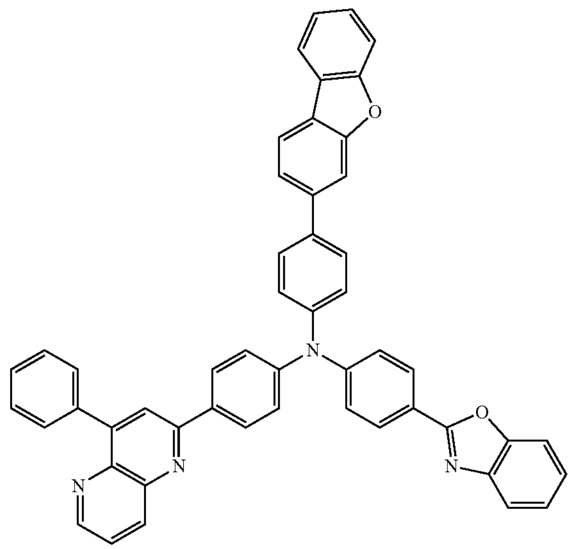
P158
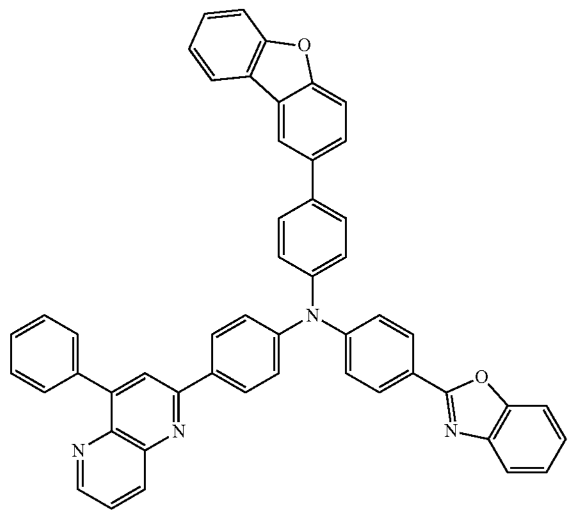
P159
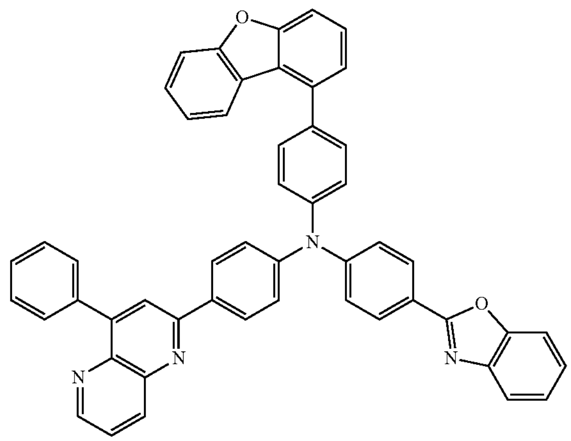

-continued
P160
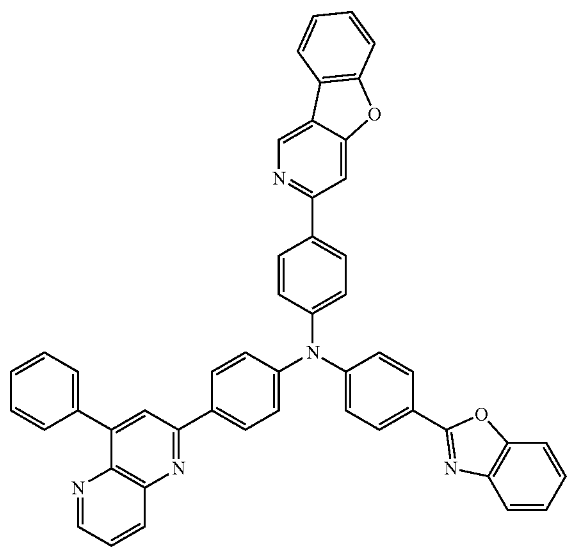
P161
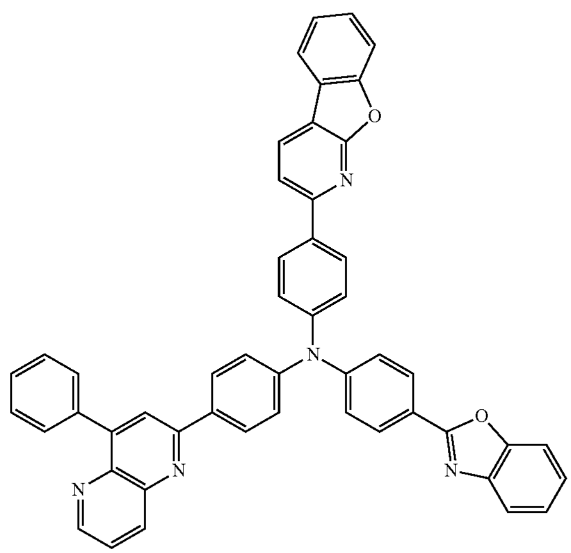
P162
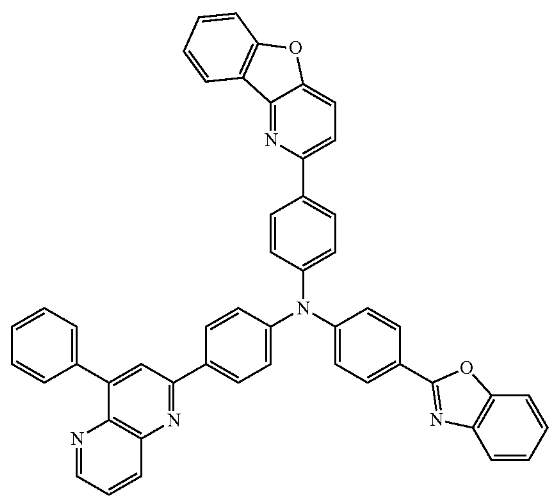
-continued
P163
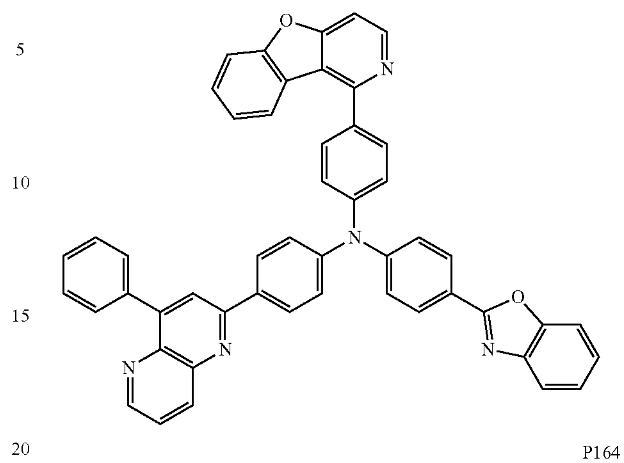
P164
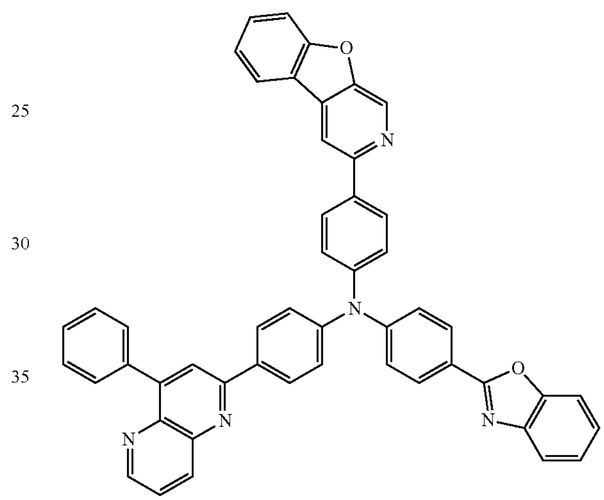
P165
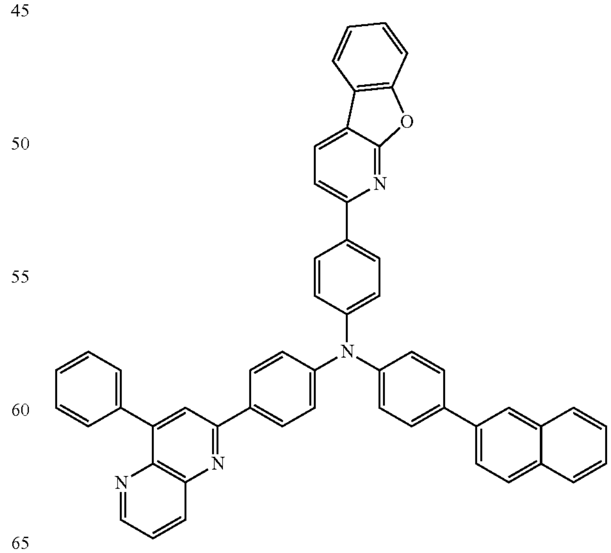

-continued
P166
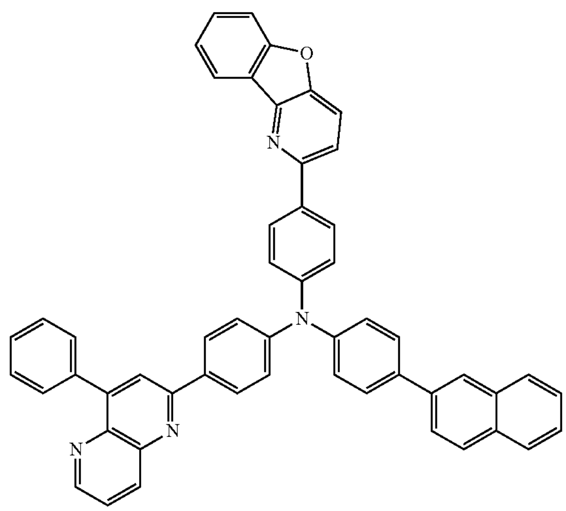
P167
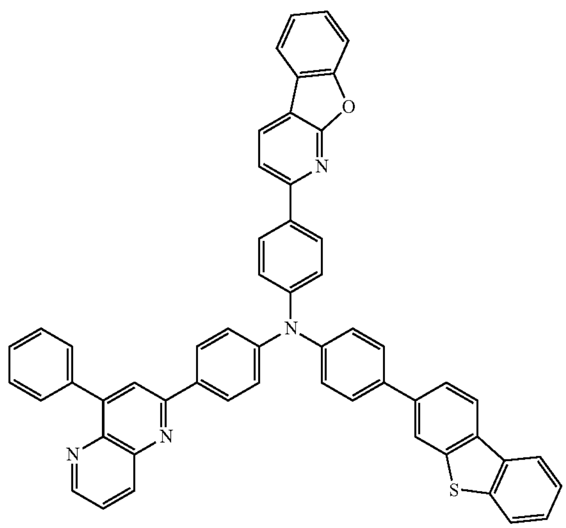
P168
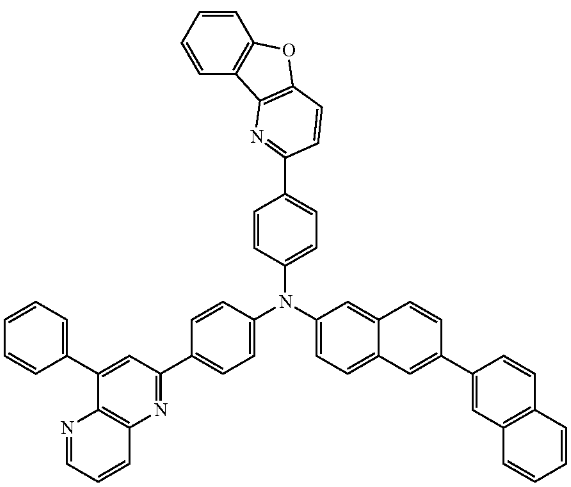
-continued
P169
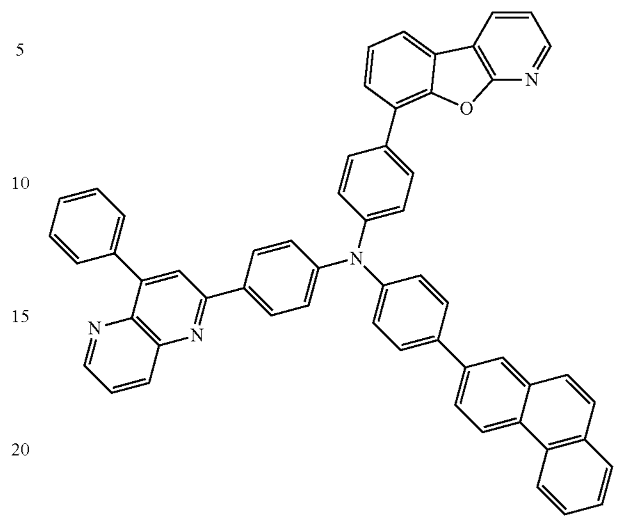
P170
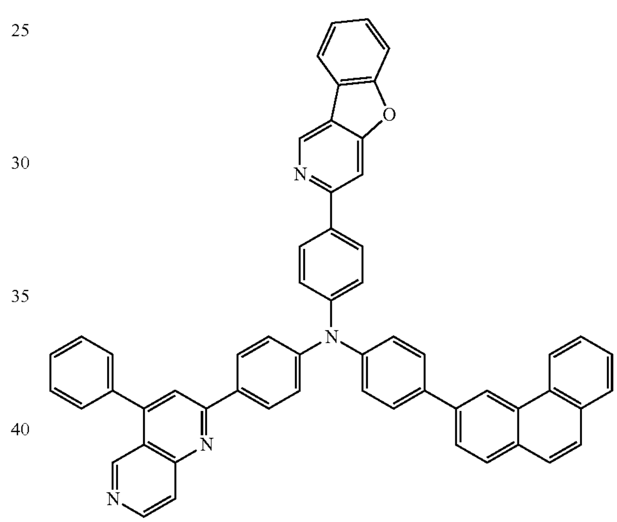
P171
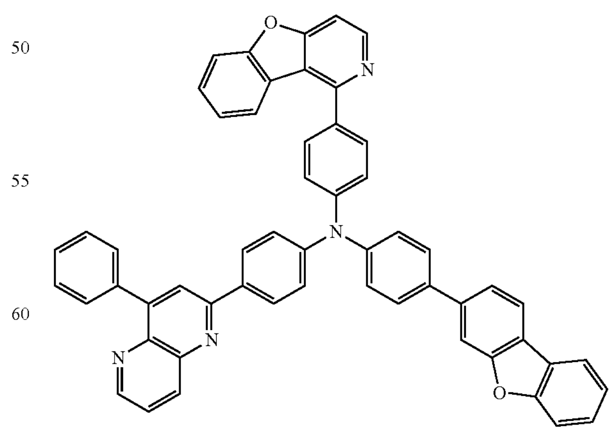

-continued
P172
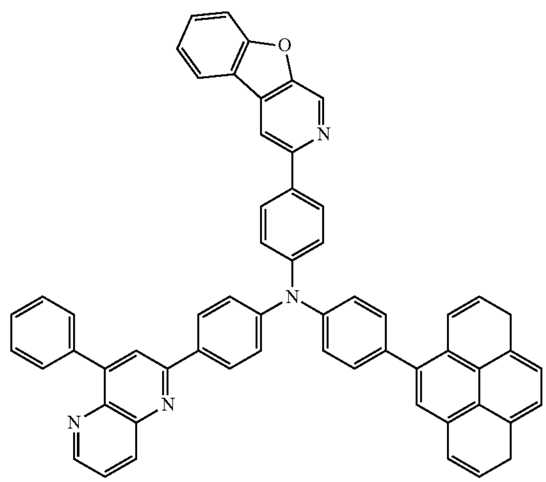
P173
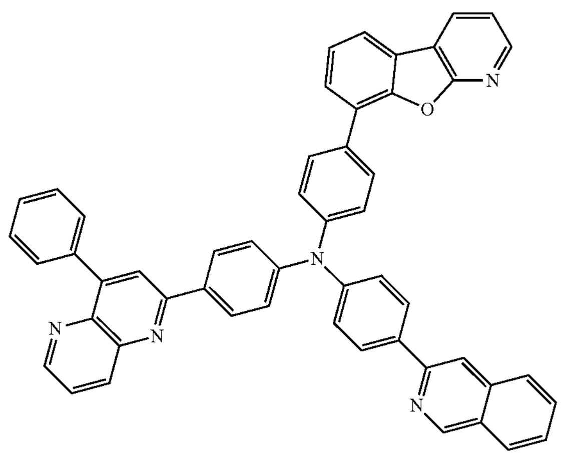
P174
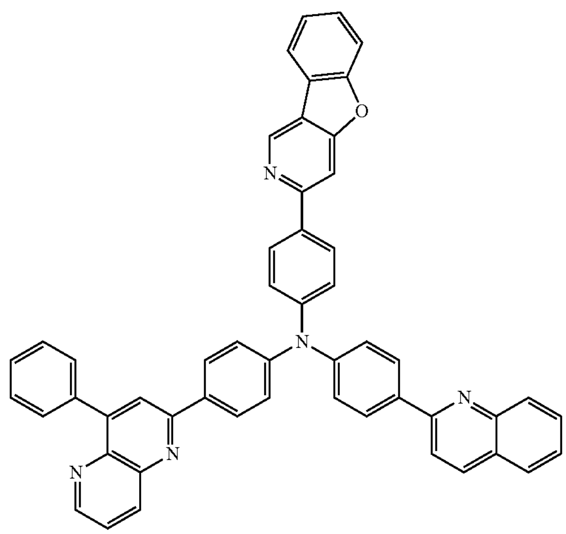
-continued
P175
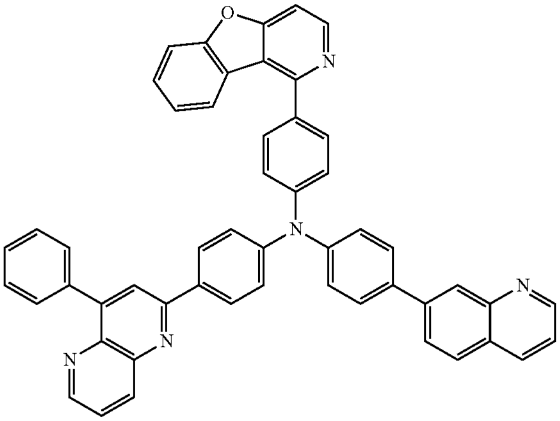
P176
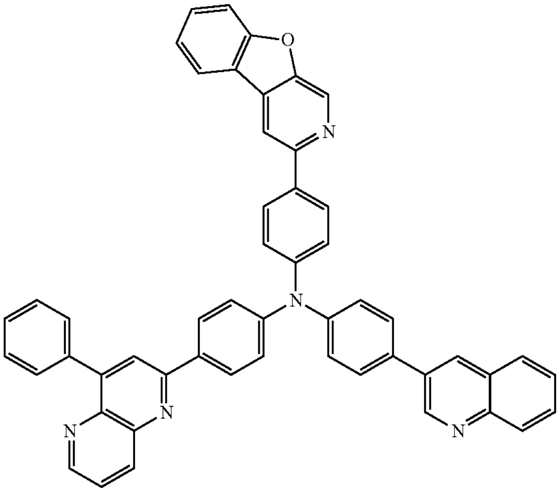
P177
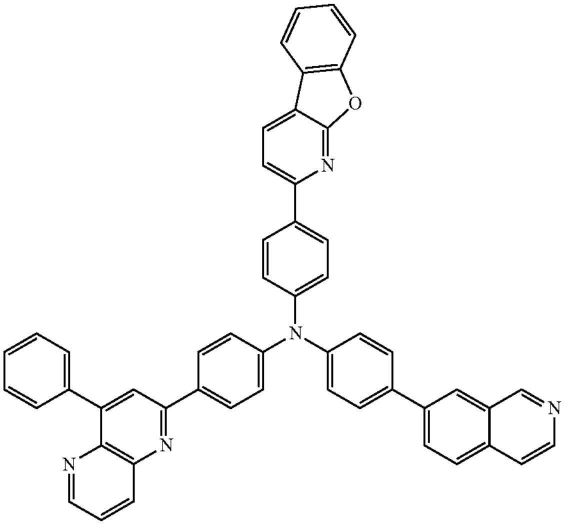

-continued
P178
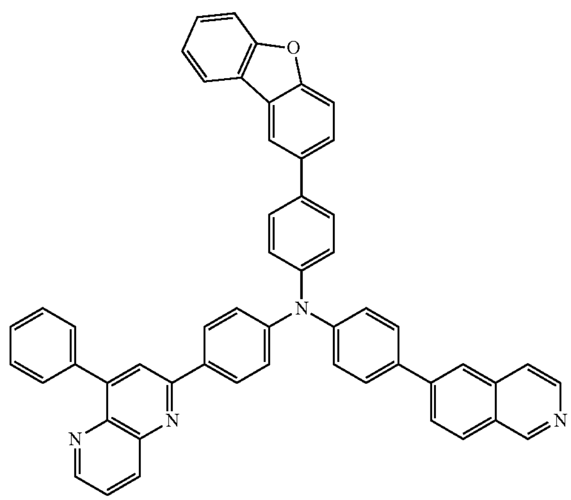
P179
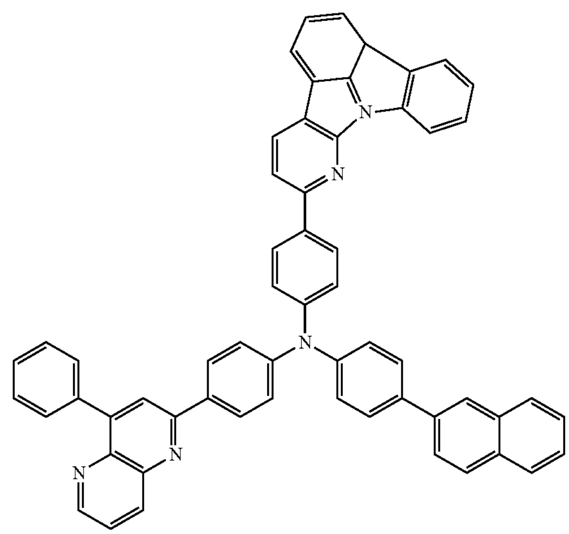
P180
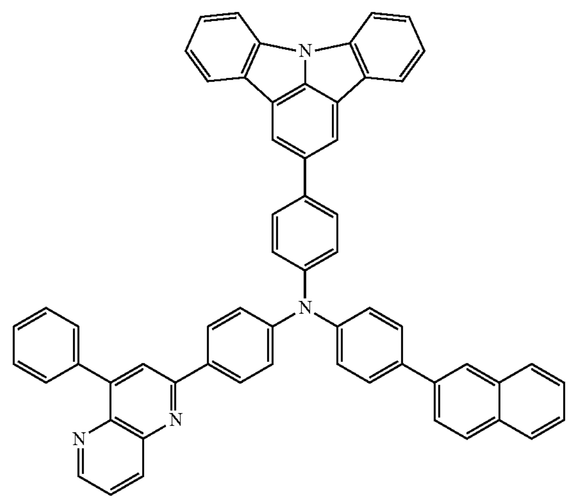
-continued
P181
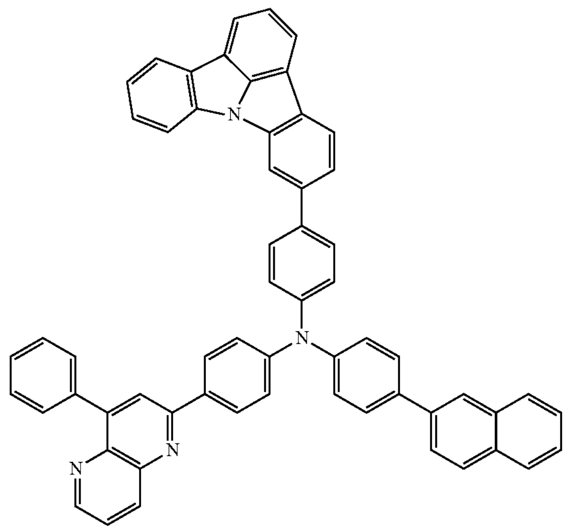
P182
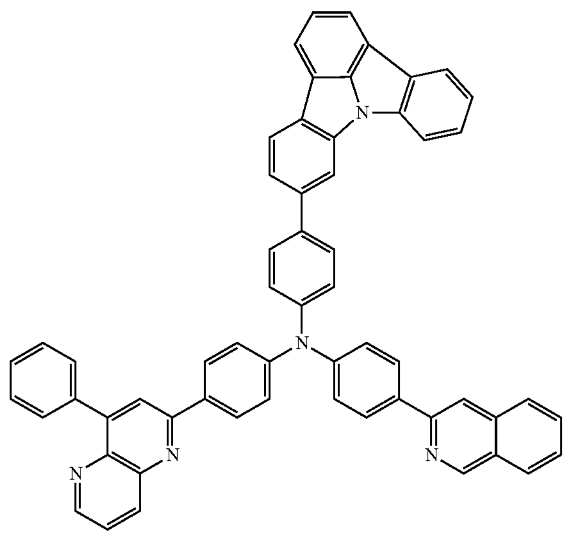
P183
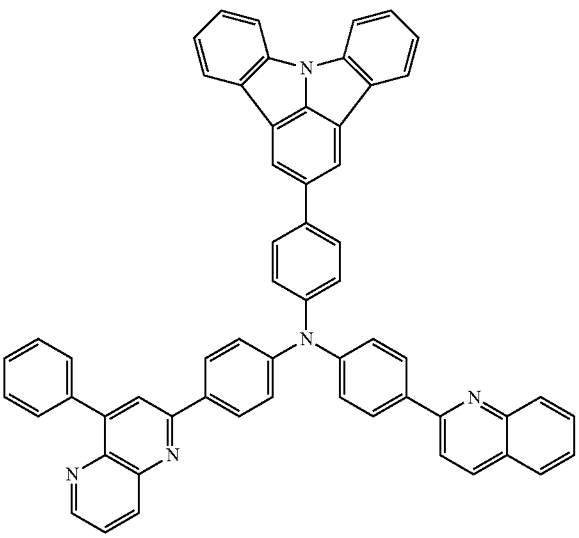

-continued
P184
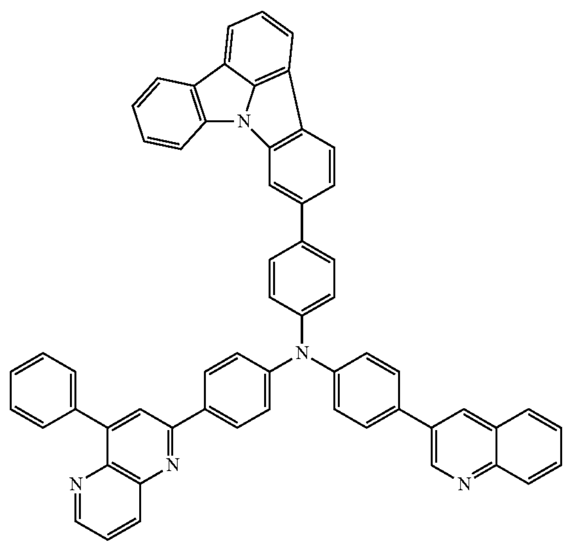
P185
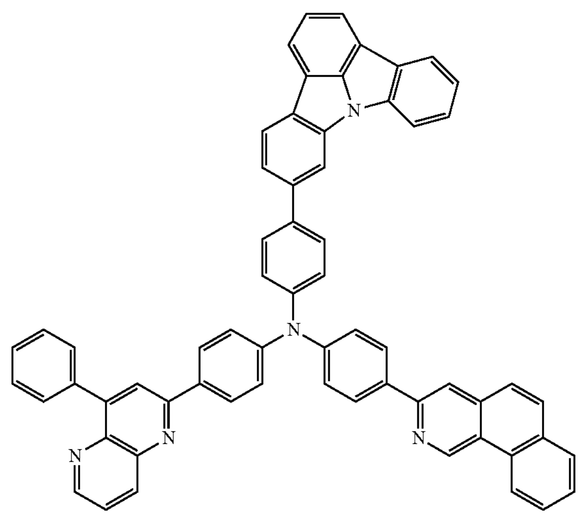
-continued
P186
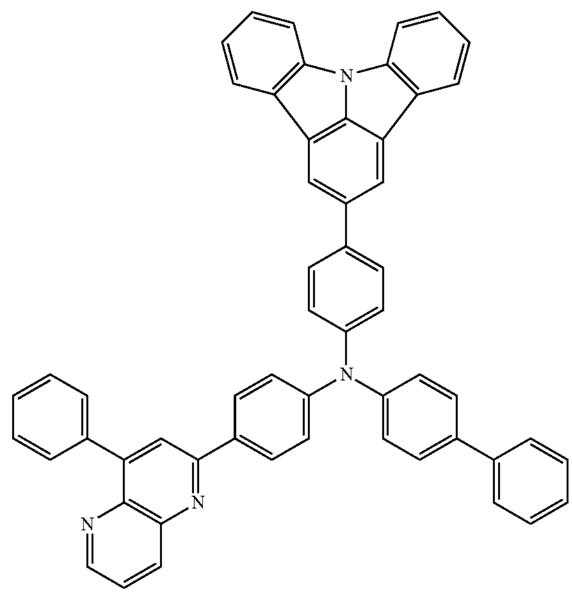
P187
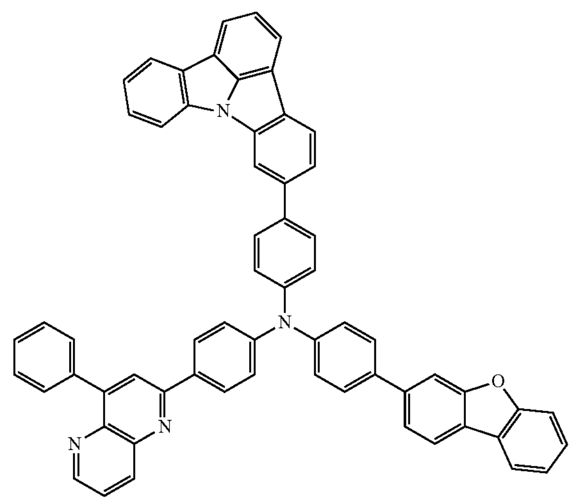
P188
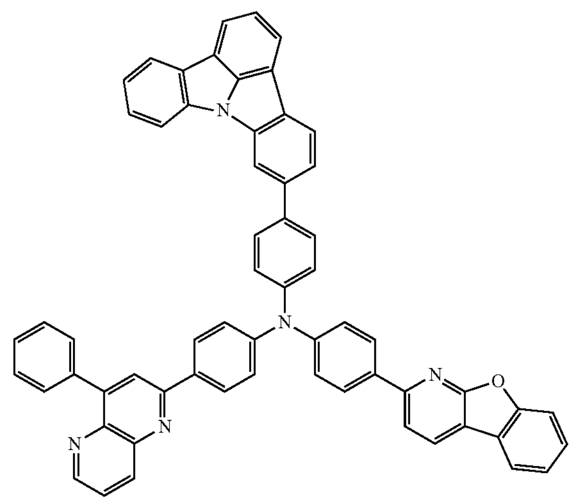

-continued
P189
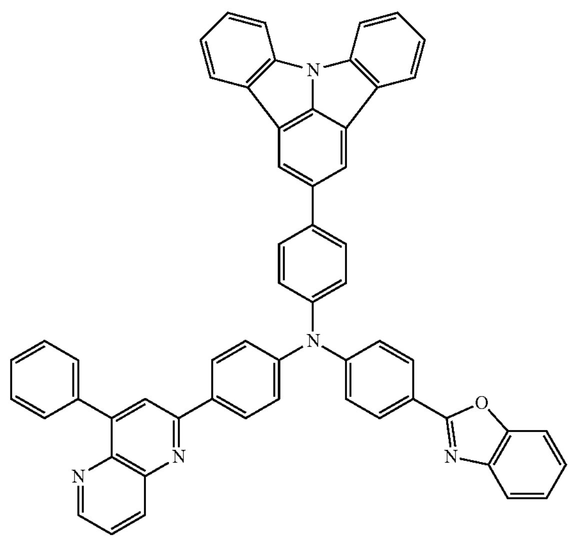
P190
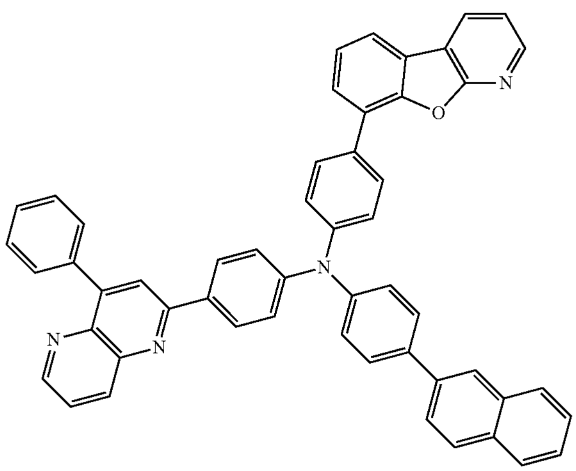
P191
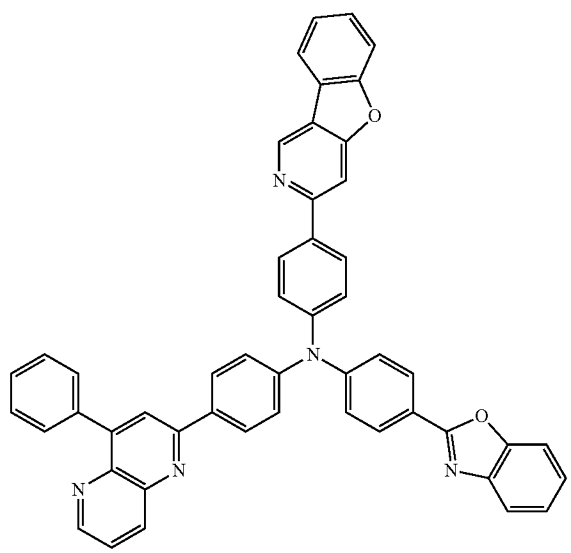
-continued
P192
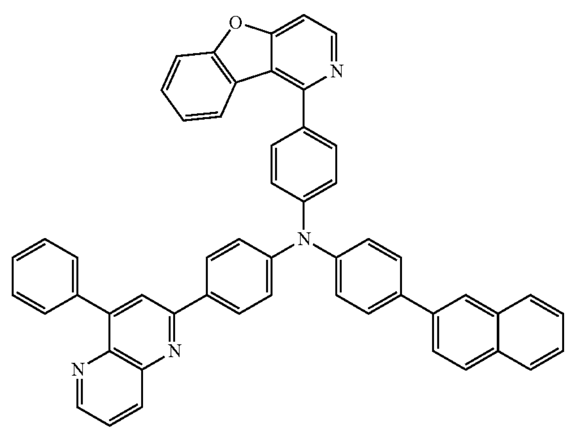
P193
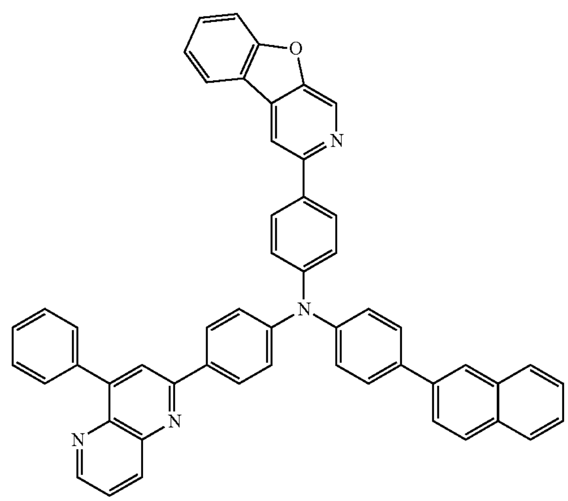
P194
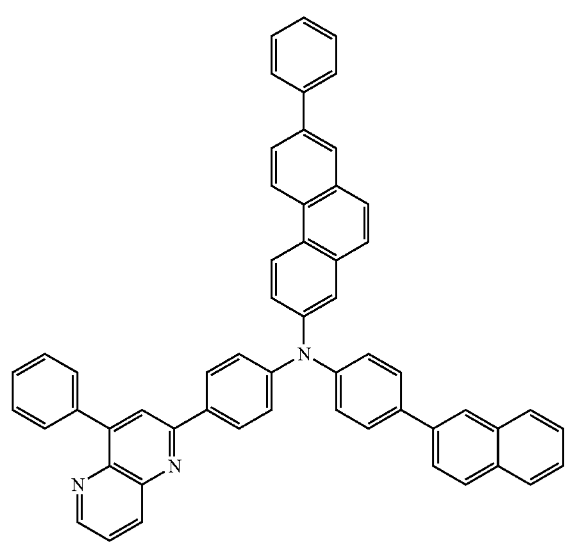

-continued
P195
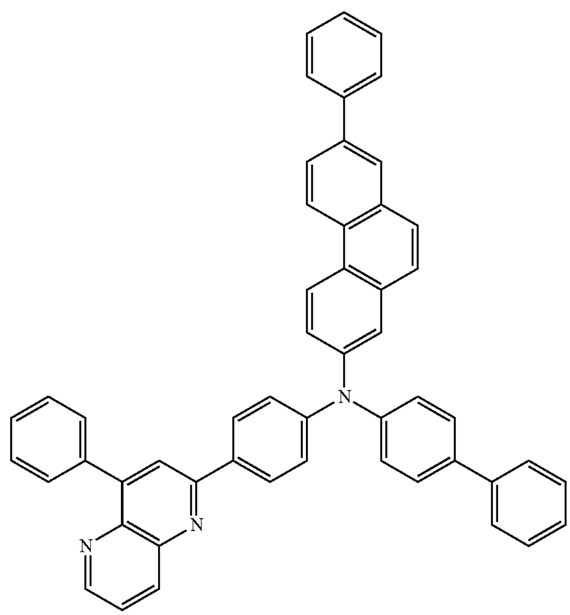
P196
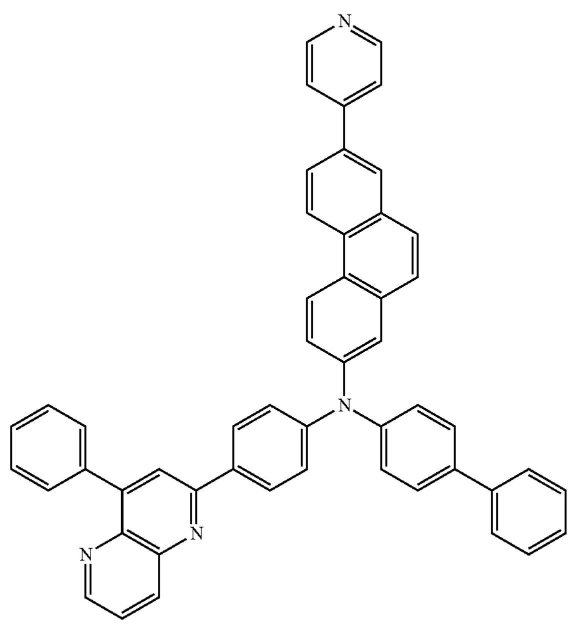
-continued
P197
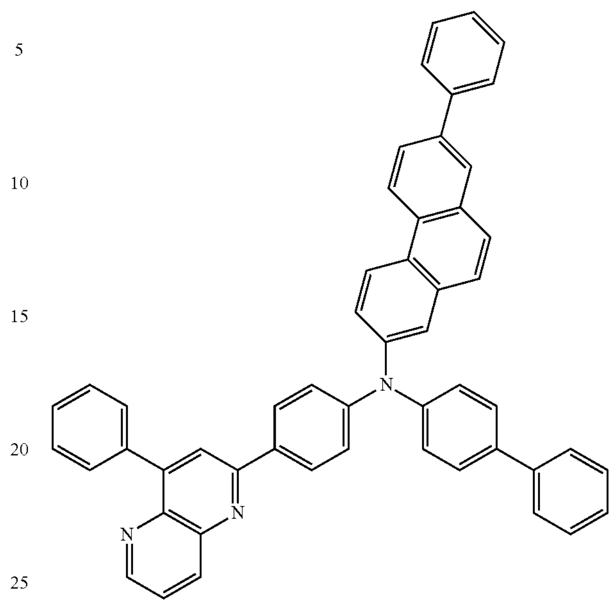
P198
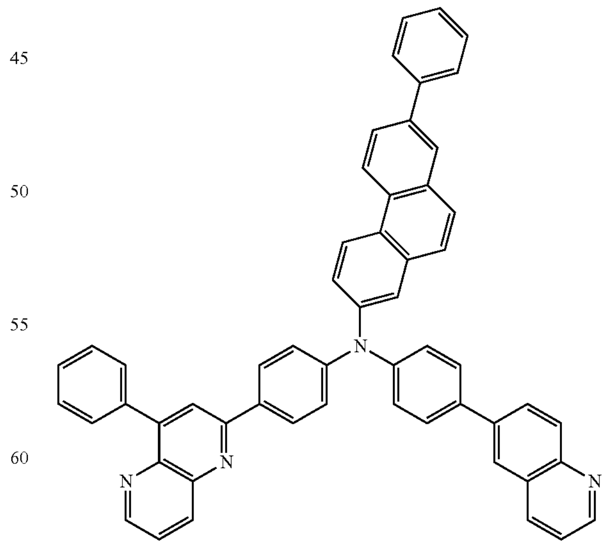

-continued

P199

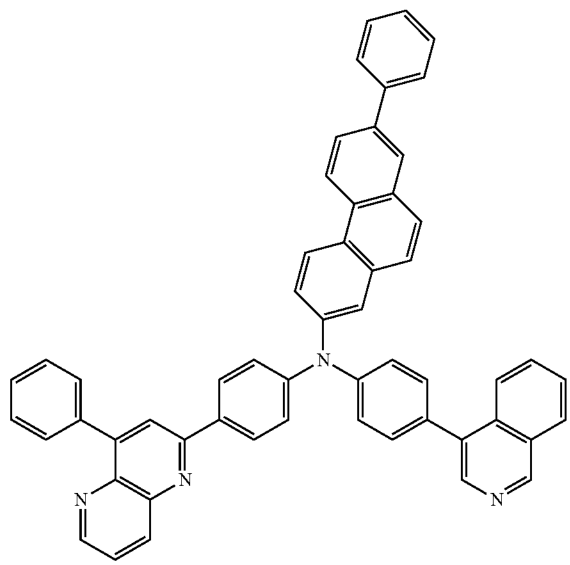

P200

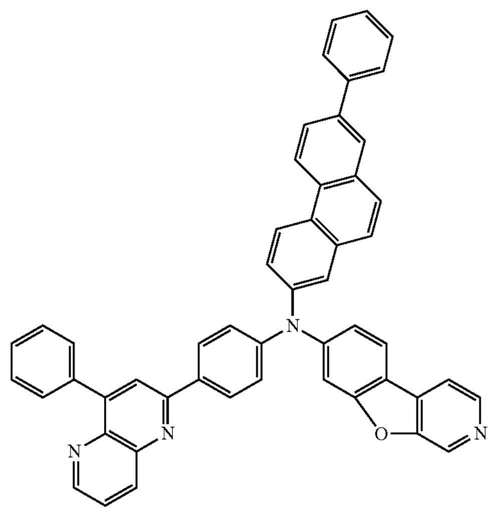

-continued

P201

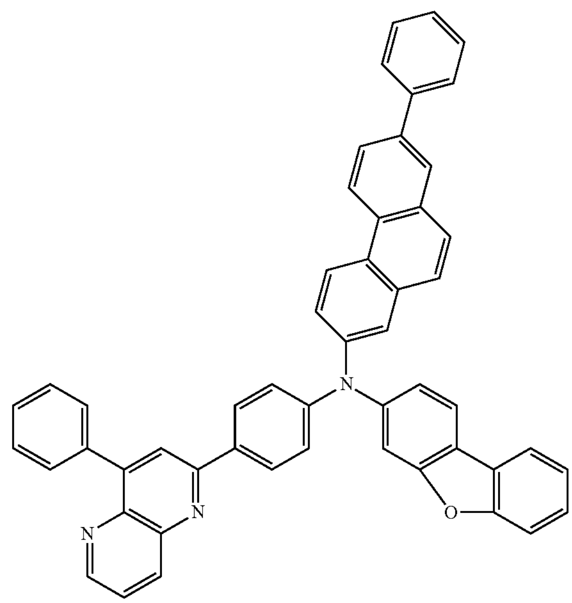

P202

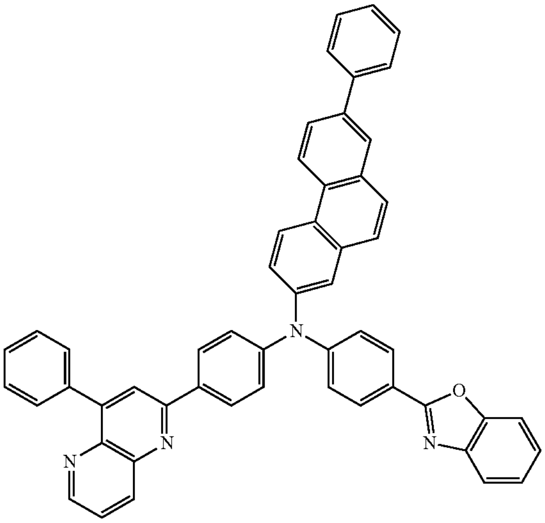

.

The present disclosure provides an organic light-emitting device. The organic light-emitting device includes an anode, a cathode, and an organic thin film layer between the anode and the cathode. The organic thin film layer includes a capping layer, and the capping layer includes a heterocyclic aromatic amine compound described herein.

The present disclosure provides a display panel including the organic light-emitting device described herein.

The organic light-emitting device provided by the present disclosure includes a substrate, an ITO anode, a first hole transport layer, a second hole transport layer, an electron blocking layer, a light-emitting layer, a first electron transport layer, a second electron transport layer, a cathode (magnesium-silver electrode, the mass ratio of magnesium-silver is 1:9), and a capping layer (CPL).

The anode material of the organic light-emitting device may be selected from metals such as copper, gold, silver, iron, chromium, nickel, manganese, palladium, platinum, and their alloys; may include metal oxides such as indium oxide, zinc oxide, indium tin oxide (ITO), and indium zinc oxide (IZO); may include conductive polymers such as polyaniline, polypyrrole, poly(3-methylthiophene); and in addition to the materials that contribute to hole injection and their combinations, may also include any existing materials suitable for anodes.

The cathode material of the organic light-emitting device may be selected from metals such as aluminum, magnesium, silver, indium, tin, titanium, and their alloys; and may be selected from multi-layer metal materials such as LiF/Al, $LiO_2$/Al, $BaF_2$/Al. In addition to the materials and alloys that facilitate electron injection, the cathode material may also include other suitable cathode materials.

The organic light-emitting device includes an organic thin film layer, which includes at least one light-emitting layer (EML), and may also include other functional layers, including hole injection layer (HIL), hole transport layer (HTL), electron blocking layer (EBL), hole blocking layer (HBL), electron transport layer (ETL), and electron injection layer (EIL).

The organic light-emitting device is prepared according to one or more methods stated herein.

The anode is formed on a transparent or opaque smooth substrate, an organic thin layer is formed on the anode, and the cathode is formed on the organic thin layer.

The organic thin layer may be formed by film forming methods such as evaporation, sputtering, spin coating, dipping, and ion plating.

The present invention provides a display device including the display panel described herein.

In certain embodiment(s) of the present disclosure, an organic light-emitting diode device (OLED device) may be used in a display device, where the organic light-emitting display device may be a mobile phone display, computer display, TV display, smart watch display, smart car display panel, VR or AR helmet displays, displays of various smart devices.

The heterocyclic aromatic amine compounds provided according to certain embodiment(s) of the present disclosure and with the structure shown in Formula I may be according to the following synthetic route,

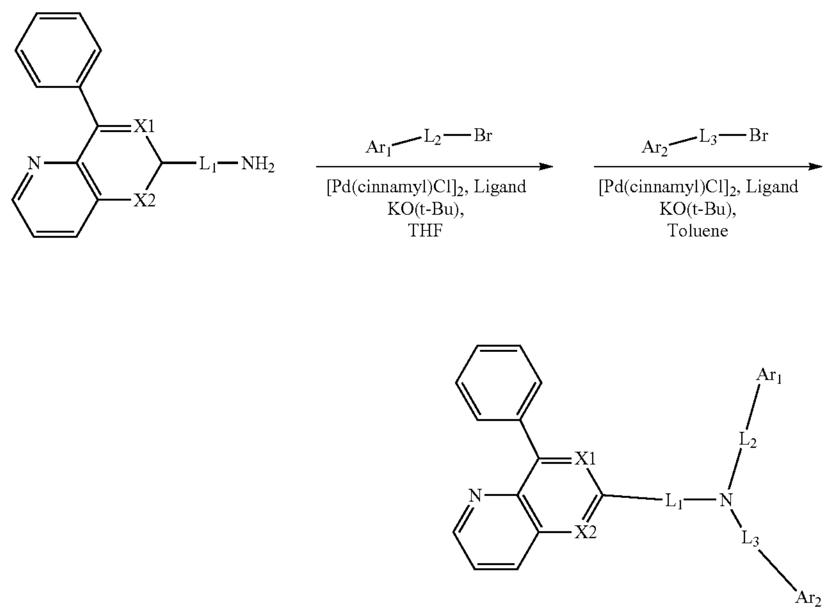

where Ligand is of a structure of:

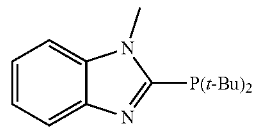

The following illustratively enumerates several heterocyclic aromatic amine compounds according to certain embodiment(s) of the present disclosure.

Example 1

In certain embodiment(s), the present disclosure provides a heterocyclic aromatic amine compound P1, a synthetic route of the heterocyclic aromatic amine compound P1 is illustrated below.

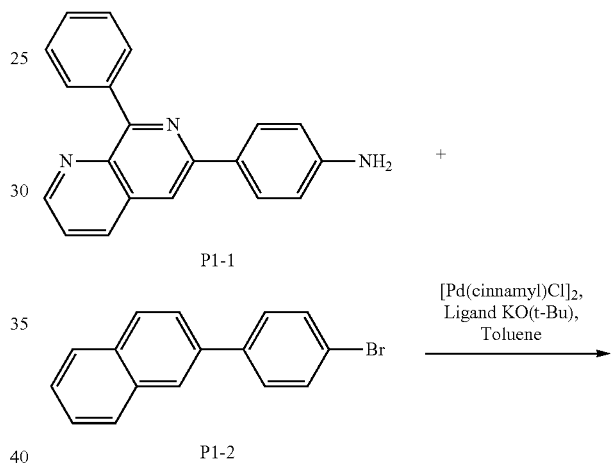

P1-1

P1-2

-continued

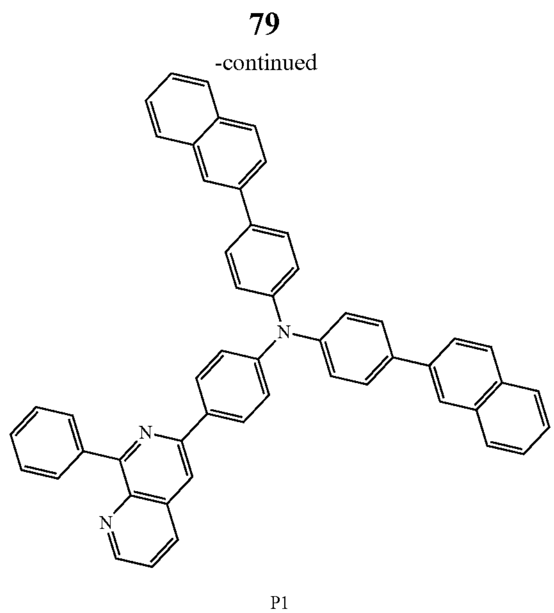

P1

To 3 mL of toluene is added an intermediate product P1-1 (0.5 mmol), compound P1-2 (1.2 mmol), KO(t-Bu) (2.0 mmol), $[Pd(cinnamyl)Cl]_2$ (0.04 mol), and Ligand (0.04 mol), and the resultant mixture is put into a 50 mL flask. After reacting at 110° C. for 12 hours, the mixture is cooled to room temperature, and to the mixture is slowly added a saturated $MgSO_4$ aqueous solution and ethyl acetate, to extract three times. Solvent is removed from the organic layer by a rotary evaporator, and the resultant organic layer passes through column chromatography to result in the target product P1.

The structure of the target product P1 is tested: MALDI-TOF MS (m/z): $C_{52}H_{35}N_3$ is obtained by matrix-assisted laser desorption ionization time-of-flight mass spectrometry, of which the calculated value is 701.3, and the tested value is 701.1.

Elemental Analysis Theoretical Values: C, 88.99; H, 5.03; N, 5.99; Tested Values: C, 88.99; H, 5.02; N, 5.99.

Example 2

In certain embodiment(s), the present disclosure provides a heterocyclic aromatic amine compound P2, a synthetic route of the heterocyclic aromatic amine compound P2 is illustrated below.

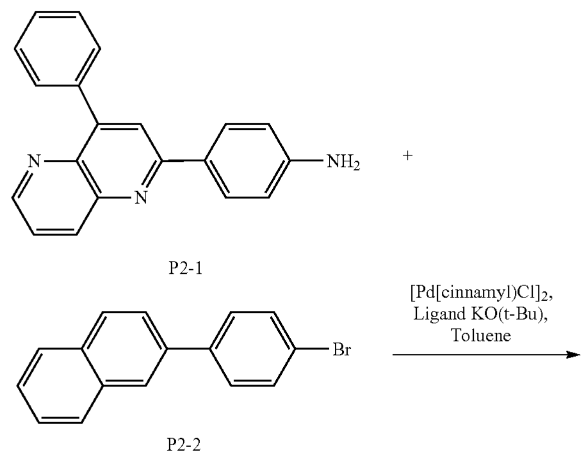

P2-1

P2-2

-continued

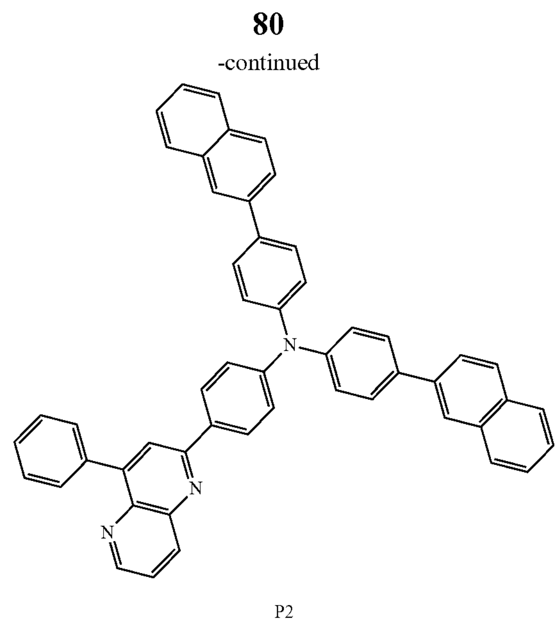

P2

To 3 mL of toluene is added an intermediate product P2-1 (0.5 mmol), compound P2-2 (1.2 mmol), KO(t-Bu) (2.0 mmol), $[Pd(cinnamyl)Cl]_2$ (0.04 mol), and Ligand (0.04 mol), and the resultant mixture is put into a 50 mL flask. After reacting at 110° C. for 12 hours, the mixture is cooled to room temperature, and to the mixture is slowly added a saturated $MgSO_4$ aqueous solution and ethyl acetate, to extract three times. Solvent is removed from the organic layer by a rotary evaporator, and the resultant organic layer passes through column chromatography to result in the target product P2.

The structure of the target product P2 is tested: MALDI-TOF MS (m/z): $C_{52}H_{35}N_3$ is obtained by matrix-assisted laser desorption ionization time-of-flight mass spectrometry, of which the calculated value is 701.3, and the tested value is 701.2.

Elemental Analysis Theoretical Values: C, 88.99; H, 5.03; N, 5.99; Tested Values: C, 88.98; H, 5.03; N, 5.99.

Example 3

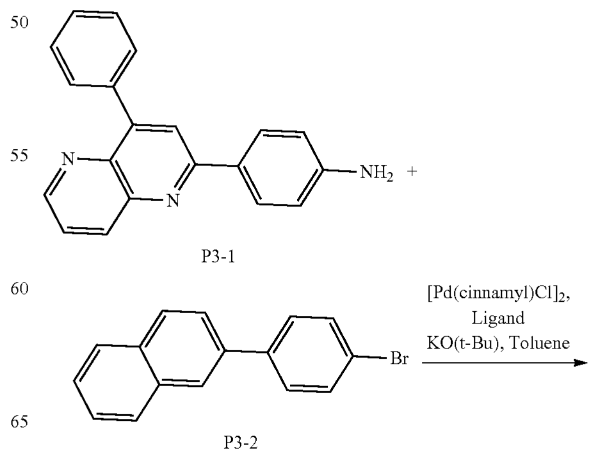

P3-1

P3-2

-continued

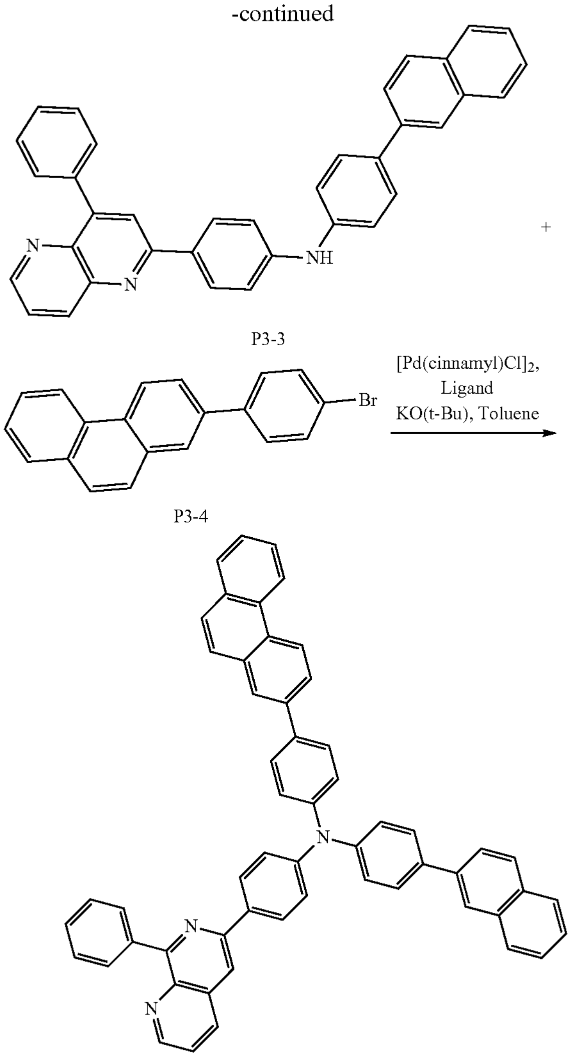

P3-3

P3-4

P3

To 3 mL of toluene is added compound P3-1 (0.5 mmol), compound P3-2 (0.5 mmol), KO(t-Bu) (1.0 mmol), [Pd(cinnamyl)Cl]$_2$ (0.02 mol), Ligand (0.02 mol), and the resultant mixture is put into a 50 mL flask. After reacting at 78° C. for 12 hours, the mixture is cooled to room temperature, and to the mixture is slowly added a saturated $MgSO_4$ aqueous solution and ethyl acetate, to extract three times. Solvent is removed from the organic layer by a rotary evaporator, and the resultant organic layer passes through column chromatography to result in the intermediate product P3-3.

To 3 mL of toluene is added the intermediate product P3-3 (0.5 mmol), compound P3-4 (0.6 mmol), KO(t-Bu) (1.0 mmol), [Pd(cinnamyl)Cl]$_2$ (0.02 mol), and Ligand (0.02 mol), and the resultant mixture is put into a 50 mL flask. After reacting at 110° C. for 12 hours, the mixture is cooled to room temperature, and to the mixture is slowly added a saturated $MgSO_4$ aqueous solution and ethyl acetate, to extract three times. Solvent is removed from the organic layer by a rotary evaporator, and the resultant organic layer passes through column chromatography to result in the target product P3.

The structure of the target product P3 is tested: MALDI-TOF MS (m/z): $C_{56}H_{37}N_3$ is obtained by matrix-assisted laser desorption ionization time-of-flight mass spectrometry, of which the calculated value is 751.3, and the tested value is 751.1. Elemental Analysis Theoretical Values: C, 89.45; H, 4.96; N, 5.59; Tested Values: C, 89.45; H, 4.97; N, 5.59.

Example 4

In certain embodiment(s), the present disclosure provides a heterocyclic aromatic amine compound P12, a synthetic route of the heterocyclic aromatic amine compound P12 is illustrated below.

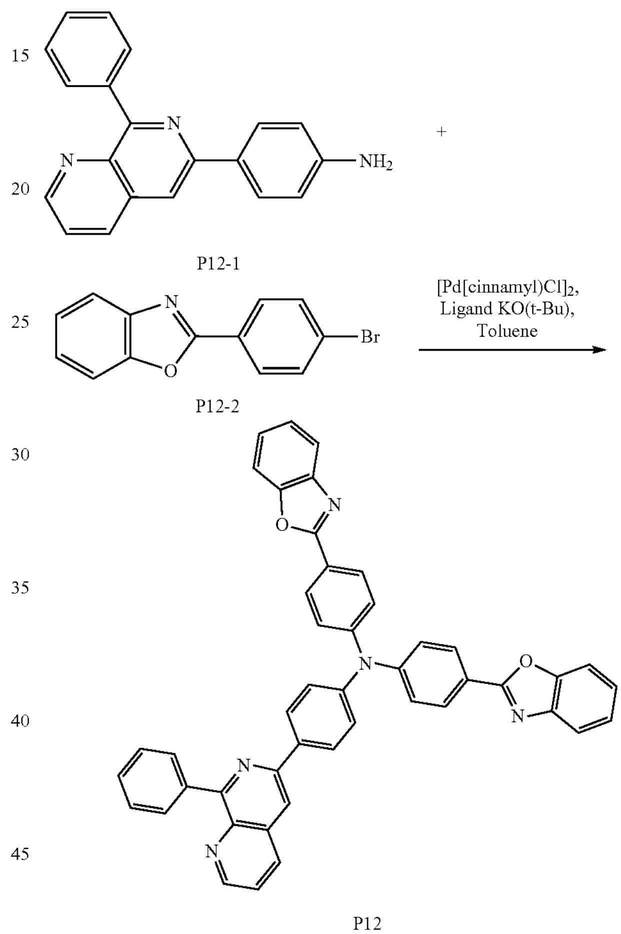

P12-1

P12-2

P12

To 3 mL of toluene is added an intermediate product P12-1 (0.5 mmol), compound P12-2 (1.2 mmol), KO(t-Bu) (2.0 mmol), [Pd(cinnamyl)Cl]$_2$ (0.04 mol), and Ligand (0.04 mol), and the resultant mixture is put into a 50 mL flask. After reacting at 110° C. for 12 hours, the mixture is cooled to room temperature, and to the mixture is slowly added a saturated $MgSO_4$ aqueous solution and ethyl acetate, to extract three times. Solvent is removed from the organic layer by a rotary evaporator, and the resultant organic layer passes through column chromatography to result in the target product P12.

The structure of the target product P12 is tested: MALDI-TOF MS (m/z): $C_{46}H_{29}N_5O_2$ is obtained by matrix-assisted laser desorption ionization time-of-flight mass spectrometry, of which the calculated value is 683.2, and the tested value is 683.1.

Elemental Analysis Theoretical Values: C, 80.80; H, 4.27; N, 10.24; Tested Values: C, 80.80; H, 4.26; N, 10.24.

Example 5

In certain embodiment(s), the present disclosure provides a heterocyclic aromatic amine compound P15, a synthetic route of the heterocyclic aromatic amine compound P15 is illustrated below.

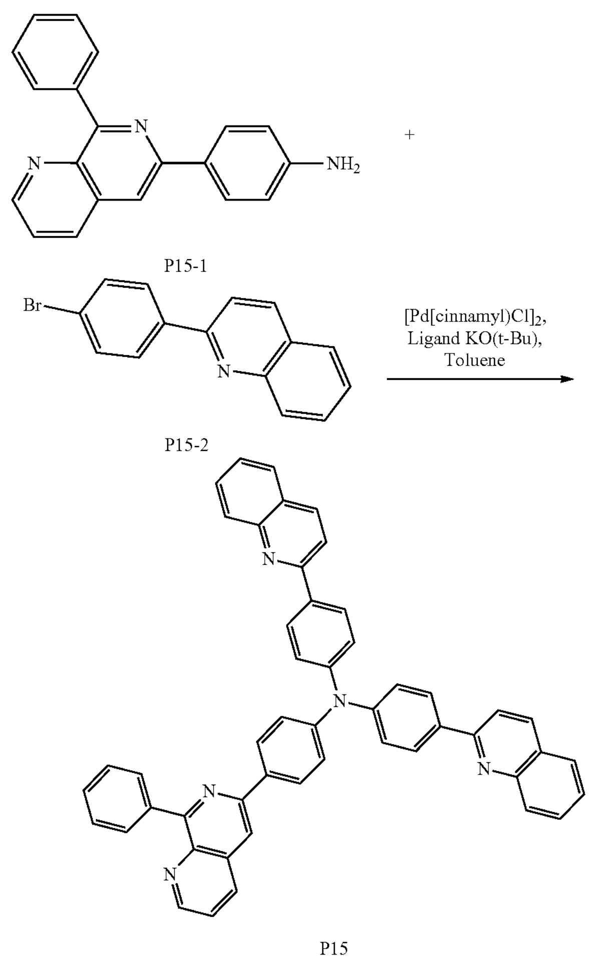

P15-1

P15-2

P15

To 3 mL of toluene is added an intermediate product P15-1 (0.5 mmol), compound P15-2 (1.2 mmol), KO(t-Bu) (2.0 mmol), $[Pd(cinnamyl)Cl]_2$ (0.04 mol), and Ligand (0.04 mol), and the resultant mixture is put into a 50 mL flask. After reacting at 110° C. for 12 hours, the mixture is cooled to room temperature, and to the mixture is slowly added a saturated $MgSO_4$ aqueous solution and ethyl acetate, to extract three times. Solvent is removed from the organic layer by a rotary evaporator, and the resultant organic layer passes through column chromatography to result in the target product P15.

The structure of the target product P15 is tested: MALDI-TOF MS (m/z): $C_{50}H_{33}N_5$ is obtained by matrix-assisted laser desorption ionization time-of-flight mass spectrometry, of which the calculated value is 703.3, and the tested value is 703.1.

Elemental Analysis Theoretical Values: C, 85.32; H, 4.73; N, 9.95; Tested Values: C, 85.31; H, 4.73; N, 9.96.

Example 6

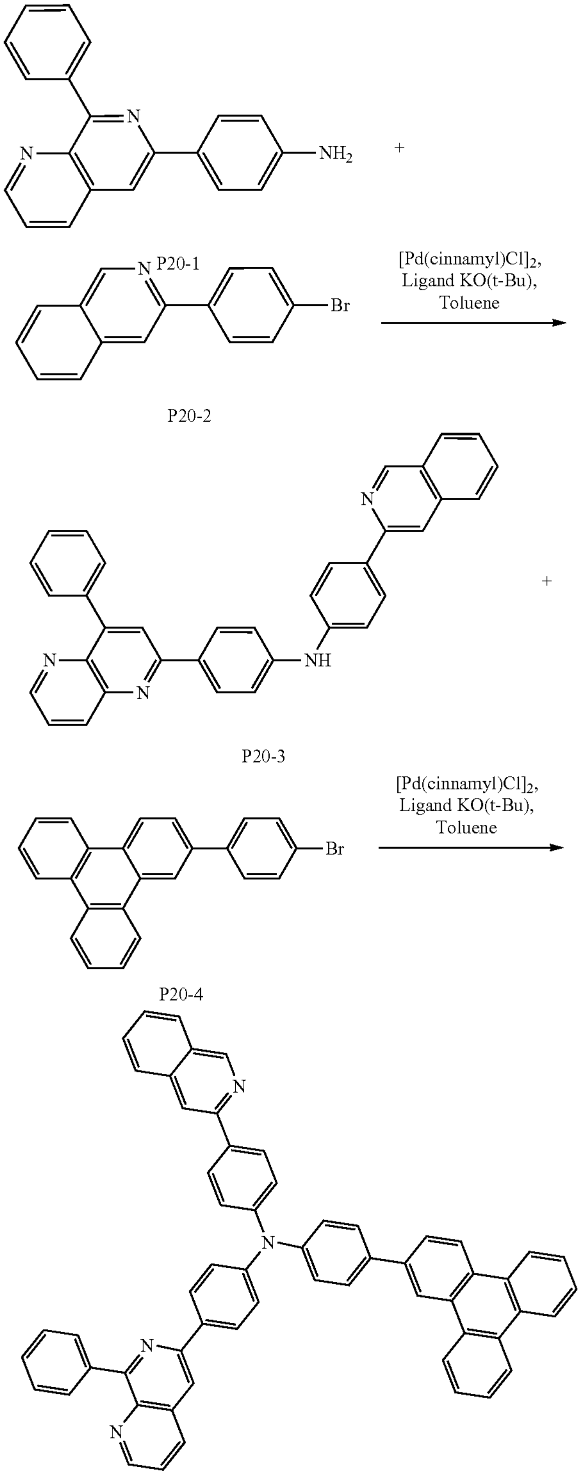

P20-1

P20-2

P20-3

P20-4

P20

To 3 mL of toluene is added compound P20-1 (0.5 mmol), compound P20-2 (0.5 mmol), KO(t-Bu) (1.0 mmol), $[Pd(cinnamyl)Cl]_2$ (0.02 mol), and Ligand (0.04 mol), and the resultant mixture is put into a 50 mL flask. After reacting at 78° C. for 12 hours, the mixture is cooled to room temperature, and to the mixture is slowly added a saturated $MgSO_4$ aqueous solution and ethyl acetate, to extract three times. Solvent is removed from the organic layer by a rotary evaporator, and the resultant organic layer passes through column chromatography to result in intermediate product P20-3.

To 3 mL of toluene is added the intermediate product P20-3 (0.5 mmol), compound P20-4 (0.6 mmol), KO(t-Bu) (1.0 mmol), $[Pd(cinnamyl)Cl]_2$ (0.02 mol), and Ligand (0.02 mol), and the resultant mixture is put into a 50 mL flask. After reacting at 110° C. for 12 hours, the mixture is cooled to room temperature, and to the mixture is slowly added a saturated $MgSO_4$ aqueous solution and ethyl acetate, to extract three times. Solvent is removed from the organic layer by a rotary evaporator, and the resultant organic layer passes through column chromatography to result in the target product P20.

The structure of the target product P20 is tested: MALDI-TOF MS (m/z): $C_{59}H_{38}N_4$ is obtained by matrix-assisted laser desorption ionization time-of-flight mass spectrometry, of which the calculated value is 802.3, and the tested value is 802.1.

Elemental Analysis Theoretical Values: C, 88.25; H, 4.77; N, 6.98; Tested Values: C, 88.25; H, 4.78; N, 6.98.

The preparation methods of other heterocyclic aromatic amine compounds are similar to the methods described herein, and are not repeated herein for brevity. Characterization results are provided, however, and the results of mass spectrometry and elemental analysis are shown in Table 1.

TABLE 1

| | Mass Spectrometry Results | | Elemental Analysis Results | |
|---|---|---|---|---|
| Compound | Calculated Value | Test Value | Theoretical Value | Test Value |
| P44 | 742.3 | 742.1 | C, 85.69; H, 4.61; N, 7.54; | C, 85.69; H, 4.60; N, 7.54; |
| P55 | 732.3 | 732.2 | C, 83.59; H, 4.40; N, 7.65; | C, 83.59; H, 4.41; N, 7.65; |
| P60 | 733.3 | 733.1 | C, 81.84; H, 4.26; N, 9.54; | C, 81.84; H, 4.27; N, 9.54; |
| P62 | 733.3 | 733.2 | C, 81.84; H, 4.26; N, 9.54; | C, 81.84; H, 4.26; N, 9.55; |
| P72 | 818.3 | 818.2 | C, 86.53; H, 4.68; N, 6.84; | C, 86.53; H, 4.69; N, 6.84; |
| P80 | 814.3 | 814.2 | C, 88.43; H, 4.70; N, 6.87; | C, 88.43; H, 4.71; N, 6.87; |
| P94 | 751.3 | 751.2 | C, 89.45; H, 4.96; N, 5.59; | C, 89.45; H, 4.96; N, 5.60; |
| P112 | 683.2 | 683.1 | C, 80.80; H, 4.27; N, 10.24; | C, 80.80; H, 4.27; N, 10.24; |
| P192 | 742.3 | 742.1 | C, 85.69; H, 4.61; N, 7.54; | C, 85.69; H, 4.61; N, 7.53; |

The performances of the heterocyclic aromatic amine compounds and compounds A-C are tested, where the structural formulas of compounds A-C are stated below:

Compound A

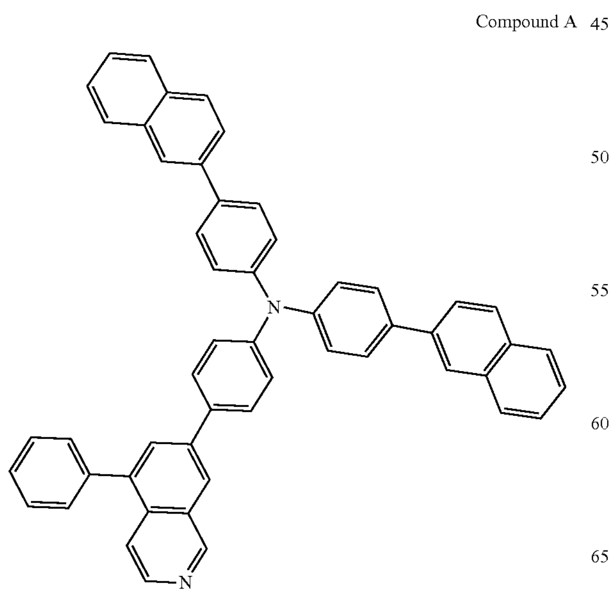

-continued

Compound B

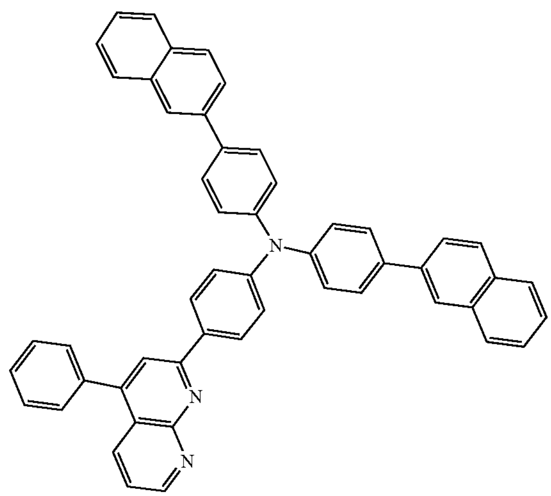

-continued

Compound C

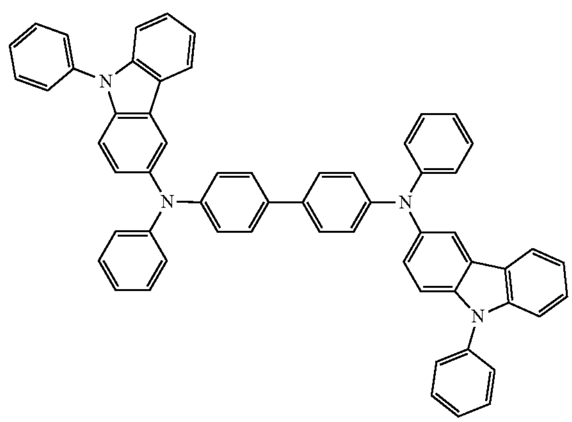

Test methods are stated below.

The refractive index values of the heterocyclic aromatic amine compounds at wavelengths of 460 nm, 530 nm and 620 nm are tested by an ellipsometer, and the test results are tabulated in Table 2 stated below.

TABLE 2

| Compound | Refractive Index | | |
|---|---|---|---|
| | $n_{460\ nm}$ | $n_{530\ nm}$ | $n_{620\ nm}$ |
| P1 | 2.36 | 2.19 | 2.08 |
| P2 | 2.34 | 2.17 | 2.06 |
| P3 | 2.38 | 2.20 | 2.09 |
| P12 | 2.34 | 2.17 | 2.05 |
| P15 | 2.37 | 2.13 | 2.02 |
| P20 | 2.39 | 2.21 | 2.10 |
| P44 | 2.36 | 2.18 | 2.08 |
| P55 | 2.33 | 2.17 | 2.07 |
| P60 | 2.35 | 2.18 | 2.08 |
| P62 | 2.33 | 2.16 | 2.06 |
| P72 | 2.38 | 2.20 | 2.09 |
| P80 | 2.37 | 2.18 | 2.08 |
| P94 | 2.35 | 2.17 | 2.06 |
| P112 | 2.33 | 2.19 | 2.08 |
| P192 | 2.34 | 2.17 | 2.05 |
| Compound A | 2.19 | 2.07 | 1.99 |
| Compound B | 2.25 | 2.12 | 2.00 |
| Compound C | 2.03 | 1.95 | 1.90 |

The following enumerates implementation examples of organic compounds according to certain embodiment(s) of the present disclosure applied in organic electroluminescent devices:

Implementation Example 1

This implementation example provides an organic electroluminescent device, for which the preparation steps are stated below:

(1) A glass substrate having an indium tin oxide (ITO) anode layer (thickness of 15 nm) is cut into a size of 50 mm×50 mm×0.7 mm, ultrasonicated in isopropanol and deionized water, respectively, for 30 min, and is cleaned by being exposed to ozone for about 10 min. The substrate thus cleaned is installed onto a vacuum deposition equipment.

(2) On the ITO anode layer, the hole injection layer material compound b and the p-doped compound a are evaporated by vacuum evaporation, the doping ratio is 3% (mass ratio), and the thickness is 5 nm, to form the hole injection layer.

(3) The hole transport layer material compound b is vacuum evaporated onto the hole injection layer at a thickness of 100 nm, to form the first hole transport layer.

(4) The hole transport type material compound c is vacuum evaporated onto the first hole transport layer at a thickness of 5 nm, to form the second hole transport layer.

(5) A light-emitting layer is vacuum-evaporated onto the second hole transport layer, where compound d is used as the host material, compound e is used as the dopant material, the doping ratio is 3% (mass ratio), and the thickness is 30 nm.

(6) Electron transport type material compound f is vacuum-evaporated onto the light-emitting layer at a thickness of 30 nm, to form the first electron transport layer.

(7) Electron transport material compound g and n-doped compound h are vacuum evaporated onto the first electron transport layer, at a doping mass ratio of 1:1, and at a thickness of 5 nm, to form the second electron transport layer.

(8) A magnesium-silver electrode is vacuum-evaporated onto the second electron transport layer, at Mg:Ag radio of 9:1, and at thickness of 10 nm, to form the cathode.

(9) The heterocyclic aromatic amine compound P001 of the present disclosure is vacuum evaporated onto the cathode at a thickness of 100 nm, to be used as a capping layer.

The structures of the compounds referenced in the description are illustrated below.

Compound a

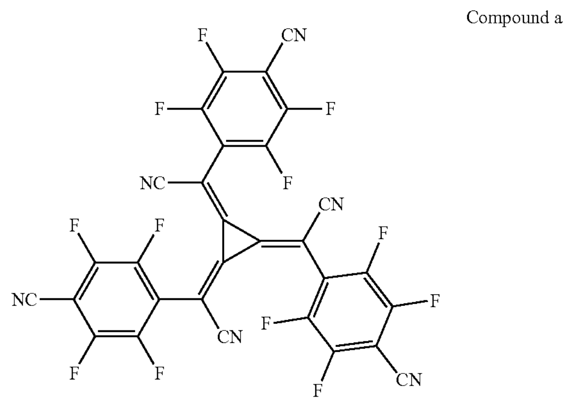

Compound b

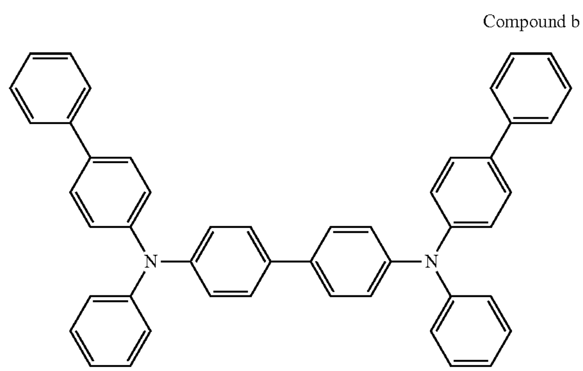

Compound c

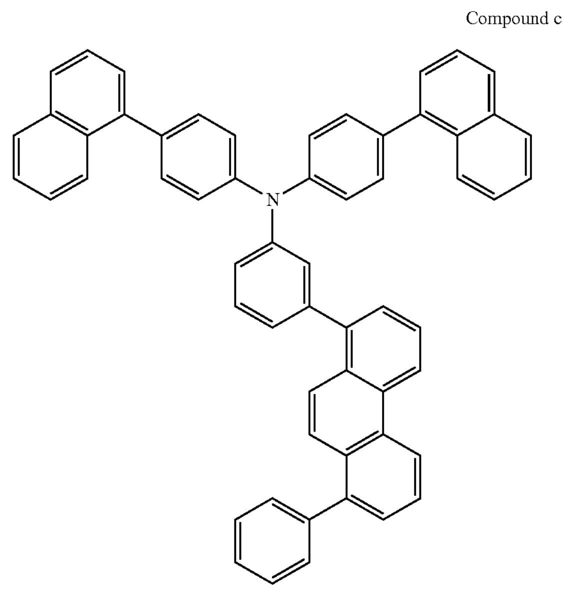

-continued

Compound d

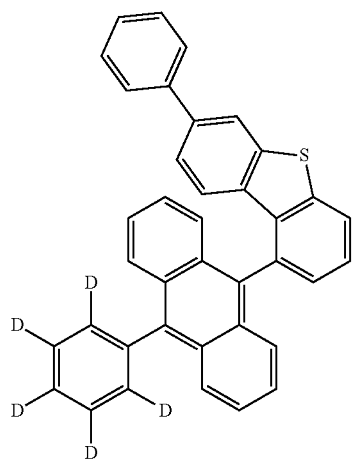

Compound e

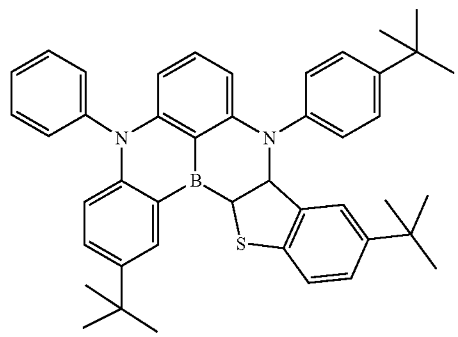

Compound f

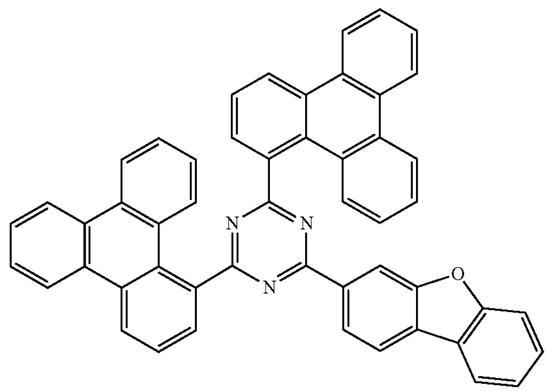

-continued

Compound g

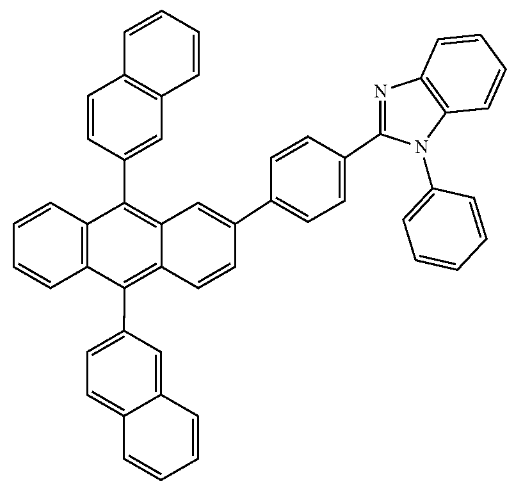

Compound h

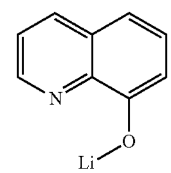

Implementation Examples 2-15

The difference between these implementation examples and implementation example 1 is that the heterocyclic arylamine compound P001 at step (9) is replaced with an equivalent amount of another heterocyclic arylamine compounds (as shown in Table 3 below), and other preparation steps remain the same.

Comparative Implementation Example 1

This comparative implementation example differs from implementation example 1 only in that the heterocyclic aromatic amine compound P001 at step (9) is replaced with an equivalent amount of compound A, and other preparation steps remain the same.

Comparative Implementation Example 2

This comparative implementation example differs from implementation example 1 only in that the heterocyclic aromatic amine compound P001 at step (9) is replaced with an equivalent amount of compound B, and other preparation steps remain the same.

Comparative Implementation Example 3

This comparative implementation example differs from implementation example 1 only in that the heterocyclic aromatic amine compound P001 at step (9) is replaced with an equivalent amount of compound C, and other preparation steps remain the same.

Performance Evaluation of the OLED Devices

A Keithley 2365A digital nanovoltmeter is employed to test the current of OLED devices at different voltages, and then the current is divided by the light-emitting area to obtain the current density of OLED devices at different voltages. Konicaminolta CS-2000 spectroradiance meter is employed to test the brightness and radiant energy flux density of the OLED devices under different voltages. According to the current density and brightness of the OLED device at different voltages, the current efficiency (CE, Cd/A) at the same current density (10 mA/cm2) is obtained. The lifetime LT95 is obtained by measuring the time at which the brightness of the OLED device reaches 95% of the initial brightness (under the test condition of 50 $mA/cm^2$). Resulting data are shown in Table 3 below.

TABLE 3

| Number | CPL Material | Current Efficiency (cd/A) | LT95 |
|---|---|---|---|
| Example 1 | P1 | 109% | 107% |
| Example 2 | P2 | 108% | 105% |
| Example 3 | P3 | 110% | 106% |
| Example 4 | P12 | 108% | 110% |
| Example 5 | P15 | 109% | 106% |
| Example 6 | P20 | 110% | 105% |
| Example 7 | P44 | 109% | 106% |
| Example 8 | P55 | 107% | 105% |
| Example 9 | P60 | 108% | 109% |
| Example 10 | P62 | 107% | 108% |
| Example 11 | P72 | 110% | 104% |
| Example 12 | P80 | 109% | 104% |
| Example 13 | P94 | 108% | 106% |
| Example 14 | P112 | 108% | 110% |
| Example 15 | P192 | 107% | 106% |
| Comparison 1 | Compound A | 103% | 104% |
| Comparison 2 | Compound B | 104% | 103% |
| Comparison 3 | Compound C | 100% | 100% |

As shown in Table 2 and Table 3, the heterocyclic aromatic amine compound provided by the examples of the present disclosure has a higher refractive index at 460 nm, 530 nm and 620 nm wavelengths relative to comparative compounds A, B, and C, and corresponding OLED devices fabricated as a capping layer have higher current efficiency and lifetime. The heterocyclic aromatic amine compounds provided according to certain embodiment(s) of the present disclosure effectively improve the efficiency and lifespan of OLED devices.

The embodiments are described to help with understanding of the method and the idea of the present disclosure. For those skilled in the art, without departing from the principle of the present disclosure, improvements and modifications may be made to the present disclosure, and these improvements and modifications also fall within the protection scope of the claims of the present disclosure.

What is claimed is:

1. A compound, having a structure of Formula I:

Formula I

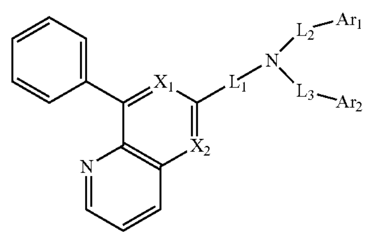

wherein $X_1$ and $X_2$ are each independently a nitrogen atom or a C—R group, C is a carbon atom, R is a hydrogen atom, a deuterium atom, a halogen atom, or a cyano group, and at least one of $X_1$ and $X_2$ is N;

$L_1$, $L_2$, and $L_3$ are each independently a single bond, a substituted or unsubstituted aryl group, or a substituted or unsubstituted aryl heteroaryl group; and $Ar_1$, $Ar_2$ are each independently a substituted or unsubstituted aryl group or a substituted or unsubstituted heteroaryl group.

2. The compound of claim 1, wherein the compound is of a structure of Formula I-a or Formula I-b:

Formula I-a

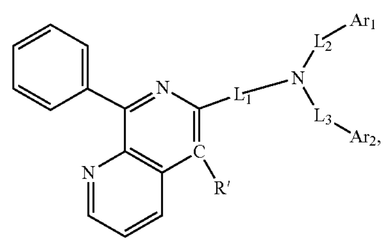

Formula I-b

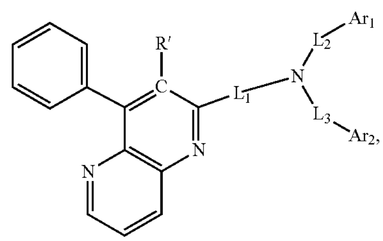

R' is the hydrogen atom, the deuterium atom, the halogen atom, or the cyano group.

3. The compound of claim 1, wherein $L_1$, $L_2$, and $L_3$ are each independently the single bond, a substituted or unsubstituted C6-C18 aryl group, or a substituted or unsubstituted C5-C18 heteroaryl group.

4. The compound of claim 3, wherein $L_1$, $L_2$, and $L_3$ are each independently the single bond, a substituted or unsubstituted monocyclic aryl group, a substituted or unsubstituted monocyclic heteroaryl group, a condensed aryl group formed by condensing 2-5 rings, or a condensed heteroaryl group formed by condensing 2 to 4 rings.

5. The compound of claim 4, wherein heteroatoms of the substituted or unsubstituted monocyclic heteroaryl group and the condensed heteroaryl group are each independently a nitrogen atom, an oxygen atom, or a sulfur atom.

6. The compound of claim 5, wherein $L_1$, $L_2$, and $L_3$ are each independently the single bond, a substituted or unsubstituted phenyl group, a substituted or unsubstituted furyl group, a substituted or unsubstituted thienyl group, a substituted or unsubstituted pyrrolyl group, a substituted or unsubstituted pyridyl group, a substituted or unsubstituted pyranyl group, a substituted or unsubstituted pyrimidinyl group, a substituted or unsubstituted pyrazinyl group, a substituted or unsubstituted pyridazinyl group, a substituted or unsubstituted triazinyl group, a substituted or unsubstituted naphthyl group, a substituted or unsubstituted quinolinyl group, a substituted or unsubstituted quinoxalinyl group, a substituted or unsubstituted isoquinolinyl group, a substituted or unsubstituted quinazolinyl group, a substituted or unsubstituted anthracenyl group, or a substituted or unsubstituted phenanthrenyl group.

7. The compound of claim 6, wherein $L_1$, $L_2$, and $L_3$ are each independently the single bond or the substituted or unsubstituted phenyl group.

8. The compound of claim 1, wherein $Ar_1$ and $Ar_2$ are each independently a substituted or unsubstituted C6-C30 aryl group or a substituted or unsubstituted C3-C30 heteroaryl group.

9. The compound of claim 8, wherein $Ar_1$ and $Ar_2$ are each independently the substituted or unsubstituted monocyclic aryl group, the substituted or unsubstituted monocyclic heteroaryl group, a condensed aryl group formed by condensing the 2-5 rings, or a condensed heteroaryl group formed by condensing 2 to 5 rings.

10. The compound of claim 9, wherein heteroatoms of the substituted or unsubstituted monocyclic heteroaryl group and the condensed heteroaryl group are each independently the nitrogen atom, the oxygen atom, or the sulfur atom.

11. The compound of claim 9, wherein the 2-5 rings forming the condensed heteroaryl group are each independently a phenyl group, a pyridyl group, a furyl group, a thienyl group, a pyrrolyl group, a pyranyl group, a pyrimidinyl group, a pyrazinyl group, a pyridazinyl group, a triazinyl group, an oxazolyl group, an isoxazolyl group, a pyrazolyl group, an imidazolyl group, or a thiazolyl group.

12. The compound of claim 9, wherein $Ar_1$ and $Ar_2$ are each independently a substituted or unsubstituted phenyl group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted perylenyl group, a substituted or unsubstituted benzophenanthrenyl group, a substituted or unsubstituted benzopyrenyl group, a substituted or unsubstituted benzanthracenyl group, a substituted or unsubstituted furyl group, a substituted or unsubstituted thienyl group, a substituted or unsubstituted pyrrolyl group, a substituted or unsubstituted pyridyl group, a substituted or unsubstituted pyranyl group, a substituted or unsubstituted pyrimidinyl group, a substituted or unsubstituted pyrazinyl group, a substituted or unsubstituted pyridazinyl group, a substituted or unsubstituted triazinyl group, a substituted or unsubstituted quinolinyl group, a substituted or unsubstituted quinoxalinyl group, a substituted or unsubstituted isoquinolinyl group, a substituted or unsubstituted quinazolinyl group, a substituted or unsubstituted acridinyl group, a substituted or unsubstituted carbazolyl group, a substituted or unsubstituted indolyl group, a substituted or unsubstituted benzofuryl group, a substituted or unsubstituted benzothienyl group, a substituted or unsubstituted benzoxazolyl group, a substituted or unsubstituted dibenzofuryl group, a substituted or unsubstituted dibenzothienyl group, a substituted or unsubstituted 2-N heterodibenzofuryl group, a substituted or unsubstituted 3-N heterodibenzofuryl group, a substituted or unsubstituted 4-N heterodibenzofuryl group, a substituted or unsubstituted 5-N heterodibenzofuryl group, a substituted or unsubstituted 2-N heterodibenzothienyl group, a substituted or unsubstituted 1,10-phenanthroline group, a substituted or unsubstituted 2-phenanthroline group, or a substituted or unsubstituted indolocarbazolyl group.

13. The compound of claim 12, wherein $Ar_1$ and $Ar_2$ are each independently of a structure of any one of:

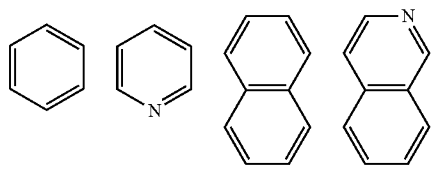

-continued

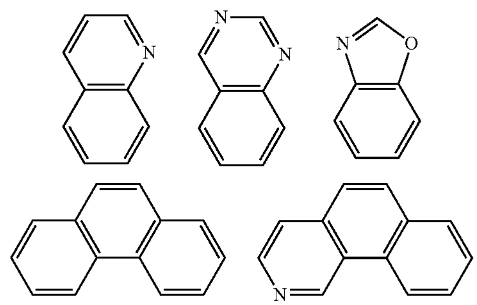

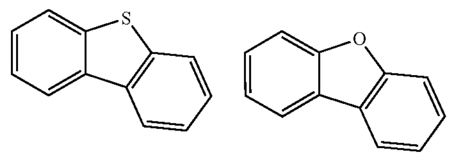

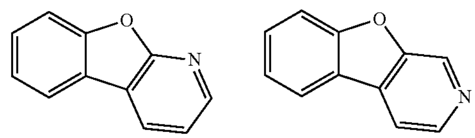

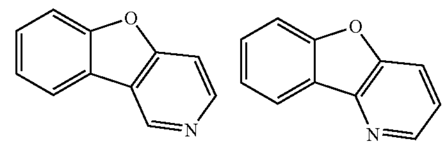

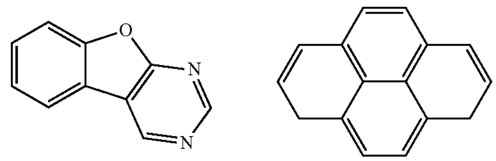

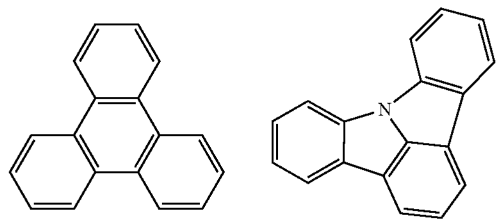

wherein L2 or L3 can occur at any open position in any of above structures.

14. The compound according to claim 1, wherein the compound is of a structure of any one of:

-continued
P1
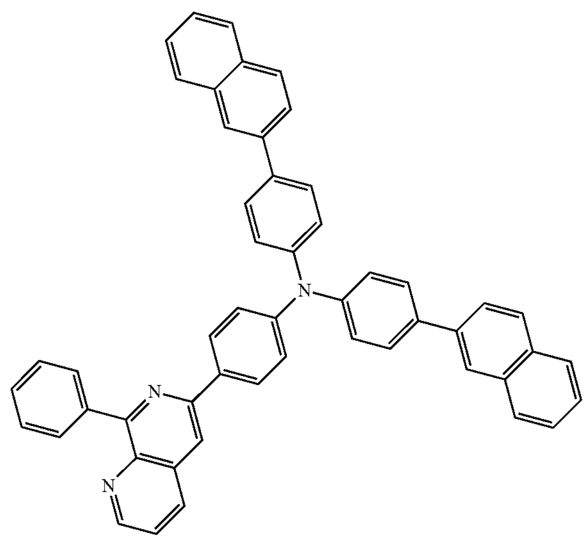
P2
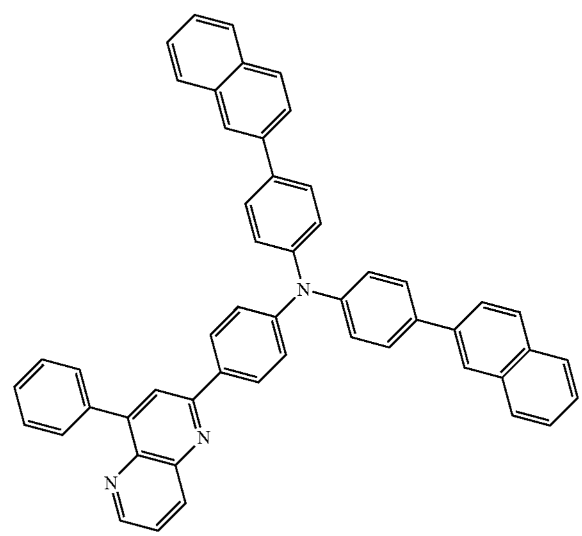
P3
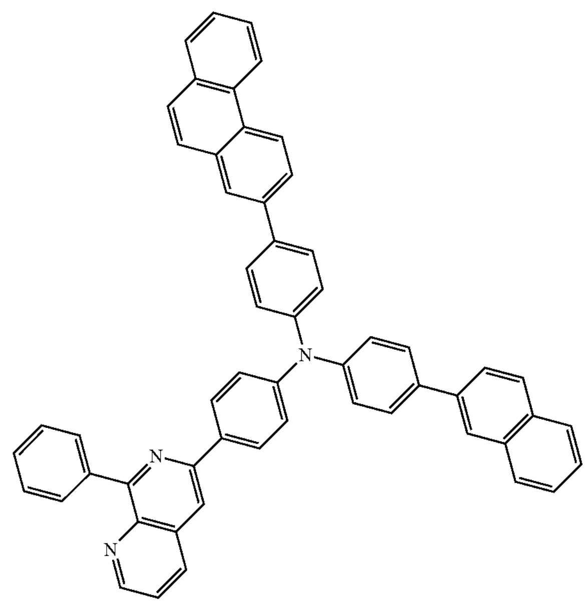
P4
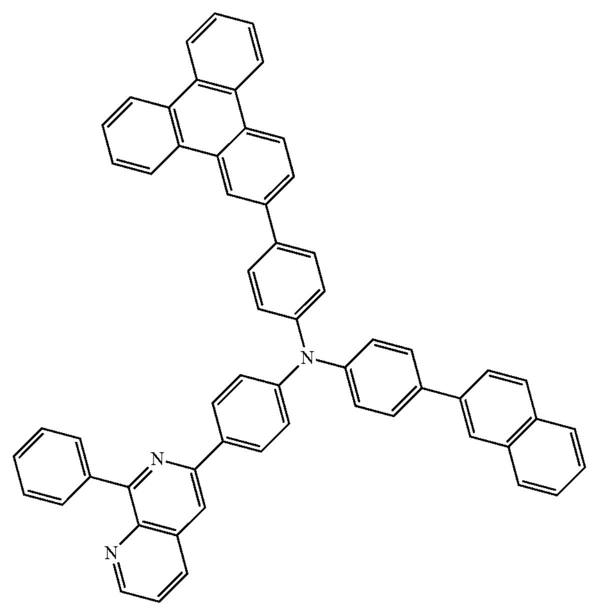

P5
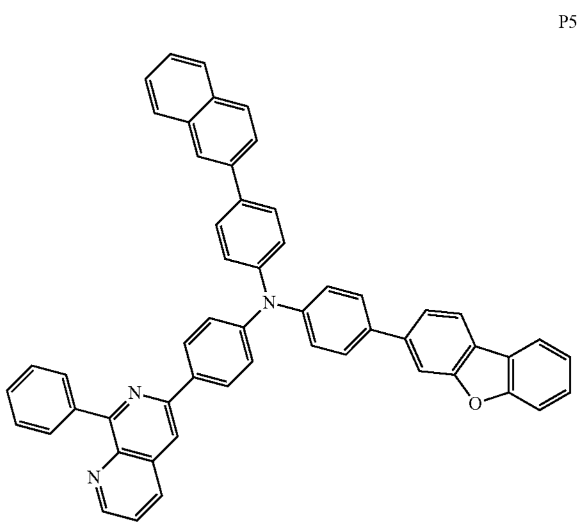
P6
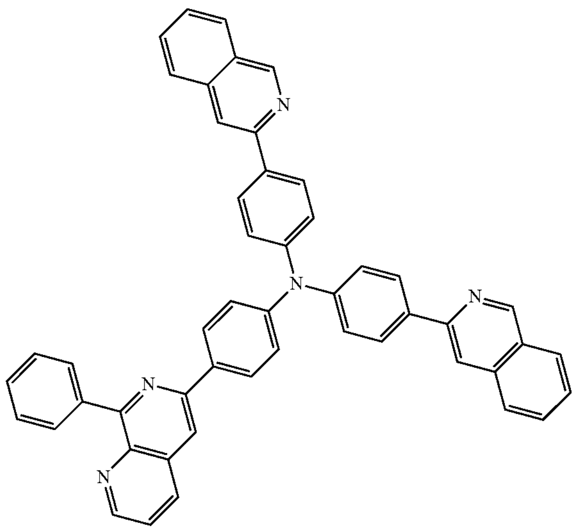
P7
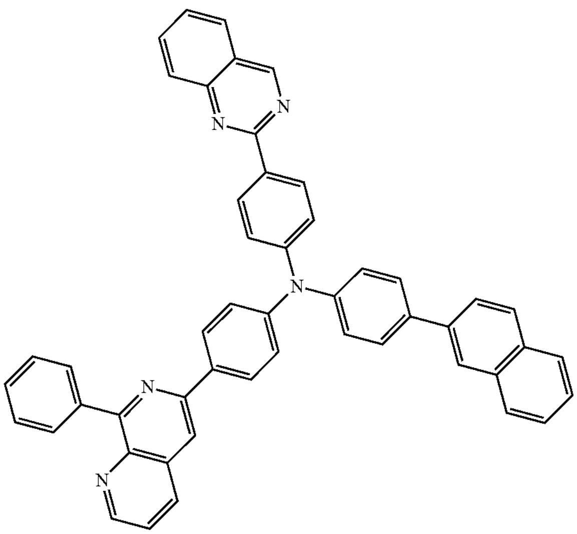
P8
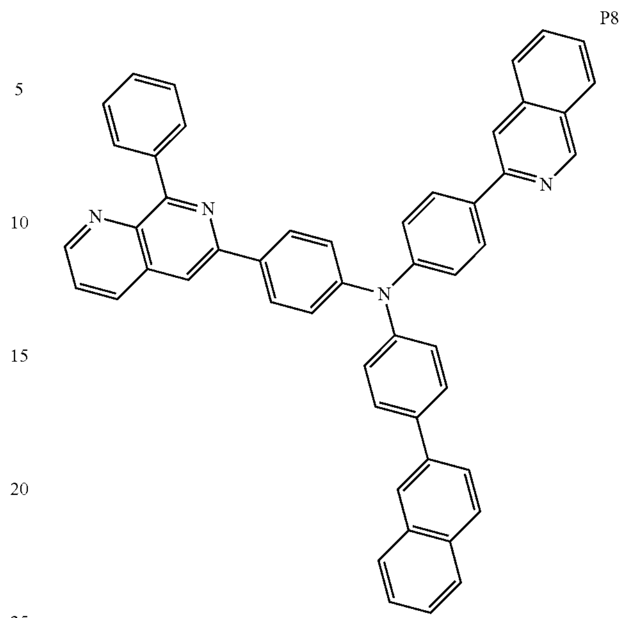
P9
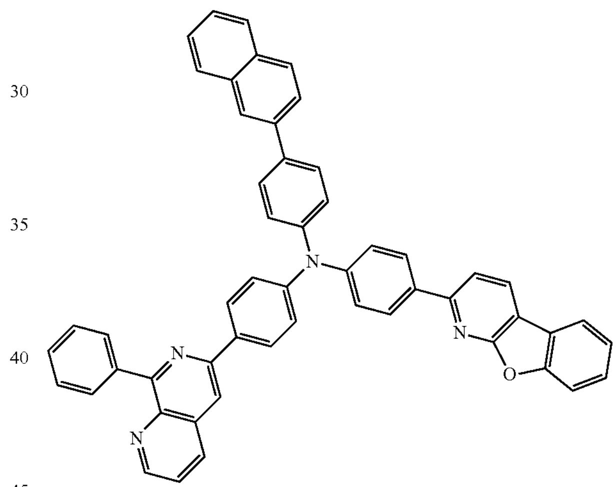
P10
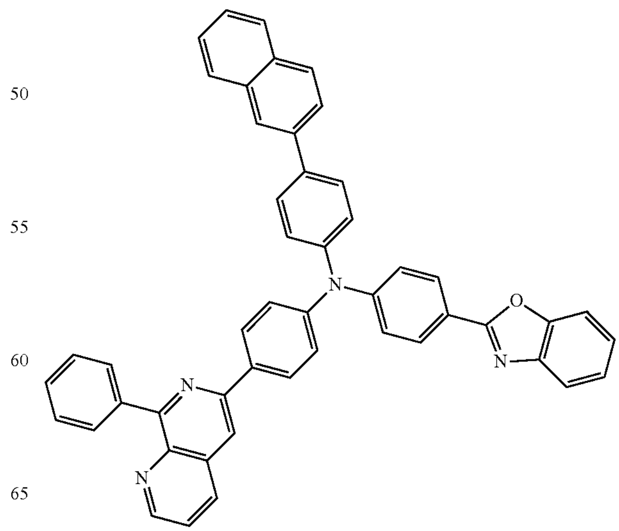

-continued
P11
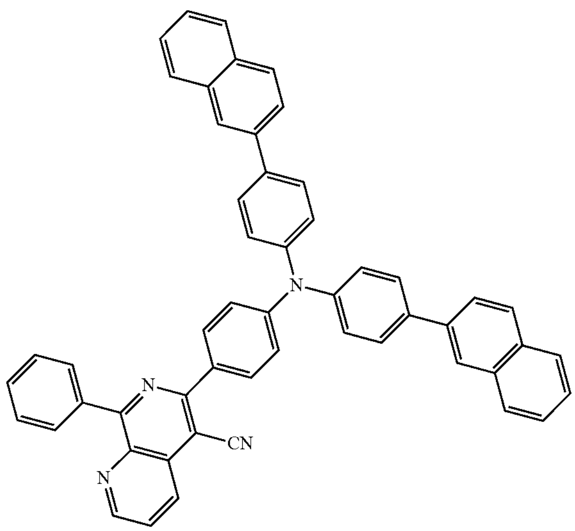
P12
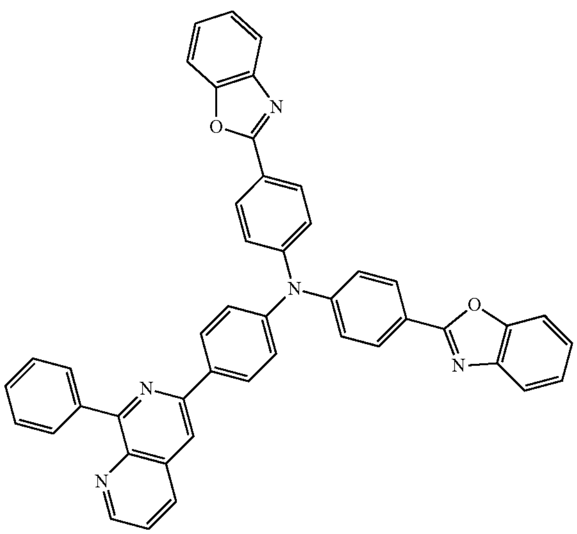
P13
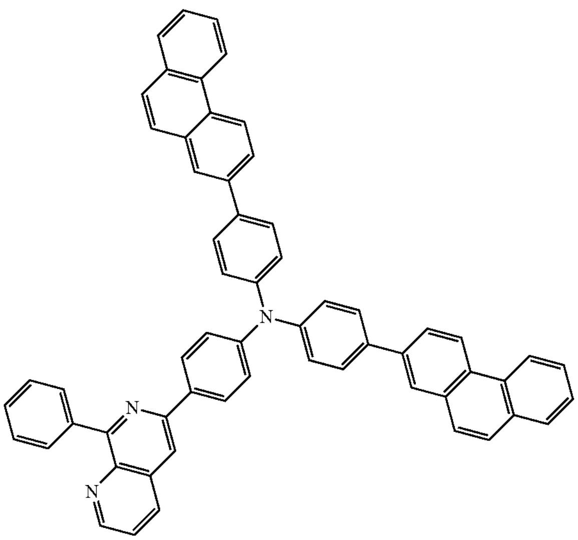
-continued
P14
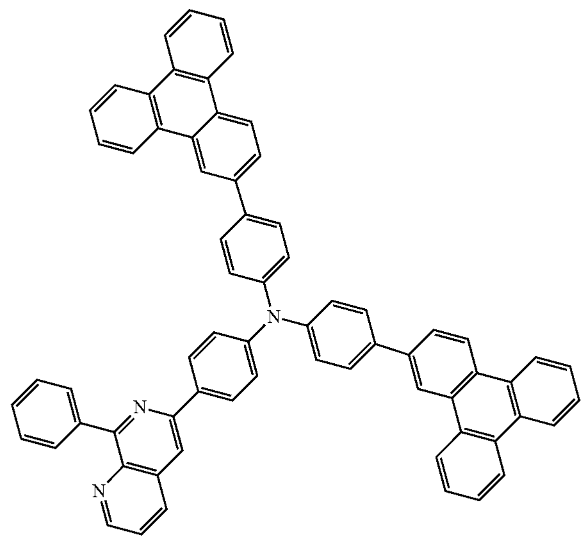
P15
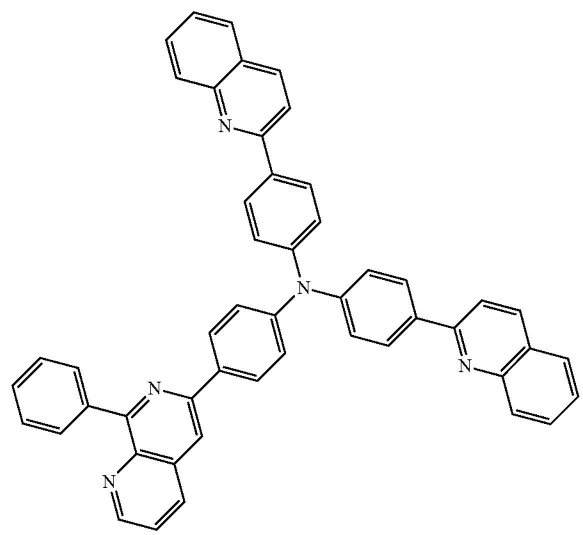
P16
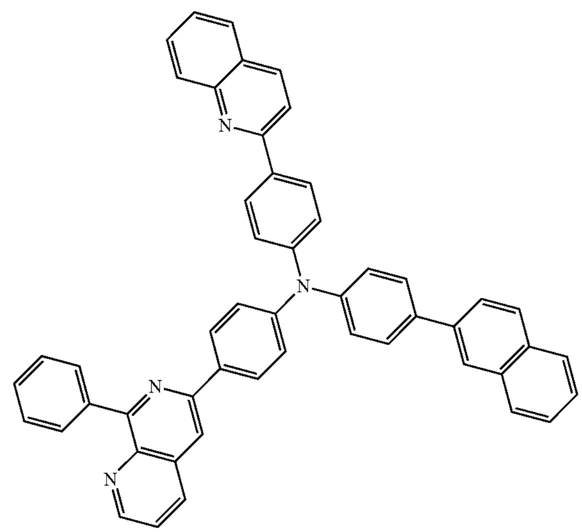

-continued
P17
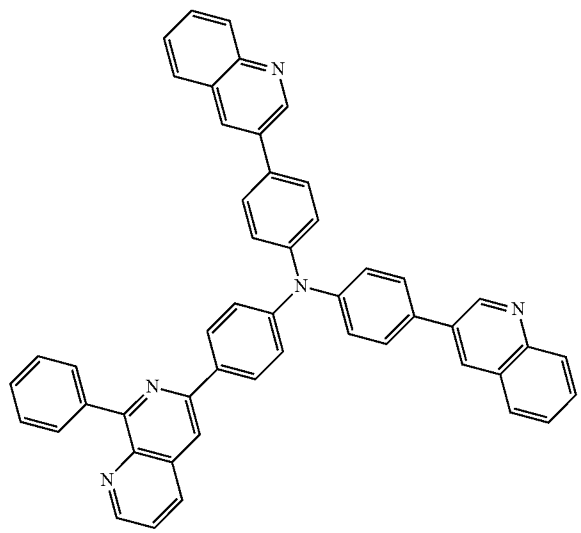
P18
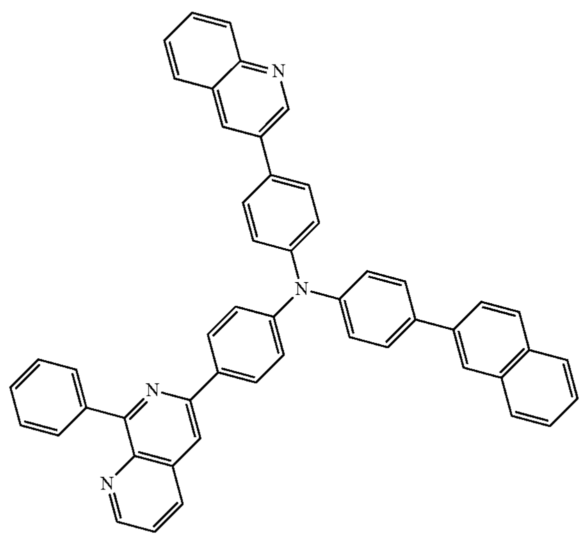
P19
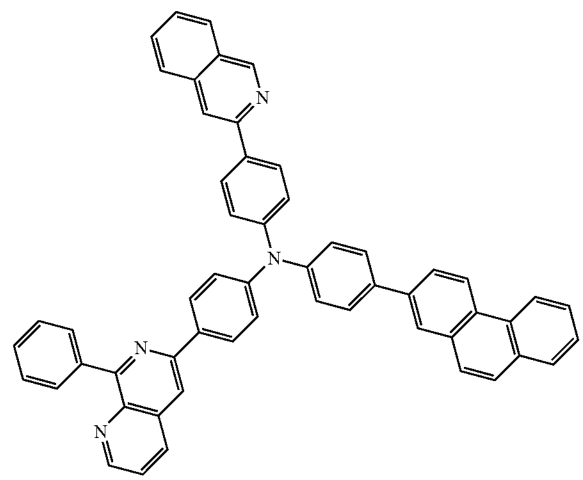
-continued
P20
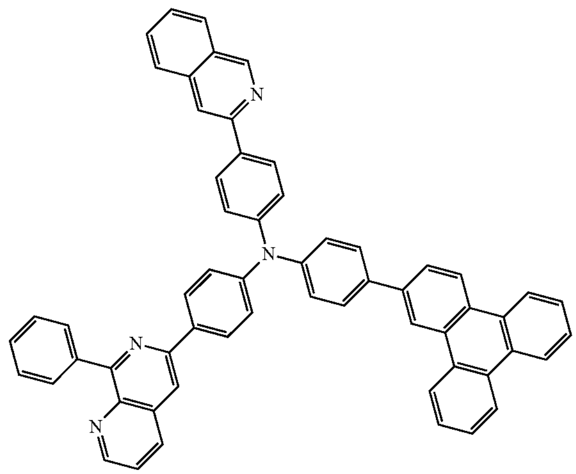
P21
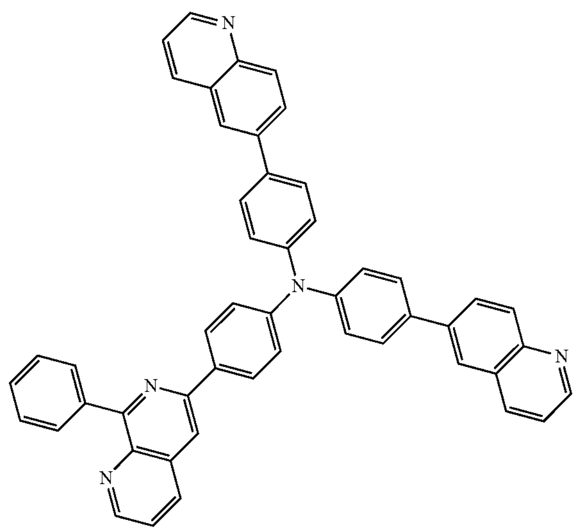
P22
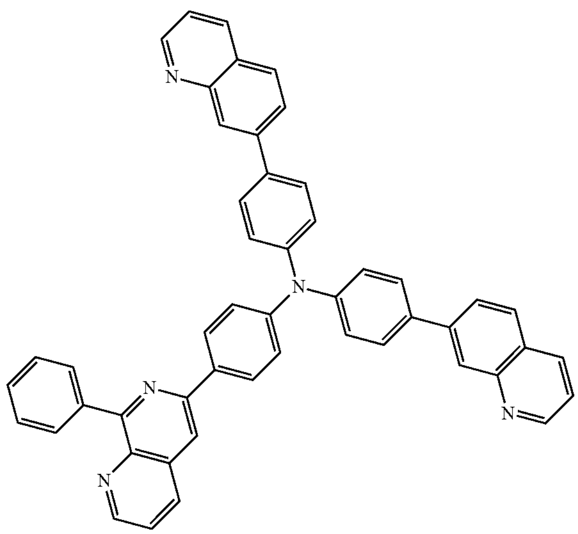

-continued
P23
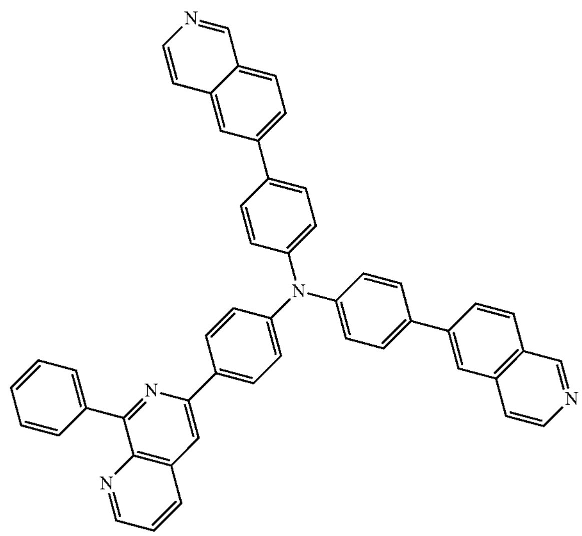
P24
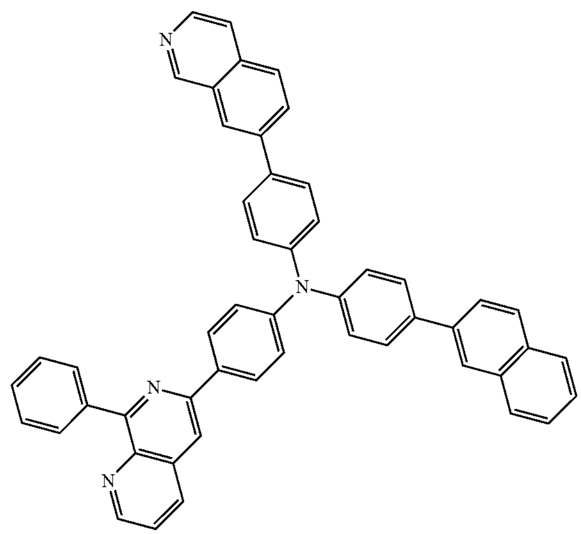
P25
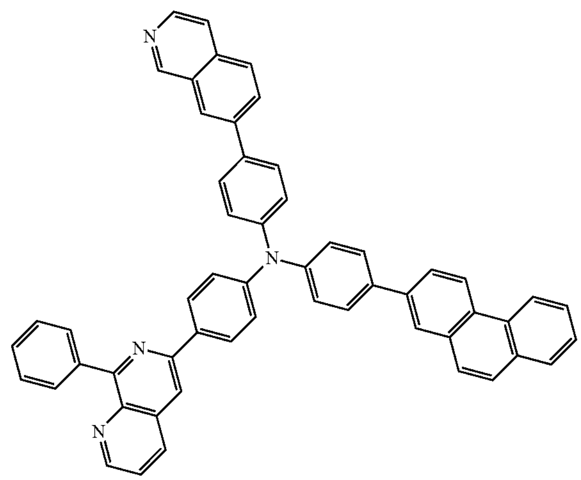
-continued
P26
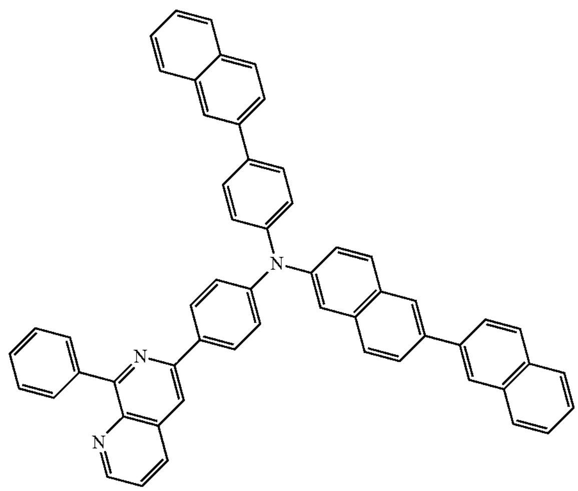
P27
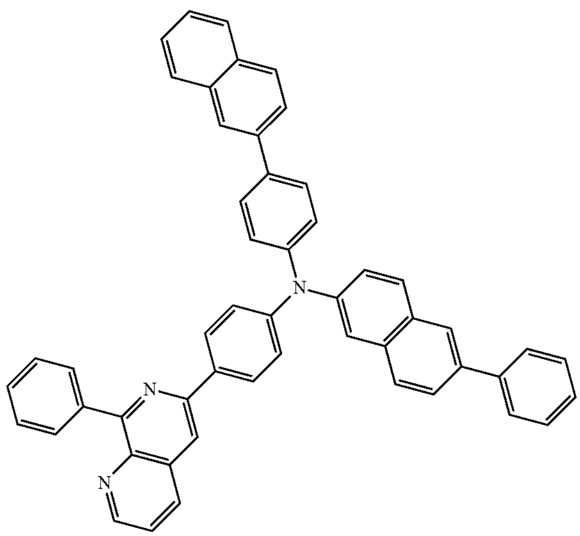
P28
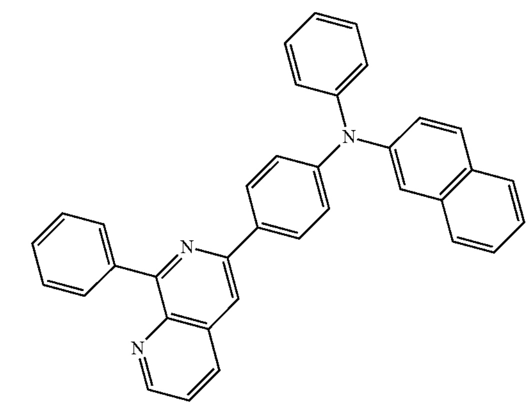

-continued
P29
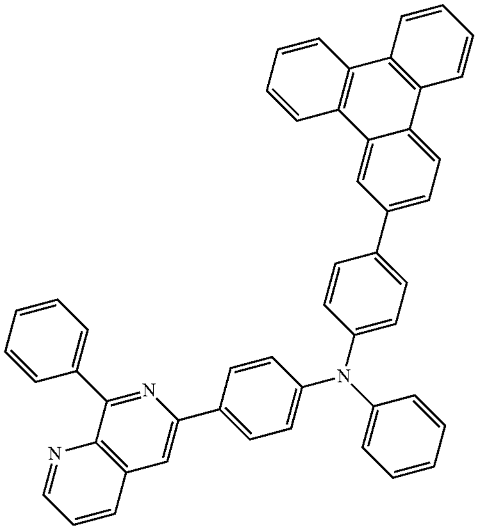
P30
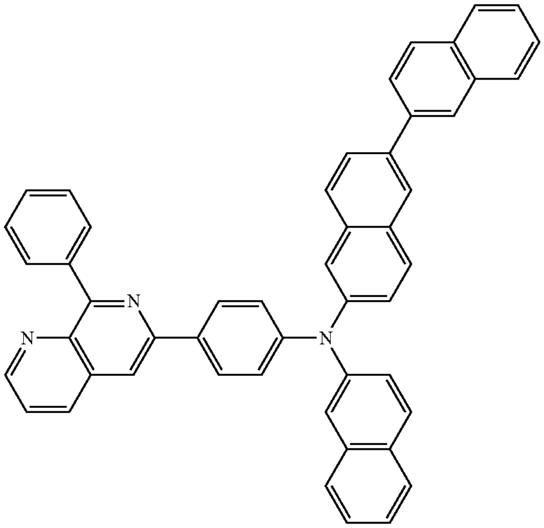
P31
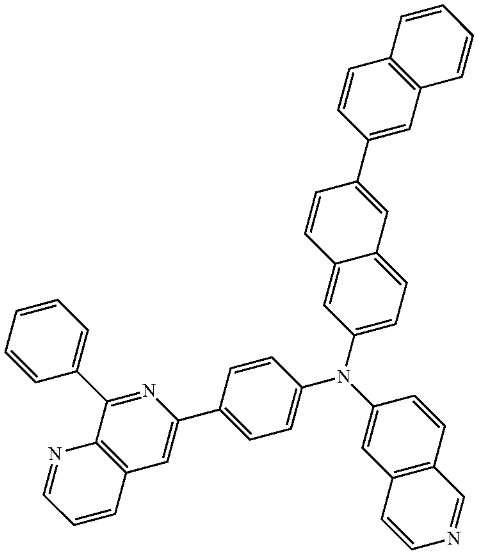
-continued
P32
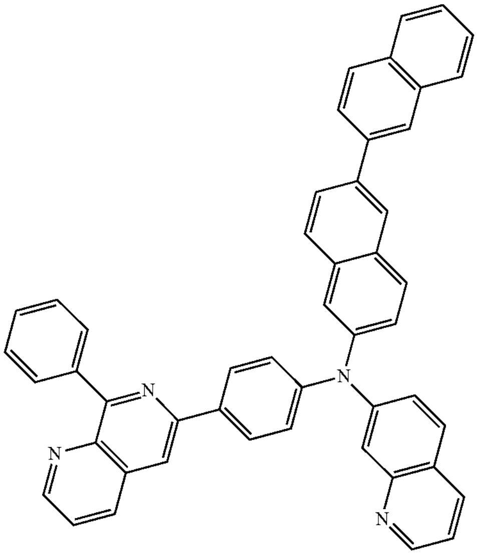
P33
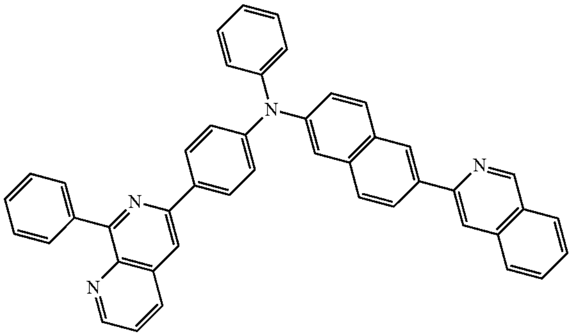
P34
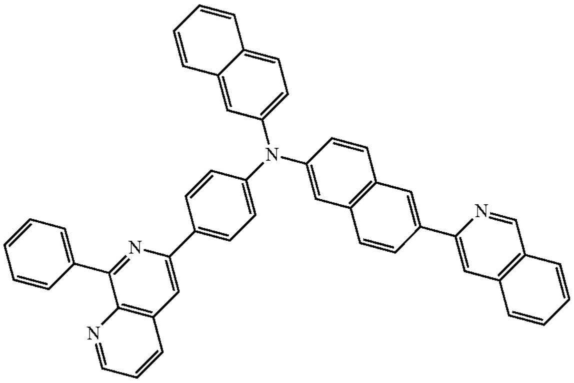

-continued
P35
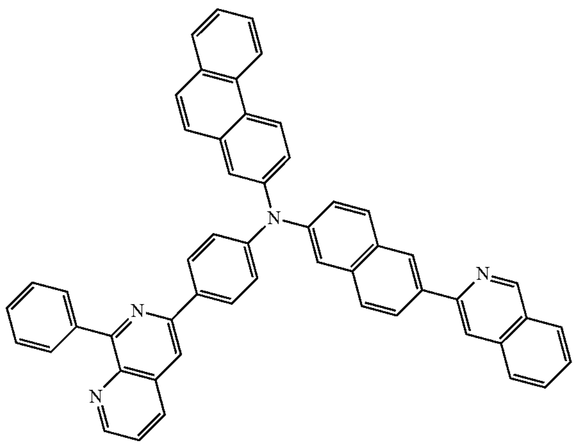
P36
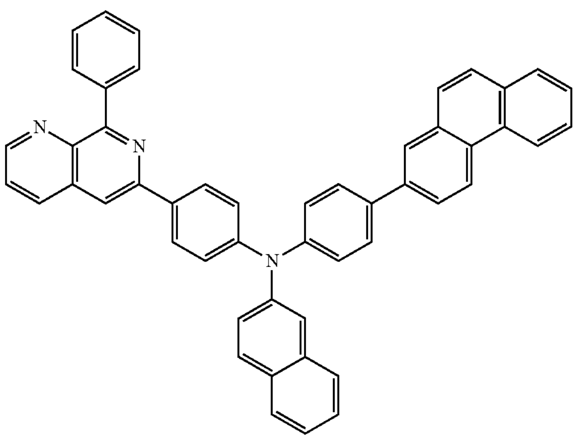
P37
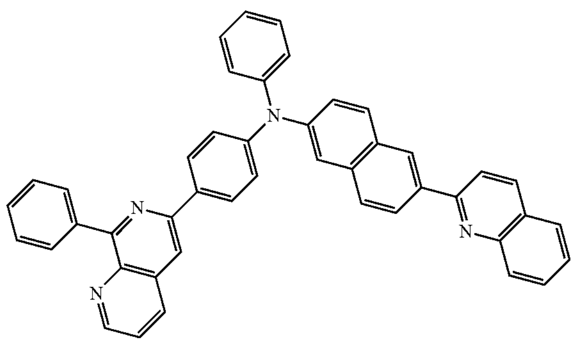
-continued
P38
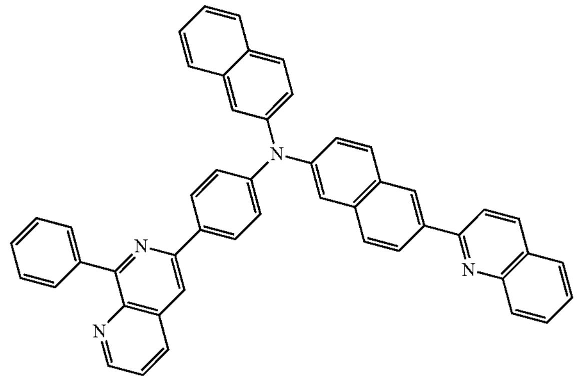
P39
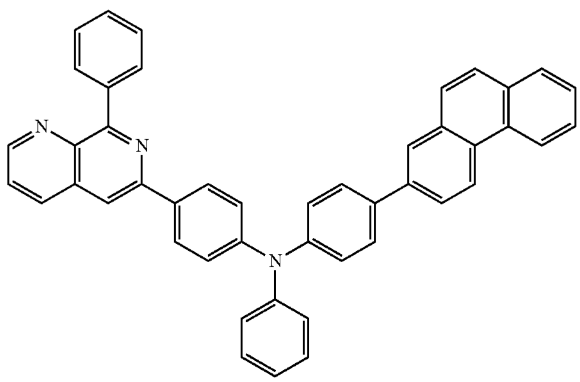
P40
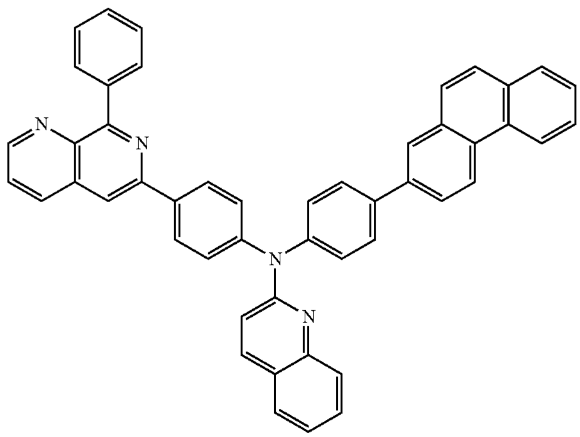

-continued
P41
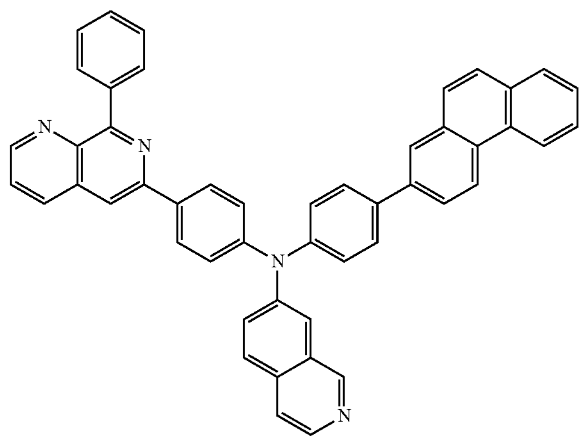
P42
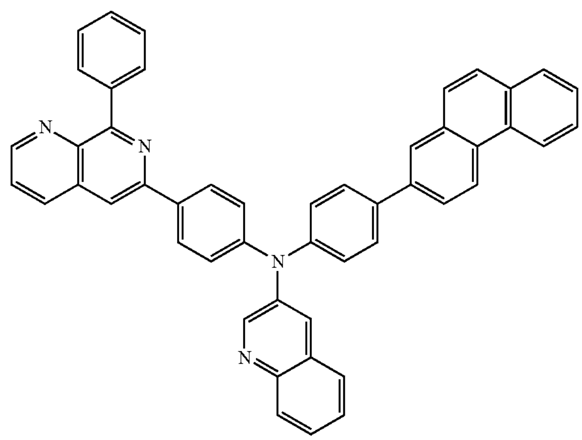
P43
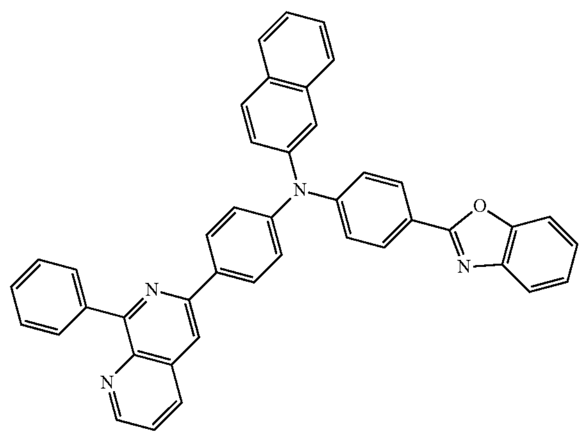
-continued
P44
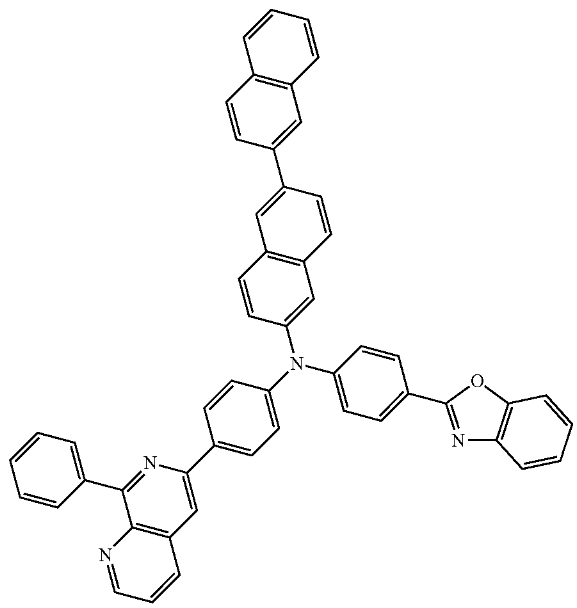
P45
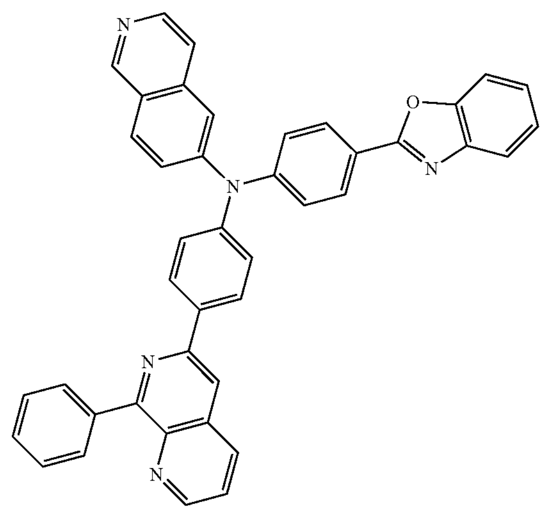

-continued
P46
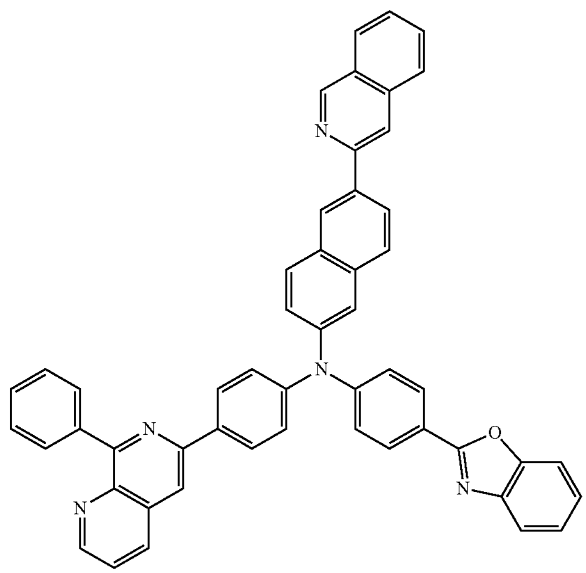
P47
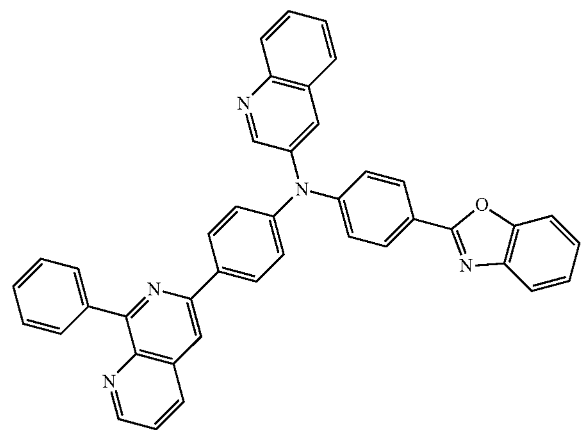
P48
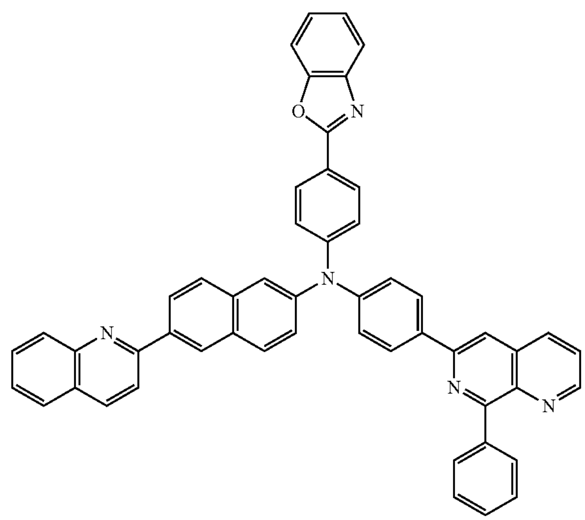
-continued
P49
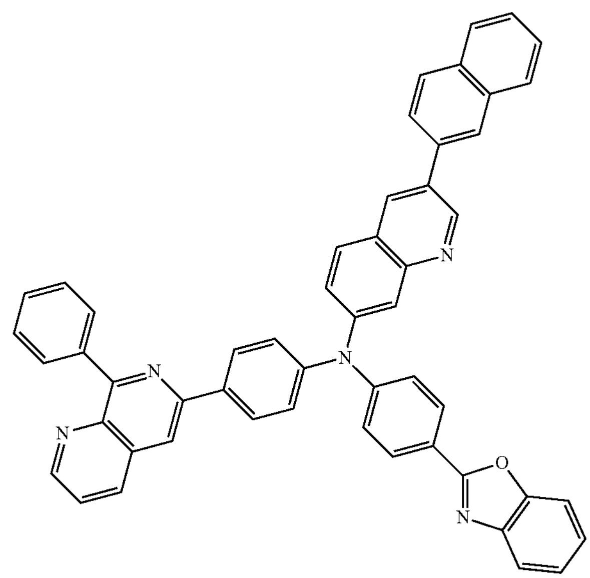
P50
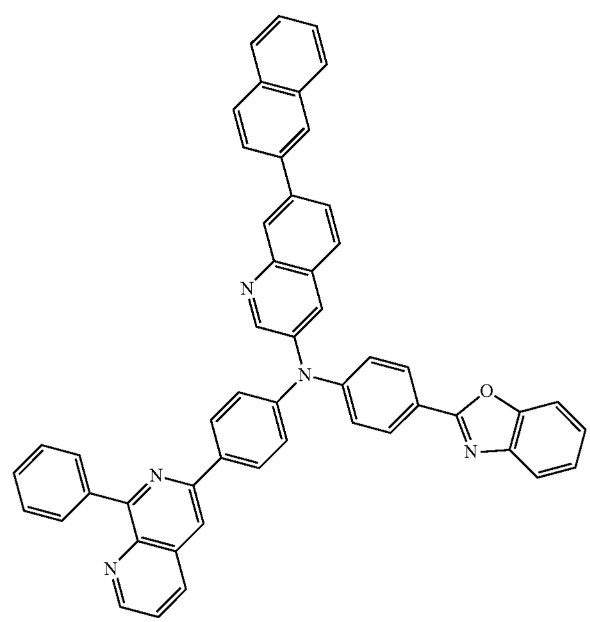

-continued
P51
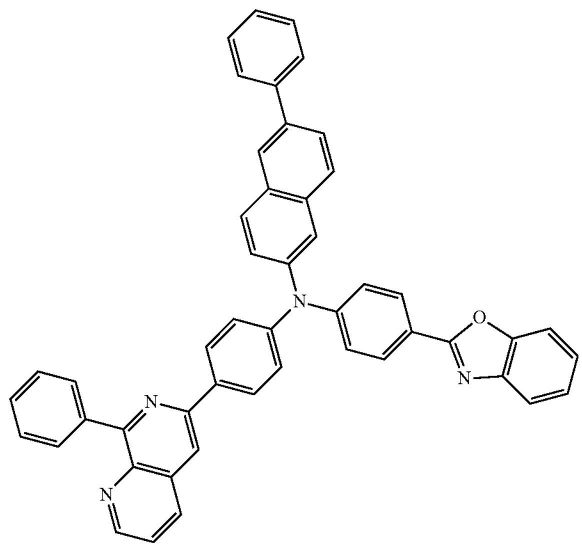
P52
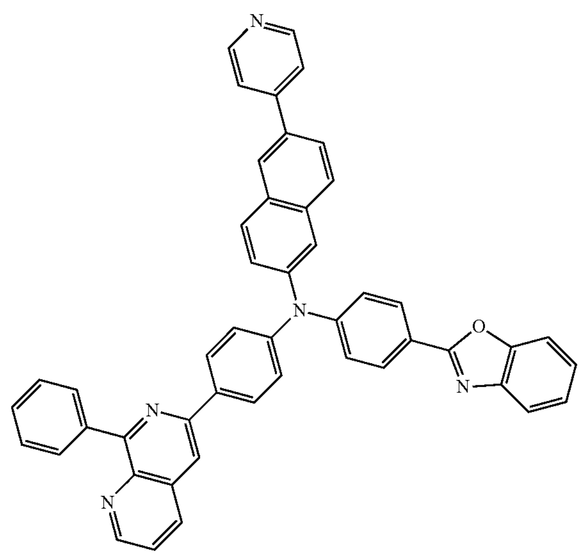
-continued
P53
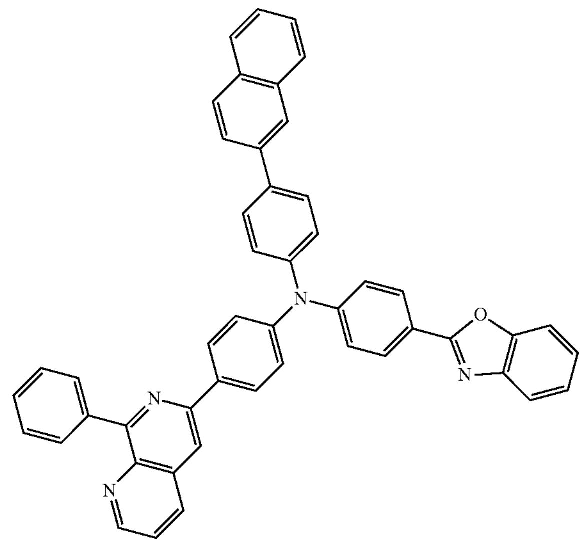
P54
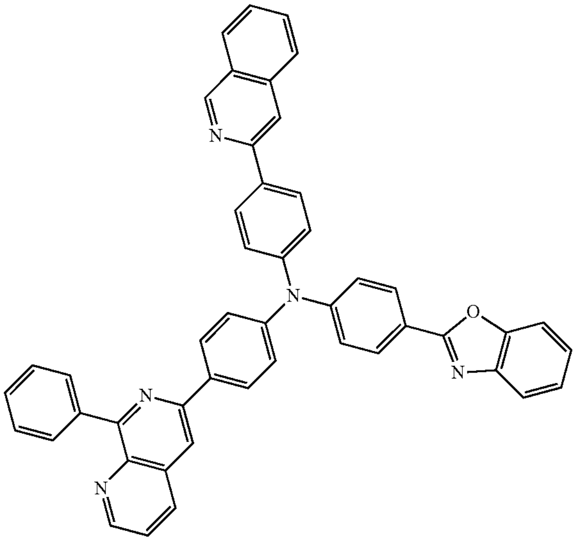
P55
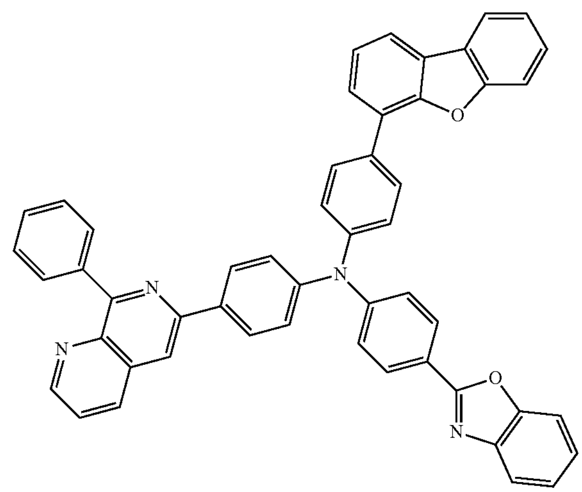

-continued
P56
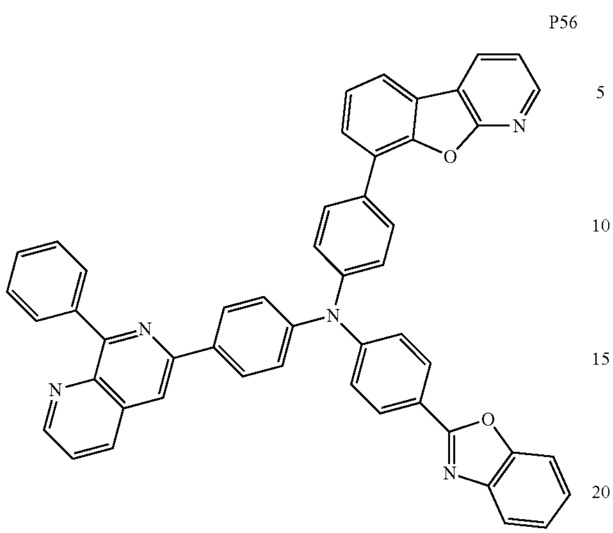
P57
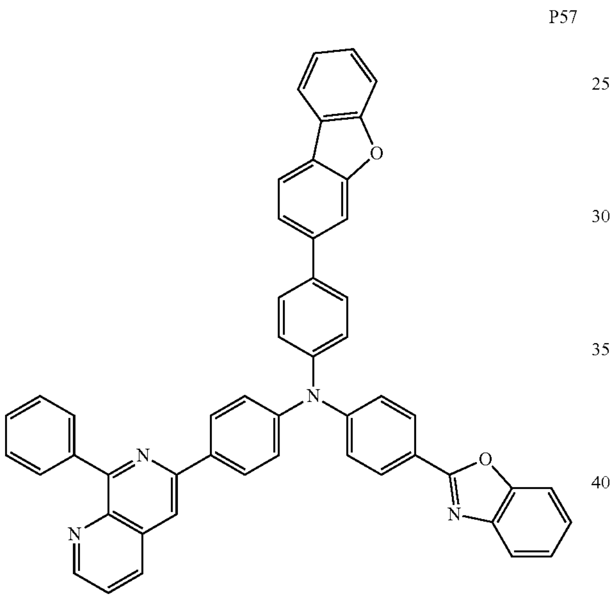
P58
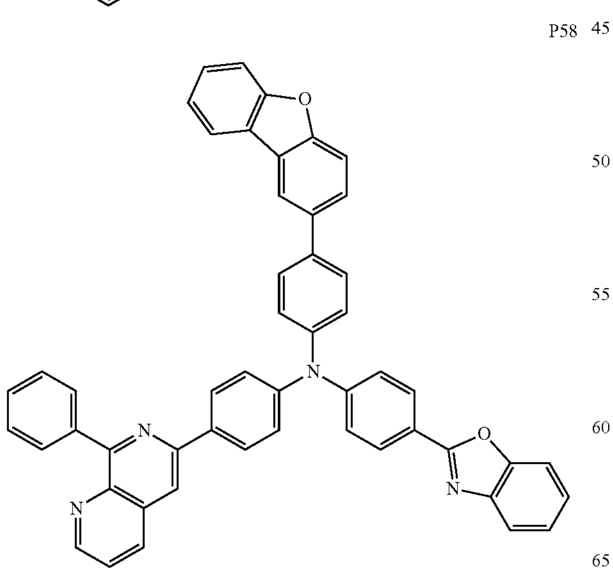
-continued
P59
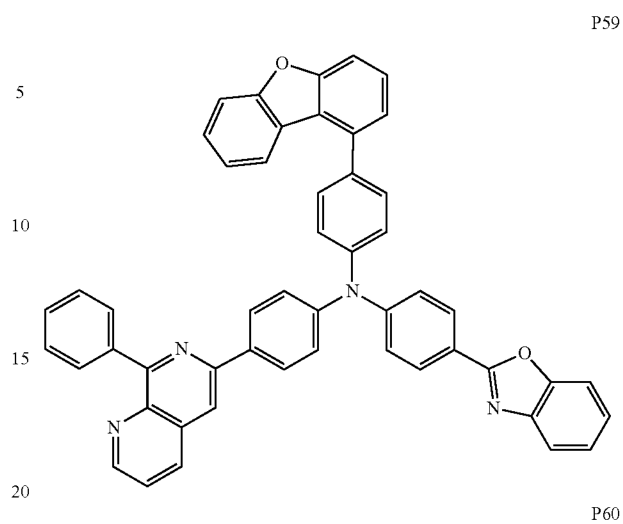
P60
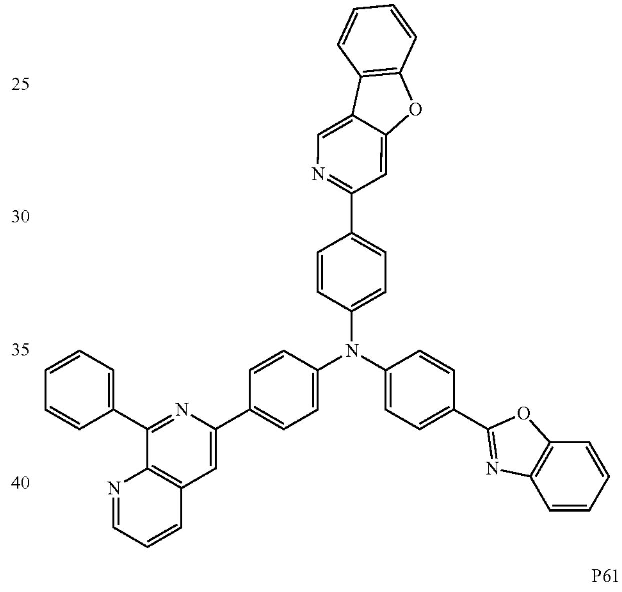
P61
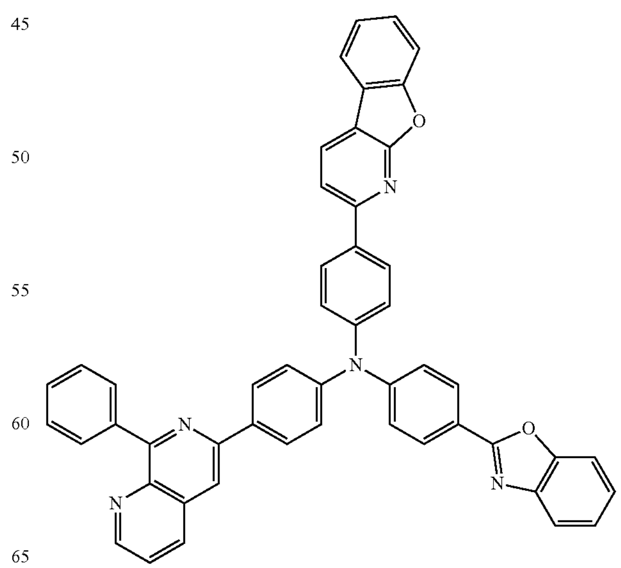

-continued
P62
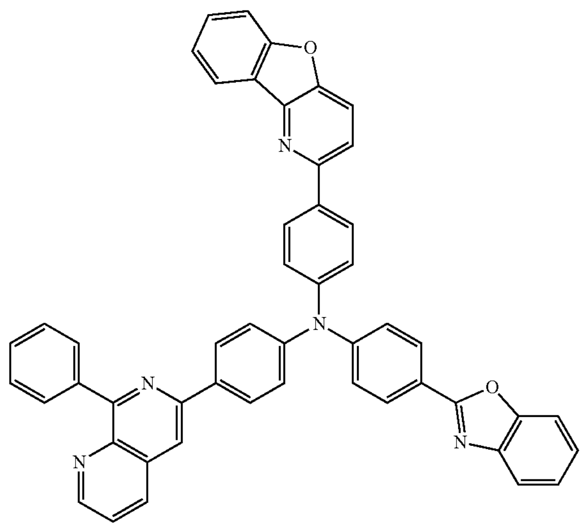
P63
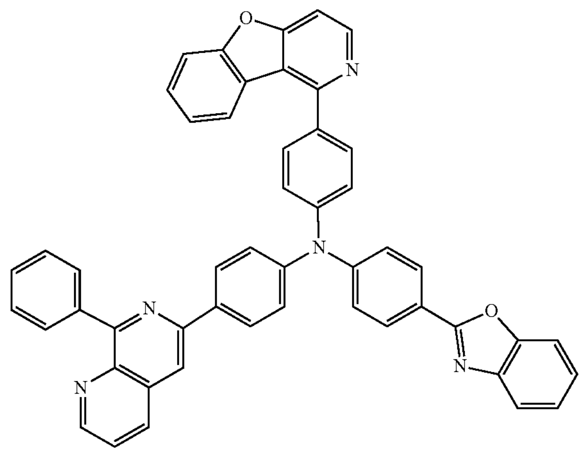
P64
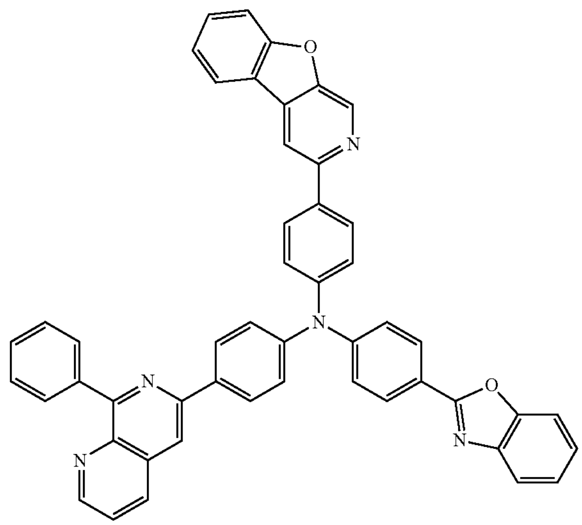
P65
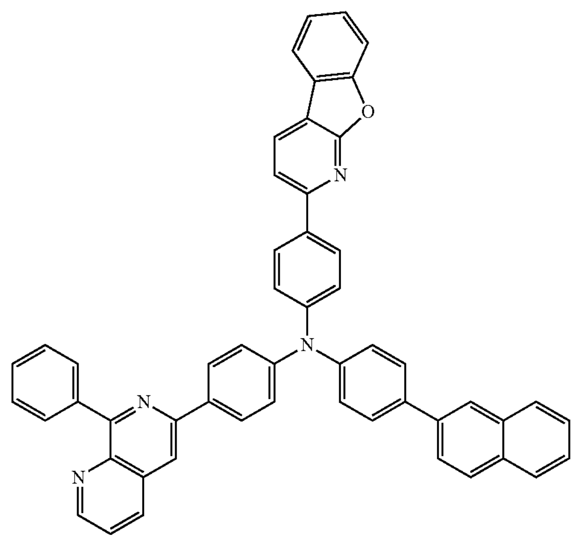
P66
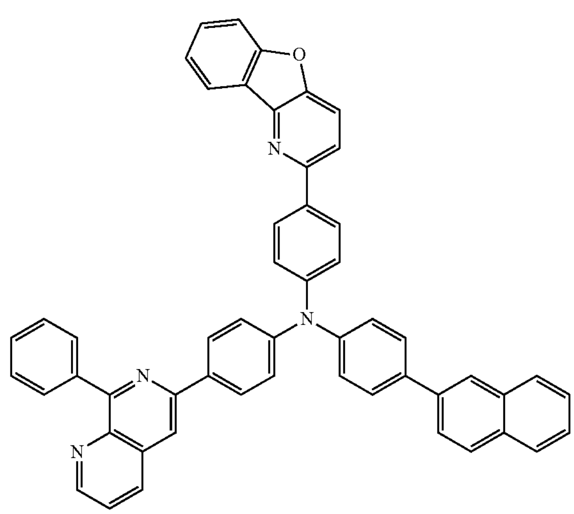
P67
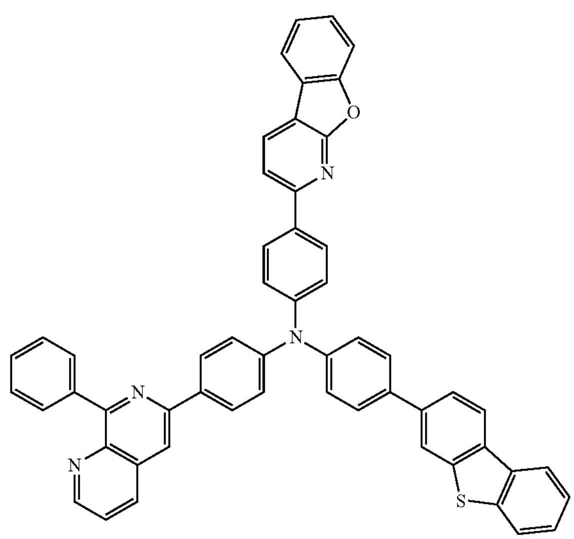

-continued
P68
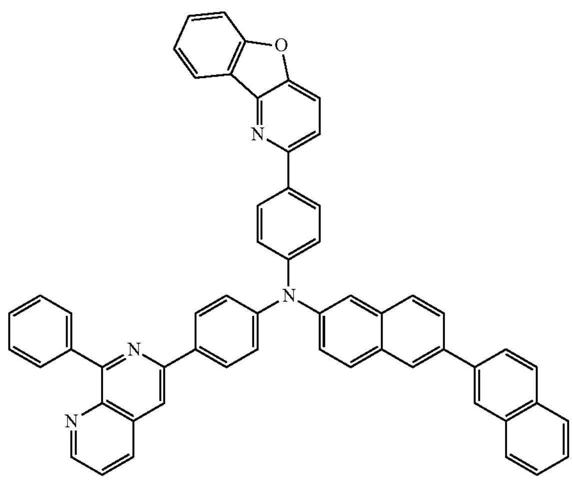
P69
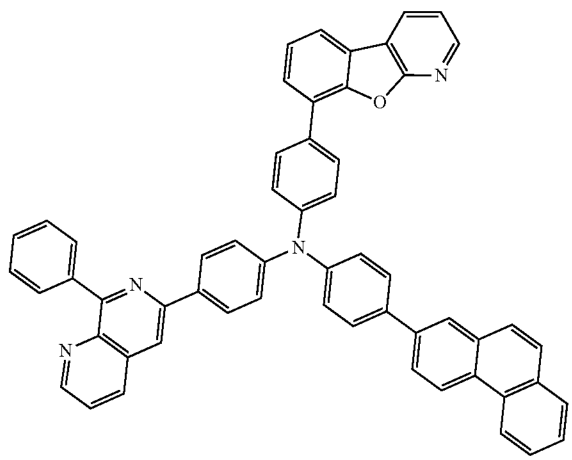
P70
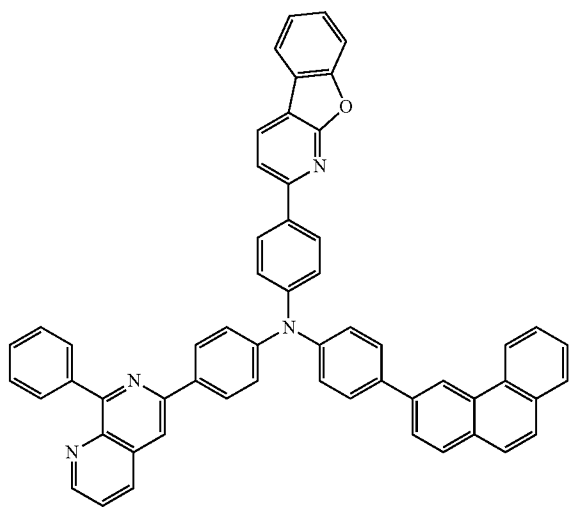
-continued
P71
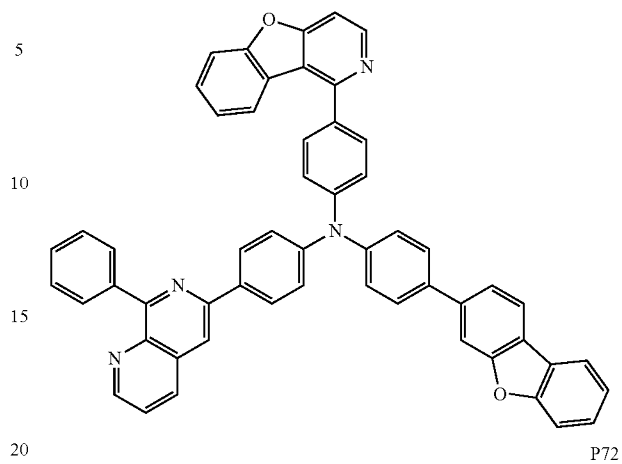
P72
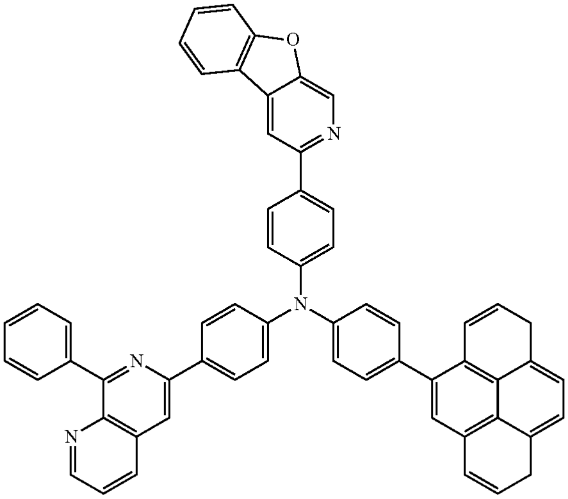
P73
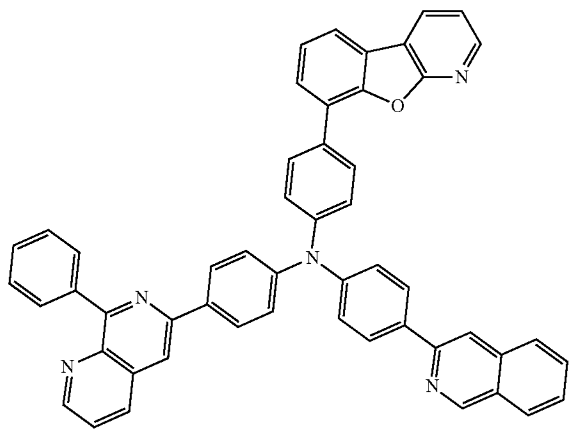

P74
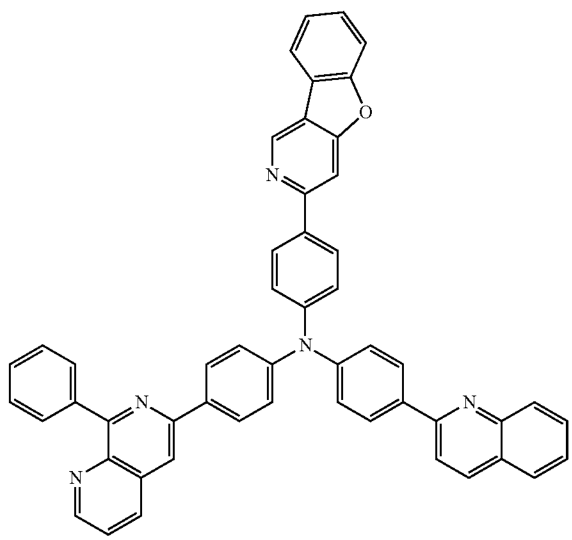
P75
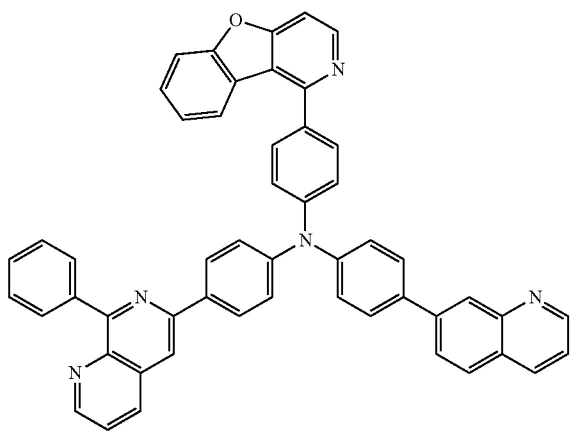
P76
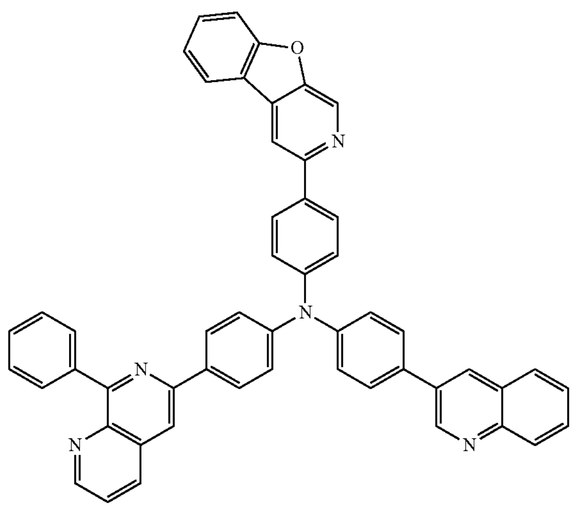
P77
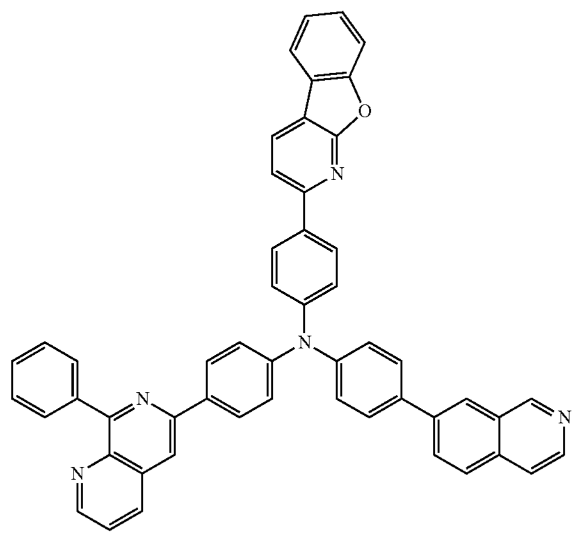
P78
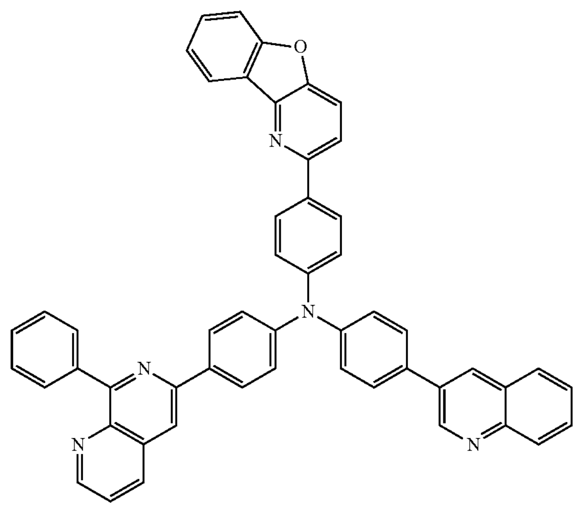
P79
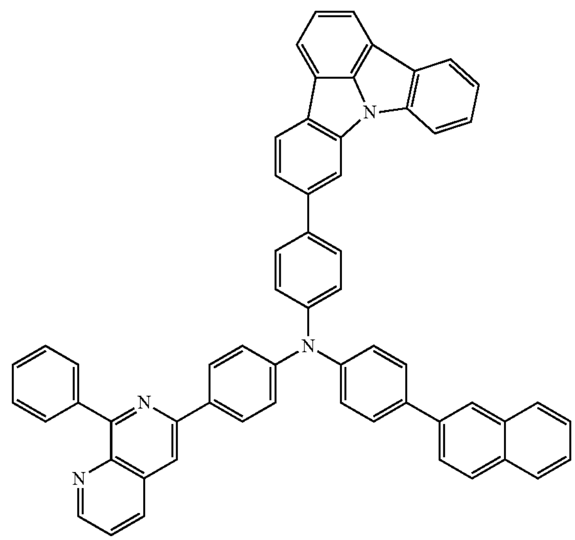

P80
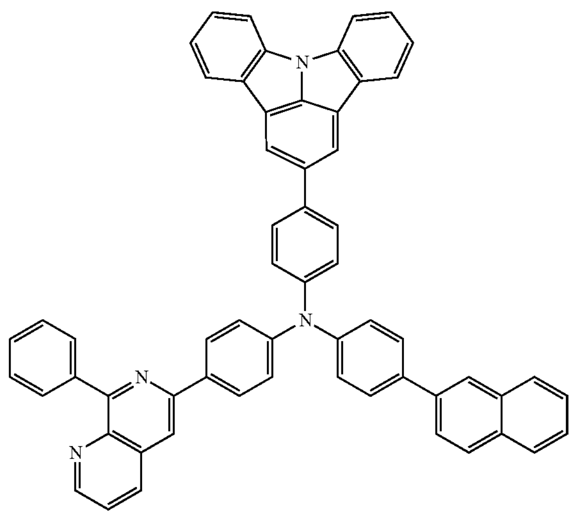
P81
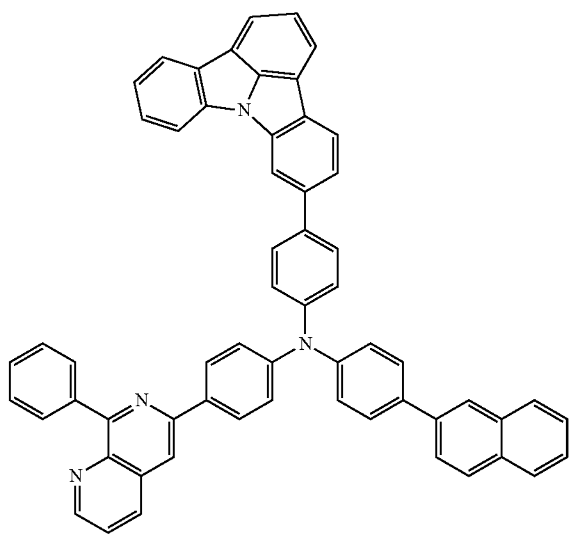
P82
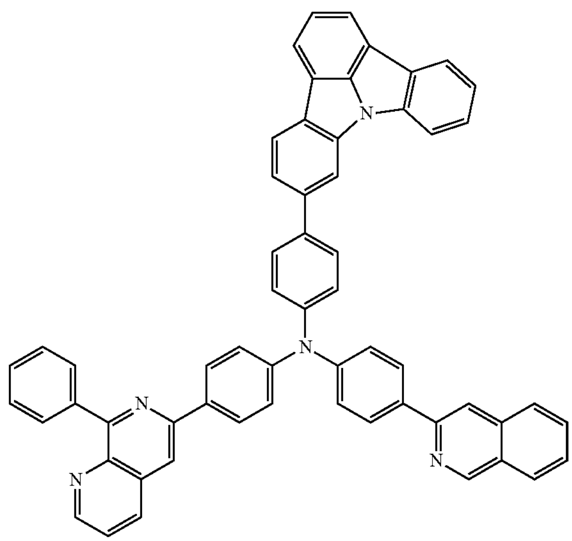
P83
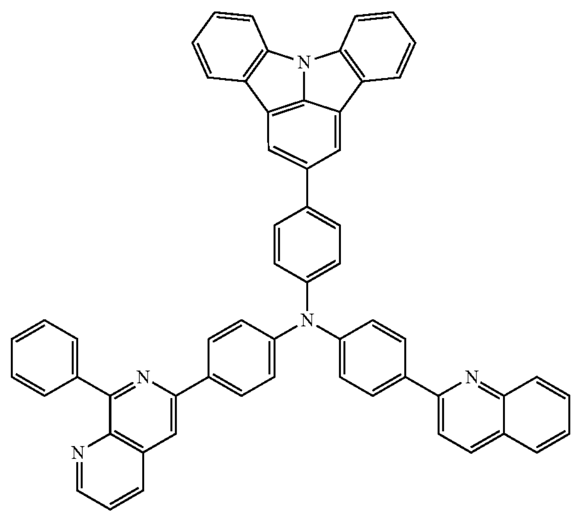
P84
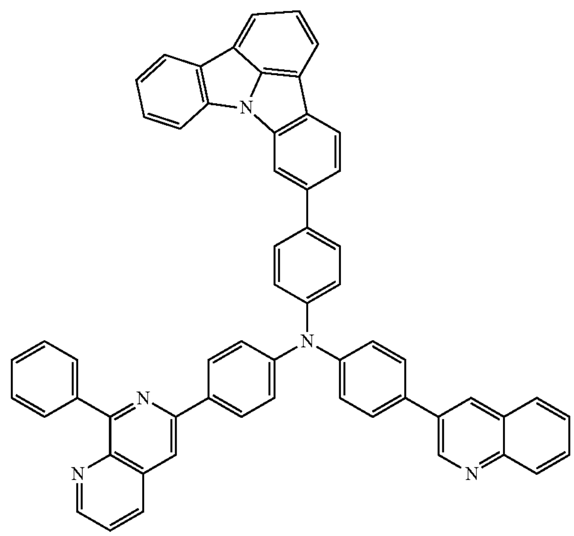
P85
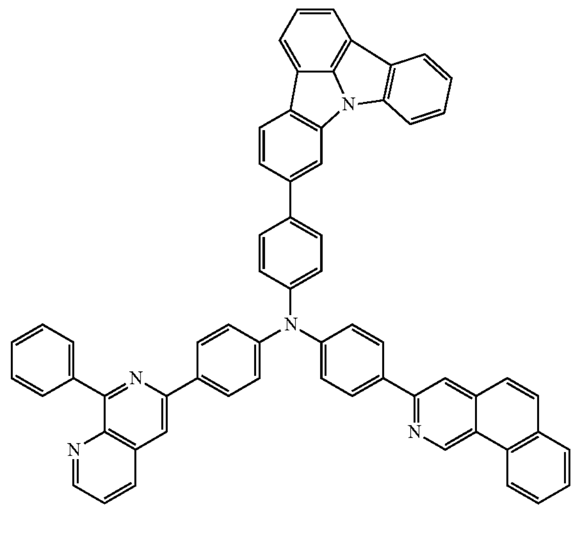

-continued
P86
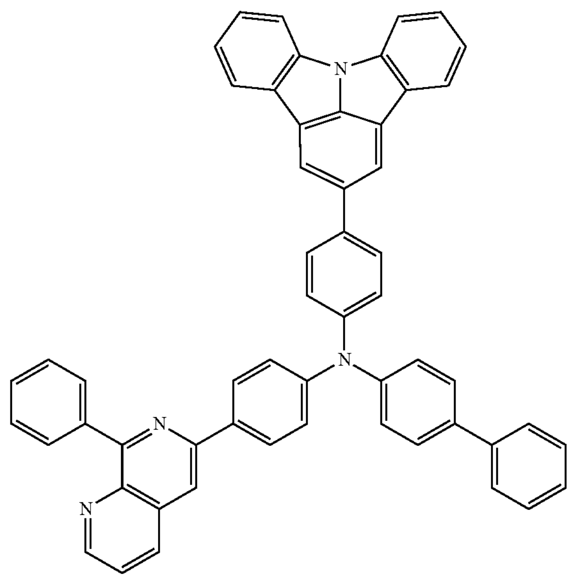
P87
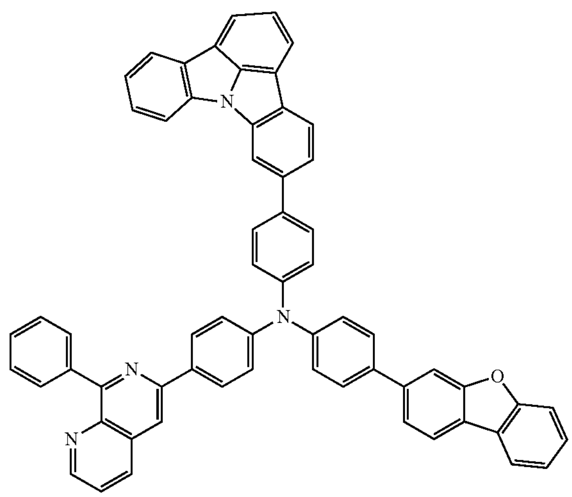
P88
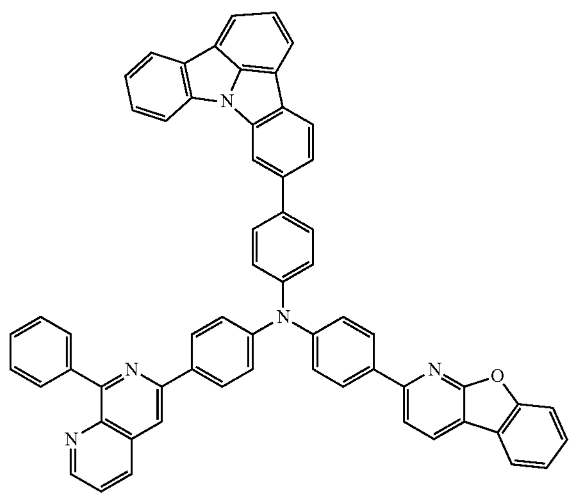
-continued
P89
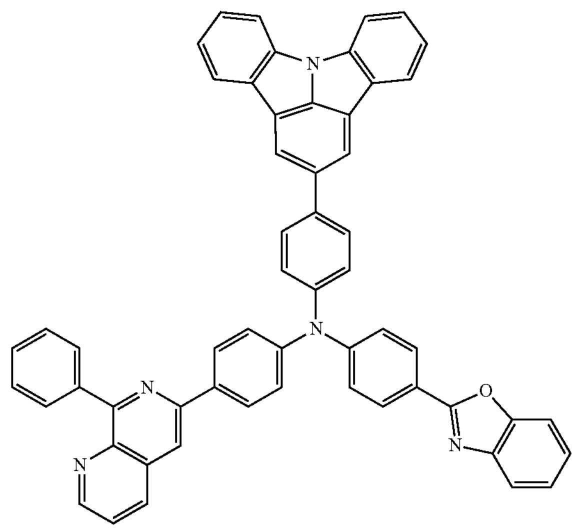
P90
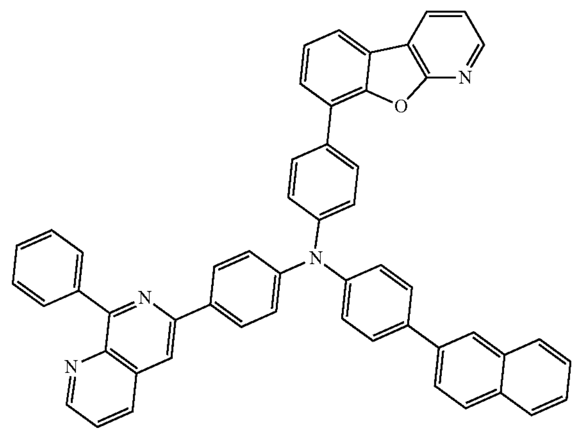
P91
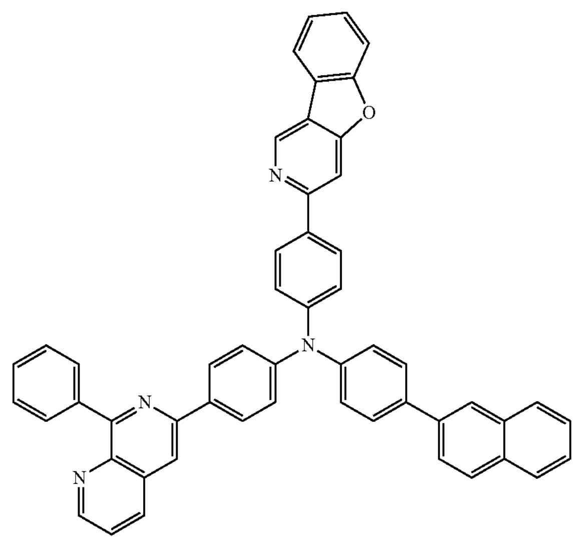

-continued
P92
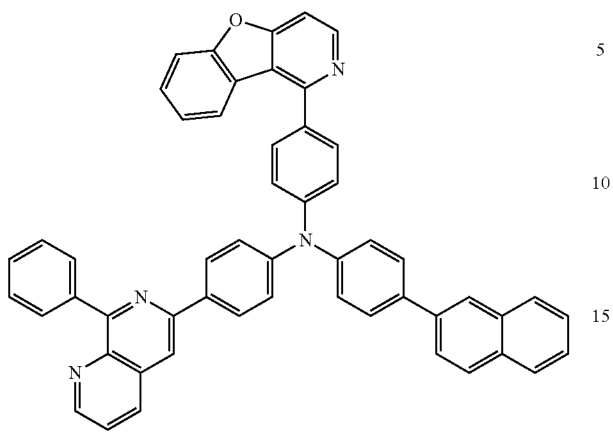
P93
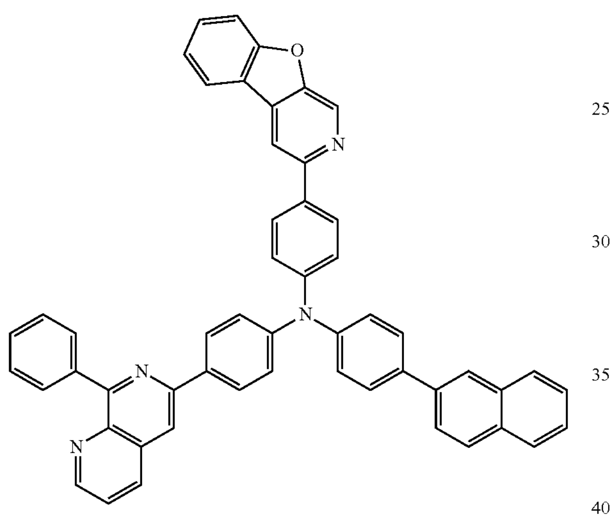
P94
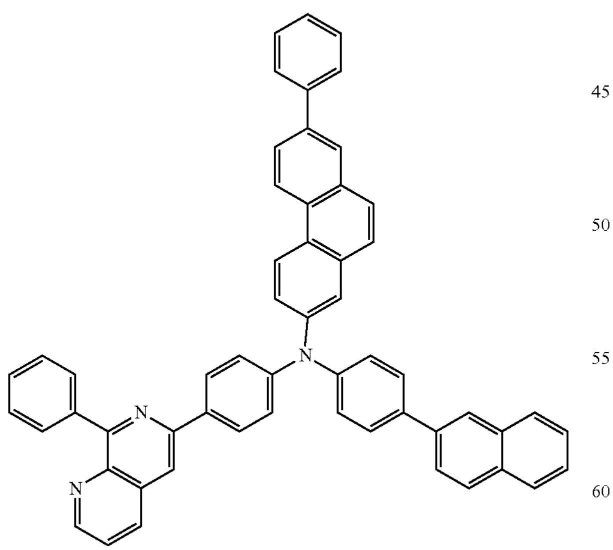
-continued
P95
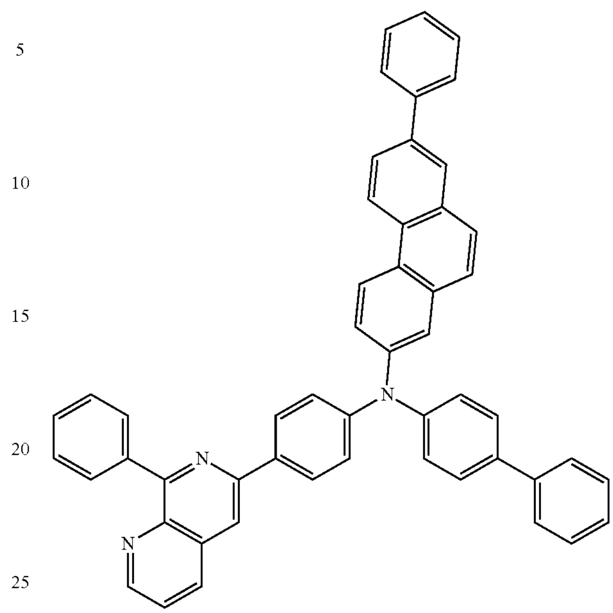
P96
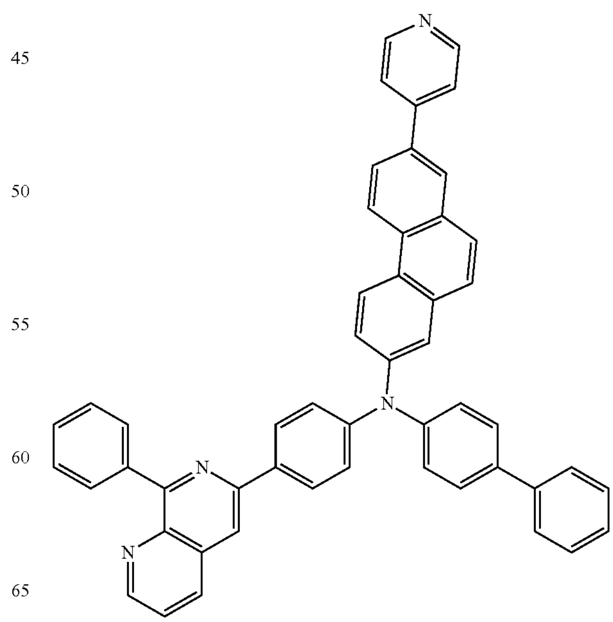

-continued
P97
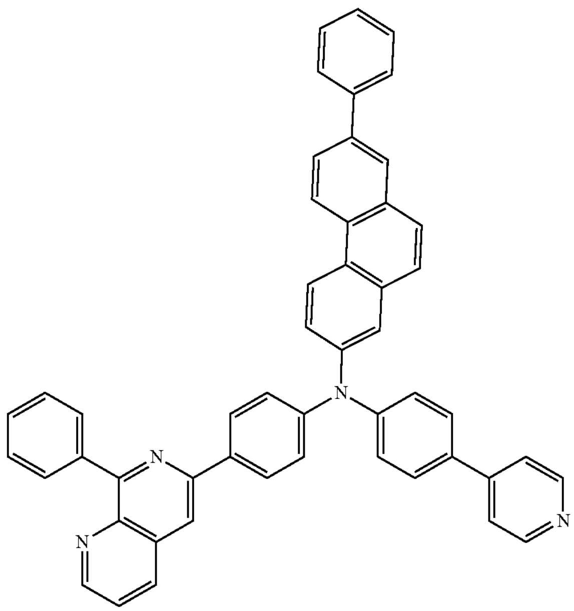
P98
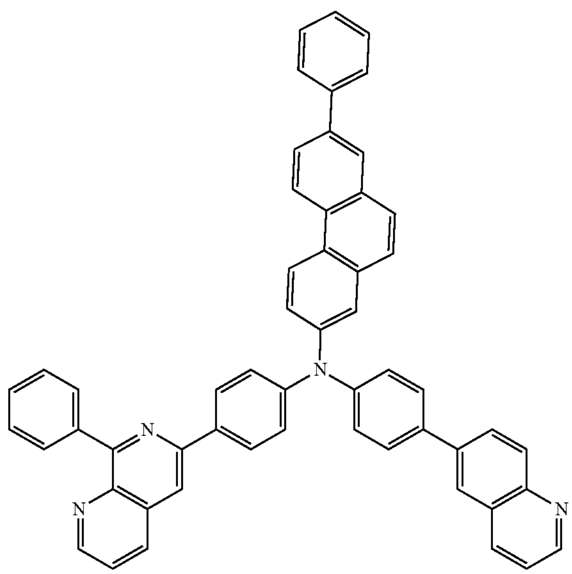
-continued
P99
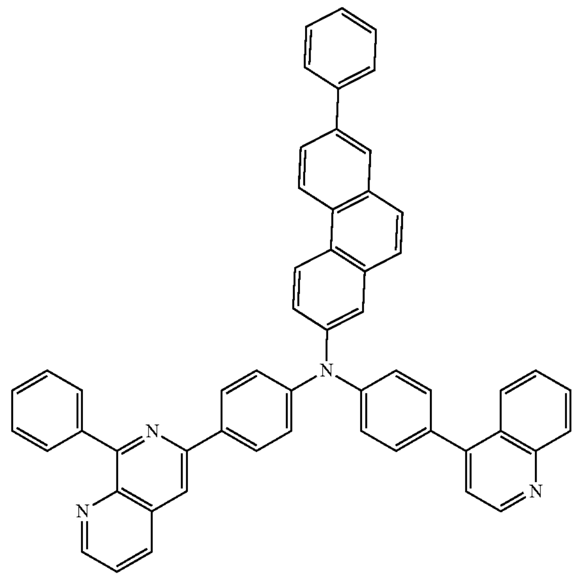
P100
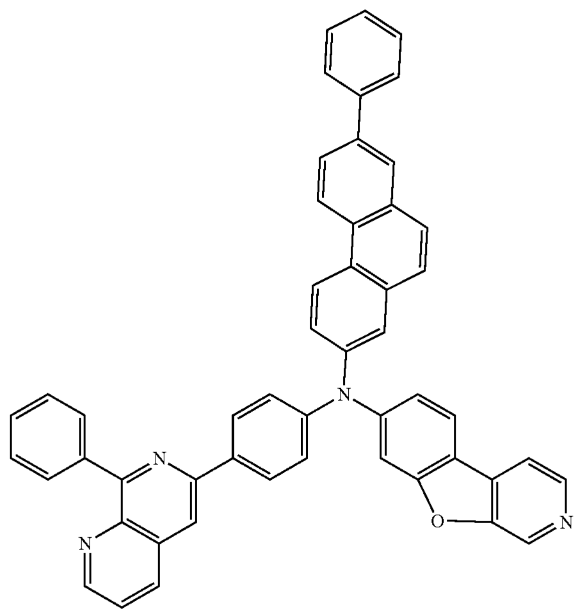

-continued
P101
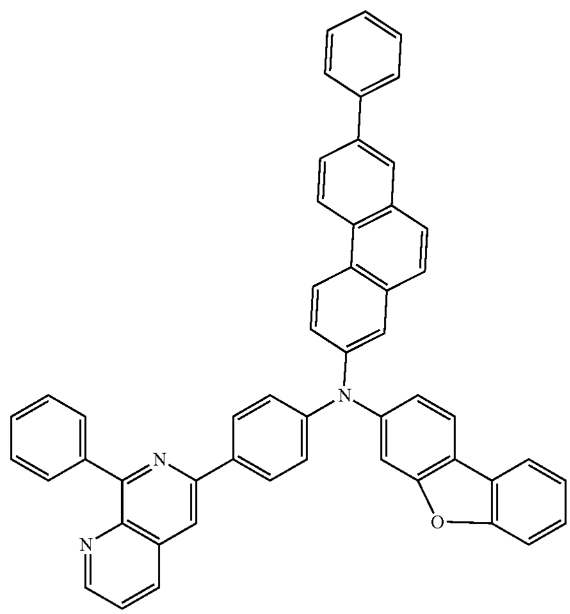
P102
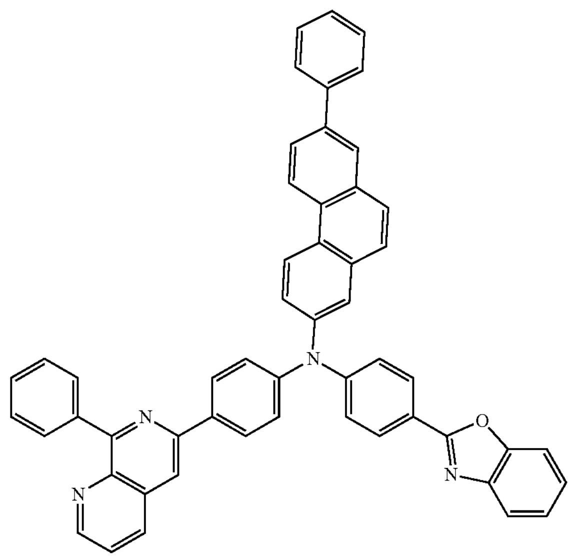
-continued
P103
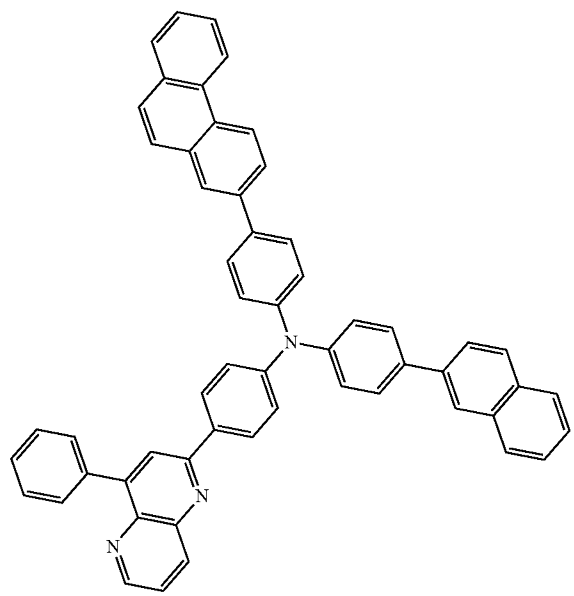
P104
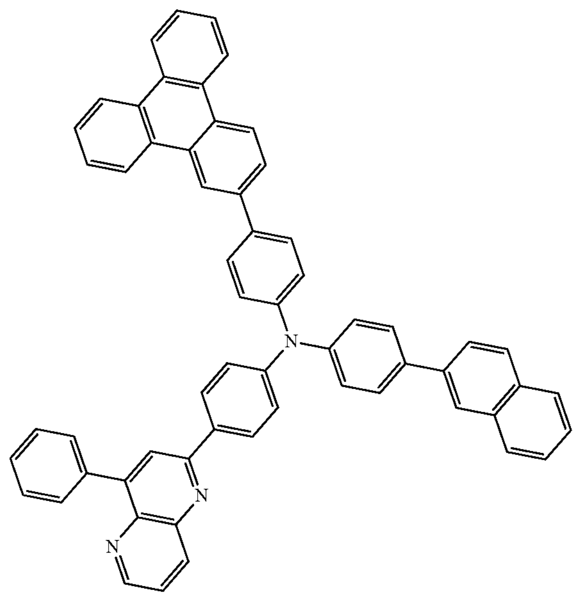

-continued
P105
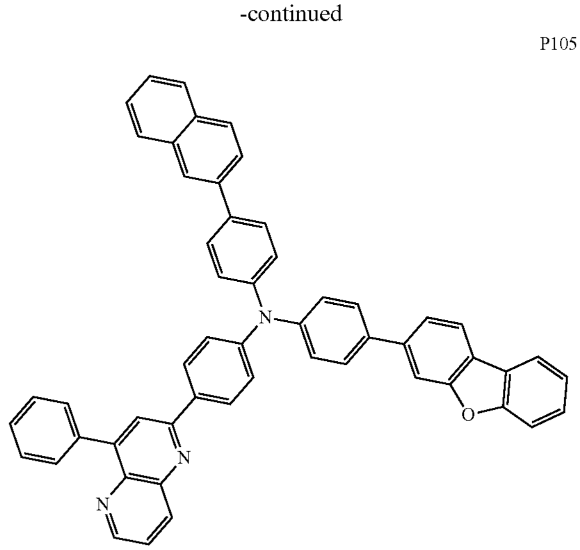
P106
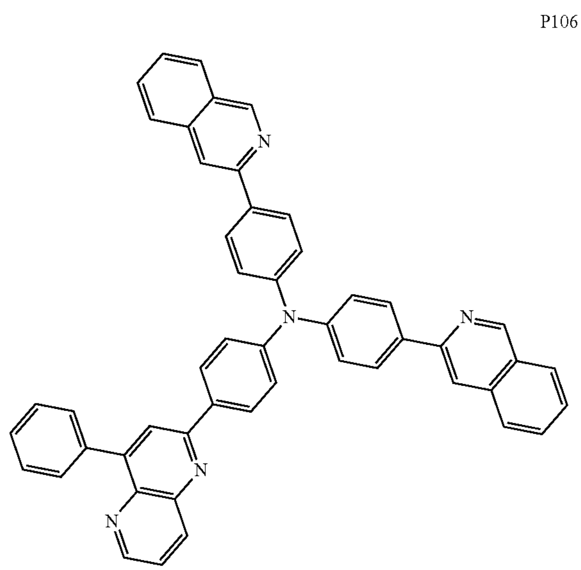 [SMILES: c1ccc(-c2cc(-c3ccc(N(c4ccc(-c5ccc6ccccc6c5)cc4)c4ccc(-c5ccc6ccncc6c5)cc4)cc3)nc3cccnc23)cc1]
P107
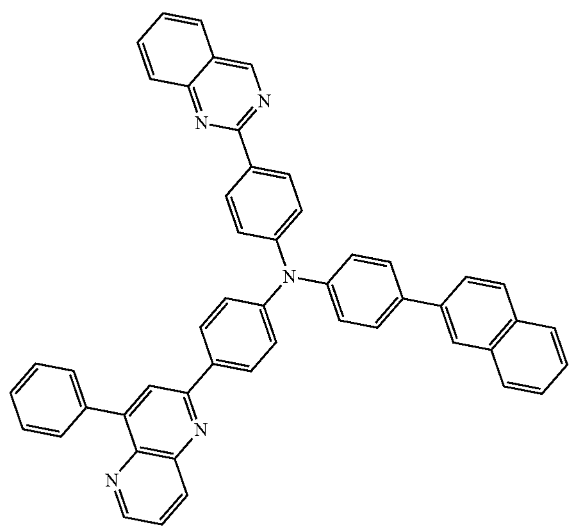
-continued
P108
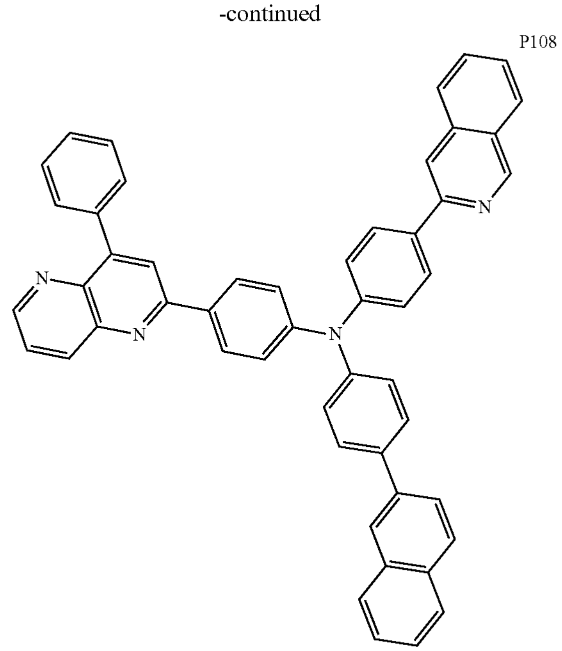
P109
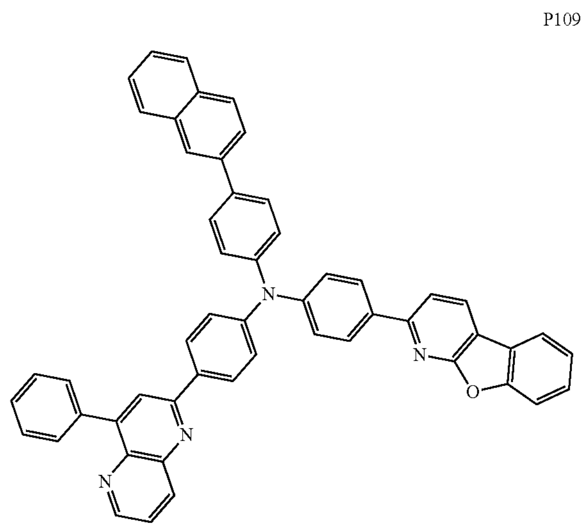
P110
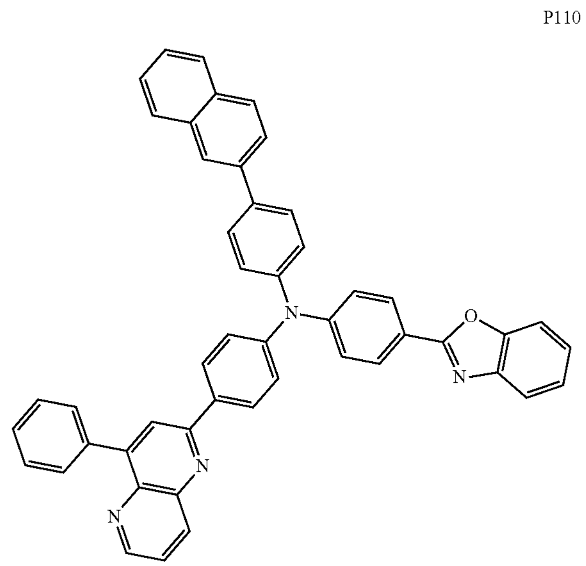

-continued
P111
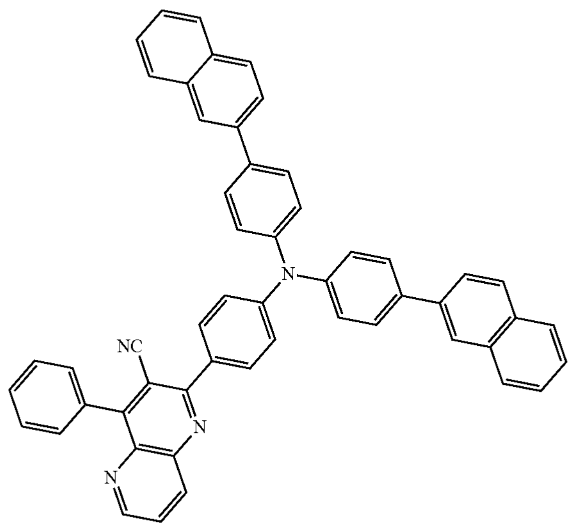
P112
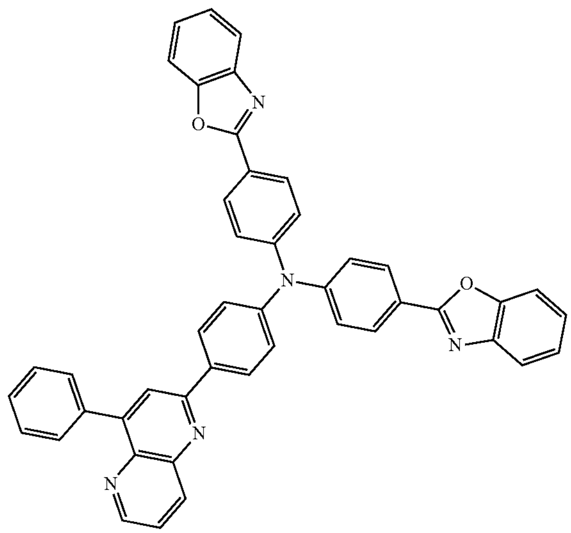
P113
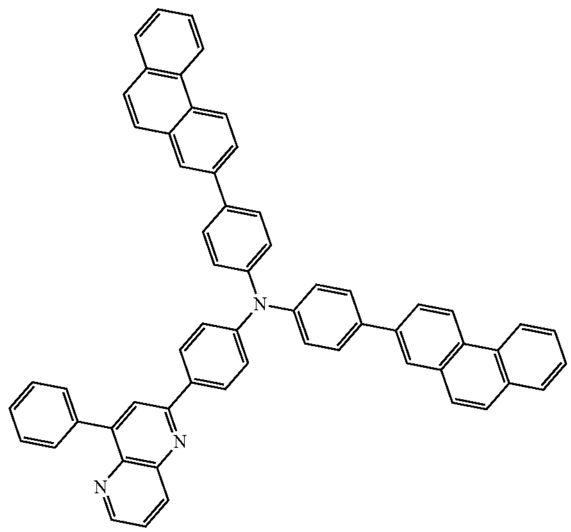
-continued
P114
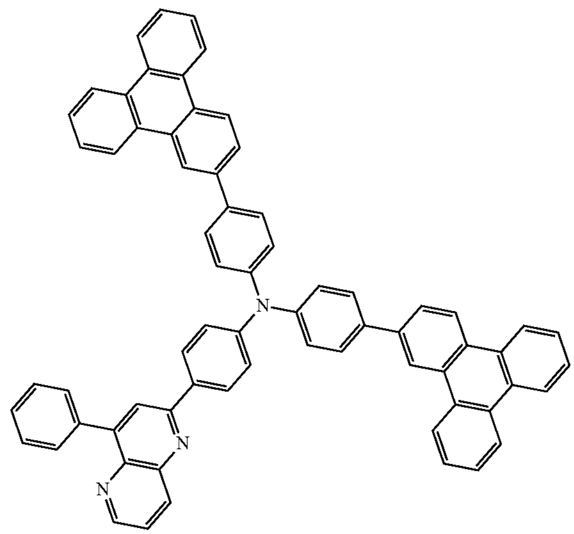
P115
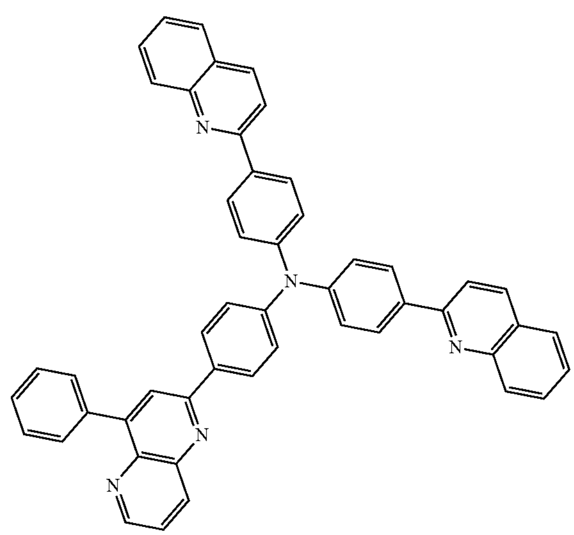
P116
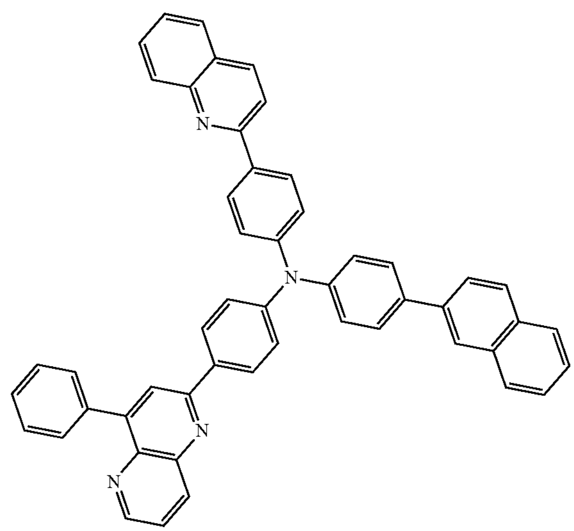

-continued
P117
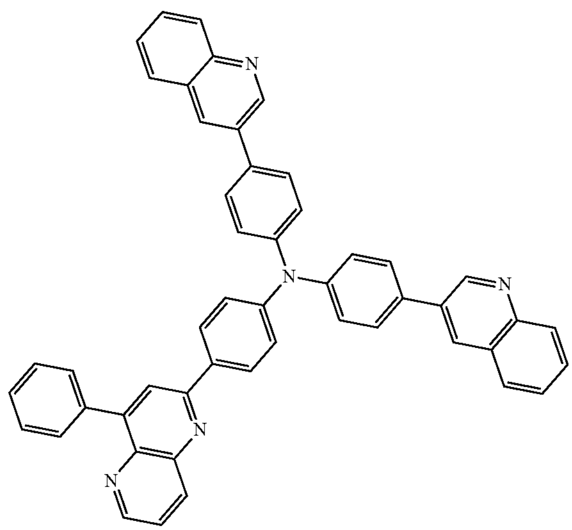
P118
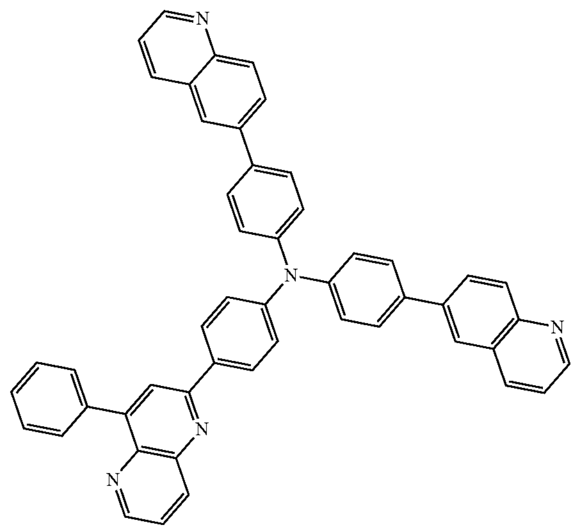
P119
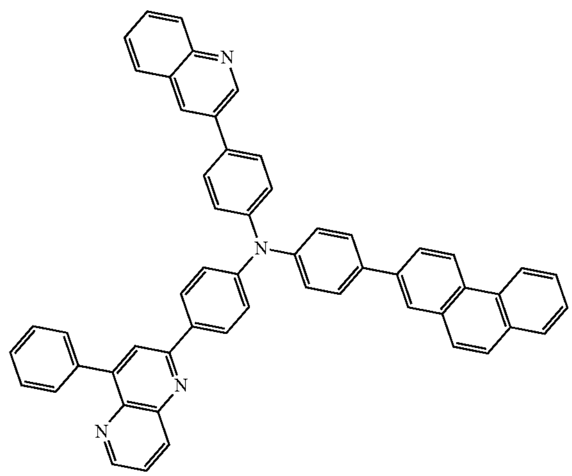
-continued
P120
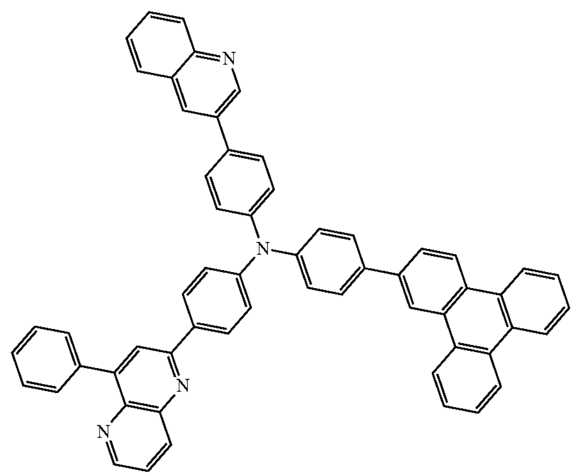
P121
P122
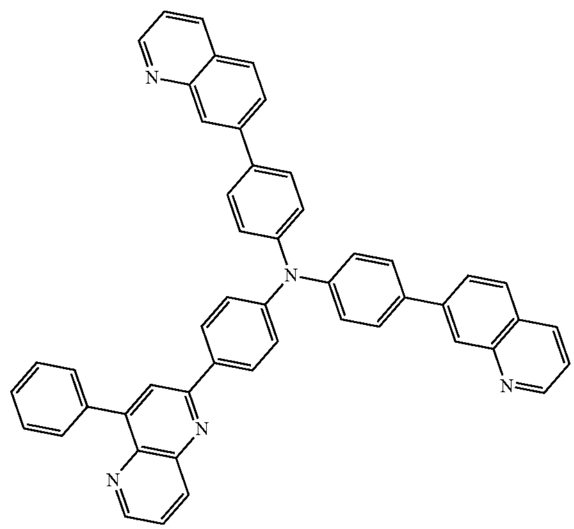

-continued
P123
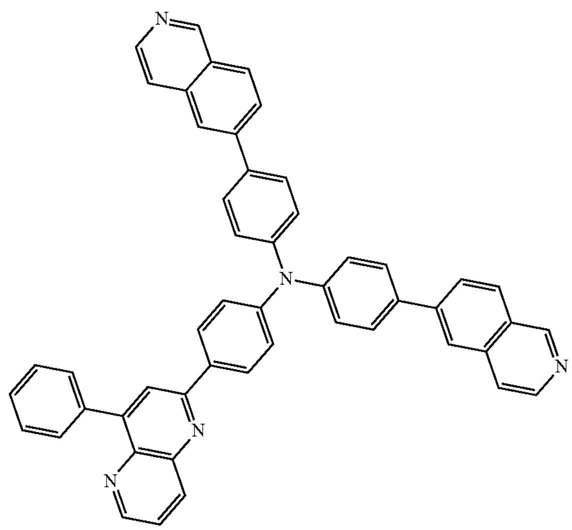
P124
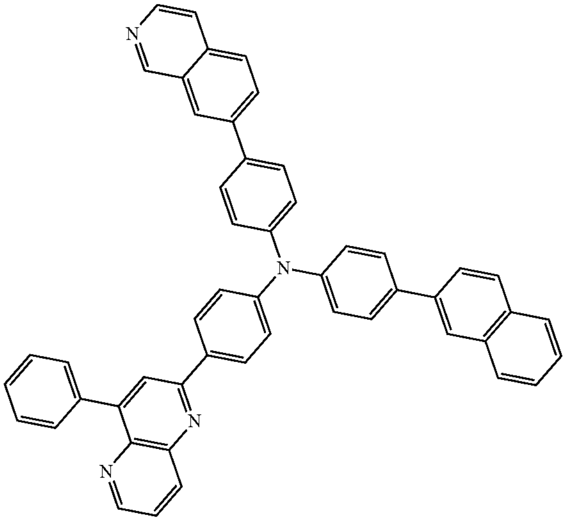
P125
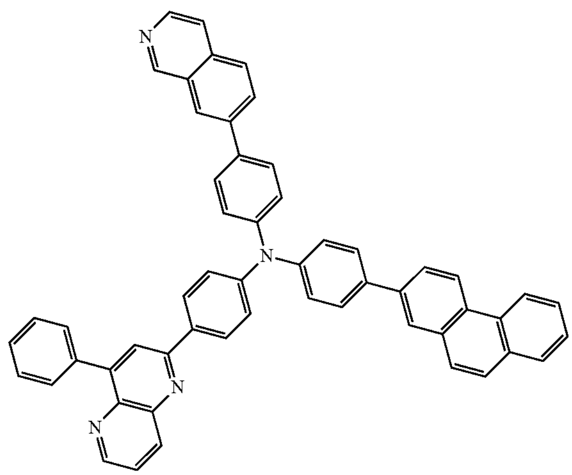
-continued
P126
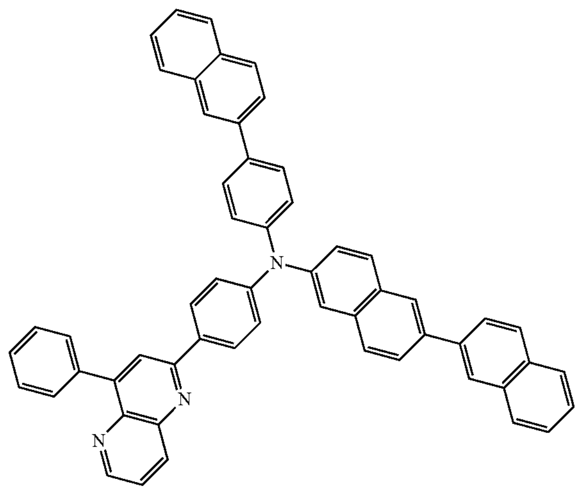
P127
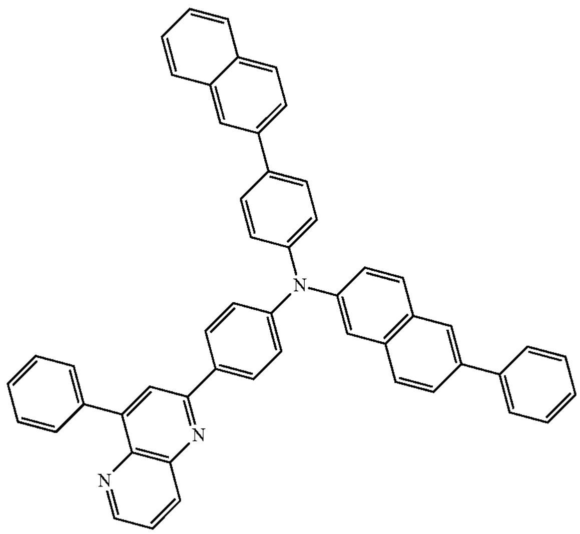
P128
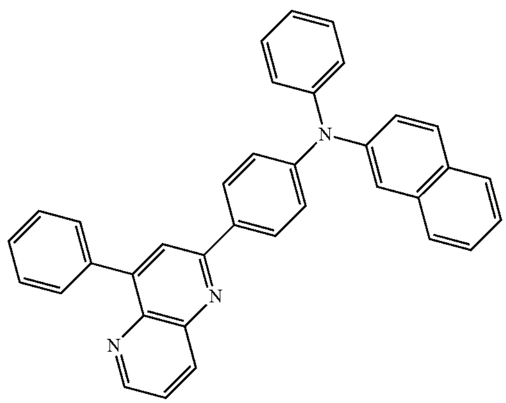

-continued
P129
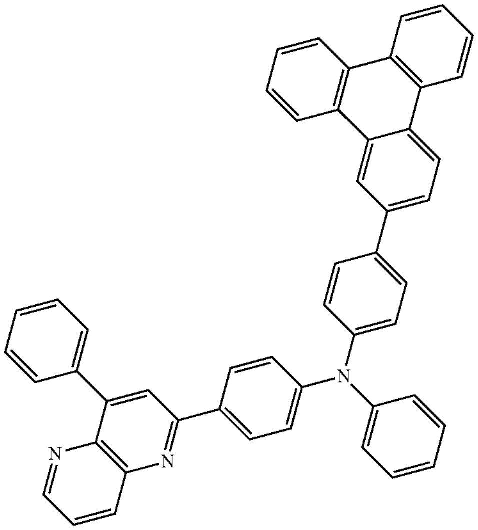
P130
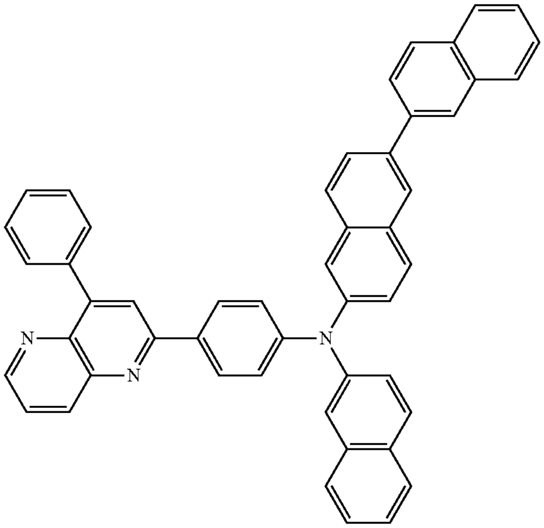
P131
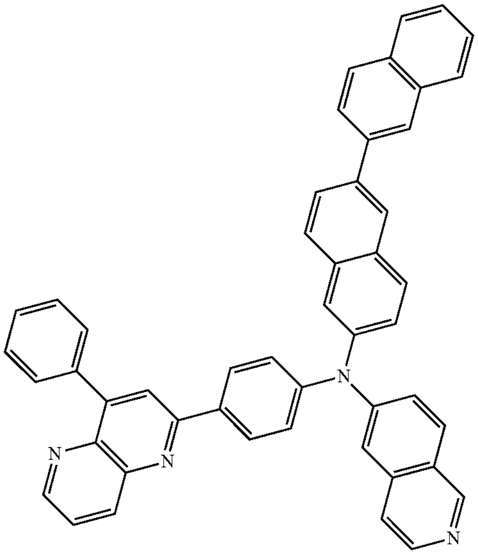
-continued
P132
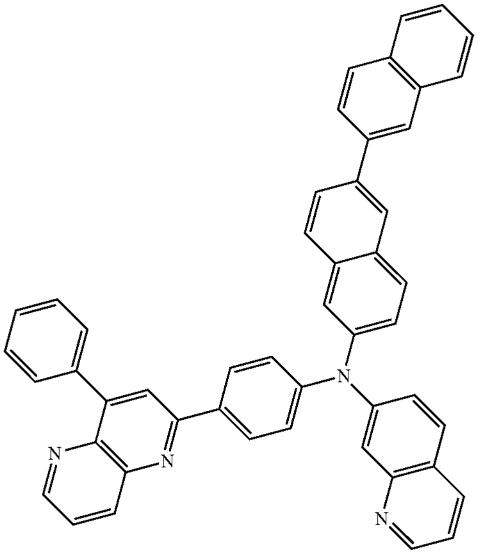
P133
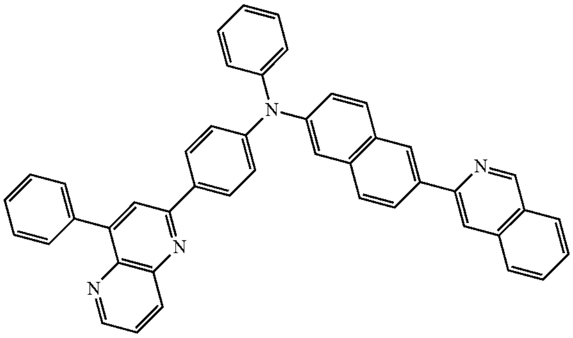
P134
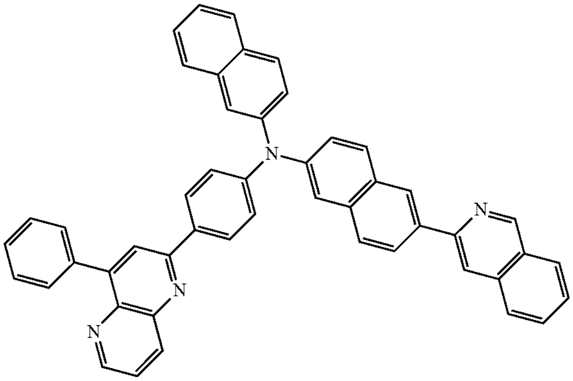

-continued
P135
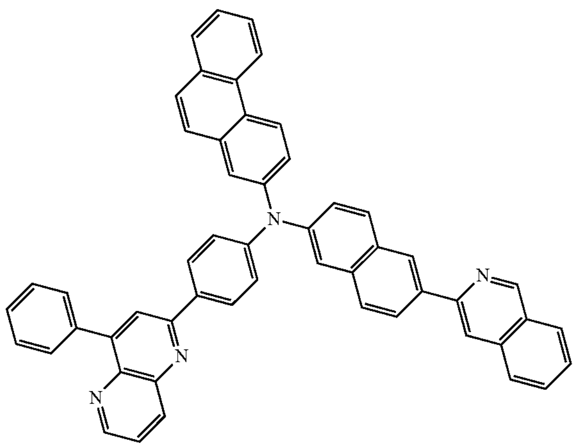
P136
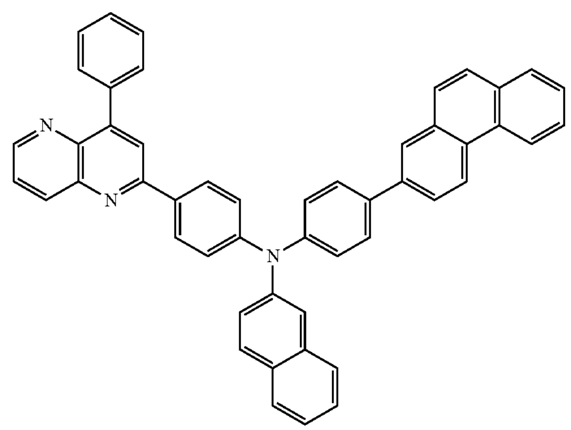
P137
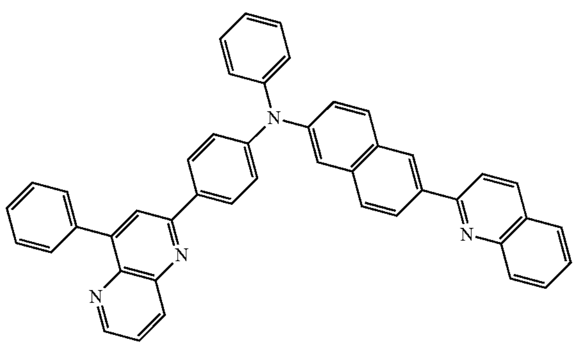
-continued
P138
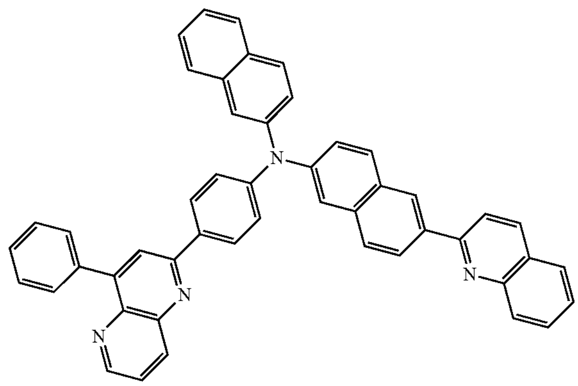
P139
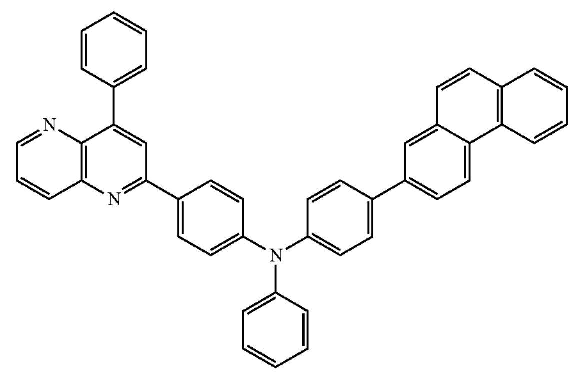
P140
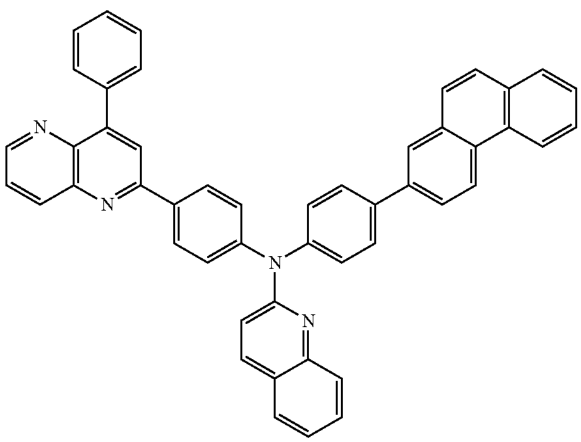

-continued
P141
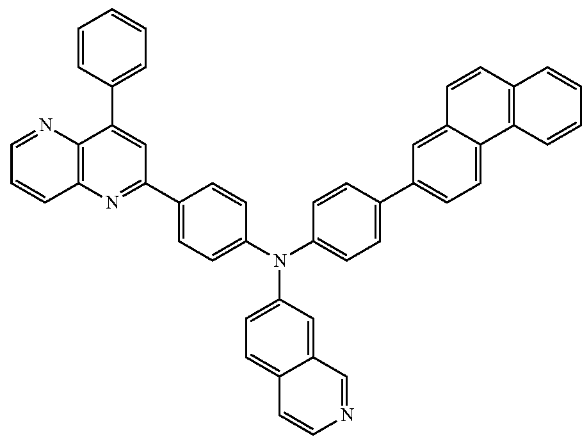
P142
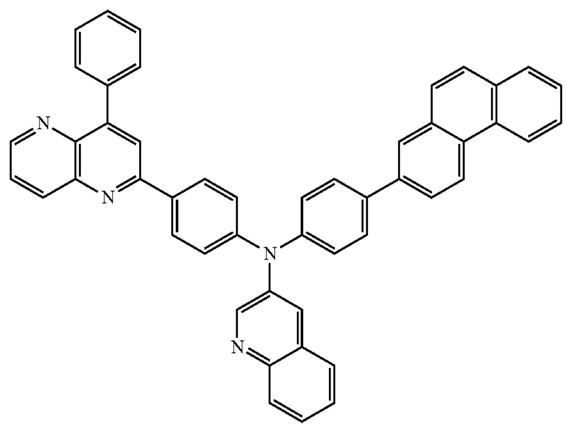
P143
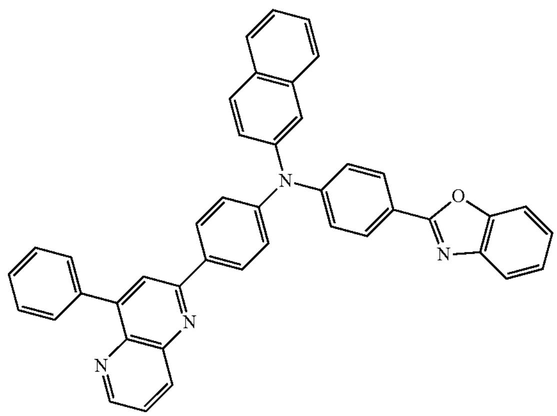
-continued
P144
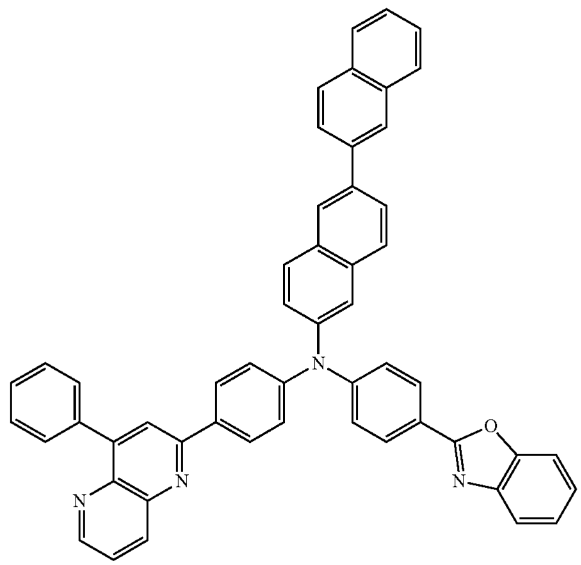
P145
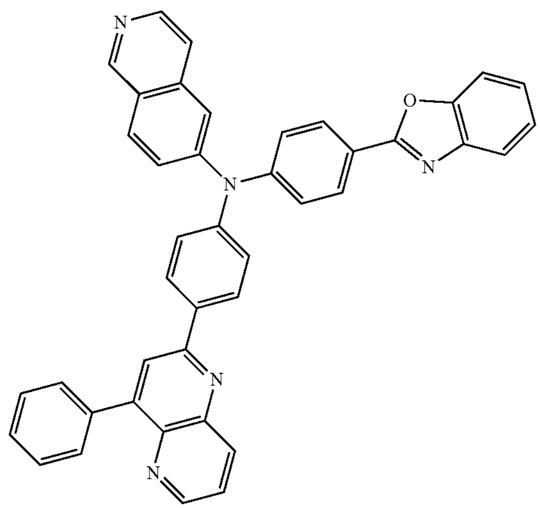

-continued
P146
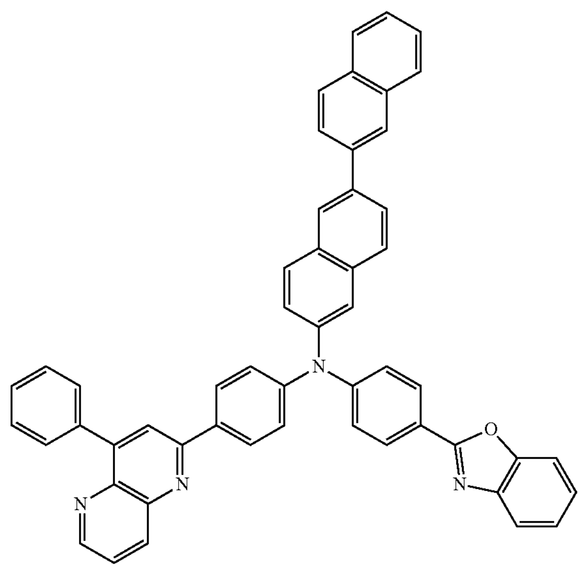
P147
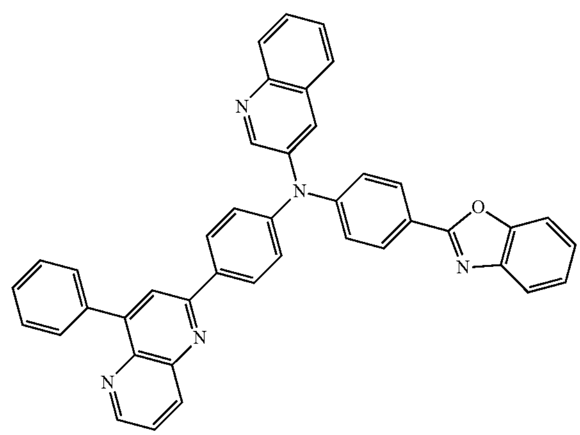
P148
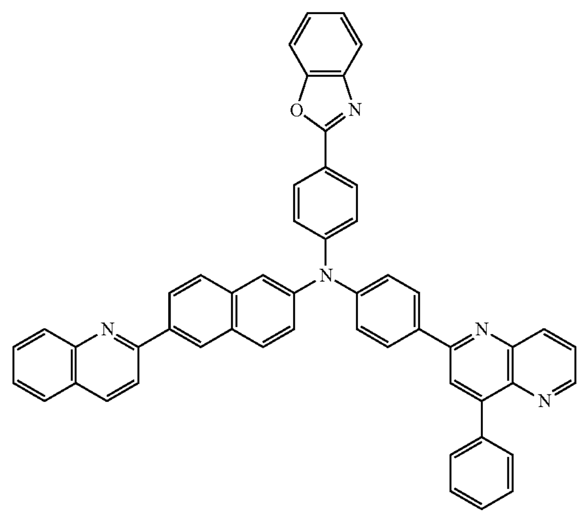
-continued
P149
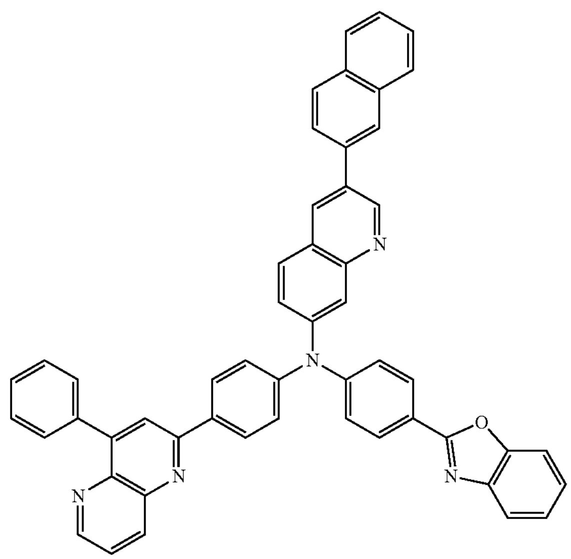
P150
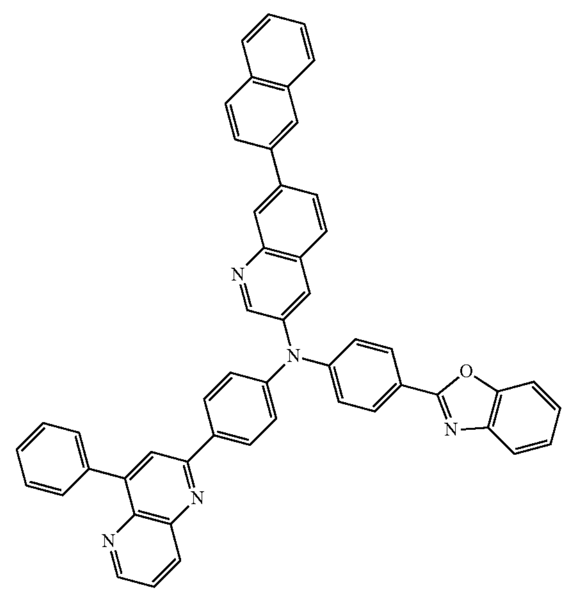

-continued
P151
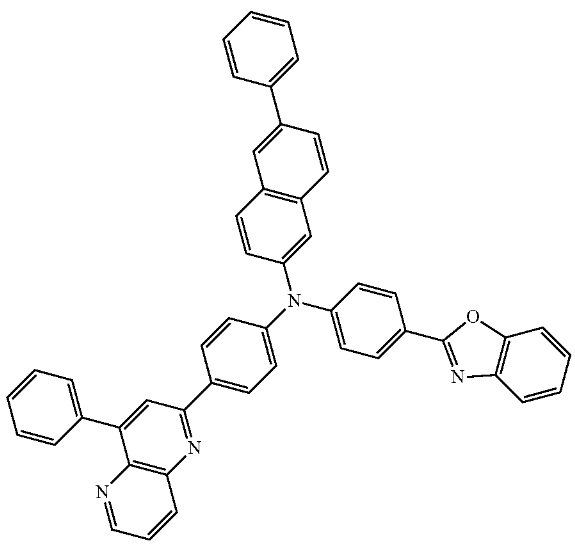
P152
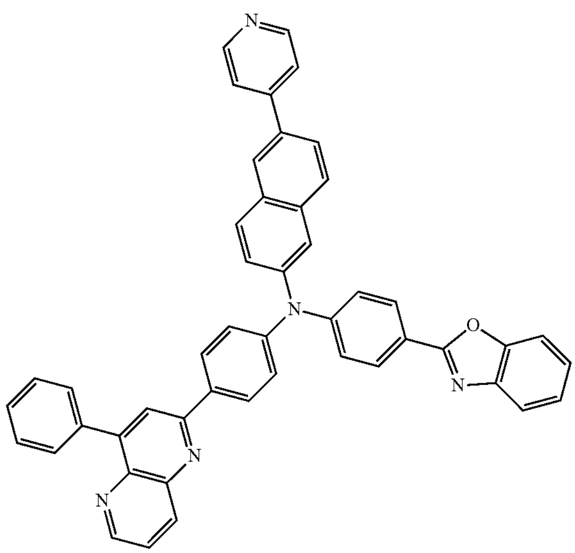
-continued
P153
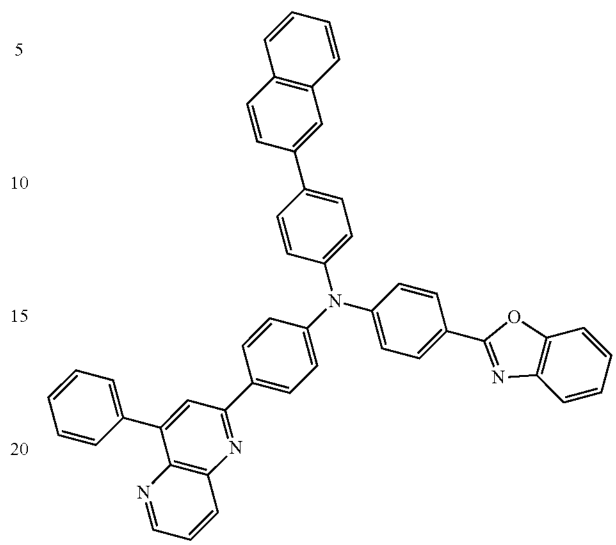
P154
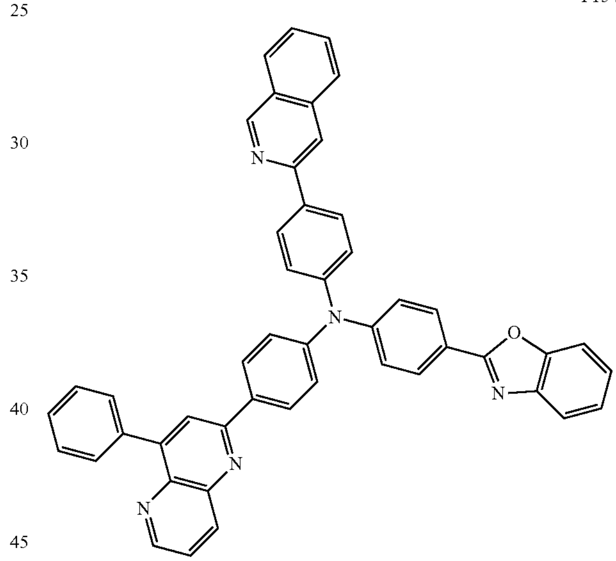
P155
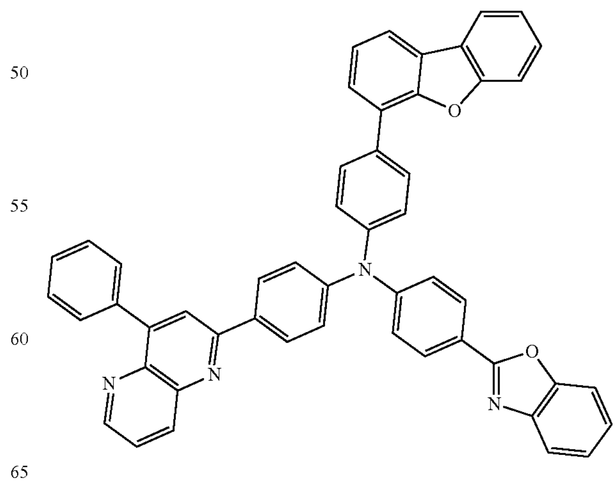

-continued
P156
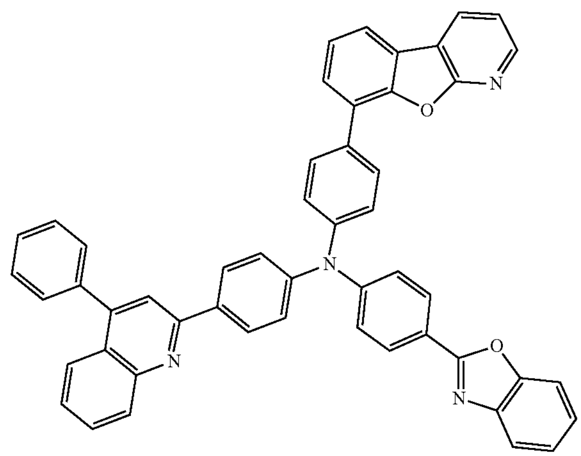
P157
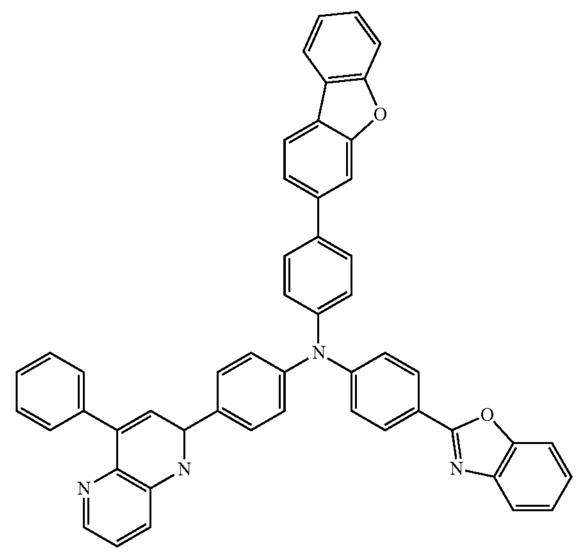
P158
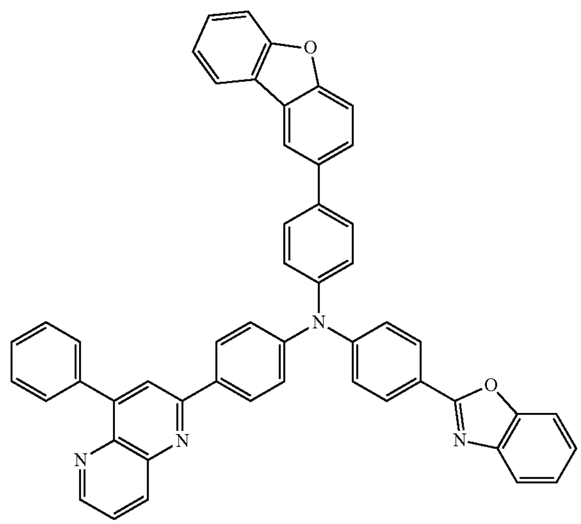
-continued
P159
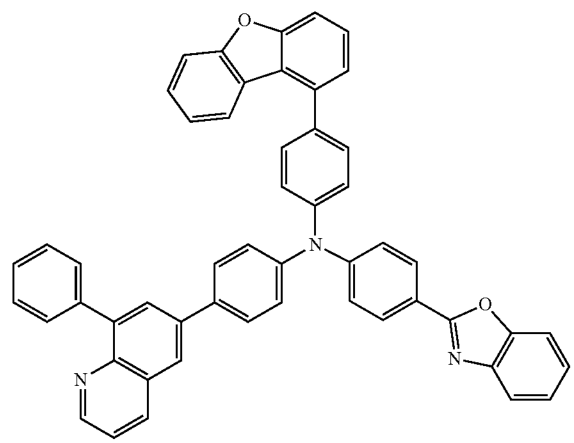
P160
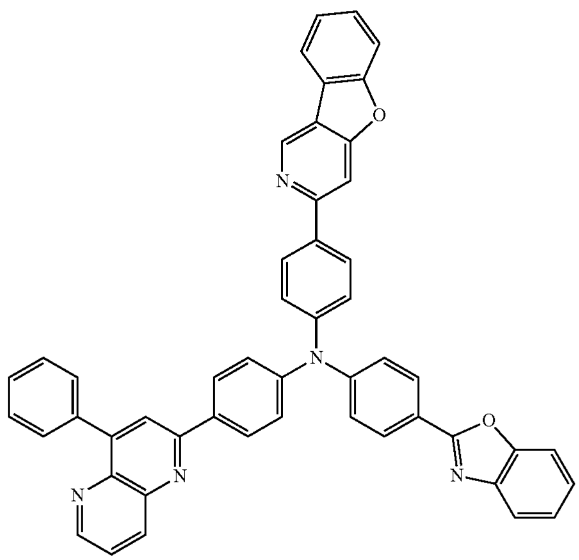
P161
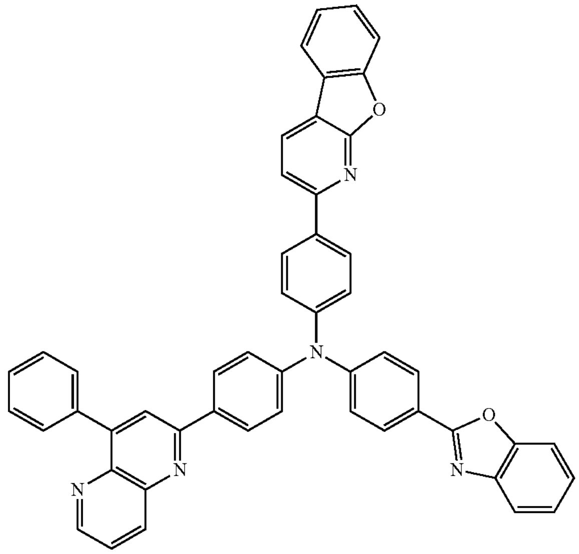

P162
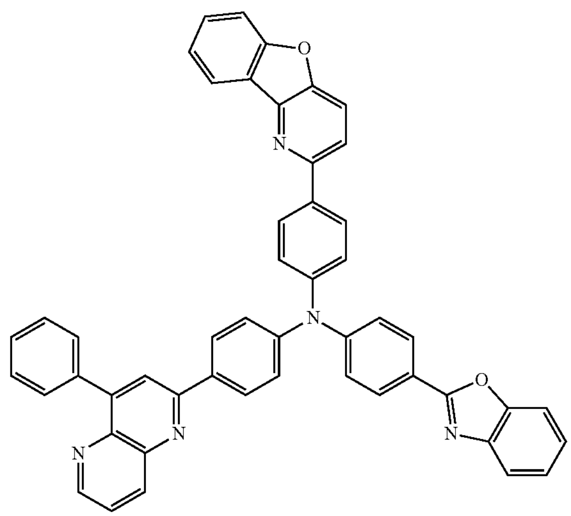
P163
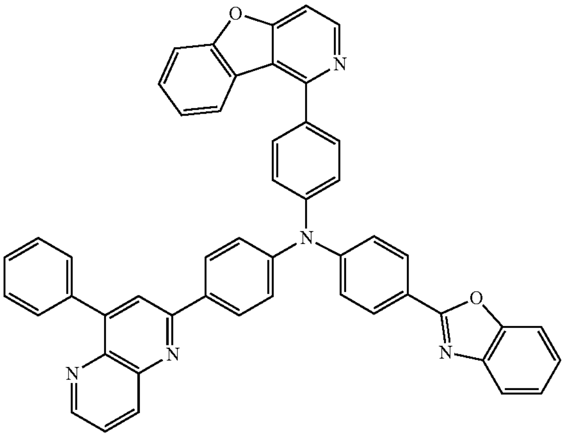
P164
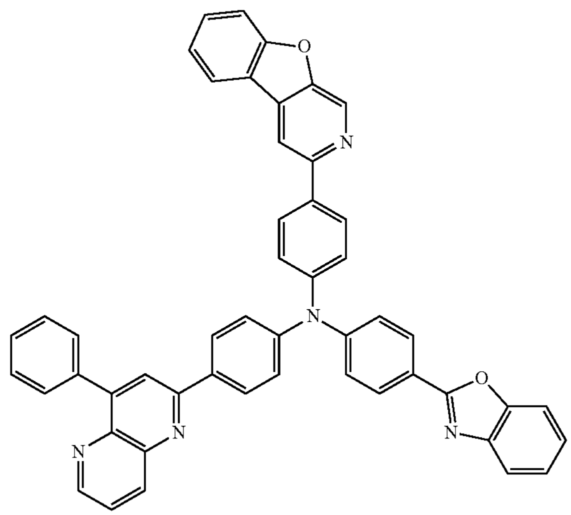
P165
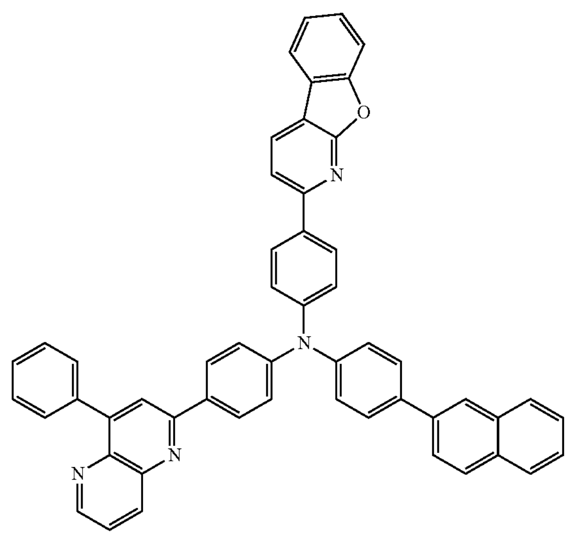
P166
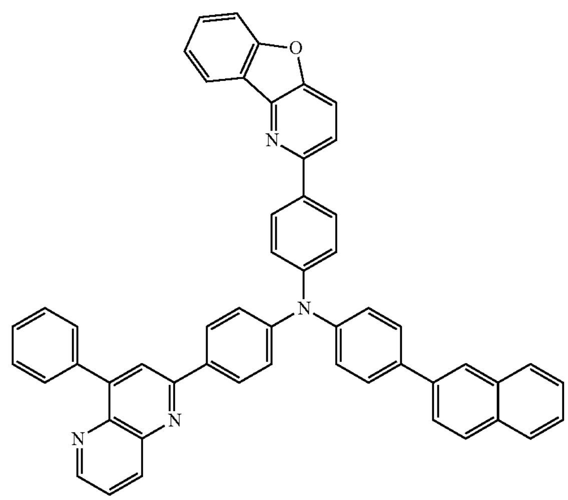
P167
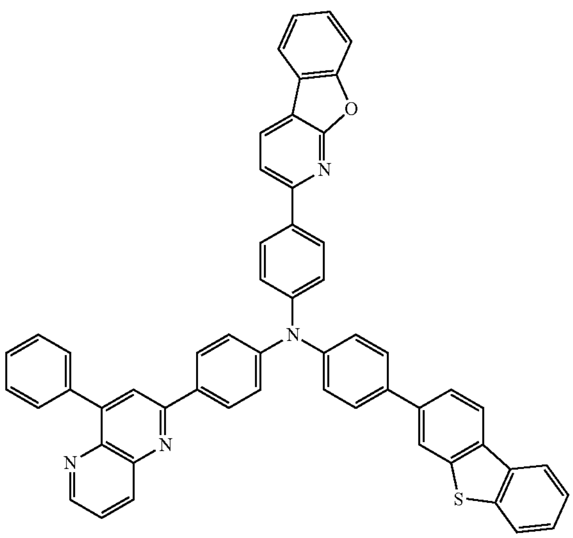

-continued
P168
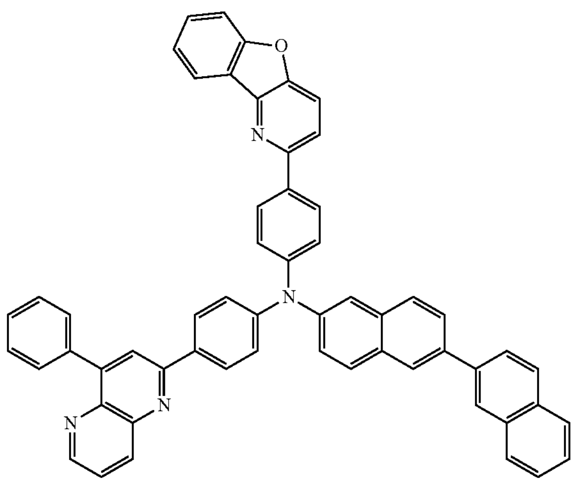
P169
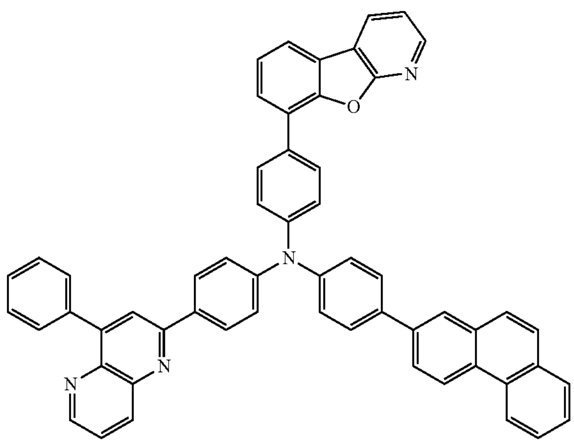
P170
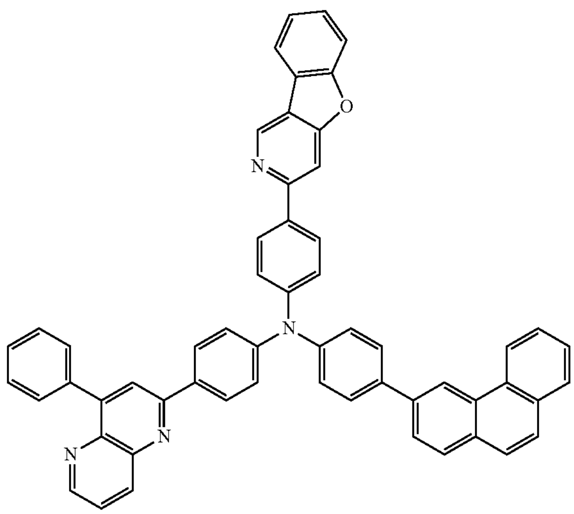
-continued
P171
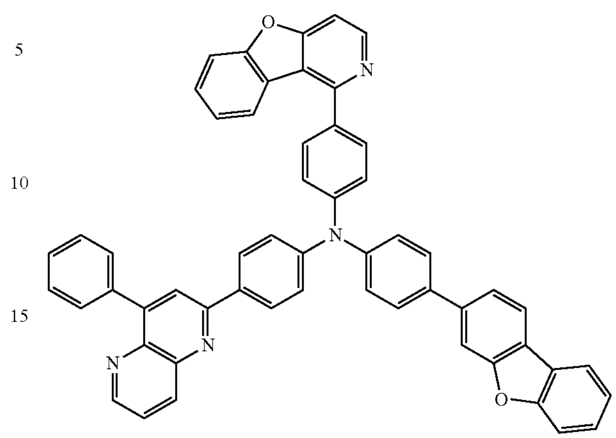
P172
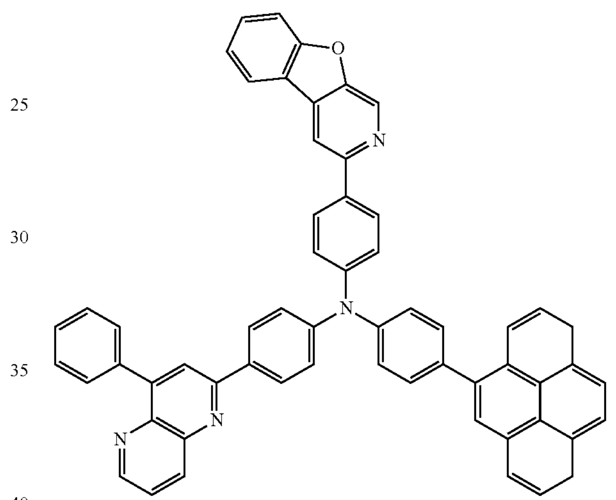
P173
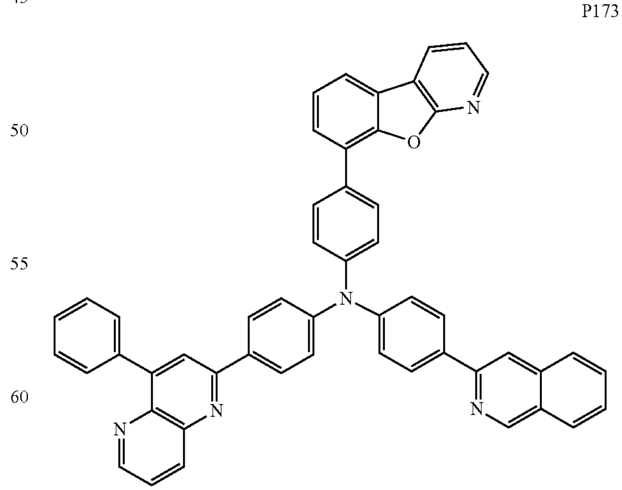

-continued
P174
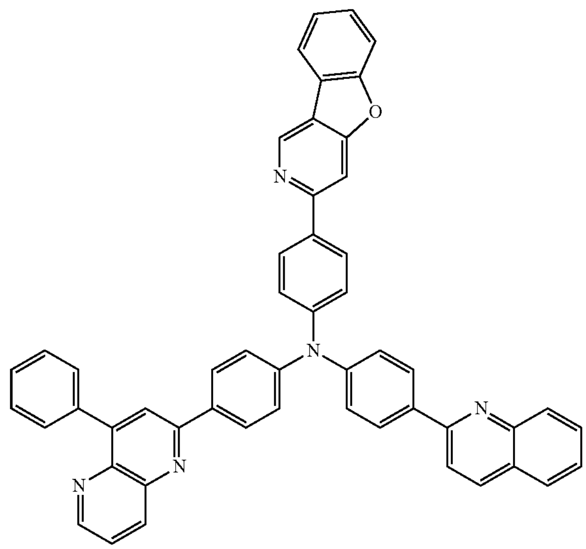
P175
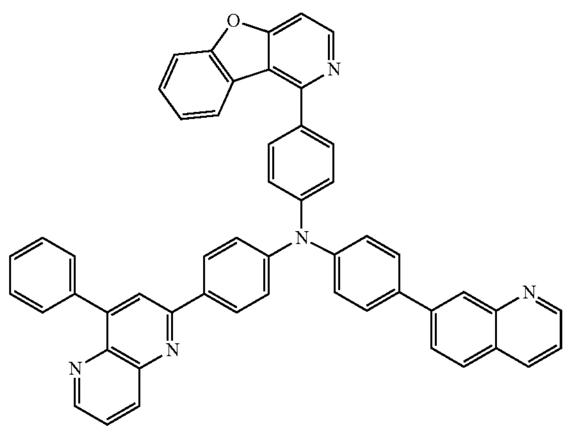
P176
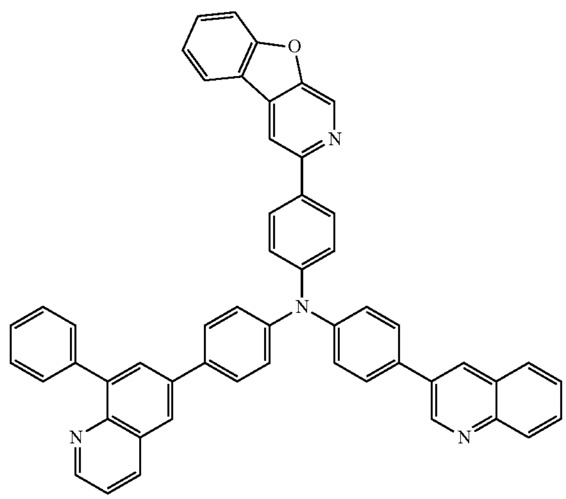
-continued
P177
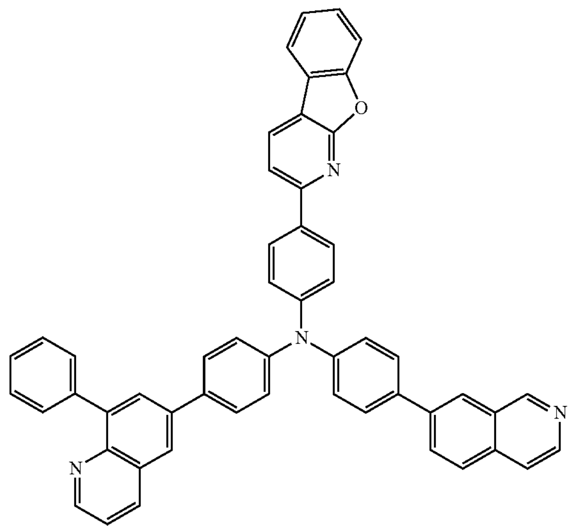
P178
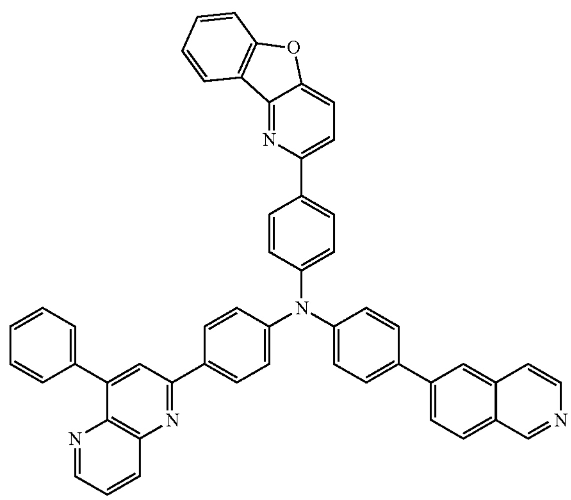
P179
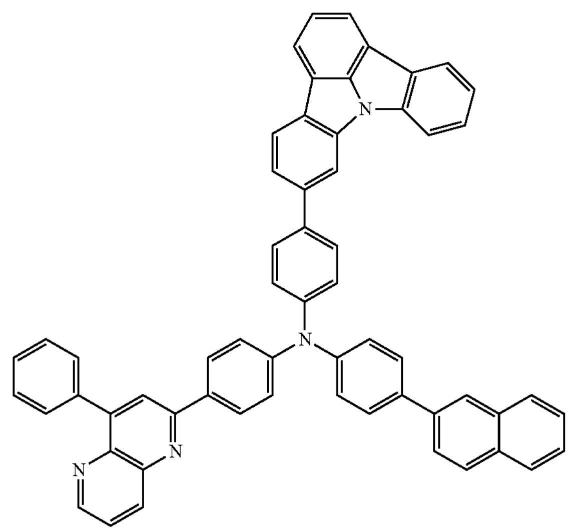

-continued
P180
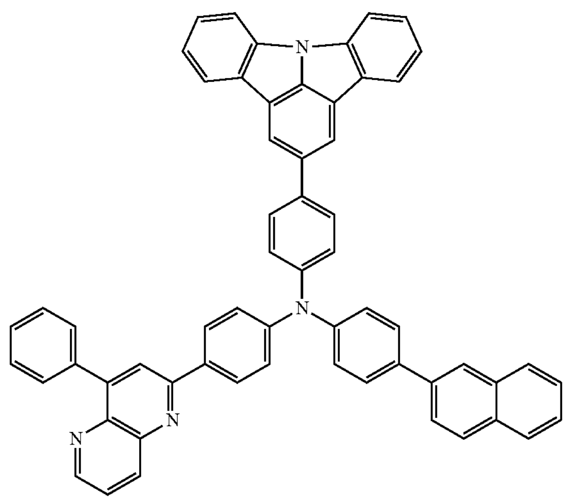
P181
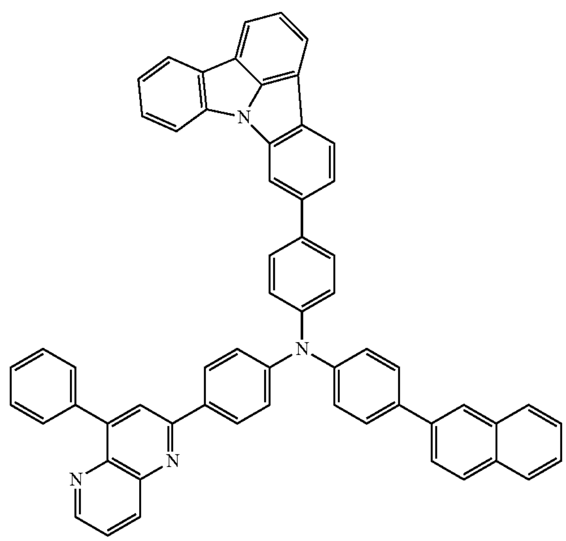
P182
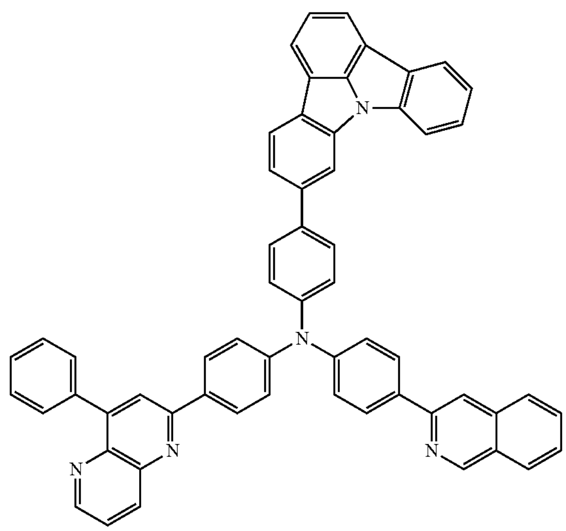
-continued
P183
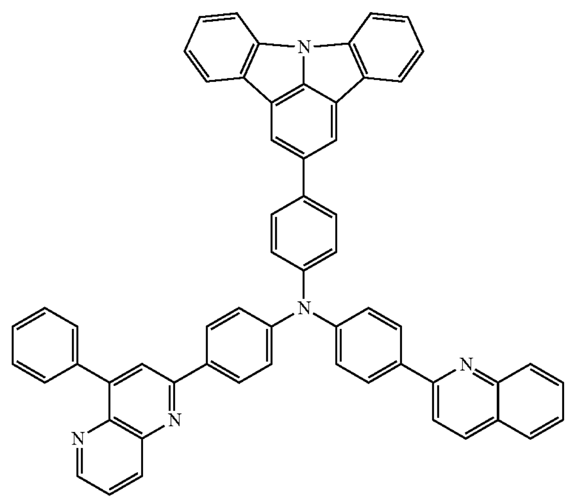
P184
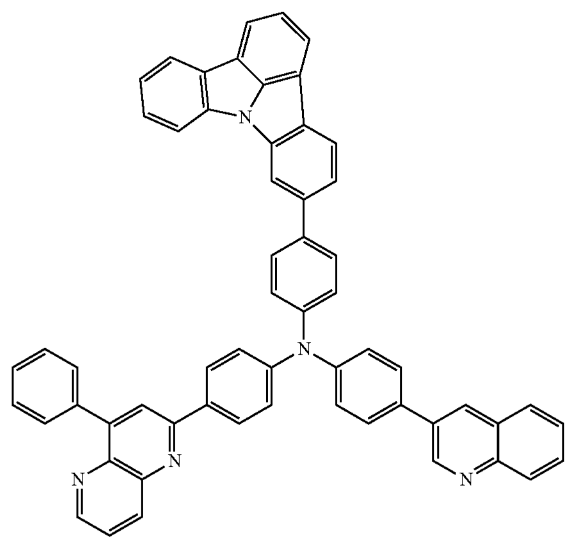
P185
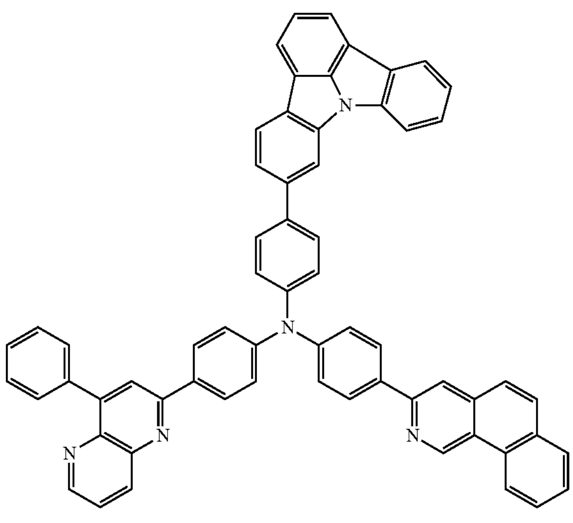

P186
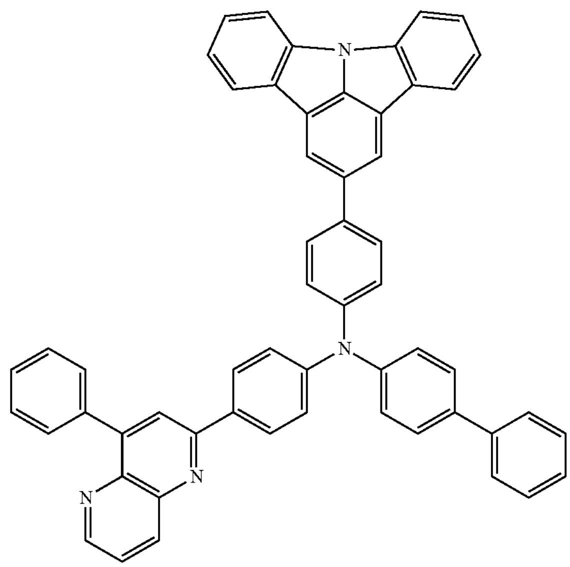
P187
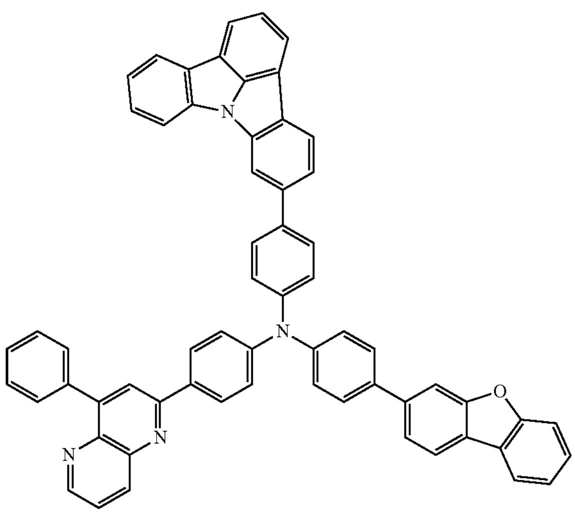
P188
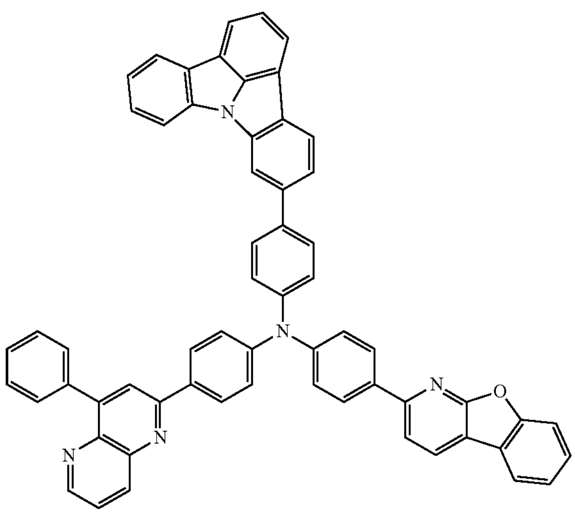
P189
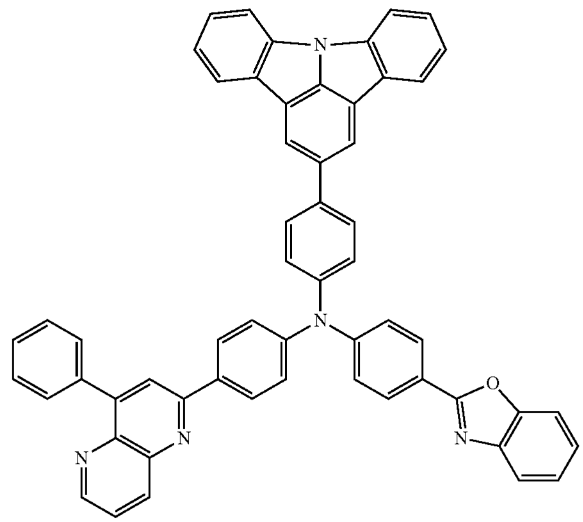
P190
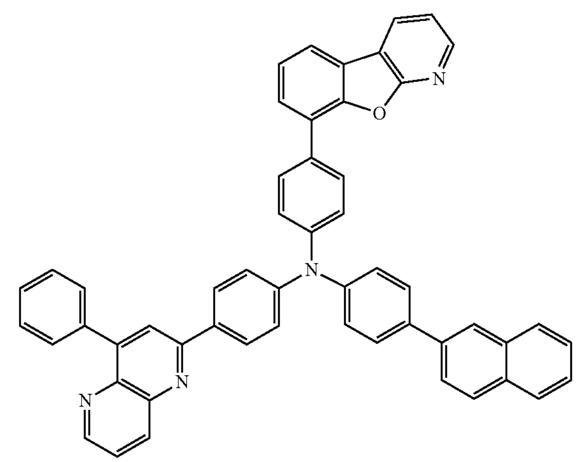
P191
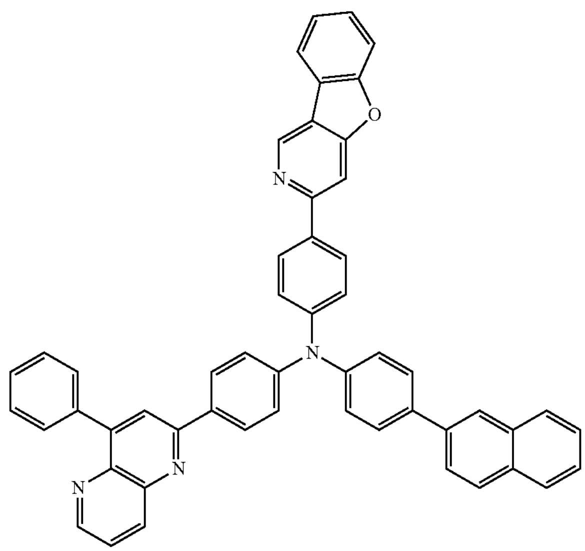

-continued
P192
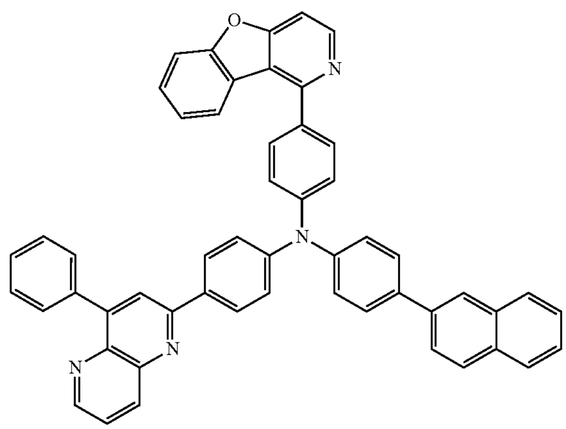
P193
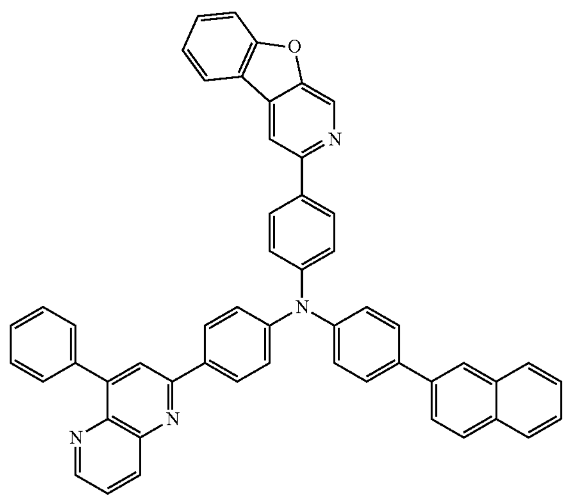
P194
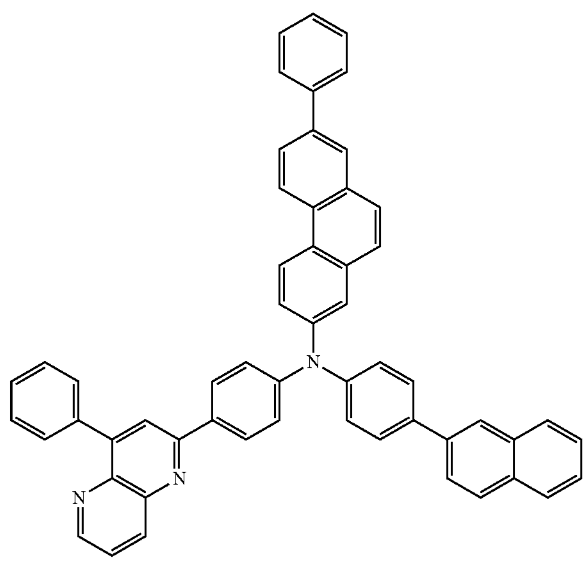
-continued
P195
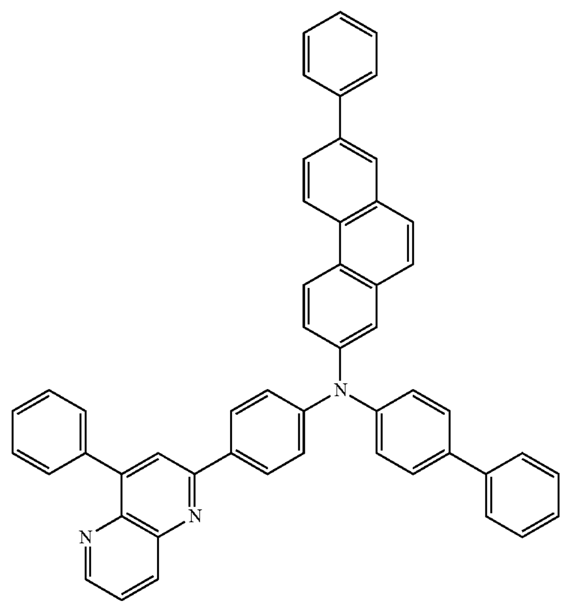
P196
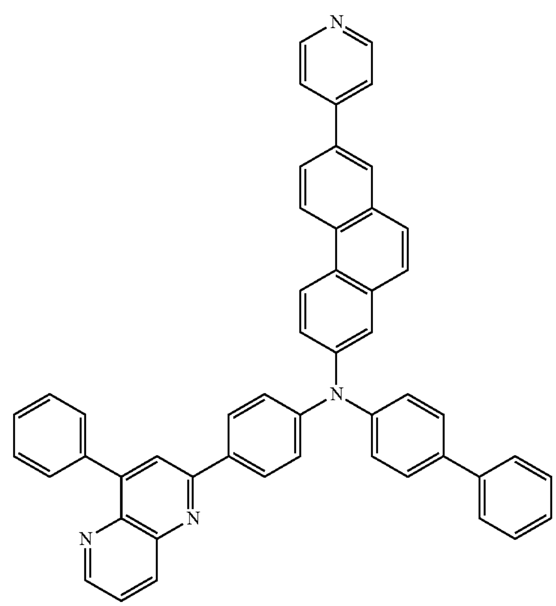

-continued
P197
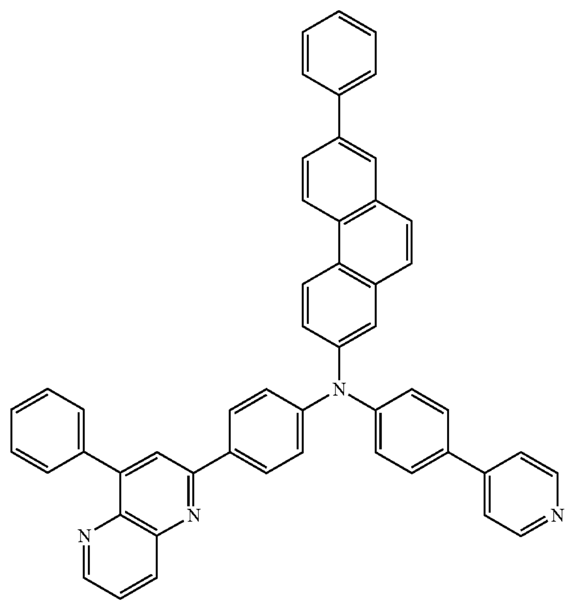
P198
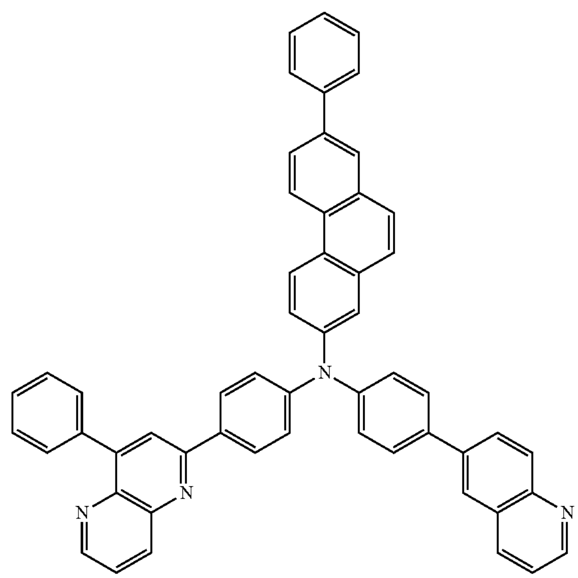
-continued
P199
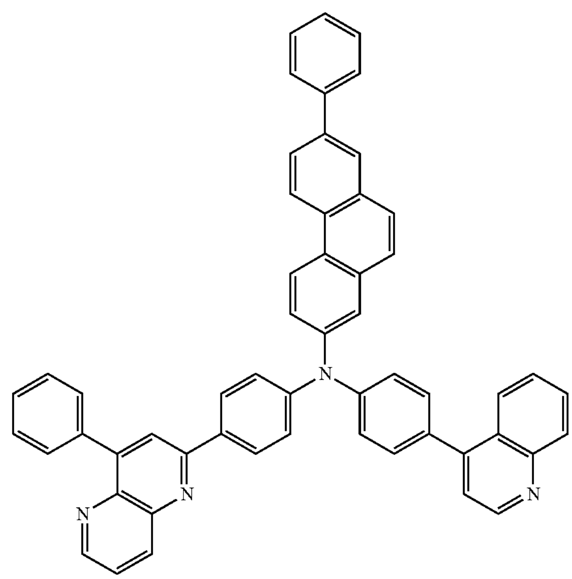
P200
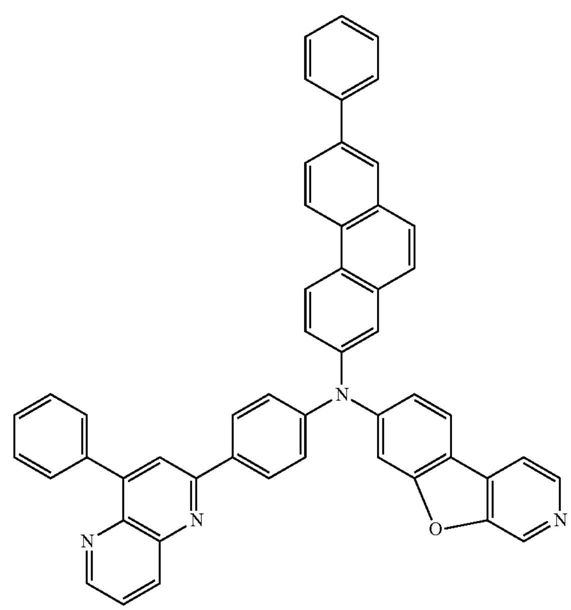

-continued

P201

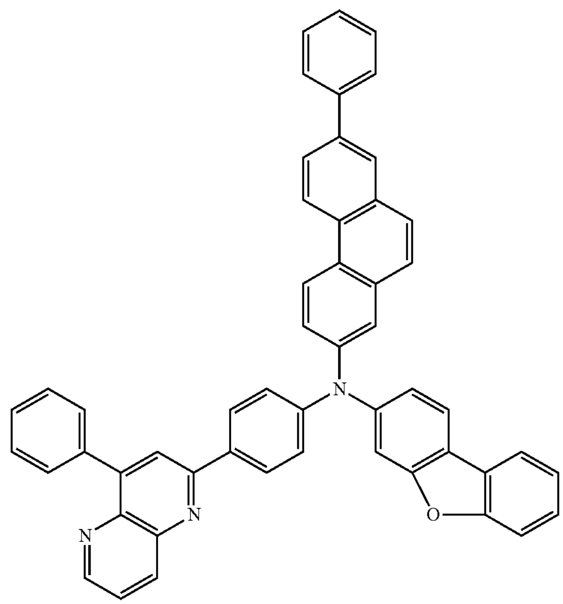

P202

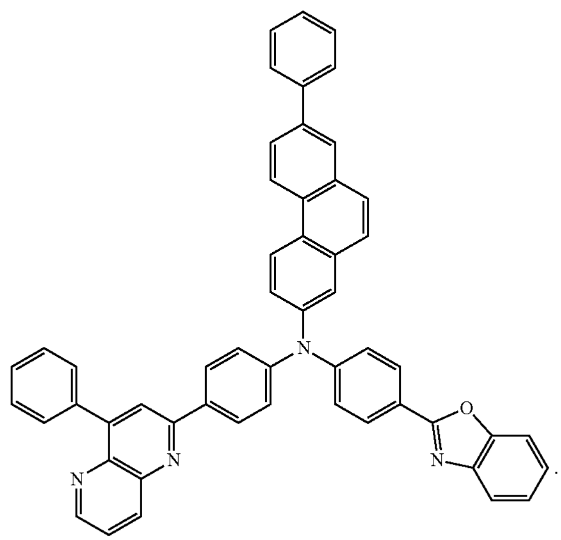

15. An organic light-emitting device, comprising: an anode; a cathode; and an organic thin film layer positioned between the anode and the cathode, the organic thin film layer includes a capping layer, and the capping layer includes a compound of a structure of Formula I:

Formula I

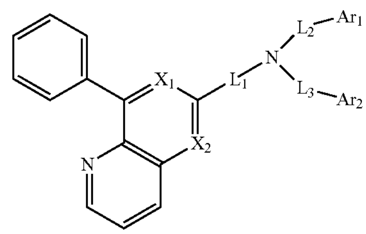

wherein $X_1$ and $X_2$ are each independently a nitrogen atom or a C—R group, C is a carbon atom, R is a hydrogen atom, a deuterium atom, a halogen atom, or a cyano group, and at least one of $X_1$ and $X_2$ is N;

$L_1$, $L_2$, and $L_3$ are each independently a single bond, a substituted or unsubstituted aryl group, or substituted or unsubstituted aryl heteroaryl group; and $Ar_1$, $Ar_2$ are each independently a substituted or unsubstituted aryl group or a substituted or unsubstituted heteroaryl group.

16. A display panel, comprising: the organic light emitting device of claim 15.

* * * * *